US007829531B2

(12) United States Patent
Senter et al.

(10) Patent No.: US 7,829,531 B2
(45) Date of Patent: *Nov. 9, 2010

(54) DRUG CONJUGATES AND THEIR USE FOR TREATING CANCER, AN AUTOIMMUNE DISEASE OR AN INFECTIOUS DISEASE

(75) Inventors: Peter D. Senter, Seattle, WA (US); Svetlana O. Doronina, Snohomish, WA (US); Brian E. Toki, Shoreline, WA (US)

(73) Assignee: Seattle Genetics Inc., Bothell, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/408,646

(22) Filed: Mar. 20, 2009

(65) Prior Publication Data

US 2009/0324621 A1 Dec. 31, 2009

Related U.S. Application Data

(63) Continuation of application No. 10/522,911, filed as application No. PCT/US03/24209 on Jul. 31, 2003, now Pat. No. 7,659,241.

(60) Provisional application No. 60/400,403, filed on Jul. 31, 2002.

(51) Int. Cl.
*A61K 38/00* (2006.01)
(52) U.S. Cl. .......................................................... 514/2
(58) Field of Classification Search .................. None
See application file for complete search history.

(56) References Cited

U.S. PATENT DOCUMENTS

| | | | |
|---|---|---|---|
| 3,445,518 A | 5/1969 | Shavel, Jr. et al. |
| 4,414,205 A | 11/1983 | Pettit |
| 4,753,894 A | 6/1988 | Frankel et al. |
| 4,764,368 A | 8/1988 | Blatter et al. |
| 4,816,444 A | 3/1989 | Pettit et al. |
| 4,879,278 A | 11/1989 | Pettit et al. |
| 4,943,628 A | 7/1990 | Rosen et al. |
| 4,978,744 A | 12/1990 | Pettit et al. |
| 5,122,368 A | 6/1992 | Greenfield et al. |
| 5,165,923 A | 11/1992 | Thorpe et al. |
| 5,169,774 A | 12/1992 | Frankel et al. |
| 5,286,637 A | 2/1994 | Veronese et al. |
| 5,410,024 A | 4/1995 | Pettit et al. |
| 5,521,284 A | 5/1996 | Pettit et al. |
| 5,530,097 A | 6/1996 | Pettit et al. |
| 5,554,725 A | 9/1996 | Pettit |
| 5,585,089 A | 12/1996 | Queen et al. |
| 5,599,902 A | 2/1997 | Pettit et al. |
| 5,629,197 A | 5/1997 | Ring et al. |
| 5,635,483 A | 6/1997 | Pettit et al. |
| 5,654,399 A | 8/1997 | Sakakibara et al. |
| 5,663,149 A | 9/1997 | Pettit et al. |
| 5,665,860 A | 9/1997 | Pettit et al. |
| 5,708,146 A | 1/1998 | Willner et al. |
| 5,714,586 A | 2/1998 | Kunstmann et al. |
| 5,741,892 A | 4/1998 | Barlozzari et al. |
| 5,767,236 A | 6/1998 | Kim et al. |
| 5,767,237 A | 6/1998 | Sakakibara et al. |
| 5,780,588 A | 7/1998 | Pettit et al. |
| 5,821,337 A | 10/1998 | Carter et al. |
| 5,840,699 A | 11/1998 | Sakakibara et al. |
| 5,965,537 A | 10/1999 | Ritter et al. |
| 6,004,934 A | 12/1999 | Sakakibara et al. |
| 6,033,876 A | 3/2000 | Lemke et al. |
| 6,034,065 A | 3/2000 | Pettit et al. |
| 6,048,720 A | 4/2000 | Dalborg et al. |
| 6,054,297 A | 4/2000 | Carter et al. |
| 6,054,561 A | 4/2000 | Ring et al. |
| 6,124,431 A | 9/2000 | Sakakibara et al. |
| 6,143,721 A | 11/2000 | Janssen et al. |
| 6,162,930 A | 12/2000 | Pinney et al. |
| 6,214,345 B1 | 4/2001 | Firestone et al. |
| 6,239,104 B1 | 5/2001 | Pettit et al. |
| 6,323,315 B1 | 11/2001 | Pettit et al. |
| 6,342,219 B1 | 1/2002 | Thorpe et al. |
| 6,342,221 B1 | 1/2002 | Thorpe et al. |
| 6,407,213 B1 | 6/2002 | Carter et al. |
| 6,569,834 B1 | 5/2003 | Pettit et al. |
| 6,620,911 B1 | 9/2003 | Pettit et al. |
| 6,639,055 B1 | 10/2003 | Carter et al. |
| 6,884,869 B2 | 4/2005 | Senter et al. |
| 6,913,748 B2 | 7/2005 | Widdison |
| 7,090,843 B1 | 8/2006 | Francisco et al. |
| 7,091,186 B2 | 8/2006 | Senter et al. |
| 7,097,840 B2 | 8/2006 | Erickson et al. |
| 7,098,305 B2 | 8/2006 | Deghenghi et al. |
| 7,098,308 B2 | 8/2006 | Senter et al. |
| 7,276,372 B2 | 10/2007 | Law et al. |
| 7,425,541 B2 | 9/2008 | Dubois et al. |
| 7,498,298 B2 | 3/2009 | Doronina et al. |

(Continued)

FOREIGN PATENT DOCUMENTS

AU 199478159 B2 4/1995

(Continued)

OTHER PUBLICATIONS

In The United States Patent and Trademark Office: Non-Final Rejection Office Action Summary of U.S. Appl. No. 12/016,978, Dated Apr. 14, 2010, 21 pages.

(Continued)

*Primary Examiner*—Christina Bradley
(74) *Attorney, Agent, or Firm*—Townsend and Townsend and Crew LLP

(57) ABSTRACT

Drug-Linker-Ligand Conjugates are disclosed in which a Drug is linked to a Ligand via a peptide-based Linker unit. In one embodiment, the Ligand is an Antibody. Drug-Linker compounds and Drug compounds are also disclosed. Methods for treating cancer, an autoimmune disease or an infectious disease using the compounds and compositions of the invention are also disclosed.

81 Claims, 8 Drawing Sheets

U.S. PATENT DOCUMENTS

| | | | |
|---|---|---|---|
| 7,553,816 | B2 | 6/2009 | Senter et al. |
| 7,659,241 | B2 | 2/2010 | Senter et al. |
| 7,662,387 | B2 | 2/2010 | Law et al. |
| 7,674,883 | B2 | 3/2010 | Bhaskar et al. |
| 2001/0018422 | A1 | 8/2001 | Ritter et al. |
| 2003/0083263 | A1 | 5/2003 | Doronina et al. |
| 2003/0130189 | A1 | 7/2003 | Senter et al. |
| 2004/0018194 | A1 | 1/2004 | Francisco et al. |
| 2004/0096392 | A1 | 5/2004 | Bhaskar et al. |
| 2004/0141983 | A1 | 7/2004 | Law et al. |
| 2004/0197325 | A1 | 10/2004 | Law et al. |
| 2004/0235068 | A1 | 11/2004 | Levinson |
| 2005/0014687 | A1 | 1/2005 | Anderson et al. |
| 2005/0084449 | A1 | 4/2005 | Landes et al. |
| 2005/0106644 | A1 | 5/2005 | Cairns et al. |
| 2005/0107595 | A1 | 5/2005 | Cairns et al. |
| 2005/0123536 | A1 | 6/2005 | Law et al. |
| 2005/0180972 | A1 | 8/2005 | Wahl et al. |
| 2005/0238649 | A1 | 10/2005 | Doronina et al. |
| 2005/0238650 | A1 | 10/2005 | Crowley et al. |
| 2005/0256030 | A1 | 11/2005 | Feng |
| 2005/0260212 | A1 | 11/2005 | Zhang et al. |
| 2005/0272665 | A1 | 12/2005 | Schmid et al. |
| 2006/0073152 | A1 | 4/2006 | Dennis |
| 2006/0074008 | A1 | 4/2006 | Senter et al. |
| 2006/0128970 | A1 | 6/2006 | Bliss et al. |
| 2006/0233794 | A1 | 10/2006 | Law et al. |
| 2007/0092940 | A1 | 4/2007 | Eigenbrot et al. |
| 2007/0098715 | A1 | 5/2007 | Ettenberg et al. |
| 2007/0160617 | A1 | 7/2007 | Ma et al. |
| 2007/0258987 | A1 | 11/2007 | Francisco et al. |
| 2008/0226657 | A1 | 9/2008 | Doronina et al. |
| 2008/0248051 | A1 | 10/2008 | Doronina et al. |
| 2008/0248053 | A1 | 10/2008 | Doronina et al. |
| 2009/0041791 | A1 | 2/2009 | Feng |
| 2009/0304721 | A1 | 12/2009 | Kinch et al. |

FOREIGN PATENT DOCUMENTS

| | | |
|---|---|---|
| CA | 2114156 A1 | 7/1994 |
| EP | 0 598 129 A1 | 5/1994 |
| EP | 0 659 759 A2 | 2/1996 |
| EP | 0 695 757 A2 | 2/1996 |
| EP | 0 695 758 A2 | 2/1996 |
| EP | 0 695 759 A2 | 2/1996 |
| JP | 06-234790 A | 8/1994 |
| JP | 8-59693 A | 3/1996 |
| JP | 09-077791 A | 3/1997 |
| JP | 9-502993 A | 3/1997 |
| JP | 2002-513402 A | 5/2002 |
| JP | 2002-520335 A | 7/2002 |
| WO | WO 93/03054 A1 | 2/1993 |
| WO | WO 95/09864 A1 | 4/1995 |
| WO | WO 96/14856 A1 | 5/1996 |
| WO | WO 96/22384 A1 | 7/1996 |
| WO | WO 96/33212 A1 | 10/1996 |
| WO | WO 98/36765 A1 | 8/1998 |
| WO | WO 99/35164 A1 | 7/1999 |
| WO | WO 00/02906 A1 | 1/2000 |
| WO | WO 00/47228 A1 | 8/2000 |
| WO | WO 01/03734 A1 | 1/2001 |
| WO | WO 01/18032 A2 | 3/2001 |
| WO | WO 01/77342 A1 | 10/2001 |
| WO | WO 02/43661 A2 | 6/2002 |
| WO | WO 02/43661 A3 | 6/2002 |
| WO | WO 02/088172 A2 | 11/2002 |
| WO | WO 03/008378 A1 | 1/2003 |
| WO | WO 03/034903 A2 | 5/2003 |
| WO | WO 03/043583 A2 | 5/2003 |
| WO | WO 03074551 | 9/2003 |
| WO | WO 2004/010957 A2 | 2/2004 |
| WO | WO 2004/032828 A2 | 4/2004 |
| WO | WO 2005/084390 A2 | 9/2005 |
| WO | WO 2006/071441 A2 | 7/2006 |
| WO | WO 2006/083936 A2 | 8/2006 |
| WO | WO 2007/030642 A2 | 3/2007 |
| WO | WO 2007/059082 A1 | 5/2007 |
| WO | WO 2007/062138 A2 | 5/2007 |
| WO | WO 2007/070538 A2 | 6/2007 |
| WO | WO 2007/109567 A1 | 9/2007 |

OTHER PUBLICATIONS

Afar et al., "Preclinical validation of anti-TMEFF2-auristatin E-conjugated antibodies in the treatment of prostate cancer," *Molecular Cancer Therapeutics*, 2004, 921-932.

Aherne et al., "Antitumour evaluation of dolastatins 10 and 15 and their measurements in plasma by radioimmunoassay," *Cancer Chemother. Phamiacol.*, 1996, 38, 225-323.

Alley et al., "Controlling the location of drug attachment in antibody-drug conjugates," *Proceedings of the AACR*, 2004, 45, Abstract #627.

Bhaskar et al., "E-Selectin Up-Regulation Allows for Targeted Drug Delivery in Prostate Cancer," *Cancer Research*, 2003, 63, 6387-6394.

Bowman et al. 1950, "N-substituted amino-acids. Part I. A new method of preparation of dimethylamino-acids,". J. Chem. Soc. :1342-1351.

Carter., "Improving the Efficacy of Antibody-Based Cancer Therapies," *Nature Reviews*, 1989, 1, 118-129.

Carter, P.J. et al., "Antibody-Drug Conjugates for Cancer Therapy," *The Cancer Journal*, May/Jun. 2008, vol. 14, No. 3, pp. 154-169.

Dillman., "Monoclonal Antibodies for Treating Cancer," *Annals of Internal Medicine*, 1989, 11.1, 592-603.

Doronina et al., "Development of potent monoclonal antibody auristatin conjugates for cancer therapy," *Nature Biotechnology*, 2003, 21(7), 778-784.

Doronina et al., "Errata and Corrigenda," *Nature Biotechnology*, 2003, 21(8), 941.

Doronina et al., "Immunoconjugates comprised of drugs with impaired cellular permeability: A new approach to targeted therapy," *SciFinder*, 2005, 10 pages.

Doronina et al., "Enhanced Activity of Monomethylauristatin F through Monoclonal Antibody Delivery: Effects of Linker Technology on Efficacy and Toxicity," *Bioconjugate Chem.*, 2006, 17, 114-124.

Doronina, S.O. et al., "Potent Monoclonal Antibody-Drug Conjugates: The Role of Linker Stability in Efficacy, Toxicity and Specificity," poster #6425 at the annual meeting of the American Association for Cancer Research, AACR, Toronto, Ontario, CA, Apr. 5-9, 2003.

Dubowchik et al. ("Cathepsin B-Sensitive Dipeptide Prodrugs. 2. Models Of Anticancer Drug Paclitaxel (Taxon®), Mitomycin C And Doxorubicin," Bloorganic & Medicinal Chemistry Letters, 1998, 8, 3347-52).

Emery et al., "Humanized monoclonal antibodies for therapeutic applications," *Exp. Opin. Invest. Drugs*, 1994, 3(3), 241-251.

Engert et al., "Evaluation of Ricin A Chain-containing Immunotoxins Directed against the CD30 Antigen as Potential Reagents for the Treatment of Hodgkin's Disease," *Cancer Research*, 1990, 50, 84-88.

Falini et al, "Responses of refractory Hodgkin's disease to monoclonal anti-CD30 immunotoxin," *The Lancet*, 1992, 339, 1195-1196.

Francisco, J.A. et al., "SGN-35, an Anti-CD30 Antibody-Drug Conjugate with Potent Antitumor Activity," poster #770 at the annual meeting of the American Association for Cancer Research, AACR, Toronto, Ontario, CA, Apr. 5-9, 2003.

Fransico et al., "cAC10-vcMMAE, an anti-CD30-monomethyl auristatin E conjugate with potent and selective antitumor activity," *Blood*, 2003, 102(4), 1458-1465.

Frisch et al., "Synthesis of Short Polyoxyethylene-Based Heterobifunctional Cross-Linking Reagents. Application to the Coupling o Peptides to Liposomes," *Bioconjugate Chem.*, 1996, 7, 180-186.

Gaertner et al., "Site-Specific Attachment of Functionalized Poly-(ethylene glycol) to the Amino Terminus of Proteins," *Bioconjugate Chem.*, 1996, 7, 38-44.

Garteiz, D.A. et al., "Quantitation of dolastatin-10 using HPLC/electrospray ionization mass spectrometry: application in a phase 1 clinical trial," *Cancer Chemother. Pharmacol.*, 1998, vol. 41, pp. 299-306.

Genet, J.P., "Recent studies on asymmetric hydrogenation. New catalysts and synthetic applications in organic synthesis," *Pure Appl. Chem.*, 2002, 74(1), 77-83.

Hamann, P.R. et al., "Gemtuzumab Ozogamicin, A Potent and Selective Anti-CD33 Antibody-Calicheamicin Conjugate for Treatment of Acute Myeloid Leukemia," *Bioconjugate Chem.*, 2002, vol. 13, No. 1, pp. 47-58.

Hamblett et al., "Effect of drug loading on the pharmacology, pharmacokinetics, and toxicity of an anti-CD30 antibody-drug conjugate" *Proceedings of the AACR*, vol. 45, Abstract # 624, 2004.

In the United States Patent and Trademark Office: Non-Final Rejection Office Action Summary of U.S. Appl. No. 10/447,257, Dated Apr. 19, 2007, 18 pages.

In the United States Patent and Trademark Office: Non-Final Rejection Office Action Summary of U.S. Appl. No. 10/983,340, Dated Oct. 4, 2007, 17 pages.

Inada et al., "Modifications of Proteins with Polyethylene Glycol Derivatives," *Methods Enzymology*, 1994, 242, 65-90.

International search report of International Application No. PCT/US03/24209, Apr. 16, 2004.

King et al., "Monoclonal Antibody Conjugates of Doxorubicin Prepared with Branched Linkers: A Novel Method for Increasing the Potency of Doxorubicin Immunoconjugates," *Bioconjugate Chem.*, 1999, 10, 279-288.

King et al., "Monoclonal Antibody Conjugates of Doxorubicin with Branched Peptide Linkers: Inhibition of Aggregation by Methoxytriethyleneglycol Chains," *J. Med. Chem.*, 2002, 45, 4336-4343.

Kline et al., "Novel Antitumor Prodrugs Designed for Activation by Matrix Metalloproteinases-2 and -9," *Molecular Pharmaceutics*, 2003, 1(1), 9-22.

Klussman et al., "Secondary mAb-vcMMAE Conjugates Are Highly Sensitive Reporters of Antibody Internalization via the Lysosome Pathway," *Bioconjugate Chem.*, 2004, 15, 765-773.

Law et al., "CD70 is expressed on renal cell carcinoma and is a potential target for tumor cell elimination by antibody-drug conjugates," *Proceedings of the AACR*, vol. 45, Abstract # 625, 2004.

Mao et al., "EphB2 as a Therapeutic Antibody Drug target for the Treatment of Colorectal Cancer," *Cancer Research*, 2004, 64, 781-788.

May et al., "Evaluation of Ricin a Chain- Containing Immunotoxins Directed Against Different Epitopes on the δ-Chain of Cell Surface-Associated IgD on Murine B Cells," *The Journal of Immunology*, 1990, 144(9), 3637-3642.

Meyer et al., "Chapter 23. Recent Advances In Antibody Drug Conjugates for Cancer Therapy," *Annual Reports in Medicinal Chemistry*, 2003, 229-237.

Meyer, D. et al., "Proteolytic vs. Hydrolytic Released Drug from Anti-Tumor Immunochemotherapeutic Agents." poster presentation at Gordon Research Conference on Drug Carriers In Medicine & Biology, Feb. 24-Mar. 1, 2002, Ventura, California, USA.

Miyazaki et al., 1995, "Synthesis and antitumor activity of novel dolastatin 10 analogs," *Chem. Pharm. Bull.* (Tokyo) 43(10):1706-1718.

Mohammad et al., "An Orthotopic Model of Human Pancreatic Cancer in Severe Combined Immunodeficient Mice: Potential Application for Preclinical Studies[1]," *Clinical Cancer Research*, 1998, 4, 887-894.

Natsume et al., "Characterization of the Interaction of TZT-1027, a Potent Antitumor Agent, with Tubulin," *Jpn. J. CancerRes.*, 2000, 91, 737-747.

Office Action mailed on Mar. 26, 2008, for U.S. Appl. No. 10/496,628, filed Dec. 17, 2004, 19 pages.

Pettit et al., "The Absolute Configuration and Synthesis of Natual (−)-Dolastin10," *J. Am. Chem. Soc.*, 1989, 111, 5463-5465.

Pettit et al., 1994, "The Dolastatins. 17. Synthesis of dolaproine and related diastereoisomers," J. Org. Chem.. 59(21):6287-6295.

Pettit et al., 1994, "The Dolastatins. 19. Synthesis of dolaisoleuine," J. Org. Chem. 59(7):1796-1800.

Pettit et al., 1995, "Antineoplastic agents 337. Synthesis of dolastatin 10 structural modifications," Anticancer Drug Des. 10(7):529-544.

Pettit et al., 1996, "The Dolastatins. 18. Stereospecific synthesis of dolaproine," Synthesis 6:719-725.

Pettit et al., 1996, "Dolastatins. 23: Stereospecific synthesis of dolaisoleuine," J. Chem Soc. Perkin. Trans. 1:853-858.

Pettit et al., 1996, "Dolastatins 24. Synthesis of (−)-dolastatin 10. X-ray molecular structure of N,N-dimethylvalyl-valyl-dolaisoleuine, tert-butyl ester," J. Chem. Soc. Perk Trans. 1:859-863.

Pettit, 1997, "The Dolastatins," (reprint) Springer-Verlag, New York 70:1-79.

Pettit, 1998, "Antineoplastic agents 365. Dolastatin 10 SAR probes," Anticancer Drug Des. 13(4):243-277.

Pettit et al., "Specific Activites of Dolastatin 10 and Peptide Derivatives against Cryptococcus neoformans," *Antimicrobial Agents and Chemotherapy*, 1998, 42(11), 2961-2965.

Pettit et al., "A Cobalt-Phosphine Complex Directed Reformatsky Approach to a stereospecific Synthesis of the Dolastatin 10 Unit Dolaproine (DAP)[1]," *J. Org. Chem.*, 2001, 66, 8640-8642.

Press et al., "Ricin A-Chain Containing Immunotoxins directed Against Different Epitopes on the CD2 Molecule Differ In Their Ability to Kill Normal and Malignant T Cells," *The Journal of Immunology*, 1988, 141(12), 4410-4417.

Press Release, "Seattle Genetics, Inc. (SGEN) To Present Advances in Preclinical Research At American Cancer Research Annual Meeting," downloaded from internet on Aug. 31, 2004.

Restriction Requirement mailed on Mar. 3, 2009, for U.S. Appl. No. 10/558,811, filed Feb. 5, 2007 8 pages.

Schnell et al., "Development of New Ricin A-Chain Immunotoxins With Potent Anti-Tumor effects Against human Hodgkin Cells In Vitro And Disseminated Hodgkin Tumors in Scid Mice Using High-Affinity Monoclonal Antibodies Directed Against the CD30 Antigen," *Int. J. Cancer*, 1995, 63, 238-244.

Schöffski et al., "Phase I and pharmacokinetic study of TZT-1027, a novel synthetic dolastatin 10 derivative, administered as a 1-hour intravenous infusion every 3 weeks in patients with advanced refractory cancer," *Annals of Oncology*, 2004, 15, 671-679.

Senter et al., "Immunoconjugates comprised of drugs with impaired cellular permeability: A new approach to targeted therapy," *Proceedings of the AACR*, vol. 45, Abstract # 623, 2004.

Senter, P. et al., "Cures and Regressions of Established Tumors with Monoclonal Antibody-Auristatin E Conjugates." poster presentation at the annual meeting of the American Association for Cancer Research, Apr. 6-10, 2002, San Francisco, California, USA.

Shioiri et al., 1993, "Stereoselective synthesis of dolastatin 10 and its congeners," Tetrahedron 49(9):1913-1924.

Supplementary European Search Report for EP Application No. 03772186.7, filed on Jul. 31, 2003, 2 pages.

Thornber, C.W., "Isoterism and Molecular Modification in Drug design," *Imperial Chemical Industries Limited*, downloaded 2007, 563-580.

Toki et al. 223rd ACS National Meeting in Orlando, FL on Apr. 7-11 "Cures and regressions of established tumor xenografts with monoclonal antibody auristatin" (CAS 2002:190266).

Toki et al., "Cures and regressions of established tumor xenographs with monoclonal antibody," 223rd ACS Metting, Orlando FL, Apr. 7-11, 2002, Abstract 147.

Toki, B.E. et al., "Cures and Regressions of Established Tumor Xenografts With Monoclonal Antibody Auristatin E Conjugates," slides accompanying the oral presentation at the 223rd National Meeting of the American Chemical Society in Orlando, Florida USA, Apr. 7-11, 2002, 17 pages.

Toki et al., "Protease-Mediated Fragmentation of p-Amidobenzyl Ethers: A New Strategy for the Activation of Anticancer Prodrugs," *J. Org. Chem.*, 2002, 67, 1866-1872.

Tomioka et al., 1991, "An expeditious synthesis of dolastatin 10," Tetrahedron Letters 32(21):2395-2398.

Trail et al., "Cure of Xenografted Human Carcinomas by BR-96-Doxorubicin Immunoconjugates," *Science*, 1993, 261, 212-215.

Trail et al., "Effects of Linker Variation on the Stability, Potency, and Efficacy of Carcinoma-reactive BR64-Doxorubicin Immunoconjugates," *Cancer Research*, 1997, 57, 100-105.

Tsutsumi et al., "Site-specific chemical modification with polyethylene glycol of recombinant immunotoxin anti-Tac(Fv)-PE38(LMB-2) improves Antitumor activity and reduces animal toxicity and immunogenicity," *PNAS*, 2000, 97(15), 8548-8553.

Verdier-Pinard, P. et al., "Sustained Intracellular Retention of Dolastatin 10 Causes Its Potent Antimitotic Activity," *Molecular Pharmacology*, 2000, vol. 57, pp. 180-187.

Vippagunta et al., "Crystalline solids," *Advanced Drug Delivery Reviews*, 2001, 48, 3-26.

Wahl, A.F. et al., "Anti-Cancer Activity of High Potency Anti-CD20 Antibody-Drug Conjugates," poster #769 at the annual meeting of the American Association for Cancer Research, AACR, Toronto, Ontario, CA, Apr. 5-9, 2003.

Woyke et al., "In Vitro Activates and Postantifungal Effects on the Potent Dolastatin 10 Derivative Auristatin PHE," *Antimicrobial Agents and Chemotherapy*, 2001, 45(12), 3580-3584.

Woyke et al., "Effects of auristatin PHE on micortube integrity and nuclear localization in Cryptococcus neoformans," *Antimicrobial Agents and Chemotherapy*, 2003, 46(12), 3802-3808.

Dubowchick, et al., Receptor-mediated and enzyme-dependent targeting of cytotoxic anticancer drugs, Pharmacology & Therapeutics 83 (1999) 67-123.

DRUG CONJUGATES AND THEIR USE FOR TREATING CANCER, AN AUTOIMMUNE DISEASE OR AN INFECTIOUS DISEASE

CROSS-REFERENCES TO RELATED APPLICATIONS

This application is a continuation of U.S. patent application Ser. No. 10/522,911, filed Jul. 7, 2005 now U.S. Pat. No. 7,659,241, which was filed under 35 U.S.C. §371 as a national stage application of International Application No. PCT/US2003/24209, filed Jul. 31, 2003; which further claims the benefit under 35 U.S.C. §119(e) of U.S. Provisional Patent Application No. 60/400,403, filed Jul. 31, 2002. The disclosures of each of the foregoing applications are hereby incorporated herein by reference.

1. FIELD OF THE INVENTION

The present invention is directed to Drug-Linker-Ligand Conjugates and to Drug-Linker Compounds, to compositions comprising a Drug-Linker-Ligand Conjugate or a Drug-Linker Compound, and to methods for using the same to treat cancer, an autoimmune disease or an infectious disease.

2. BACKGROUND OF THE INVENTION

Several short peptidic compounds have been isolated from natural sources and found to have biological activity. Analogs of these compounds have also been prepared, and some were found to have biological activity. For example, Auristatin E (U.S. Pat. No. 5,635,483 to Pettit et al.) is a synthetic analogue of the marine natural product Dolastatin 10, an agent that inhibits tubulin polymerization by binding to the same site on tubulin as the anticancer drug vincristine (G. R. Pettit, *Prog. Chem. Org. Nat. Prod.*, 70:1-79 (1997)). Dolastatin 10, auristatin PE, and auristatin E are linear peptides having four amino acids, three of which are unique to the dolastatin class of compounds. Both dolastatin 10 and auristatin PE are presently being used in human clinical trials to treat cancer. The structural differences between dolastatin 10 and auristatin E reside in the C-terminal residue, in which the thiazolephenethyl amine group of dolastatin 10 is replaced by a norephedrine unit in auristatin E.

The following references disclose dolastatin and auristatin compounds and analogs thereof, and their use for treating cancer:

International Publication No. WO 96/33212 A1 to Teikoku Hormone Mfg. Co., Ltd.;
International Publication No. WO 96/14856 A1 to Arizona Board of Regents;
European Patent Publication No. EP 695757 A2 to Arizona Board of Regents;
European Patent Publication No. EP 695758 A2 to Arizona Board of Regents;
European Patent Publication No. EP 695759 A2 to Arizona Board of Regents;
International Publication No. WO 95/09864 A1 to Teikoku Hormone Mfg. Co., Ltd.;
International Publication No. WO 93/03054 A1 to Teikoku Hormone Mfg. Co., Ltd.;
U.S. Pat. No. 6,323,315 B1 to Pettit et al.;
G. R. Pettit et al., *Anti-Cancer Drug Des.* 13(4): 243-277 (1998);
G. R. Pettit et al., *Anti-Cancer Drug Des.* 10(7): 529-544 (1995); and
K. Miyazaki et al., *Chem. Pharm. Bull.* 43(10), 1706-18 (1995).

Despite in vitro data for compounds of the dolastatin class and its analogs, significant general toxicities at doses required for achieving a therapeutic effect compromise their efficacy in clinical studies. Accordingly, there is a clear need in the art for dolastatin derivatives having significantly lower toxicity, yet useful therapeutic efficiency, compared to current dolastatin drug therapies.

The recitation of any reference in Section 2 of this application is not an admission that the reference is prior art to this application.

3. SUMMARY OF THE INVENTION

In one aspect, the present invention provides compounds of general Formula Ia:

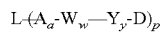

and pharmaceutically acceptable salts and solvates thereof wherein,

L- is a Ligand unit;
-A- is a Stretcher unit;
a is 0 or 1;
each —W— is independently an Amino Acid unit;
—Y— is a Spacer unit;
w is an integer ranging from 0 to 12;
y is 0, 1 or 2;
p ranges from 1 to about 20; and
-D is a Drug unit of the formula

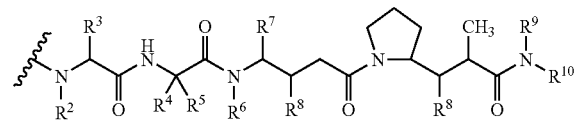

wherein, independently at each location:

$R^2$ is selected from -hydrogen and —$C_1$-$C_8$ alkyl;

$R^3$ is selected from -hydrogen, —$C_1$-$C_8$ alkyl, —$C_3$-$C_8$ carbocycle, —O—($C_1$-$C_8$ alkyl), aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle);

$R^4$ is selected from -hydrogen, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle) wherein $R^5$ is selected from —H and -methyl; or $R^4$ and $R^5$ join, have the formula —$(CR^aR^b)_n$— wherein $R^a$ and $R^b$ are independently selected from —H, —$C_1$-$C_8$ alkyl and —$C_3$-$C_8$ carbocycle and n is selected from 2, 3, 4, 5 and 6, and form a ring with the carbon atom to which they are attached;

$R^6$ is selected from —H and —$C_1$-$C_8$ alkyl;

$R^7$ is selected from —H, —$C_1$-$C_8$ alkyl, —$C_3$-$C_8$ carbocycle, —O—($C_1$-$C_8$ alkyl), aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle);

each $R^8$ is independently selected from —H, —OH, —$C_1$-$C_8$ alkyl, —$C_3$-$C_8$ carbocycle and —O—($C_1$-$C_8$ alkyl);

$R^9$ is selected from —H and —$C_1$-$C_8$ alkyl;

$R^{10}$ is selected from

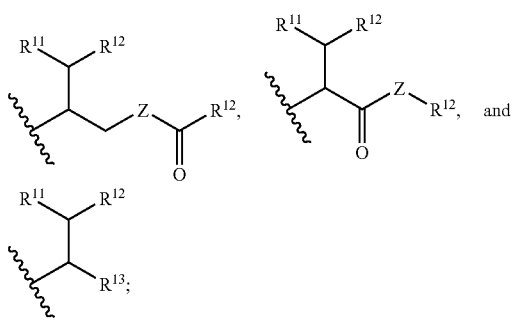

Z is —O—, —S—, —NH— or —N(R$^{14}$)—;

R$^{11}$ is selected from —H, —OH, —NH$_2$, —NHR$^{14}$, —N(R$^{14}$)$_2$, —C$_1$-C$_8$ alkyl, —C$_3$-C$_8$ carbocycle, —O—(C$_1$-C$_8$ alkyl), -aryl, —C$_1$-C$_8$ alkyl-aryl, —C$_1$-C$_8$ alkyl-(C$_3$-C$_8$ carbocycle), —C$_3$-C$_8$ heterocycle and —C$_1$-C$_8$ alkyl-(C$_3$-C$_8$ heterocycle); or R$^{11}$ is an oxygen atom which forms a carbonyl unit (C=O) with the carbon atom to which it is attached and a hydrogen atom on this carbon atom is replaced by one of the bonds in the (C=O) double bond;

each R$^{12}$ is independently selected from -aryl and —C$_3$-C$_8$ heterocycle;

R$^{13}$ is selected from —H, —OH, —NH$_2$, —NHR$^{14}$, —N(R$^{14}$)$_2$, —C$_1$-C$_8$ alkyl, —C$_3$-C$_8$ carbocycle, —O—(C$_1$-C$_8$ alkyl), -aryl, —C$_1$-C$_8$ alkyl-aryl, —C$_1$-C$_8$ alkyl-(C$_3$-C$_8$ carbocycle), C$_3$-C$_8$ heterocycle and —C$_1$-C$_8$ alkyl-(C$_3$-C$_8$ heterocycle); and each R$^{14}$ is independently —H or —C$_1$-C$_8$ alkyl.

In another aspect, the present invention provides compounds of general formula Ib:

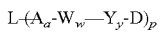

L-(A$_a$-W$_w$—Y$_y$-D)$_p$    Ib and pharmaceutically acceptable salts and solvates thereof wherein,
L- is a Ligand unit;
-A- is a Stretcher unit;
a is 0 or 1;
each —W— is independently an Amino Acid unit;
—Y— is a Spacer unit;
w is an integer ranging from 0 to 12;
y is 0, 1 or 2;
p ranges from 1 to about 20; and
-D is a Drug unit of the formula

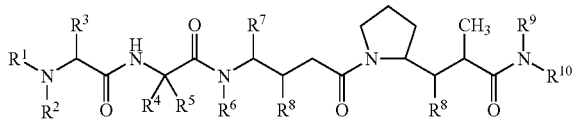

wherein, independently at each location:

R$^1$ is selected from —H, —C$_1$-C$_8$ alkyl and —C$_3$-C$_8$ carbocycle; and R$^2$ is selected from —H and —C$_1$-C$_8$ alkyl; or R$^1$ and R$^2$ join, have the formula —(CR$^a$R$^b$)$_n$— wherein R$^a$ and R$^b$ are independently selected from —H, —C$_1$-C$_8$ alkyl and —C$_3$-C$_8$ carbocycle and n is selected from 2, 3, 4, 5 and 6, and form a ring with the nitrogen atom to which they are attached;

R$^3$ is selected from —H, —C$_1$-C$_8$ alkyl, —C$_3$-C$_8$ carbocycle, —O—(C$_1$-C$_8$ alkyl), -aryl, —C$_1$-C$_8$ alkyl-aryl, —C$_1$-C$_8$ alkyl-(C$_3$-C$_8$ carbocycle), —C$_3$-C$_8$ heterocycle and —C$_1$-C$_8$ alkyl-(C$_3$-C$_8$ heterocycle);

R$^4$ is selected from —H, —C$_1$-C$_8$ alkyl, —C$_3$-C$_8$ carbocycle, —O—(C$_1$-C$_8$ alkyl), -aryl, —C$_1$-C$_8$ alkyl-aryl, —C$_1$-C$_8$ alkyl-(C$_3$-C$_8$ carbocycle), —C$_3$-C$_8$ heterocycle and —C$_1$-C$_8$ alkyl-(C$_3$-C$_8$ heterocycle) wherein R$^5$ is selected from —H and -methyl; or R$^4$ and R$^5$ join, have the formula —(CR$^a$R$^b$)$_n$— wherein R$^a$ and R$^b$ are independently selected from —H, —C$_1$-C$_8$ alkyl and —C$_3$-C$_8$ carbocycle and n is selected from 2, 3, 4, 5 and 6, and form a ring with the carbon atom to which they are attached;

R$^6$ is selected from —H and —C$_1$-C$_8$ alkyl;

R$^7$ is selected from —H, —C$_1$-C$_8$ alkyl, —C$_3$-C$_8$ carbocycle, —O—(C$_1$-C$_8$ alkyl), -aryl, —C$_1$-C$_8$ alkyl-aryl, —C$_1$-C$_8$ alkyl-(C$_3$-C$_8$ carbocycle), —C$_3$-C$_8$ heterocycle and —C$_1$-C$_8$ alkyl-(C$_3$-C$_8$ heterocycle);

each R$^8$ is independently selected from —H, —OH, —C$_1$-C$_8$ alkyl, —C$_3$-C$_8$ carbocycle and —O—(C$_1$-C$_8$ alkyl);

R$^9$ is selected from —H and —C$_1$-C$_8$ alkyl;

R$^{10}$ is selected from

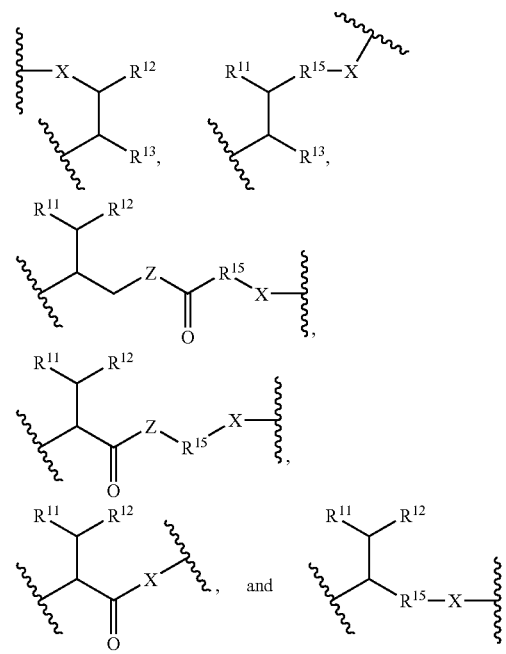

X is —O—, —S—, —NH— or —N(R$^{14}$)—, where X is bonded to Y when y is 1 or 2, or X is bonded to W when y is 0;

Z is —O—, —S—, —NH— or —N(R$^{14}$)—;

R$^{11}$ is selected from —H, —OH, —NH$_2$, —NHR$^{14}$, —N(R$^{14}$)$_2$, —C$_1$-C$_8$ alkyl, —C$_3$-C$_8$ carbocycle, —O—(C$_1$-C$_8$ alkyl), -aryl, —C$_1$-C$_8$ alkyl-aryl, —C$_1$-C$_8$ alkyl-(C$_3$-C$_8$ carbocycle), —C$_3$-C$_8$ heterocycle and —C$_1$-C$_8$ alkyl-(C$_3$-C$_8$ heterocycle); or R$^{11}$ is an oxygen atom which forms a carbonyl unit (C=O) with the carbon atom to which it is attached and a hydrogen atom on this carbon atom is replaced by one of the bonds in the (C=O) double bond;

each R$^{12}$ is independently selected from -aryl and —C$_3$-C$_8$ heterocycle;

R$^{13}$ is selected from —H, —OH, —NH$_2$, —NHR$^{14}$, —N(R$^{14}$)$_2$, —C$_1$-C$_8$ alkyl, —C$_3$-C$_8$ carbocycle, —O—(C$_1$-C$_8$ alkyl), -aryl, —C$_1$-C$_8$ alkyl-aryl, —C$_1$-C$_8$ alkyl-(C$_3$-C$_8$ carbocycle), C$_3$-C$_8$ heterocycle and —C$_1$-C$_8$ alkyl-(C$_3$-C$_8$ heterocycle);

each $R^{14}$ is independently —H or —$C_1$-$C_8$ alkyl; and $R^{15}$ is -arylene-, —$C_3$-$C_8$ carbocyclo- or —$C_3$-$C_8$ heterocyclo-.

In another aspect, the present invention provides compounds of general formula Ic:

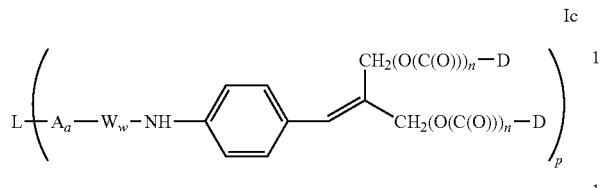

and pharmaceutically acceptable salts and solvates thereof wherein,

L- is a Ligand unit;

-A- is a Stretcher unit;

a is 0 or 1;

each —W— is independently an Amino Acid unit;

w is an integer ranging from 0 to 12;

each n is independently 0 or 1;

p ranges from 1 to about 20; and each -D is independently:

(a) a Drug unit of the formula:

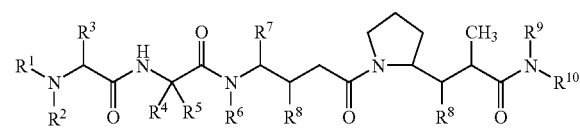

wherein, independently at each location:

$R^1$ is selected from —H, —$C_1$-$C_8$ alkyl and —$C_3$-$C_8$ carbocycle; and $R^2$ is selected from —H and —$C_1$-$C_8$ alkyl; or $R^1$ and $R^2$ join, have the formula —$(CR^aR^b)_n$— wherein $R^a$ and $R^b$ are independently selected from —H, —$C_1$-$C_8$ alkyl and —$C_3$-$C_8$ carbocycle and n is selected from 2, 3, 4, 5 and 6, and form a ring with the nitrogen atom to which they are attached;

$R^3$ is selected from —H, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle);

$R^4$ is selected from —H, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle) wherein $R^5$ is selected from —H and -methyl; or $R^4$ and $R^5$ join, have the formula —$(CR^aR^b)_n$— wherein $R^a$ and $R^b$ are independently selected from —H, —$C_1$-$C_8$ alkyl and —$C_3$-$C_8$ carbocycle and n is selected from 2, 3, 4, 5 and 6, and form a ring with the carbon atom to which they are attached;

$R^6$ is selected from —H and —$C_1$-$C_8$ alkyl;

$R^7$ is selected from —H, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle);

each $R^8$ is independently selected from —H, —OH, —$C_1$-$C_8$ alkyl, —$C_3$-$C_8$ carbocycle and —O—($C_1$-$C_8$ alkyl);

$R^9$ is selected from —H and —$C_1$-$C_8$ alkyl;

$R^{10}$ is selected from

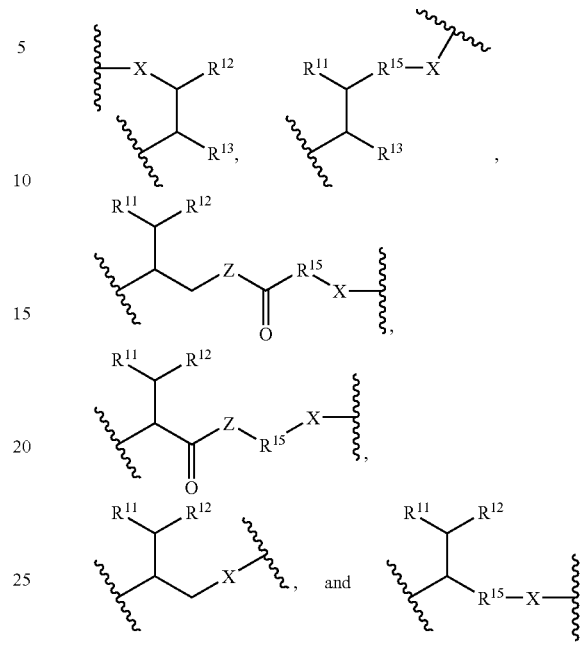

X is —O—, —S—, —NH— or —N($R^{14}$)—, where X is bonded to —C(O)— when y is 1 or 2, or X is bonded to —$CH_2$— when n is 0;

Z is —O—, —S—, —NH— or —N($R^{14}$)—;

$R^{11}$ is selected from —H, —OH, —$NH_2$, —$NHR^{14}$, —$N(R^{14})_2$, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle); or $R^{11}$ is an oxygen atom which forms a carbonyl unit (C=O) with the carbon atom to which it is attached and a hydrogen atom on this carbon atom is replaced by one of the bonds in the (C=O) double bond;

each $R^{12}$ is independently selected from -aryl and —$C_3$-$C_8$ heterocycle;

$R^{13}$ is selected from —H, —OH, —$NH_2$, —$NHR^{14}$, —$N(R^{14})_2$, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), $C_3$-$C_8$ heterocycle and —$C_1$-$C_8$ alkyl-($C_3$-$C_8$ heterocycle);

each $R^{14}$ is independently —H or —$C_1$-$C_8$ alkyl; and $R^{15}$ is -arylene-, —$C_3$-$C_8$ carbocyclo- or —$C_3$-$C_8$ heterocyclo-; or (b) a Drug unit of the formula:

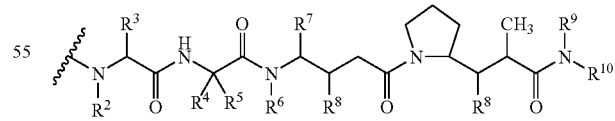

wherein, independently at each location:

$R^2$ is selected from —H and —$C_1$-$C_8$ alkyl;

$R^3$ is selected from —H, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle);

$R^4$ is selected from —H, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle) wherein $R^5$ is selected from —H and -methyl; or $R^4$ and $R^5$ join, have the formula —$(CR^aR^b)_n$— wherein $R^a$ and $R^b$ are independently selected from —H, —$C_1$-$C_8$ alkyl and —$C_3$-$C_8$ carbocycle and n is selected from 2, 3, 4, 5 and 6, and form a ring with the carbon atom to which they are attached;

$R^6$ is selected from —H and —$C_1$-$C_8$ alkyl;

$R^7$ is selected from —H, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle);

each $R^8$ is independently selected from —H, —OH, —$C_1$-$C_8$ alkyl, —$C_3$-$C_8$ carbocycle and —O—($C_1$-$C_8$ alkyl);

$R^9$ is selected from —H and —$C_1$-$C_8$ alkyl;

$R^{10}$ is selected from

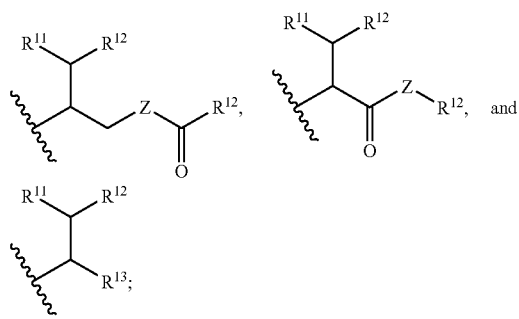

Z is —O—, —S—, —NH— or —N($R^{14}$)—;

$R^{11}$ is selected from —H, —OH, —$NH_2$, —$NHR^{14}$, —$N(R^{14})_2$, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle); or $R^{11}$ is an oxygen atom which forms a carbonyl unit (C=O) with the carbon atom to which it is attached and a hydrogen atom on this carbon atom is replaced by one of the bonds in the (C=O) double bond;

each $R^{12}$ is independently selected from -aryl and —$C_3$-$C_8$ heterocycle;

$R^{13}$ is selected from —H, —OH, —$NH_2$, —$NHR^{14}$, —$N(R^{14})_2$, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), $C_3$-$C_8$ heterocycle and —$C_1$-$C_8$ alkyl-($C_3$-$C_8$ heterocycle); and each $R^{14}$ is independently —H or —$C_1$-$C_8$ alkyl.

A compound of formula Ia, formula Ib, formula Ic or a pharmaceutically acceptable salt or solvate thereof (a "Drug-Linker-Ligand Conjugate") is useful for treating or preventing cancer, an autoimmune disease or an infectious disease in an animal.

In another aspect, the present invention provides compounds of the formula IIa:

and pharmaceutically acceptable salts and solvates thereof wherein, independently at each location:

$R^1$ is selected from —H, —$C_1$-$C_8$ alkyl and —$C_3$-$C_8$ carbocycle; and $R^2$ is selected from —H and —$C_1$-$C_8$ alkyl; or $R^1$ and $R^2$ join, have the formula —$(CR^aR^b)_n$— wherein $R^a$ and $R^b$ are independently selected from —H, —$C_1$-$C_8$ alkyl and —$C_3$-$C_8$ carbocycle and n is selected from 2, 3, 4, 5 and 6, and form a ring with the nitrogen atom to which they are attached;

$R^3$ is selected from —H, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle);

$R^4$ is selected from —H, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle) wherein $R^5$ is selected from —H and -methyl; or $R^4$ and $R^5$ join, have the formula —$(CR^aR^b)_n$— wherein $R^a$ and $R^b$ are independently selected from —H, —$C_1$-$C_8$ alkyl and —$C_3$-$C_8$ carbocycle and n is selected from 2, 3, 4, 5 and 6, and form a ring with the carbon atom to which they are attached;

$R^6$ is selected from —H and —$C_1$-$C_8$ alkyl;

$R^7$ is selected from —H, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle);

each $R^8$ is independently selected from —H, —OH, —$C_1$-$C_8$ alkyl, —$C_3$-$C_8$ carbocycle and —O—($C_1$-$C_8$ alkyl);

$R^9$ is selected from —H and —$C_1$-$C_8$ alkyl;

X is —O—, —S—, —NH— or —N($R^{14}$)—;

$R^{11}$ is selected from —H, —OH, —$NH_2$, —$NHR^{14}$, —$N(R^{14})_2$, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle); or $R^{11}$ is an oxygen atom which forms a carbonyl unit (C=O) with the carbon atom to which it is attached and a hydrogen atom on this carbon atom is replaced by one of the bonds in the (C=O) double bond;

each $R^{12}$ is independently selected from -aryl and —$C_3$-$C_8$ heterocycle;

each $R^{14}$ is independently —H or —$C_1$-$C_8$ alkyl; and $R^{16}$ is —Yy-Ww-A' wherein each —W— is independently an Amino Acid unit;

—Y— is a Spacer unit;

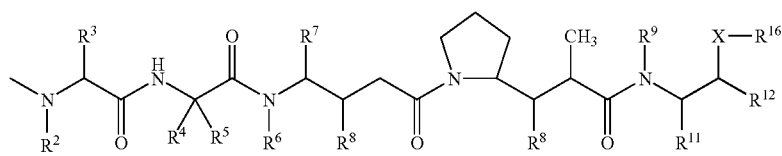

w is an integer ranging from 0 to 12;
y is 0, 1 or 2; and
-A' is selected from

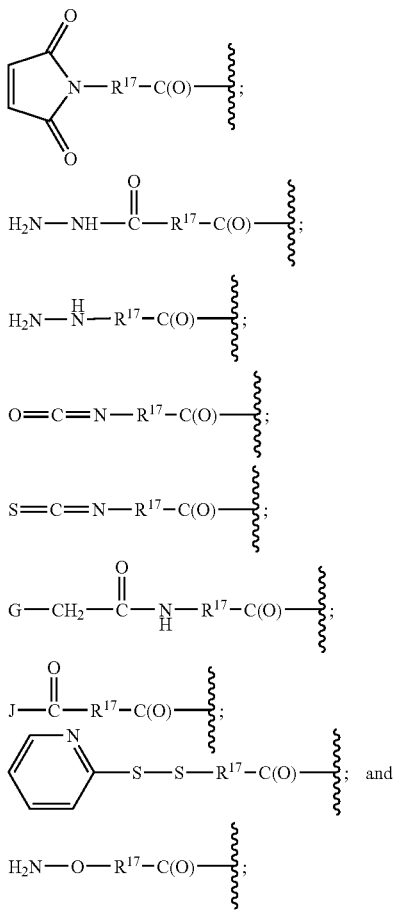

wherein
G is selected from —Cl, —Br, —I, —O-mesyl and —O-tosyl;
J is selected from —Cl, —Br, —I, —F, —OH, —O—N-succinimide, —O-(4-nitrophenyl), —O-pentafluorophenyl, —O-tetrafluorophenyl and —O—C(O)—OR$^{18}$;
R$^{17}$ is selected from —C$_1$-C$_{10}$ alkylene-, —C$_3$-C$_8$ carbocyclo-, —O—(C$_1$-C$_8$ alkyl)-, -arylene-, —C$_1$-C$_{10}$ alkylene-arylene-, -arylene-C$_1$-C$_{10}$ alkylene-, —C$_1$-C$_{10}$ alkylene-(C$_3$-C$_8$ carbocyclo)-, —(C$_3$-C$_8$ carbocyclo)-C$_1$-C$_{10}$ alkylene-, —C$_3$-C$_8$ heterocyclo-, —C$_1$-C$_{10}$ alkylene-(C$_3$-C$_8$ heterocyclo)-, —(C$_3$-C$_8$ heterocyclo)-C$_1$-C$_{10}$ alkylene-, —(CH$_2$CH$_2$O)$_r$—, and —(CH$_2$CH$_2$O)$_r$—CH$_2$—; r is an integer ranging from 1-10; and
R$^{18}$ is —C$_1$-C$_8$ alkyl or -aryl.

In another aspect, the present invention provides compounds of the formula IIb:

and pharmaceutically acceptable salts and solvates thereof
wherein, independently at each location:

R$^1$ is selected from —H, —C$_1$-C$_8$ alkyl and —C$_3$-C$_8$ carbocycle; and R$^2$ is selected from —H and —C$_1$-C$_8$ alkyl; or R$^1$ and R$^2$ join, have the formula —(CR$^a$R$^b$)$_n$— wherein R$^a$ and R$^b$ are independently selected from —H, —C$_1$-C$_8$ alkyl and —C$_3$-C$_8$ carbocycle and n is selected from 2, 3, 4, 5 and 6, and form a ring with the nitrogen atom to which they are attached;

R$^3$ is selected from —H, —C$_1$-C$_8$ alkyl, —C$_3$-C$_8$ carbocycle, —O—(C$_1$-C$_8$ alkyl), -aryl, —C$_1$-C$_8$ alkyl-aryl, —C$_1$-C$_8$ alkyl-(C$_3$-C$_8$ carbocycle), —C$_3$-C$_8$ heterocycle and —C$_1$-C$_8$ alkyl-(C$_3$-C$_8$ heterocycle);

R$^4$ is selected from —H, —C$_1$-C$_8$ alkyl, —C$_3$-C$_8$ carbocycle, —O—(C$_1$-C$_8$ alkyl), -aryl, —C$_1$-C$_8$ alkyl-aryl, —C$_1$-C$_8$ alkyl-(C$_3$-C$_8$ carbocycle), —C$_3$-C$_8$ heterocycle and —C$_1$-C$_8$ alkyl-(C$_3$-C$_8$ heterocycle) wherein R$^5$ is selected from —H and -methyl; or R$^4$ and R$^5$ join, have the formula —(CR$^a$R$^b$)$_n$— wherein R$^a$ and R$^b$ are independently selected from —H, —C$_1$-C$_8$ alkyl and —C$_3$-C$_8$ carbocycle and n is selected from 2, 3, 4, 5 and 6, and form a ring with the carbon atom to which they are attached;

R$^6$ is selected from —H and —C$_1$-C$_8$ alkyl;

R$^7$ is selected from —H, —C$_1$-C$_8$ alkyl, —C$_3$-C$_8$ carbocycle, —O—(C$_1$-C$_8$ alkyl), -aryl, —C$_1$-C$_8$ alkyl-aryl, —C$_1$-C$_8$ alkyl-(C$_3$-C$_8$ carbocycle), —C$_3$-C$_8$ heterocycle and —C$_1$-C$_8$ alkyl-(C$_3$-C$_8$ heterocycle);

each R$^8$ is independently selected from —H, —OH, —C$_1$-C$_8$ alkyl, —C$_3$-C$_8$ carbocycle and —O—(C$_1$-C$_8$ alkyl);

R$^9$ is selected from —H and —C$_1$-C$_8$ alkyl;

X is —O—, —S—, —NH— or —N(R$^{14}$)—;

R$^{11}$ is selected from —H, —OH, —NH$_2$, —NHR$^{14}$, —N(R$^{14}$)$_2$, —C$_1$-C$_8$ alkyl, —C$_3$-C$_8$ carbocycle, —O—(C$_1$-C$_8$ alkyl), -aryl, —C$_1$-C$_8$ alkyl-aryl, —C$_1$-C$_8$ alkyl-(C$_3$-C$_8$ carbocycle), —C$_3$-C$_8$ heterocycle and —C$_1$-C$_8$ alkyl-(C$_3$-C$_8$ heterocycle); or R$^{11}$ is an oxygen atom which forms a carbonyl unit (C=O) with the carbon atom to which it is attached and a hydrogen atom on this carbon atom is replaced by one of the bonds in the (C=O) double bond;

R$^{13}$ is selected from hydrogen, —OH, —NH$_2$, —NHR$^{14}$, —N(R$^{14}$)$_2$, C$_1$-C$_8$ alkyl, C$_3$-C$_8$ carbocycle, —O—(C$_1$-C$_8$ alkyl), -aryl, alkyl-aryl, alkyl-(C$_3$-C$_8$ carbocycle), C$_3$-C$_8$ heterocycle and alkyl-(C$_3$-C$_8$ heterocycle);

each R$^{14}$ is independently —H or —C$_1$-C$_8$ alkyl;

R$^{15}$ is -arylene-, —C$_3$-C$_8$ carbocyclo- or —C$_3$-C$_8$ heterocyclo-; and R$^{16}$ is —Y$_y$-W$_w$-A' wherein
each —W— is independently an Amino Acid unit;
—Y— is a Spacer unit;

IIb

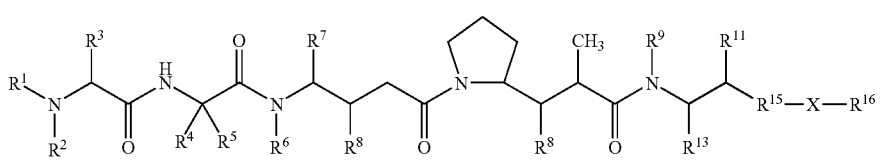

w is an integer ranging from 0 to 12;

y is 0, 1 or 2; and

-A' is selected from

—(CH$_2$CH$_2$O)$_n$—, and —(CH$_2$CH$_2$O)$_r$—CH$_2$—; r is an integer ranging from 1-10; and R$^{18}$ is —C$_1$-C$_8$ alkyl or -aryl.

In another aspect, the present invention provides compounds of the formula IIc:

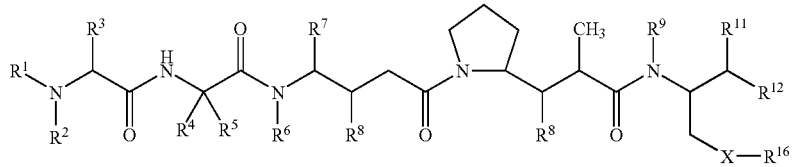

IIc

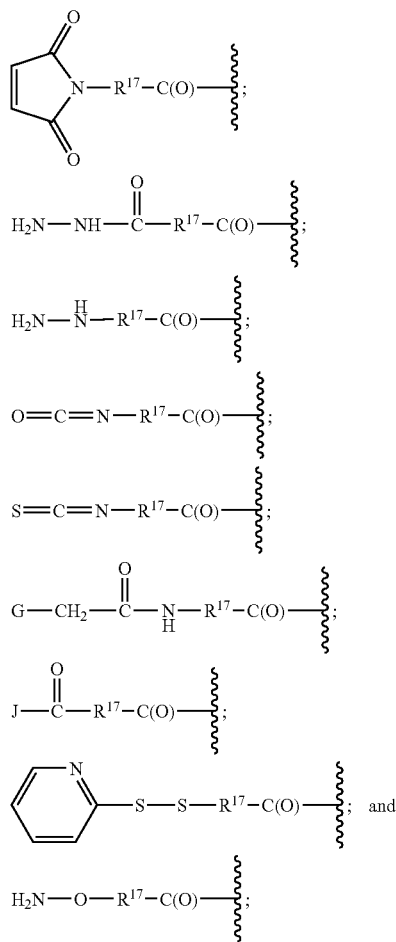

wherein

G is selected from —Cl, —Br, —I, —O-mesyl and —O-tosyl;

J is selected from —Cl, —Br, —I, —F, —OH, —O—N-succinimide, —O-(4-nitrophenyl), —O-pentafluorophenyl, —O-tetrafluorophenyl and —O—C(O)—OR$^{18}$;

R$^{17}$ is selected from —C$_1$-C$_{10}$ alkylene-, —C$_3$-C$_8$ carbocyclo-, —O—(C$_1$-C$_8$ alkyl)-, -arylene-, —C$_1$-C$_{10}$ alkylene-arylene-, -arylene-C$_1$-C$_{10}$ alkylene-, —C$_1$-C$_{10}$ alkylene-(C$_3$-C$_8$ carbocyclo)-, —(C$_3$-C$_8$ carbocyclo)-C$_1$-C$_{10}$ alkylene-, —C$_3$-C$_8$ heterocyclo-, —C$_1$-C$_{10}$ alkylene-(C$_3$-C$_8$ heterocyclo)-, —(C$_3$-C$_8$ heterocyclo)-C$_1$-C$_{10}$ alkylene-, and pharmaceutically acceptable salts and solvates thereof wherein, independently at each location:

R$^1$ is selected from —H, —C$_1$-C$_8$ alkyl and —C$_3$-C$_8$ carbocycle; and R$^2$ is selected from —H and —C$_1$-C$_8$ alkyl; or R$^1$ and R$^2$ join, have the formula —(CR$^a$R$^b$)$_n$— wherein R$^a$ and R$^b$ are independently selected from —H, —C$_1$-C$_8$ alkyl and —C$_3$-C$_8$ carbocycle and n is selected from 2, 3, 4, 5 and 6, and form a ring with the nitrogen atom to which they are attached;

R$^3$ is selected from —H, —C$_1$-C$_8$ alkyl, —C$_3$-C$_8$ carbocycle, —O—(C$_1$-C$_8$ alkyl), -aryl, —C$_1$-C$_8$ alkyl-aryl, —C$_1$-C$_8$ alkyl-(C$_3$-C$_8$ carbocycle), —C$_3$-C$_8$ heterocycle and —C$_1$-C$_8$ alkyl-(C$_3$-C$_8$ heterocycle);

R$^4$ is selected from —H, —C$_1$-C$_8$ alkyl, —C$_3$-C$_8$ carbocycle, —O—(C$_1$-C$_8$ alkyl), -aryl, —C$_1$-C$_8$ alkyl-aryl, —C$_1$-C$_8$ alkyl-(C$_3$-C$_8$ carbocycle), —C$_3$-C$_8$ heterocycle and —C$_1$-C$_8$ alkyl-(C$_3$-C$_8$ heterocycle) wherein R$^5$ is selected from —H and -methyl; or R$^4$ and R$^5$ join, have the formula —(CR$^a$R$^b$)$_n$— wherein R$^a$ and R$^b$ are independently selected from —H, —C$_1$-C$_8$ alkyl and —C$_3$-C$_8$ carbocycle and n is selected from 2, 3, 4, 5 and 6, and form a ring with the carbon atom to which they are attached;

R$^6$ is selected from —H and —C$_1$-C$_8$ alkyl;

R$^7$ is selected from —H, —C$_1$-C$_8$ alkyl, —C$_3$-C$_8$ carbocycle, —O—(C$_1$-C$_8$ alkyl), -aryl, —C$_1$-C$_8$ alkyl-aryl, —C$_1$-C$_8$ alkyl-(C$_3$-C$_8$ carbocycle), —C$_3$-C$_8$ heterocycle and —C$_1$-C$_8$ alkyl-(C$_3$-C$_8$ heterocycle);

each R$^8$ is independently selected from —H, —OH, —C$_1$-C$_8$ alkyl, —C$_3$-C$_8$ carbocycle and —O—(C$_1$-C$_8$ alkyl);

R$^9$ is selected from —H and —C$_1$-C$_8$ alkyl;

X is —O—, —S—, —NH— or —N(R$^{14}$)—;

R$^{11}$ is selected from —H, —OH, —NH$_2$, —NHR$^{14}$, —N(R$^{14}$)$_2$, —C$_1$-C$_8$ alkyl, —C$_3$-C$_8$ carbocycle, —O—(C$_1$-C$_8$ alkyl), -aryl, —C$_1$-C$_8$ alkyl-aryl, —C$_1$-C$_8$ alkyl-(C$_3$-C$_8$ carbocycle), —C$_3$-C$_8$ heterocycle and —C$_1$-C$_8$ alkyl-(C$_3$-C$_8$ heterocycle); or R$^{11}$ is an oxygen atom which forms a carbonyl unit (C═O) with the carbon atom to which it is attached and a hydrogen atom on this carbon atom is replaced by one of the bonds in the (C═O) double bond;

each R$^{12}$ is independently selected from -aryl and —C$_3$-C$_8$ heterocycle;

each R$^{14}$ is independently —H or —C$_1$-C$_8$ alkyl;

R$^{16}$ is —Yy-Ww-A' wherein each —W— is independently an Amino Acid unit;

—Y— is a Spacer unit;

w is an integer ranging from 0 to 12;
y is 0, 1 or 2; and
-A' is selected from

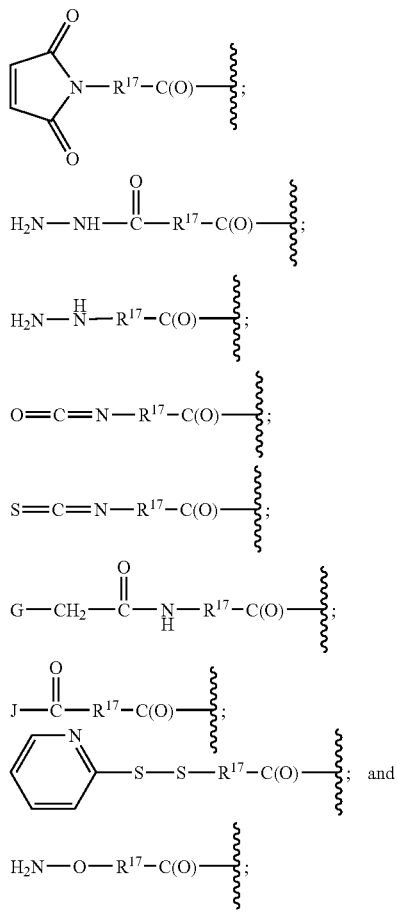

wherein
G is selected from —Cl, —Br, —I, —O-mesyl and —O-tosyl;
J is selected from —Cl, —Br, —I, —F, —OH, —O—N-succinimide, —O-(4-nitrophenyl), —O-pentafluorophenyl, —O-tetrafluorophenyl and —O—C(O)—OR$^{1'''}$;
$R^{17}$ is selected from —$C_1$-$C_{10}$ alkylene-, —$C_3$-$C_8$ carbocyclo-, —O—($C_1$-$C_8$ alkyl)-, -arylene-, —$C_1$-$C_{10}$ alkylene-arylene-, -arylene-$C_1$-$C_{10}$ alkylene-, —$C_1$-$C_{10}$ alkylene-($C_3$-$C_8$ carbocyclo)-, —($C_3$-$C_8$ carbocyclo)-$C_1$-$C_{10}$ alkylene-, —$C_3$-$C_8$ heterocyclo-, —$C_1$-$C_{10}$ alkylene-($C_3$-$C_8$ heterocyclo)-, —($C_3$-$C_8$ heterocyclo)-$C_1$-$C_{10}$ alkylene-, —($CH_2CH_2O$)$_r$—, and —($CH_2CH_2O$)$_r$—$CH_2$—; r is an integer ranging from 1-10; and
$R^{18}$ is —$C_1$-$C_8$ alkyl or -aryl.

In another aspect, the present invention provides compounds of the formula IId:

and pharmaceutically acceptable salts and solvates thereof
wherein, independently at each location:
$R^1$ is selected from —H, —$C_1$-$C_8$ alkyl and —$C_3$-$C_8$ carbocycle; and $R^2$ is selected from —H and —$C_1$-$C_8$ alkyl; or $R^1$ and $R^2$ join, have the formula —($CR^aR^b$)$_n$— wherein $R^a$ and $R^b$ are independently selected from —H, —$C_1$-$C_8$ alkyl and —$C_3$-$C_8$ carbocycle and n is selected from 2, 3, 4, 5 and 6, and form a ring with the nitrogen atom to which they are attached;
$R^3$ is selected from —H, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle);
$R^4$ is selected from —H, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle) wherein $R^5$ is selected from —H and -methyl; or $R^4$ and $R^5$ join, have the formula —($CR^aR^b$)$_n$— wherein $R^a$ and $R^b$ are independently selected from —H, —$C_1$-$C_8$ alkyl and —$C_3$-$C_8$ carbocycle and n is selected from 2, 3, 4, 5 and 6, and form a ring with the carbon atom to which they are attached;
$R^6$ is selected from —H and —$C_1$-$C_8$ alkyl;
$R^7$ is selected from —H, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle);
each $R^8$ is independently selected from —H, —OH, —$C_1$-$C_8$ alkyl, —$C_3$-$C_8$ carbocycle and —O—($C_1$-$C_8$ alkyl);
$R^9$ is selected from —H and —$C_1$-$C_8$ alkyl;
X is —O—, —S—, —NH— or —N($R^{14}$)—;
$R^{11}$ is selected from —H, —OH, —$NH_2$, —$NHR^{14}$, —N($R^{14}$)$_2$, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle); or $R^{11}$ is an oxygen atom which forms a carbonyl unit (C=O) with the carbon atom to which it is attached and a hydrogen atom on this carbon atom is replaced by one of the bonds in the (C=O) double bond;
each $R^{12}$ is independently selected from -aryl and —$C_3$-$C_8$ heterocycle;
each $R^{14}$ is independently —H or —$C_1$-$C_8$ alkyl;
$R^{15}$ is -arylene-, —$C_3$-$C_8$ carbocyclo- or —$C_3$-$C_8$ heterocyclo-;
$R^{16}$ is —$Y_y$-$W_w$-A'
wherein
each —W— is independently an Amino Acid unit;
—Y— is a Spacer unit;
w is an integer ranging from 0 to 12;

IId

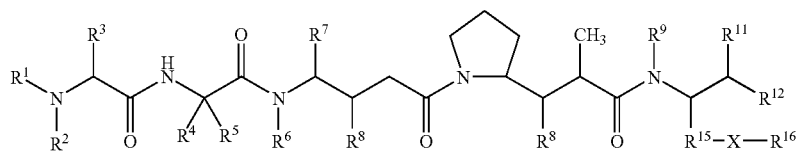

y is 0, 1 or 2; and

-A' is selected from

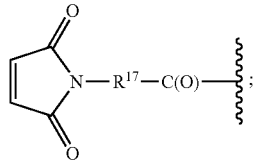

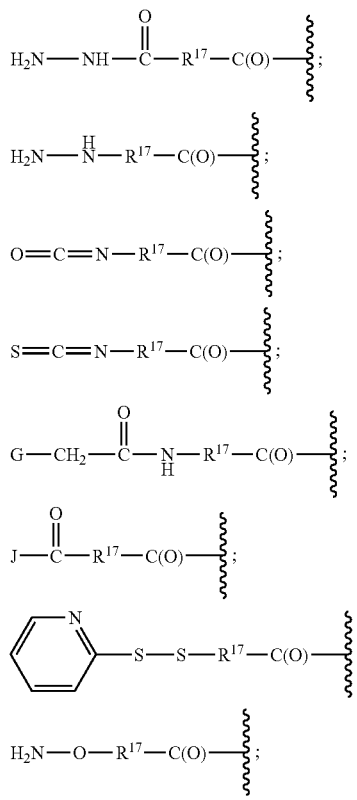

wherein

G is selected from —Cl, —Br, —I, —O-mesyl and —O-tosyl;

J is selected from —Cl, —Br, —I, —F, —OH, —O—N-succinimide, —O-(4-nitrophenyl), —O-pentafluorophenyl, —O-tetrafluorophenyl and —O—C(O)—$OR^{18}$;

$R^{17}$ is selected from —$C_1$-$C_{10}$ alkylene-, —$C_3$-$C_8$ carbocyclo-, —O—($C_1$-$C_8$ alkyl)-, -arylene-, —$C_1$-$C_{10}$ alkylene-arylene-, -arylene-$C_1$-$C_{10}$ alkylene-, —$C_1$-$C_{10}$ alkylene-($C_3$-$C_8$ carbocyclo)-, —($C_3$-$C_8$ carbocyclo)-$C_1$-$C_{10}$ alkylene-, —$C_3$-$C_8$ heterocyclo-, —$C_1$-$C_{10}$ alkylene-($C_3$-$C_8$ heterocyclo)-, —($C_3$-$C_8$ heterocyclo)-$C_1$-$C_{10}$ alkylene-, —($CH_2CH_2O$)$_r$—, and —($CH_2CH_2O$)$_r$—$CH_2$—; r is an integer ranging from 1-10; and $R^{18}$ is —$C_1$-$C_8$ alkyl or -aryl In another aspect, the present invention provides compounds of the formula IIe:

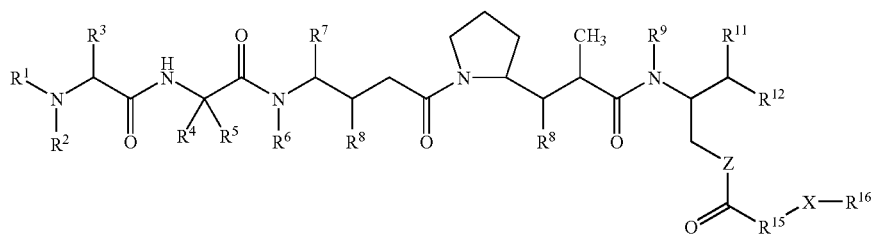

IIe and pharmaceutically acceptable salts and solvates thereof wherein, independently at each location:

$R^1$ is selected from —H, —$C_1$-$C_8$ alkyl and —$C_3$-$C_8$ carbocycle; and $R^2$ is selected from —H and —$C_1$-$C_8$ alkyl; or $R^1$ and $R^2$ join, have the formula —$(CR^aR^b)_n$— wherein $R^a$ and $R^b$ are independently selected from —H, —$C_1$-$C_8$ alkyl and —$C_3$-$C_8$ carbocycle and n is selected from 2, 3, 4, 5 and 6, and form a ring with the nitrogen atom to which they are attached;

$R^3$ is selected from —H, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle);

$R^4$ is selected from —H, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle) wherein $R^5$ is selected from —H and -methyl; or $R^4$ and $R^5$ join, have the formula —$(CR^aR^b)_n$— wherein $R^a$ and $R^b$ are independently selected from —H, —$C_1$-$C_8$ alkyl and —$C_3$-$C_8$ carbocycle and n is selected from 2, 3, 4, 5 and 6, and form a ring with the carbon atom to which they are attached;

$R^6$ is selected from —H and —$C_1$-$C_8$ alkyl;

$R^7$ is selected from —H, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle);

each $R^8$ is independently selected from —H, —OH, —$C_1$-$C_8$ alkyl, —$C_3$-$C_8$ carbocycle and —O—($C_1$-$C_8$ alkyl);

$R^9$ is selected from —H and —$C_1$-$C_8$ alkyl;

X is —O—, —S—, —NH— or —N($R^{14}$)—;

Z is —O—, —S—, —NH— or —N($R^{14}$)—;

$R^{11}$ is selected from —H, —OH, —$NH_2$, —$NHR^{14}$, —N($R^{14}$)$_2$, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle); or $R^{11}$ is an oxygen atom which forms a carbonyl unit (C=O) with the carbon atom to which it is attached and a hydrogen atom on this carbon atom is replaced by one of the bonds in the (C=O) double bond;

each $R^{12}$ is independently selected from -aryl and $—C_3-C_8$ heterocycle;

each $R^{14}$ is independently $—H$ or $—C_1-C_8$ alkyl;

$R^{15}$ is -arylene-, $—C_3-C_8$ carbocyclo- or $—C_3-C_8$ heterocyclo-;

$R^{16}$ is $—Y_y-W_w-A'$ wherein each $—W—$ is independently an Amino Acid unit;

$—Y—$ is a Spacer unit;

w is an integer ranging from 0 to 12;

y is 0, 1 or 2; and

-A' is selected from

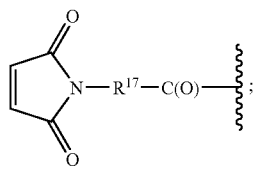

-continued

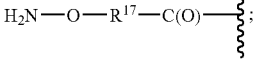

wherein

G is selected from $—Cl, —Br, —I, —O$-mesyl and $—O$-tosyl;

J is selected from $—Cl, —Br, —I, —F, —OH, —O—N$-succinimide, $—O$-(4-nitrophenyl), $—O$-pentafluorophenyl, $—O$-tetrafluorophenyl and $—O—C(O)—OR^{18}$;

$R^{17}$ is selected from $—C_1-C_{10}$ alkylene-, $—C_3-C_8$ carbocyclo-, $—O—(C_1-C_8$ alkyl)-, -arylene-, $—C_1-C_{10}$ alkylene-arylene-, -arylene-$C_1-C_{10}$ alkylene-, $—C_1-C_{10}$ alkylene-($C_3$-$C_8$ carbocyclo)-, $—(C_3-C_8$ carbocyclo)-$C_1-C_{10}$ alkylene-, $—C_3-C_8$ heterocyclo-, $—C_1-C_{10}$ alkylene-($C_3-C_8$ heterocyclo)-, $—(C_3-C_8$ heterocyclo)-$C_1-C_{10}$ alkylene-, $—(CH_2CH_2O)_n—$, and $—(CH_2CH_2O)_r—CH_2—$; r is an integer ranging from 1-10; and $R^{18}$ is $—C_1-C_8$ alkyl or -aryl.

In another aspect, the present invention provides compounds of the formula IIf:

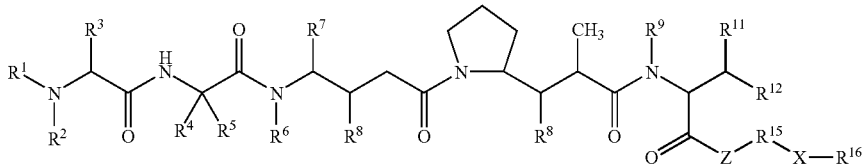

IIf and pharmaceutically acceptable salts and solvates thereof wherein, independently at each location:

$R^1$ is selected from $—H, —C_1-C_8$ alkyl and $—C_3-C_8$ carbocycle; and $R^2$ is selected from $—H$ and $—C_1-C_{10}$ alkyl; or $R^1$ and $R^2$ join, have the formula $—(CR^aR^b)_n—$ wherein $R^a$ and $R^b$ are independently selected from $—H, —C_1-C_{10}$ alkyl and $—C_3-C_8$ carbocycle and n is selected from 2, 3, 4, 5 and 6, and form a ring with the nitrogen atom to which they are attached;

$R^3$ is selected from $—H, —C_1-C_8$ alkyl, $—C_3-C_8$ carbocycle, $—O—(C_1-C_8$ alkyl), -aryl, $—C_1-C_8$ alkyl-aryl, $—C_1-C_8$ alkyl-($C_3-C_8$ carbocycle), $—C_3-C_8$ heterocycle and $—C_1-C_8$ alkyl-($C_3-C_8$ heterocycle);

$R^4$ is selected from $—H, —C_1-C_8$ alkyl, $—C_3-C_8$ carbocycle, $—O—(C_1-C_8$ alkyl), -aryl, $—C_1-C_8$ alkyl-aryl, $—C_1-C_8$ alkyl-($C_3-C_8$ carbocycle), $—C_3-C_8$ heterocycle and $—C_1-C_8$ alkyl-($C_3-C_8$ heterocycle) wherein $R^5$ is selected from $—H$ and -methyl; or $R^4$ and $R^5$ join, have the formula $—(CR^aR^b)_n—$ wherein $R^a$ and $R^b$ are independently selected from $—H, —C_1-C_8$ alkyl and $—C_3-C_8$ carbocycle and n is selected from 2, 3, 4, 5 and 6, and form a ring with the carbon atom to which they are attached;

$R^6$ is selected from $—H$ and $—C_1-C_8$ alkyl;

$R^7$ is selected from $—H, —C_1-C_8$ alkyl, $—C_3-C_8$ carbocycle, $—O—(C_1-C_8$ alkyl), -aryl, $—C_1-C_8$ alkyl-aryl, $—C_1-C_8$ alkyl-($C_3-C_8$ carbocycle), $—C_3-C_8$ heterocycle and $—C_1-C_8$ alkyl-($C_3-C_8$ heterocycle);

each $R^8$ is independently selected from $—H, —OH, —C_1-C_8$ alkyl, $—C_3-C_8$ carbocycle and $—O—(C_1-C_8$ alkyl);

$R^9$ is selected from $—H$ and $—C_1-C_8$ alkyl;

X is $—O—, —S—, —NH—$ or $—N(R^{14})—$;

-continued

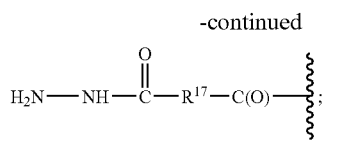

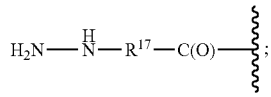

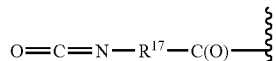

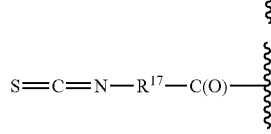

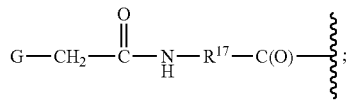

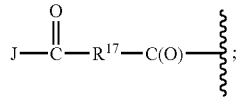

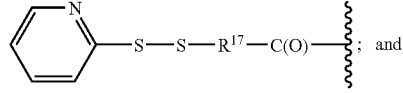; and

Z is —O—, —S—, —NH— or —N(R$^{14}$)—;

R$^{11}$ is selected from —H, —OH, —NH$_2$, —NHR$^{14}$, —N(R$^{14}$)$_2$, —C$_1$-C$_8$ alkyl, —C$_3$-C$_8$ carbocycle, —O—(C$_1$-C$_8$ alkyl), -aryl, —C$_1$-C$_8$ alkyl-aryl, —C$_1$-C$_8$ alkyl-(C$_3$-C$_8$ carbocycle), —C$_3$-C$_8$ heterocycle and —C$_1$-C$_8$ alkyl-(C$_3$-C$_8$ heterocycle); or R$^{11}$ is an oxygen atom which forms a carbonyl unit (C=O) with the carbon atom to which it is attached and a hydrogen atom on this carbon atom is replaced by one of the bonds in the (C=O) double bond;

each R$^{12}$ is independently selected from -aryl and —C$_3$-C$_8$ heterocycle;

each R$^{14}$ is independently —H or —C$_1$-C$_8$ alkyl;

R$^{15}$ is -arylene-, —C$_3$-C$_8$ carbocyclo- or —C$_3$-C$_8$ heterocyclo-;

R$^{16}$ is —Yy-Ww-A' wherein each —W— is independently an Amino Acid unit;

—Y— is a Spacer unit;

w is an integer ranging from 0 to 12;

y is 0, 1 or 2; and

-A' is selected from

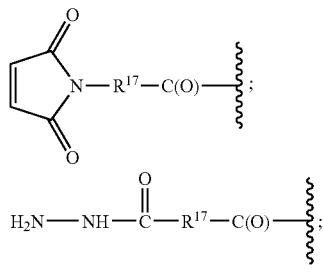

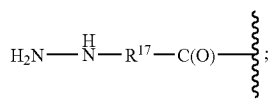

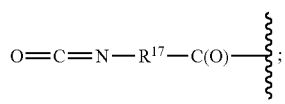

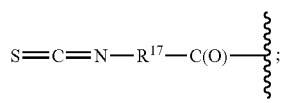

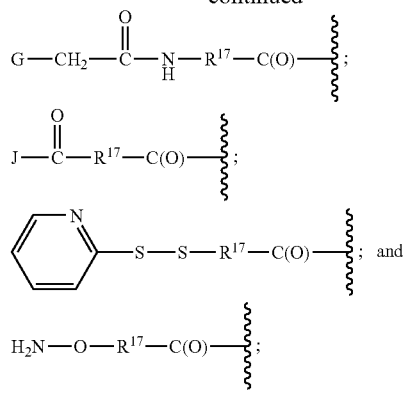

wherein

G is selected from —Cl, —Br, —I, —O-mesyl and —O-tosyl;

J is selected from —Cl, —Br, —I, —F, —OH, —O—N-succinimide, —O-(4-nitrophenyl), —O-pentafluorophenyl, —O-tetrafluorophenyl and —O—C(O)—OR$^{18}$;

R$^{17}$ is selected from —C$_1$-C$_{10}$ alkylene-, —C$_3$-C$_8$ carbocyclo-, —O—(C$_1$-C$_8$ alkyl)-, -arylene-, —C$_1$-C$_{10}$ alkylene-arylene-, -arylene-C$_1$-C$_{10}$ alkylene-, —C$_1$-C$_{10}$ alkylene-(C$_3$-C$_8$ carbocyclo)-, —(C$_3$-C$_8$ carbocyclo)-C$_1$-C$_{10}$ alkylene-, —C$_3$-C$_8$ heterocyclo-, —C$_1$-C$_{10}$ alkylene-(C$_3$-C$_8$ heterocyclo)-, —(C$_3$-C$_8$ heterocyclo)-C$_1$-C$_{10}$ alkylene-, —(CH$_2$CH$_2$O)$_r$—, and —(CH$_2$CH$_2$O)$_r$—CH$_2$—; r is an integer ranging from 1-10; and R$^{18}$ is —C$_1$-C$_8$ alkyl or -aryl.

In another aspect, the present invention provides compounds of the formula IIg:

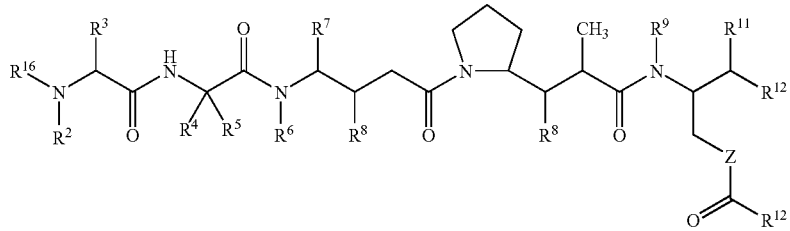

IIg and pharmaceutically acceptable salts and solvates thereof wherein, independently at each location:

R$^2$ is selected from —H and —C$_1$-C$_8$ alkyl;

R$^3$ is selected from —H, —C$_1$-C$_8$ alkyl, —C$_3$-C$_8$ carbocycle, —O—(C$_1$-C$_8$ alkyl), -aryl, —C$_1$-C$_8$ alkyl-aryl, —C$_1$-C$_8$ alkyl-(C$_3$-C$_8$ carbocycle), —C$_3$-C$_8$ heterocycle and —C$_1$-C$_8$ alkyl-(C$_3$-C$_8$ heterocycle);

R$^4$ is selected from —H, —C$_1$-C$_8$ alkyl, —C$_3$-C$_8$ carbocycle, —O—(C$_1$-C$_8$ alkyl), -aryl, —C$_1$-C$_8$ alkyl-aryl, —C$_1$-C$_8$ alkyl-(C$_3$-C$_8$ carbocycle), —C$_3$-C$_8$ heterocycle and —C$_1$-C$_8$ alkyl-(C$_3$-C$_8$ heterocycle) wherein R$^5$ is selected from —H and -methyl; or R$^4$ and R$^5$ join, have the formula —(CR$^a$R$^b$)$_n$— wherein R$^a$ and R$^b$ are independently selected from —H, —C$_1$-C$_8$ alkyl and —C$_3$-C$_8$ carbocycle and n is selected from 2, 3, 4, 5 and 6, and form a ring with the carbon atom to which they are attached;

$R^6$ is selected from —H and —$C_1$-$C_8$ alkyl;

$R^7$ is selected from —H, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle);

each $R^8$ is independently selected from —H, —OH, —$C_1$-$C_8$ alkyl, —$C_3$-$C_8$ carbocycle and —O—($C_1$-$C_8$ alkyl);

$R^9$ is selected from —H and —$C_1$-$C_8$ alkyl;

Z is —O—, —S—, —NH— or —N($R^{14}$)—;

$R^{11}$ is selected from —H, —OH, —$NH_2$, —$NHR^{14}$, —N($R^{14}$)$_2$, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle); or $R^{11}$ is an oxygen atom which forms a carbonyl unit (C=O) with the carbon atom to which it is attached and a hydrogen atom on this carbon atom is replaced by one of the bonds in the (C=O) double bond;

each $R^{12}$ is independently selected from -aryl and —$C_3$-$C_8$ heterocycle;

each $R^{14}$ is independently —H or —$C_1$-$C_8$ alkyl;

$R^{16}$ is —Yy-Ww-A' wherein each —W— is independently an Amino Acid unit;

—Y— is a Spacer unit;

w is an integer ranging from 0 to 12;

y is 0, 1 or 2; and

-A' is selected from

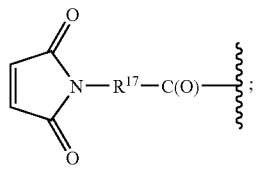

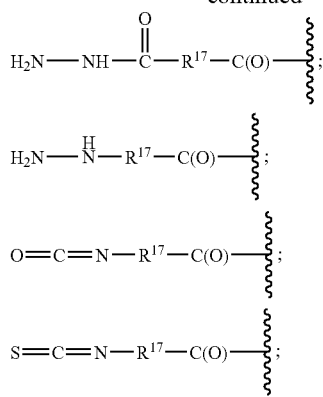

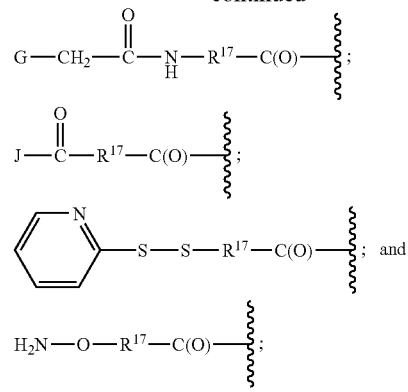

wherein

G is selected from —Cl, —Br, —I, —O-mesyl and —O-tosyl;

J is selected from —Cl, —Br, —I, —F, —OH, —O—N-succinimide, —O-(4-nitrophenyl), —O-pentafluorophenyl, —O-tetrafluorophenyl and —O—C(O)—$OR^{18}$;

$R^{17}$ is selected from —$C_1$-$C_{10}$ alkylene-, —$C_3$-$C_8$ carbocyclo-, —O—($C_1$-$C_8$ alkyl)-, -arylene-, —$C_1$-$C_{10}$ alkylene-arylene-, -arylene-$C_1$-$C_{10}$ alkylene-, —$C_1$-$C_{10}$ alkylene-($C_3$-$C_8$ carbocyclo)-, —($C_3$-$C_8$ carbocyclo)-$C_1$-$C_{10}$ alkylene-, —$C_3$-$C_8$ heterocyclo-, —$C_1$-$C_{10}$ alkylene-($C_3$-$C_8$ heterocyclo)-, —($C_3$-$C_8$ heterocyclo)-$C_1$-$C_{10}$ alkylene-, —($CH_2CH_2O$)$_r$—, and —($CH_2CH_2O$)$_r$—$CH_2$—; r is an integer ranging from 1-10; and $R^{18}$ is —$C_1$-$C_8$ alkyl or -aryl.

In another aspect, the present invention provides compounds of the formula IIh:

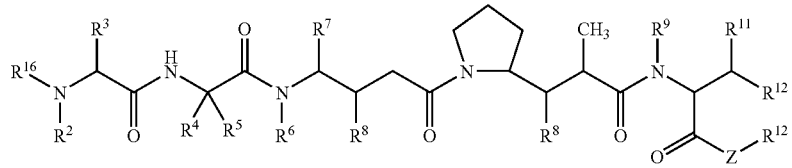

IIh and pharmaceutically acceptable salts and solvates thereof wherein, independently at each location:

$R^2$ is selected from —H and —$C_1$-$C_8$ alkyl;

$R^3$ is selected from —H, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle);

$R^4$ is selected from —H, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle) wherein $R^5$ is selected from —H and -methyl; or $R^4$ and $R^5$ join, have the formula —($CR^aR^b$)$_n$— wherein $R^a$ and $R^b$ are independently selected from —H, —$C_1$-$C_8$ alkyl and —$C_3$-$C_8$ carbocycle and n is selected from 2, 3, 4, 5 and 6, and form a ring with the carbon atom to which they are attached;

$R^6$ is selected from —H and —$C_1$-$C_8$ alkyl;

$R^7$ is selected from —H, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle);

each $R^8$ is independently selected from —H, —OH, —$C_1$-$C_8$ alkyl, —$C_3$-$C_8$ carbocycle and —O—($C_1$-$C_8$ alkyl);

$R^9$ is selected from —H and —$C_1$-$C_8$ alkyl;

Z is —O—, —S—, —NH— or —N($R^{14}$)—;

$R^{11}$ is selected from —H, —OH, —$NH_2$, —$NHR^{14}$, —$N(R^{14})_2$, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle); or $R^{11}$ is an oxygen atom which forms a carbonyl unit (C=O) with the carbon atom to which it is attached and a hydrogen atom on this carbon atom is replaced by one of the bonds in the (C=O) double bond;

each $R^{12}$ is independently selected from -aryl and —$C_3$-$C_8$ heterocycle;

each $R^{14}$ is independently —H or —$C_1$-$C_8$ alkyl;

$R^{16}$ is —Yy-Ww-A' wherein
 each —W— is independently an Amino Acid unit;
 —Y— is a Spacer unit;
 w is an integer ranging from 0 to 12;
 y is 0, 1 or 2; and
 -A' is selected from

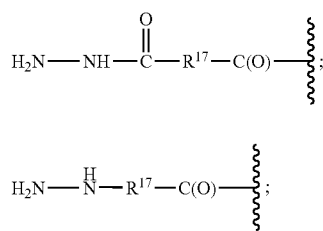

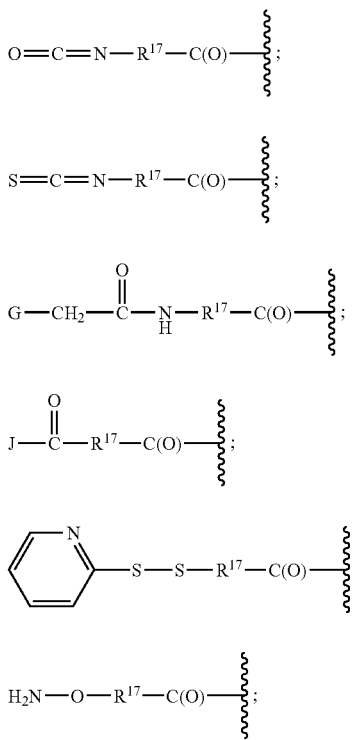

wherein
G is selected from —Cl, —Br, —I, —O-mesyl and —O-tosyl;

J is selected from —Cl, —Br, —I, —F, —OH, —O—N-succinimide, —O-(4-nitrophenyl), —O-pentafluorophenyl, —O-tetrafluorophenyl and —O—C(O)—$OR^{18}$;

$R^{17}$ is selected from —$C_1$-$C_{10}$ alkylene-, —$C_3$-$C_8$ carbocyclo-, —O—($C_1$-$C_8$ alkyl)-, -arylene-, —$C_1$-$C_{10}$ alkylene-arylene-, -arylene-$C_1$-$C_{10}$ alkylene-, —$C_1$-$C_{10}$ alkylene-($C_3$-$C_8$ carbocyclo)-, —($C_3$-$C_8$ carbocyclo)-$C_1$-$C_{10}$ alkylene-, —$C_3$-$C_8$ heterocyclo-, —$C_1$-$C_{10}$ alkylene-($C_3$-$C_8$ heterocyclo)-, —($C_3$-$C_8$ heterocyclo)-$C_1$-$C_{10}$ alkylene-, —$(CH_2CH_2O)_n$—, and —$(CH_2CH_2O)_r$—$CH_2$—; r is an integer ranging from 1-10; and $R^{18}$ is —$C_1$-$C_8$ alkyl or -aryl.

In another aspect, the present invention provides compounds of the formula IIi:

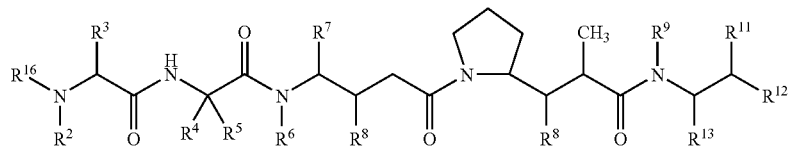

and pharmaceutically acceptable salts and solvates thereof wherein, independently at each location:

$R^2$ is selected from —H and —$C_1$-$C_8$ alkyl;

$R^3$ is selected from —H, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle);

$R^4$ is selected from —H, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle) wherein $R^5$ is selected from —H and -methyl; or $R^4$ and $R^5$ join, have the formula —$(CR^aR^b)_n$— wherein $R^a$ and $R^b$ are independently selected from —H, —$C_1$-$C_8$ alkyl and —$C_3$-$C_8$ carbocycle and n is selected from 2, 3, 4, 5 and 6, and form a ring with the carbon atom to which they are attached;

$R^6$ is selected from —H and —$C_1$-$C_8$ alkyl;

$R^7$ is selected from —H, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle);

each $R^8$ is independently selected from —H, —OH, —$C_1$-$C_8$ alkyl, —$C_3$-$C_8$ carbocycle and —O—($C_1$-$C_8$ alkyl);

$R^9$ is selected from —H and —$C_1$-$C_8$ alkyl;

$R^{11}$ is selected from —H, —OH, —$NH_2$, —$NHR^{14}$, —$N(R^{14})_2$, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle); or $R^{11}$ is an oxygen atom which forms a carbonyl unit (C=O) with the carbon atom to which it is attached and a hydrogen atom on this carbon atom is replaced by one of the bonds in the (C=O) double bond;

each $R^{12}$ is independently selected from -aryl and —$C_3$-$C_8$ heterocycle;

$R^{13}$ is selected from —H, —OH, —$NH_2$, —$NHR^{14}$, —$N(R^{14})_2$, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle);

each $R^{14}$ is independently —H or —$C_1$-$C_8$ alkyl;

$R^{16}$ is —Yy-Ww-A' wherein each —W— is independently an Amino Acid unit;

—Y— is a Spacer unit;

w is an integer ranging from 0 to 12;

y is 0, 1 or 2; and

-A' is selected from

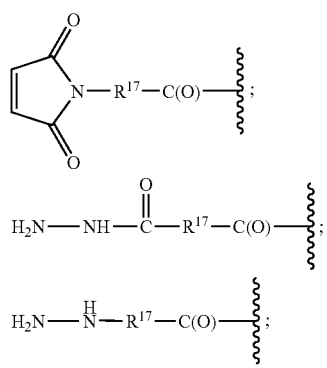

-continued

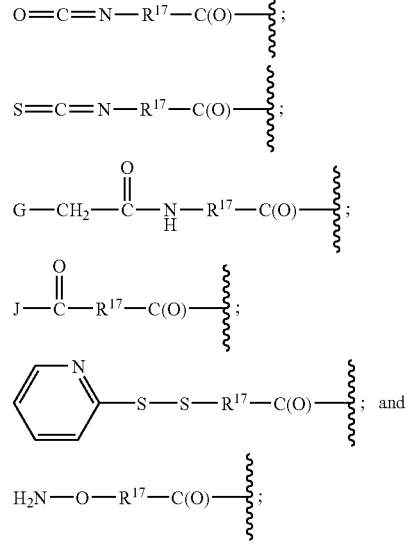

wherein

G is selected from —Cl, —Br, —I, —O-mesyl and —O-tosyl;

J is selected from —Cl, —Br, —I, —F, —OH, —O—N-succinimide, —O-(4-nitrophenyl), —O-pentafluorophenyl, —O-tetrafluorophenyl and —O—C(O)—$OR^{18}$;

$R^{17}$ is selected from —$C_1$-$C_{10}$ alkylene-, —$C_3$-$C_8$ carbocyclo-, —O—($C_1$-$C_8$ alkyl)-, -arylene-, —$C_1$-$C_{10}$ alkylene-arylene-, -arylene-$C_1$-$C_{10}$ alkylene-, —$C_1$-$C_{10}$ alkylene-($C_3$-$C_8$ carbocyclo)-, —($C_3$-$C_8$ carbocyclo)-$C_1$-$C_{10}$ alkylene-, —$C_3$-$C_8$ heterocyclo-, —$C_1$-$C_{10}$ alkylene-($C_3$-$C_8$ heterocyclo)-, —($C_3$-$C_8$ heterocyclo)-$C_1$-$C_{10}$ alkylene-, —$(CH_2CH_2O)_n$—, and —$(CH_2CH_2O)_r$—$CH_2$—; r is an integer ranging from 1-10; and $R^{18}$ is —$C_1$-$C_8$ alkyl or -aryl.

A compound of formula IIa-i or a pharmaceutically acceptable salt or solvate thereof (a "Drug-Linker Compound") is useful for treating cancer, an autoimmune disease or an infectious disease in an animal or useful as an intermediate for the synthesis of a Drug-Linker-Ligand Conjugate.

In another aspect, the present invention provides compositions comprising an effective amount of a Drug-Linker-Ligand Conjugate and a pharmaceutically acceptable carrier or vehicle.

In still another aspect, the present invention provides compositions comprising an effective amount of a Drug-Linker Compound and a pharmaceutically acceptable carrier or vehicle.

In yet another aspect, the present invention provides methods for killing or inhibiting the multiplication of a tumor cell or cancer cell, comprising administering to an animal in need thereof an effective amount of a Drug-Linker Compound.

In another aspect, the present invention provides methods for killing or inhibiting the multiplication of a tumor cell or cancer cell, comprising administering to an animal in need thereof an effective amount of a Drug-Linker-Ligand Conjugate.

In still another aspect, the invention provides methods for treating cancer, comprising administering to an animal in need thereof an effective amount of a Drug-Linker Compound.

In yet another aspect, the invention provides methods for treating cancer, comprising administering to an animal in need thereof an effective amount of a Drug-Linker-Ligand Conjugate.

In still another aspect, the invention provides methods for killing or inhibiting the replication of a cell that expresses an auto-immune antibody, comprising administering to an animal in need thereof an effective amount of a Drug-Linker Compound.

In another aspect, the invention provides methods for killing or inhibiting the replication of a cell that expresses an auto-immune antibody, comprising administering to an animal in need thereof an effective amount of a Drug-Linker-Ligand Conjugate.

In yet another aspect, the invention provides methods for treating an autoimmune disease, comprising administering to an animal in need thereof an effective amount of a Drug-Linker Compound.

In yet another aspect, the invention provides methods for treating an autoimmune disease, comprising administering to an animal in need thereof an effective amount of a Drug-Linker-Ligand Conjugate.

In still another aspect, the invention provides methods for treating an infectious disease, comprising administering to an animal in need thereof an effective amount of a Drug-Linker Compound.

In still another aspect, the invention provides methods for treating an infectious disease, comprising administering to an animal in need thereof an effective amount of a Drug-Linker-Ligand Conjugate.

In yet another aspect, the present invention provides methods for preventing the multiplication of a tumor cell or cancer cell, comprising administering to an animal in need thereof an effective amount of a Drug-Linker Compound.

In another aspect, the present invention provides methods for preventing the multiplication of a tumor cell or cancer cell, comprising administering to an animal in need thereof an effective amount of a Drug-Linker-Ligand Conjugate.

In still another aspect, the invention provides methods for preventing cancer, comprising administering to an animal in need thereof an effective amount of a Drug-Linker Compound.

In yet another aspect, the invention provides methods for preventing cancer, comprising administering to an animal in need thereof an effective amount of a Drug-Linker-Ligand Conjugate.

In still another aspect, the invention provides methods for preventing the multiplication of a cell that expresses an auto-immune antibody, comprising administering to an animal in need thereof an effective amount of a Drug-Linker Compound.

In another aspect, the invention provides methods for preventing the multiplication of a cell that expresses an auto-immune antibody, comprising administering to an animal in need thereof an effective amount of a Drug-Linker-Ligand Conjugate.

In yet another aspect, the invention provides methods for preventing an autoimmune disease, comprising administering to an animal in need thereof an effective amount of a Drug-Linker Compound.

In yet another aspect, the invention provides methods for preventing an autoimmune disease, comprising administering to an animal in need thereof an effective amount of a Drug-Linker-Ligand Conjugate.

In still another aspect, the invention provides methods for preventing an infectious disease, comprising administering to an animal in need thereof an effective amount of a Drug-Linker Compound.

In still another aspect, the invention provides methods for preventing an infectious disease, comprising administering to an animal in need thereof an effective amount of a Drug-Linker-Ligand Conjugate.

In another aspect, the invention provides a Drug-Linker Compound which can be used as an intermediate for the synthesis of a Drug-Linker-Ligand Conjugate.

The present invention may be understood more fully by reference to the following detailed description, Figures and illustrative examples, which are intended to exemplify non-limiting embodiments of the invention.

4. BRIEF DESCRIPTION OF THE DRAWINGS

Figure 6:
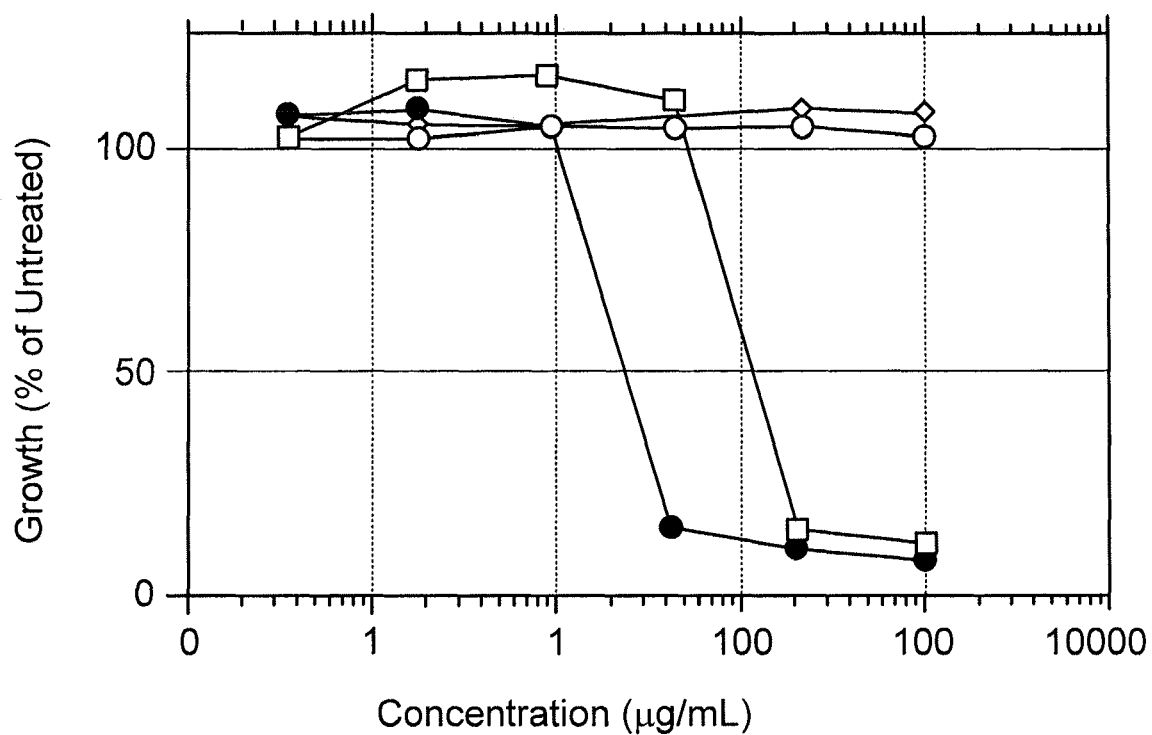

FIG. 6 shows the cytotoxicity of Compounds 66 and 67 against the H3396 cell line as a function of exposure length. The cells were either exposed to the conjugates for the entire duration of the assay without washing (96 hours), or were exposed to the conjugates for 2 hours, washed, and then incubated for an additional 94 hours. At the end of the 96 hour period, the cells were pulsed with Alamar Blue to determine cell viability. Line - - represents Compound 66 at 2 h exposure, line -- represents Compound 67 at 2 h exposure, line -●- represents Compound 66 at 96 h exposure, and line - - represents Compound 67 at 96 h exposure.

Figure 7:
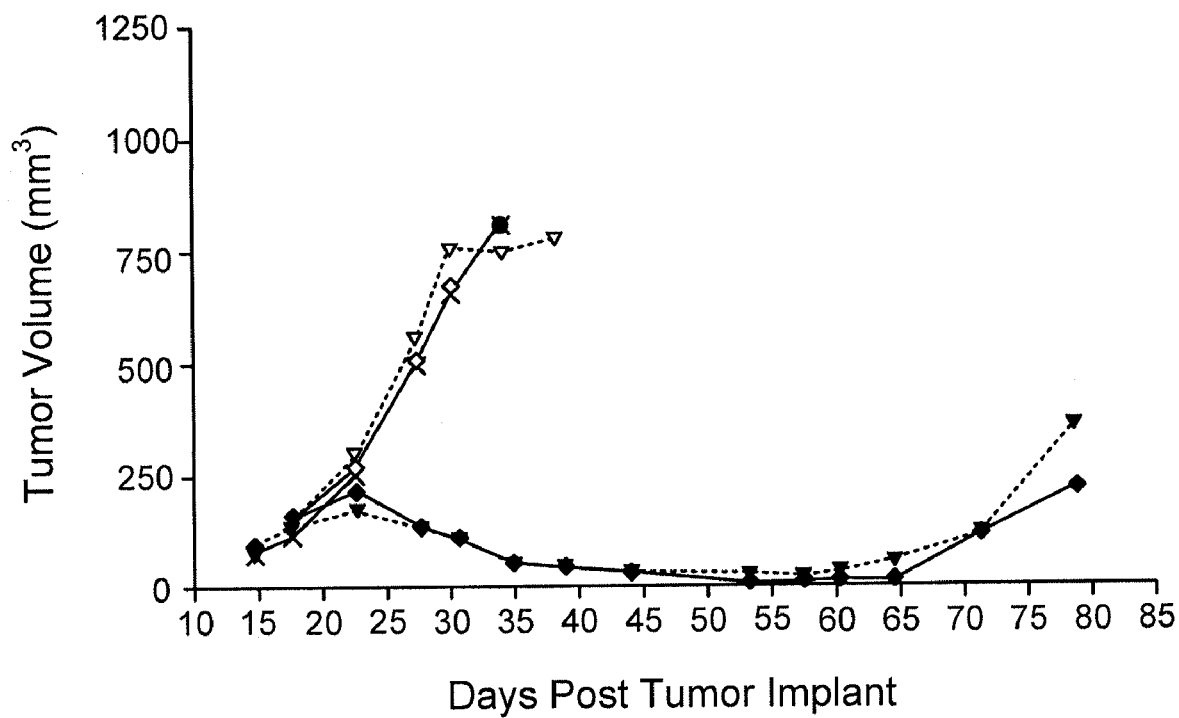

FIG. 7 shows the effect of Compounds 66-69 on the growth of L2987 human lung adenocarcinoma xenograft tumors which were implanted in nude mice. Line -X- represents untreated tumor, line -▼- represents Compound 66, line -♦- represents Compound 68, line -∇- Compound 67, and line -◇- represents Compound 69.

Figure 8:
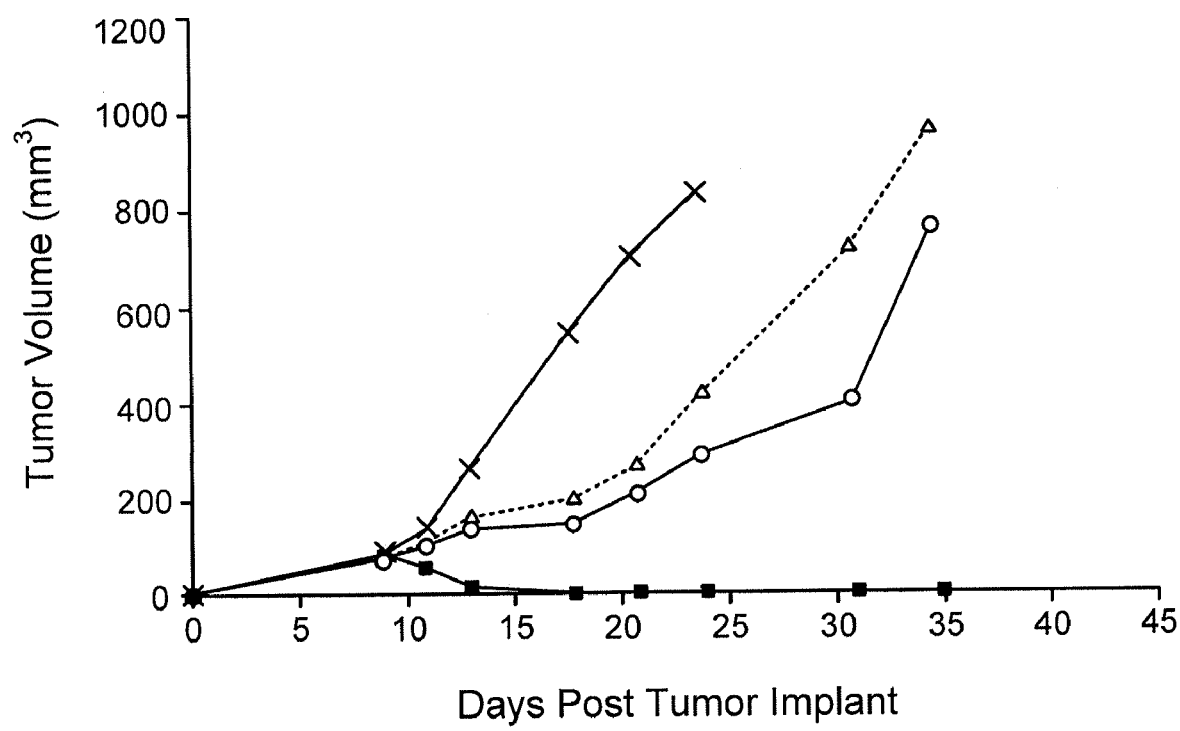

FIG. 8 shows the effects of Compounds 66-69 on the growth of Karpas human anaplastic large cell lymphoma xenograft tumors which were implanted in nude mice. Line -X- represents untreated tumor, line -▲- represents Compound 67, line represents Compound 69, line -Δ- represents Compound 66, and line -o- represents Compound 68.

5. DETAILED DESCRIPTION OF THE INVENTION

5.1 Definitions

Examples of an "animal" include, but are not limited to, a human, rat, mouse, guinea pig, monkey, pig, goat, cow, horse, dog, cat, bird and fowl.

"Aryl" refers to a carbocyclic aromatic group Examples of aryl groups include, but are not limited to, phenyl, naphthyl and anthracenyl. A carbocyclic aromatic group or a heterocyclic aromatic group can be unsubstituted or substituted with one or more groups including, but not limited to, $-C_1$-$C_8$ alkyl, $-O-(C_1$-$C_8$ alkyl), -aryl, $-C(O)R'$, $-OC(O)R'$, $-C(O)OR'$, $-C(O)NH_2$, $-C(O)NHR'$, $-C(O)N(R')_2-$NHC(O)R', $-S(O)_2R'$, $-S(O)R'$, $-OH$, -halogen, $-N_3$, $-NH_2$, $-NH(R')$, $-N(R')_2$ and $-CN$; where each R' is independently selected from $-C_1$-$C_8$ alkyl and aryl.

The term "$C_1$-$C_8$ alkyl," as used herein refers to a straight chain or branched, saturated or unsaturated hydrocarbon having from 1 to 8 carbon atoms. Representative "$C_1$-$C_8$ alkyl" groups include, but are not limited to, -methyl, -ethyl, -n-propyl, -n-butyl, -n-pentyl, -n-hexyl, -n-heptyl, -n-octyl, -n-nonly and -n-decyl; while branched $C_1$-$C_8$ alkyls include, but are not limited to, -isopropyl, -sec-butyl, -isobutyl, -tert-butyl, -isopentyl, 2-methylbutyl, unsaturated $C_1$-$C_8$ alkyls include, but are not limited to, -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, 1-hexyl, 2-hexyl, 3-hexyl, -acetylenyl, -propynyl, -1-butynyl, -2-butynyl, -1-pentynyl, -2-pentynyl, -3-methyl-1 butynyl. methyl, ethyl, propyl, isopropyl, n-butyl, isobutyl, sec-butyl, tert-butyl, n-pentyl, isopentyl, neopentyl, n-hexyl, isohexyl, 2-methylpentyl, 3-methylpentyl, 2,2-dimethylbutyl, 2,3-dimethylbutyl, 2,2-dimethylpentyl, 2,3-dimethylpentyl, 3,3-dimethylpentyl, 2,3,4-trimethylpentyl, 3-methylhexyl, 2,2-dimethylhexyl, 2,4-dimethylhexyl, 2,5-dimethylhexyl, 3,5-dimethylhexyl, 2,4-dimethylpentyl, 2-methylheptyl, 3-methylheptyl, n-heptyl, isoheptyl, n-octyl, and isooctyl. A $C_1$-$C_8$ alkyl group can be unsubstituted or substituted with one or more groups including, but not limited to, $-C_1$-$C_8$ alkyl, $-O-(C_1$-$C_8$ alkyl), -aryl, $-C(O)R'$, $-OC(O)R'$, $-C(O)OR'$, $-C(O)NH_2$, $-C(O)NHR'$, $-C(O)N(R')_2-$NHC(O)R', $-S(O)_2R'$, $-S(O)R'$, $-OH$, -halogen, $-N_3$, $-NH_2$, $-NH(R')$, $-N(R')_2$ and $-CN$; where each R' is independently selected from $-C_1$-$C_8$ alkyl and aryl.

A "$C_3$-$C_8$ carbocycle" is a 3-, 4-, 5-, 6-, 7- or 8-membered saturated or unsaturated non-aromatic carbocyclic ring. Representative $C_3$-$C_8$ carbocycles include, but are not limited to, -cyclopropyl, -cyclobutyl, -cyclopentyl, -cyclopentadienyl, -cyclohexyl, -cyclohexenyl, -1,3-cyclohexadienyl, -1,4-cyclohexadienyl, -cycloheptyl, -1,3-cycloheptadienyl, -1,3,5-cycloheptatrienyl, -cyclooctyl, and -cyclooctadienyl. A $C_3$-$C_8$ carbocycle group can be unsubstituted or substituted with one or more groups including, but not limited to, $-C_1$-$C_8$ alkyl, $-O-(C_1$-$C_8$ alkyl), -aryl, $-C(O)R'$, $-OC(O)R'$, $-C(O)OR'$, $-C(O)NH_2$, $-C(O)NHR'$, $-C(O)N(R')_2-$NHC(O)R', $-S(O)_2R'$, $-S(O)R'$, $-OH$, -halogen, $-N_3$, $-NH_2$, $-NH(R')$, $-N(R')_2$ and $-CN$; where each R' is independently selected from $-C_1$-$C_8$ alkyl and aryl.

A "$C_3$-$C_8$ carbocyclo" refers to a $C_3$-$C_8$ carbocycle group defined above wherein one of the carbocycle groups hydrogen atoms is replaced with a bond.

A "$C_1$-$C_{10}$ alkylene" is a straight chain, saturated hydrocarbon group of the formula $-(CH_2)_{1-10}-$. Examples of a $C_1$-$C_{10}$ alkylene include methylene, ethylene, propylene, butylene, pentylene, hexylene, heptylene, ocytylene, nonylene and decalene.

An "arylene" is an aryl group which has two covalent bonds and can be in the ortho, meta, or para configurations as shown in the following structures:

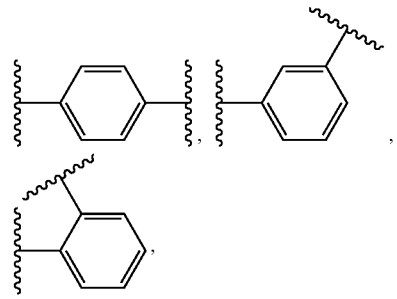

in which the phenyl group can be unsubstituted or substituted with up to four groups including, but not limited to, $-C_1$-$C_8$ alkyl, $-O-(C_1$-$C_8$ alkyl), -aryl, $-C(O)R'$, $-OC(O)R'$, $-C(O)OR'$, $-C(O)NH_2$, $-C(O)NHR'$, $-C(O)N(R')_2-$NHC(O)R', $-S(O)_2R'$, $-S(O)R'$, $-OH$, -halogen, $-N_3$, $-NH_2$, $-NH(R')$, $-N(R')_2$ and $-CN$; where each R' is independently selected from $-C_1$-$C_8$ alkyl and aryl.

A "$C_3$-$C_8$ heterocycle" refers to an aromatic or non-aromatic $C_3$-$C_8$ carbocycle in which one to four of the ring carbon atoms are independently replaced with a heteroatom from the group consisting of O, S and N. Representative examples of a $C_3$-$C_8$ heterocycle include, but are not limited to, benzofuranyl, benzothiophene, indolyl, benzopyrazolyl, coumarinyl, isoquinolinyl, pyrrolyl, thiophenyl, furanyl, thiazolyl, imidazolyl, pyrazolyl, triazolyl, quinolinyl, pyrimidinyl, pyridinyl, pyridonyl, pyrazinyl, pyridazinyl, isothiazolyl, isoxazolyl and tetrazolyl. A $C_3$-$C_8$ Heterocycle can be unsubstituted or substituted with up to seven groups including, but not limited to, $-C_1$-$C_8$ alkyl, $-O-(C_1$-$C_8$ alkyl), -aryl, $-C(O)R'$, $-OC(O)R'$, $-C(O)OR'$, $-C(O)NH_2$, $-C(O)NHR'$, $-C(O)N(R')_2-$NHC(O)R', $-S(O)_2R'$, $-S(O)R'$, $-OH$, -halogen, $-N_3$, $-NH_2$, $-NH(R')$, $-N(R')_2$ and $-CN$; where each R' is independently selected from $-C_1$-$C_8$ alkyl and aryl.

"$C_3$-$C_8$ heterocyclo" refers to a $C_3$-$C_8$ heterocycle group defined above wherein one of the heterocycle groups hydrogen atoms is replaced with a bond. A $C_3$-$C_8$ heterocyclo can be unsubstituted or substituted with up to six groups including, but not limited to, $-C_1$-$C_8$ alkyl, $-O-(C_1$-$C_8$ alkyl), -aryl, $-C(O)R'$, $-OC(O)R'$, $-C(O)OR'$, $-C(O)NH_2$, $-C(O)NHR'$, $-C(O)N(R')_2-$NHC(O)R', $-S(O)_2R'$, $-S(O)R'$, $-OH$, -halogen, $-N_3$, $-NH_2$, $-NH(R')$, $-N(R')_2$ and $-CN$; where each R' is independently selected from $-C_1$-$C_8$ alkyl and aryl.

A "Compound of the Invention" is a Drug-Linker Compound or a Drug-Linker-Ligand Conjugate.

In one embodiment, the Compounds of the Invention are in isolated or purified form. As used herein, "isolated" means separated from other components of (a) a natural source, such as a plant or animal cell or cell culture, or (b) a synthetic organic chemical reaction mixture. As used herein, "purified" means that when isolated, the isolate contains at least 95%, preferably at least 98%, of a Compound of the Invention by weight of the isolate.

Examples of a "Hydroxyl protecting group" include, but are not limited to, methoxymethyl ether, 2-methoxyethoxymethyl ether, tetrahydropyranyl ether, benzyl ether, p-methoxybenzyl ether, trimethylsilyl ether, triisopropyl silyl ether, t-butyldimethyl silyl ether, triphenylmethyl silyl ether, acetate ester, substituted acetate esters, pivaloate, benzoate, methanesulfonate and p-toluenesulfonate.

"Leaving group" refers to a functional group that can be substituted by another functional group. Such leaving groups are well known in the art, and examples include, but are not limited to, a halide (e.g., chloride, bromide, iodide), methanesulfonyl (mesyl), p-toluenesulfonyl (tosyl), trifluoromethylsulfonyl (triflate), and trifluoromethylsulfonate.

The term "antibody," as used herein, refers to a full-length immunoglobulin molecule or an immunologically active portion of a full-length immunoglobulin molecule, i.e., a molecule that contains an antigen binding site that immunospecifically binds an antigen of a target of interest or part thereof, such targets including but not limited to, cancer cell or cells that produce auto-immune antibodies associated with an autoimmune disease. The immunoglobulin disclosed herein can be of any type (e.g., IgG, IgE, IgM, IgD, IgA and IgY), class (e.g., IgG1, IgG2, IgG3, IgG4, IgA1 and IgA2) or subclass of immunoglobulin molecule. The immunoglobulins can be derived from any species. Preferably, however, the immunoglobulin is of human, murine, or rabbit origin. Antibodies useful in the invention are preferably monoclonal, and include, but are not limited to, polyclonal, monoclonal, bispecific, human, humanized or chimeric antibodies, single chain antibodies, Fv, Fab fragments, F(ab') fragments, F(ab')$_2$ fragments, fragments produced by a Fab expression library, anti-idiotypic (anti-Id) antibodies, CDR's, and epitope-binding fragments of any of the above which immunospecifically bind to cancer cell antigens, viral antigens or microbial antigens.

The phrase "pharmaceutically acceptable salt," as used herein, refers to pharmaceutically acceptable organic or inorganic salts of a Compound of the Invention. The Compounds of the Invention contain at least one amino group, and accordingly acid addition salts can be formed with this amino group. Preferred salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counterions. Hence, a pharmaceutically acceptable salt can have one or more charged atoms and/or one or more counterion.

"Pharmaceutically acceptable solvate" refers to an association of one or more solvent molecules and a Compound of the Invention. Examples of solvents that form pharmaceutically acceptable solvates include, but are not limited to, water, isopropanol, ethanol, methanol, DMSO, ethyl acetate, acetic acid, and ethanolamine.

In the context of cancer, the term "treating" includes any or all of: preventing growth of tumor cells or cancer cells, preventing replication of tumor cells or cancer cells, lessening of overall tumor burden and ameliorating one or more symptoms associated with the disease.

In the context of an autoimmune disease, the term "treating" includes any or all of: preventing replication of cells associated with an autoimmune disease state including, but not limited to, cells capable of producing an autoimmune antibody, lessening the autoimmune-antibody burden and ameliorating one or more symptoms of an autoimmune disease.

In the context of an infectious disease, the term "treating" includes any or all of: preventing the growth, multiplication or replication of the pathogen that causes the infectious disease and ameliorating one or more symptoms of an infectious disease.

The following abbreviations are used herein and have the indicated definitions: AE is auristatin E, Boc is N-(t-butoxycarbonyl), cit is citrulline, dap is dolaproine, DCC is 1,3-dicyclohexylcarbodiimide, DCM is dichloromethane, DEA is diethylamine, DEAD is diethylazodicarboxylate, DEPC is diethylphosphorylcyanidate, DIAD is diisopropylazodicarboxylate, DIEA is N,N-diisopropylethylamine, dil is dolaisoleuine, DMAP is 4-dimethylaminopyridine, DME is ethyleneglycol dimethyl ether (or 1,2-dimethoxyethane), DMF is N,N-dimethylformamide, DMSO is dimethylsulfoxide, doe is dolaphenine, dov is N,N-dimethylvaline, DTNB is 5,5'-dithiobis(2-nitrobenzoic acid), DTPA is diethylenetriaminepentaacetic acid, DTT is dithiothreitol, EDCI is 1-(3-dimethylaminopropyl)-3-ethylcarbodiimide hydrochloride, EEDQ is 2-ethoxy-1-ethoxycarbonyl-1,2-dihydroquinoline, ES-MS is electrospray mass spectrometry, EtOAc is ethyl acetate, Fmoc is N-(9-fluorenylmethoxycarbonyl), gly is glycine, HATU is O-(7-azabenzotriazol-1-yl)-N,N,N',N'-tetramethyluronium hexafluorophosphate, HOBt is 1-hydroxybenzotriazole, HPLC is high pressure liquid chromatography, ile is isoleucine, lys is lysine, MeCN is acetonitrile, MeOH is methanol, Mtr is 4-anisyldiphenylmethyl (or 4-methoxytrityl), nor is (1S,2R)-(+)-norephedrine, PAB is p-aminobenzyl, PBS is phosphate-buffered saline (pH 7.4), PEG is polyethylene glycol, Ph is phenyl, Pnp is p-nitrophenyl, MC is 6-maleimidocaproyl, Ph is phenyl, phe is L-phenylalanine, PyBrop is bromo-tris-pyrrolidino-phosphonium hexafluorophosphate, SEC is size-exclusion chromatography, Su is succinimide, TFA is trifluoroacetic acid, TLC is thin layer chromatography, UV is ultraviolet, val is valine.

5.2 Drug-Linker-Ligand Conjugates

As stated above, the invention provides compounds of the formula Ia:

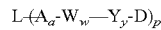

Ia and pharmaceutically acceptable salts and solvates thereof wherein,

L- is a Ligand unit;

-A- is a Stretcher unit;

a is 0 or 1;

each —W— is independently an Amino Acid unit;

—Y— is a Spacer unit;

w is an integer ranging from 0 to 12;

y is 0, 1 or 2;

p ranges from 1 to about 20; and

-D is a Drug unit of the formula

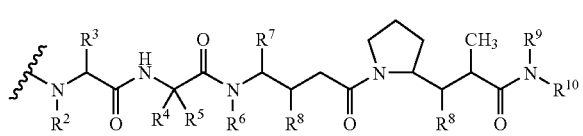

wherein, independently at each location:

$R^2$ is selected from —H and —$C_1$-$C_8$ alkyl;

$R^3$ is selected from —H, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle);

$R^4$ is selected from —H, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle) wherein $R^5$ is selected from —H and -methyl; or $R^4$ and $R^5$ join, have the formula —$(CR^aR^b)_n$— wherein $R^a$ and $R^b$ are independently selected from —H, —$C_1$-$C_8$ alkyl and —$C_3$-$C_8$ carbocycle and n is selected from 2, 3, 4, 5 and 6, and form a ring with the carbon atom to which they are attached;

$R^6$ is selected from —H and —$C_1$-$C_8$ alkyl;

$R^7$ is selected from —H, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle);

each $R^8$ is independently selected from —H, —OH, —$C_1$-$C_8$ alkyl, —$C_3$-$C_8$ carbocycle and —O—($C_1$-$C_8$ alkyl);

$R^9$ is selected from —H and —$C_1$-$C_8$ alkyl;

$R^{10}$ is selected from

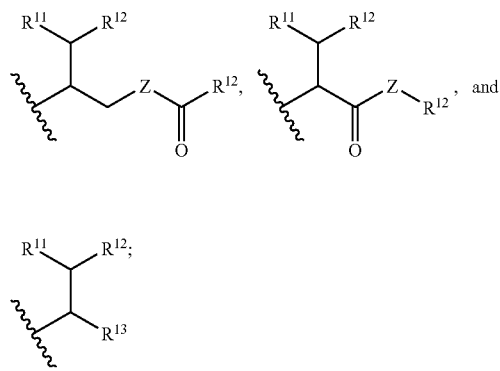

Z is —O—, —S—, —NH— or —N($R^{14}$)—;

$R^{11}$ is selected from —H, —OH, —$NH_2$, —$NHR^{14}$, —$N(R^{14})_2$, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle); or $R^{11}$ is an oxygen atom which forms a carbonyl unit (C=O) with the carbon atom to which it is attached and a hydrogen atom on this carbon atom is replaced by one of the bonds in the (C=O) double bond;

each $R^{12}$ is independently selected from -aryl and —$C_3$-$C_8$ heterocycle;

$R^{13}$ is selected from —H, —OH, —$NH_2$, —$NHR^{14}$, —$N(R^{14})_2$, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), $C_3$-$C_8$ heterocycle and —$C_1$-$C_8$ alkyl-($C_3$-$C_8$ heterocycle); and each $R^{14}$ is independently —H or —$C_1$-$C_8$ alkyl.

In one embodiment $R^{10}$ is selected from

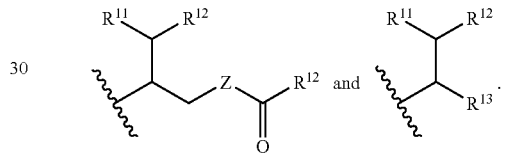

In another embodiment, w is an integer ranging from 2 to 12.

In another embodiment, p ranges from 1 to about 8.

In another embodiment, p ranges from 1 to about 3.

In another embodiment, p ranges from about 3 to about 5.

In still another embodiment, p ranges from about 7 to about 9.

In another embodiment, p is about 8.

In another embodiment, p is about 4.

In a further embodiment, p is about 2.

Illustrative classes of compounds of formula Ia have the structures:

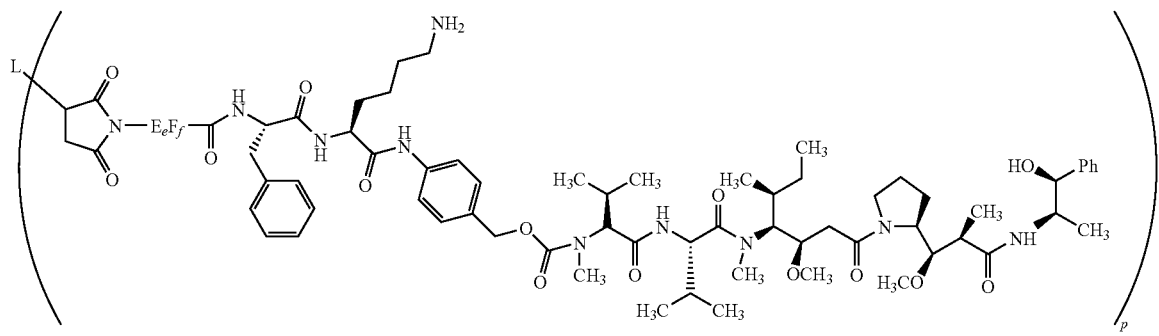

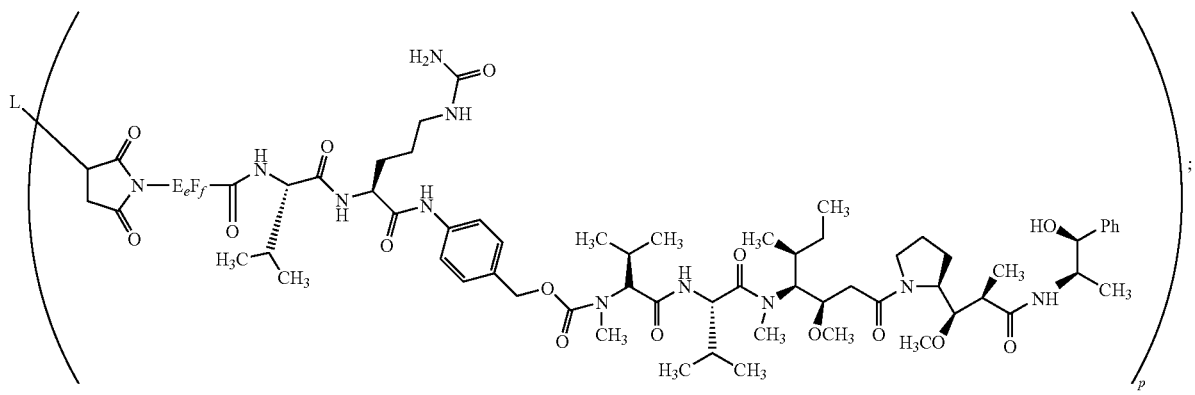
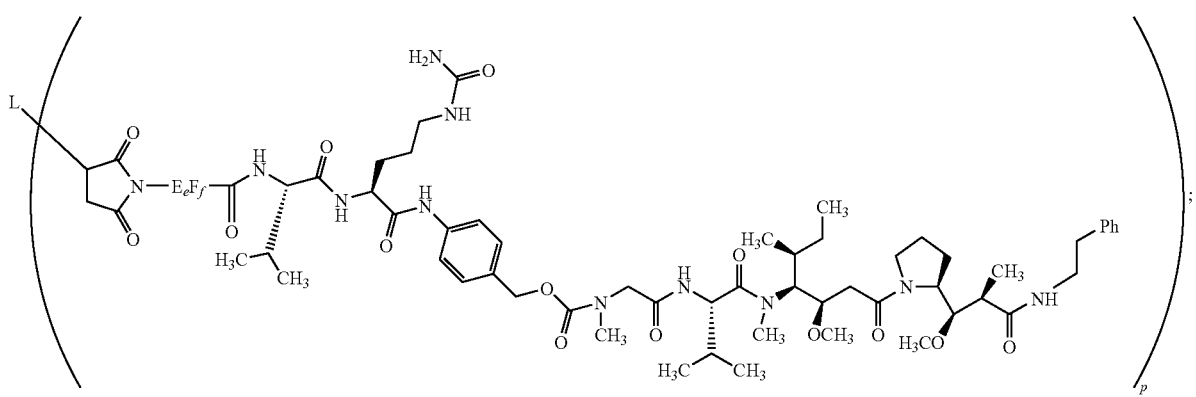
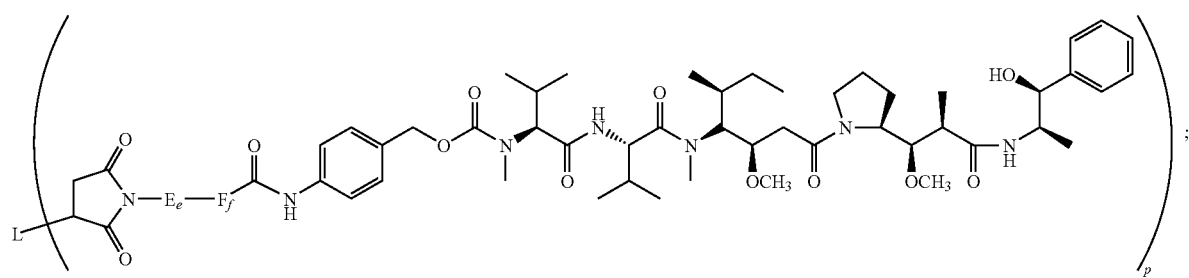
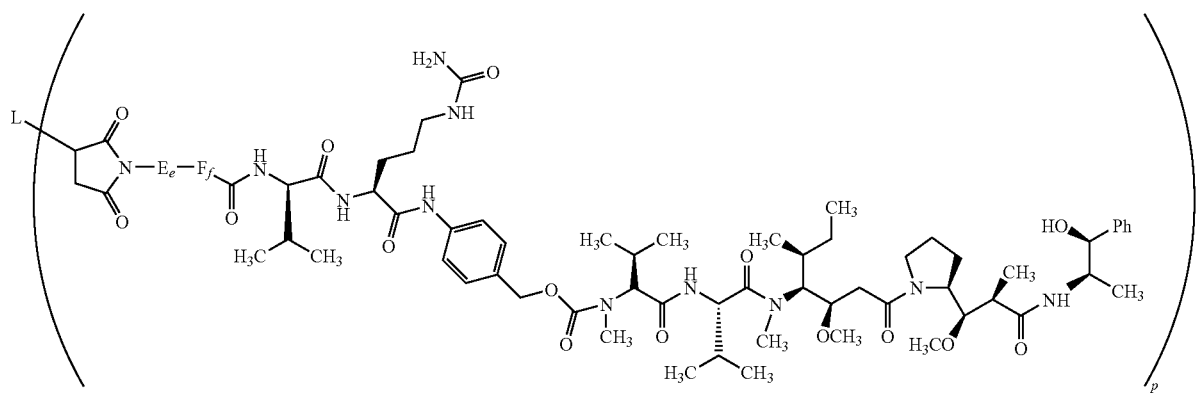

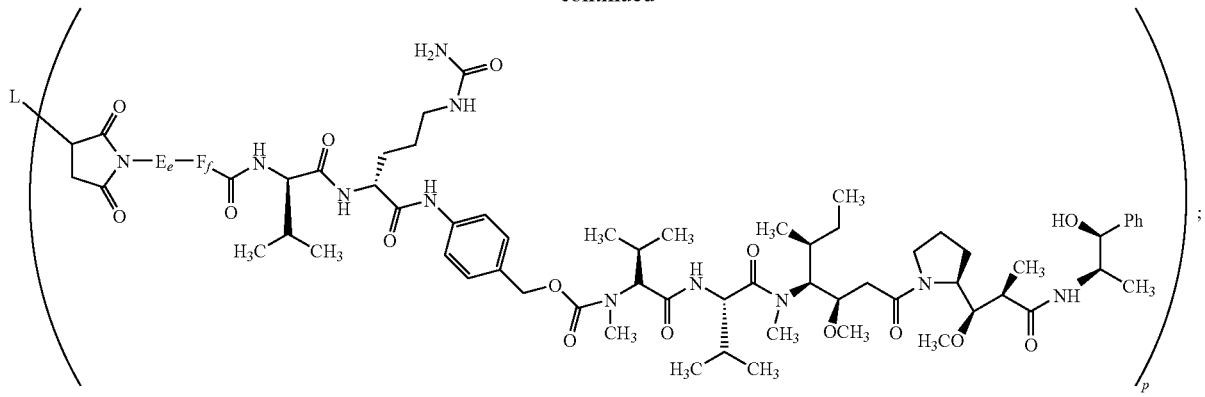

and

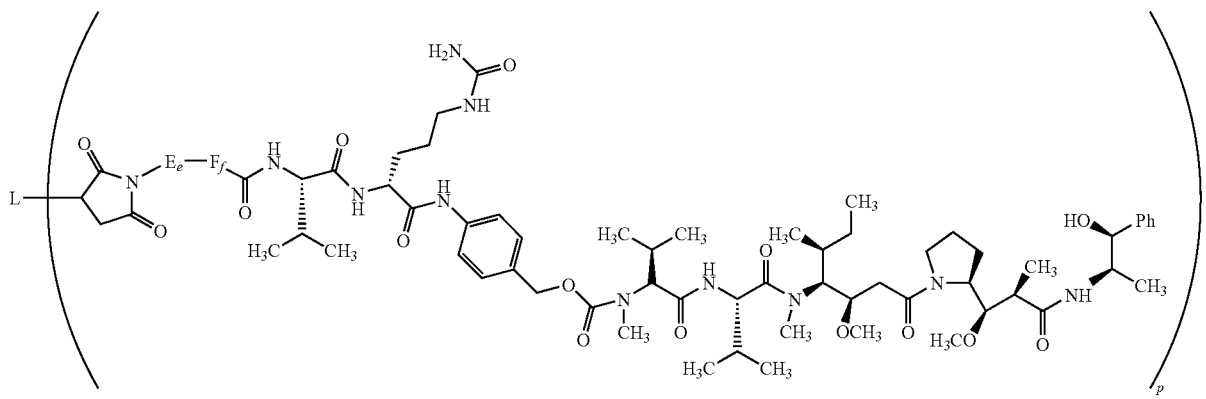

and pharmaceutically acceptable salts and solvates thereof, where L- is a Ligand unit, E is —CH$_2$— or —CH$_2$CH$_2$O—; e is an integer ranging either from 0-10 when E is —CH$_2$—, or from 1-10 when E is —CH$_2$CH$_2$—O—; F is —CH$_2$—; f is 0 or 1; and p ranges from 1 to about 20.

In another embodiment, p ranges from 1 to about 8.
In another embodiment, p ranges from 1 to about 3.
In another embodiment, p ranges from about 3 to about 5.
In still another embodiment, p ranges from about 7 to about 9.
In another embodiment, p is about 8.
In another embodiment, p is about 4.
In another embodiment L is cBR96, cAC10 or 1F6.
Illustrative compounds of formula Ia have the structure:

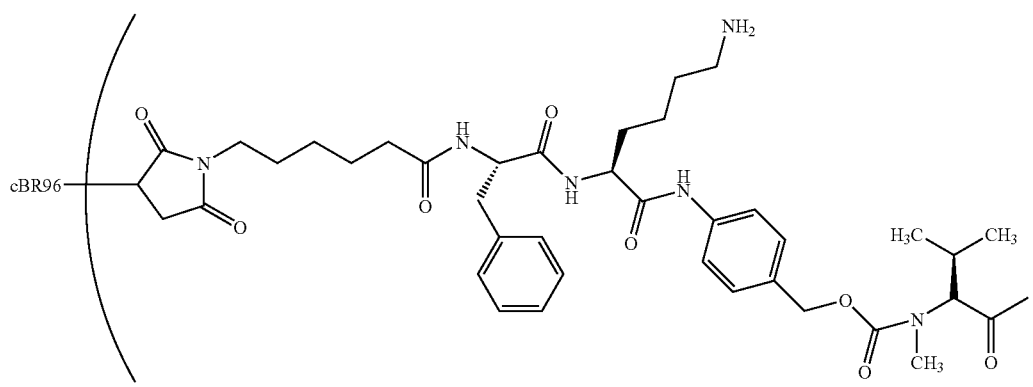

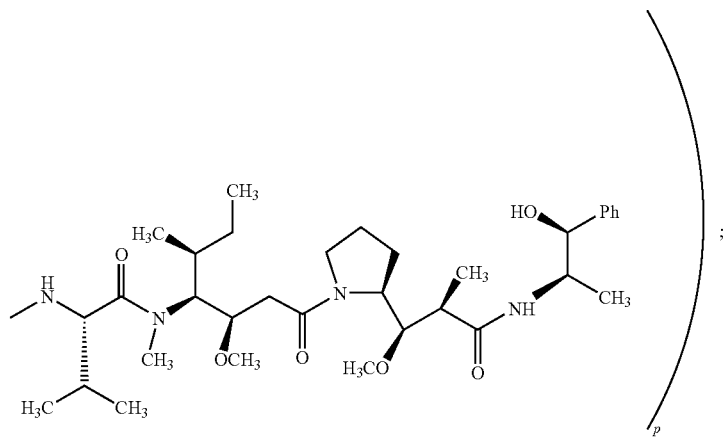
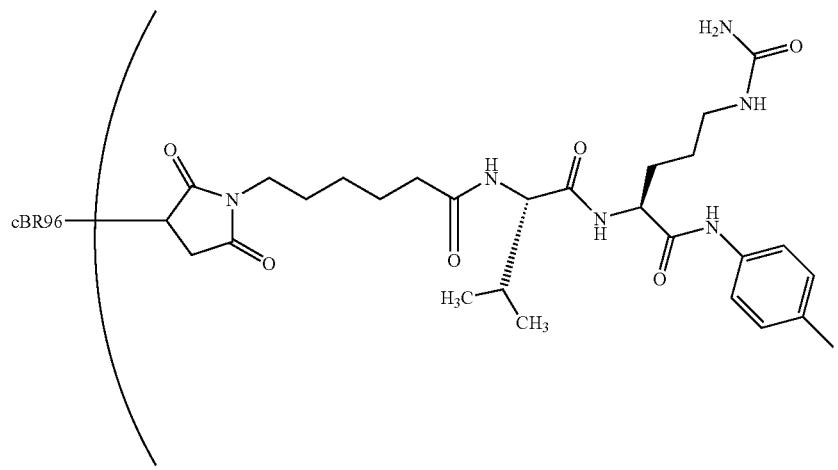
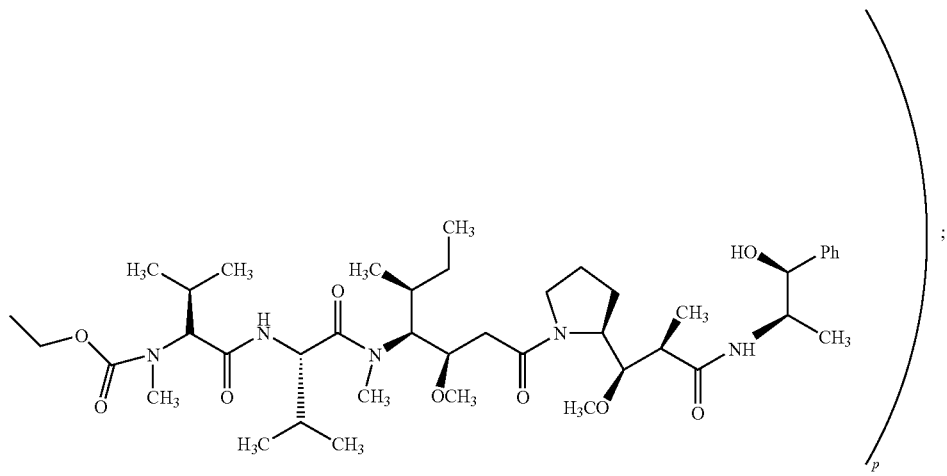

-continued
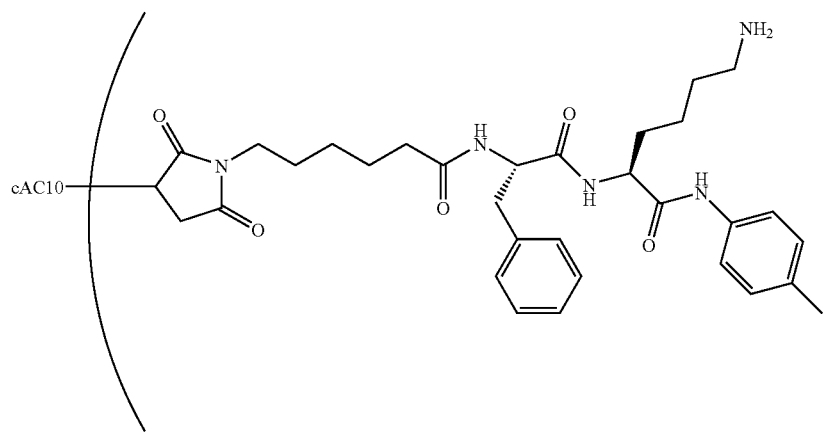
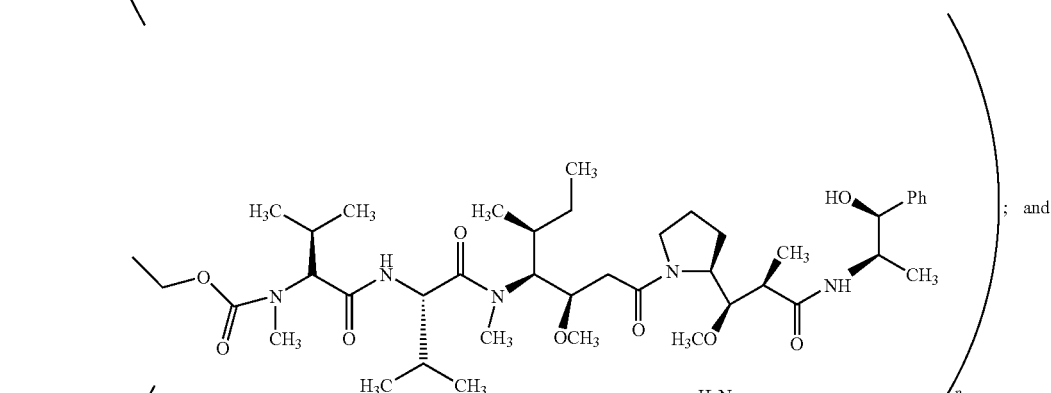
; and
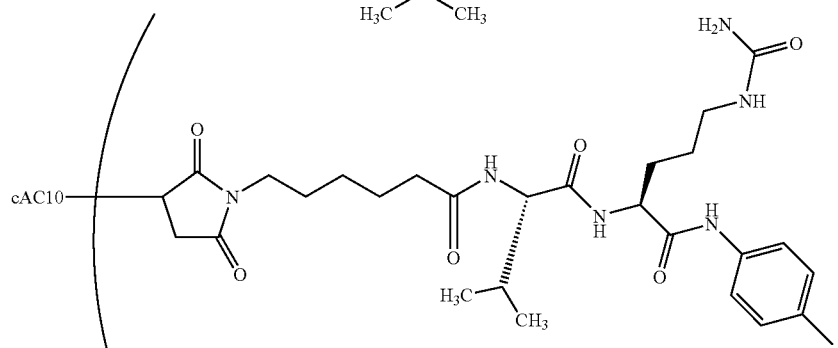
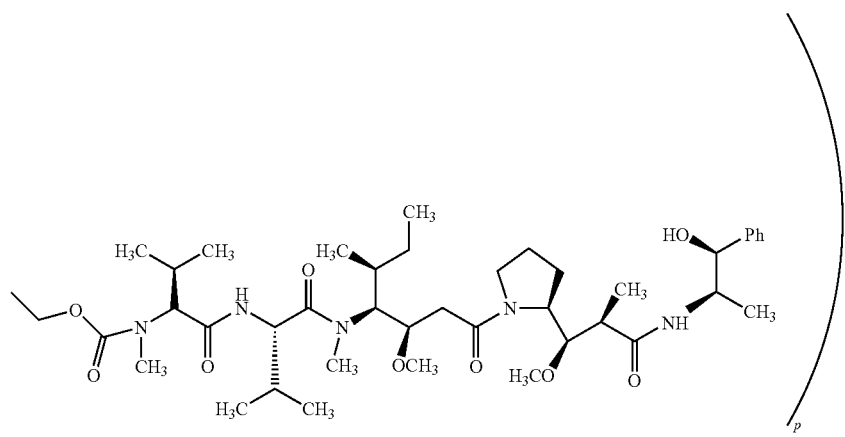

and pharmaceutically acceptable salts and solvates thereof, where p ranges from about 7 to about 9.

In one embodiment p ranges from 1 to about 3.

In another embodiment, p ranges from about 3 to about 5.

In another embodiment, p is about 8.

In yet another embodiment, p is about 4.

In a further embodiment, p is about 2.

In another aspect, the present invention provides compounds of general formula Ib:

$$L-(A_a-W_w-Y_y-D) \quad Ib$$

and pharmaceutically acceptable salts and solvates thereof wherein,

L- is a Ligand unit;

-A- is a Stretcher unit;

a is 0 or 1;

each —W— is independently an Amino Acid unit;

—Y— is a Spacer unit;

w is an integer ranging from 0 to 12;

y is 0, 1 or 2;

p ranges from 1 to about 20; and

-D is a Drug unit of the formula

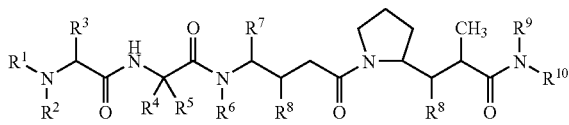

wherein, independently at each location:

$R^1$ is selected from —H, —$C_1$-$C_8$ alkyl and —$C_3$-$C_8$ carbocycle; and $R^2$ is selected from —H and —$C_1$-$C_8$ alkyl; or $R^1$ and $R^2$ join, have the formula —$(CR^aR^b)_n$— wherein $R^a$ and $R^b$ are independently selected from —H, —$C_1$-$C_8$ alkyl and —$C_3$-$C_8$ carbocycle and n is selected from 2, 3, 4, 5 and 6, and form a ring with the nitrogen atom to which they are attached;

$R^3$ is selected from —H, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle);

$R^4$ is selected from —H, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle) wherein $R^5$ is selected from —H and -methyl; or $R^4$ and $R^5$ join, have the formula —$(CR^aR^b)_n$— wherein $R^a$ and $R^b$ are independently selected from —H, —$C_1$-$C_8$ alkyl and —$C_3$-$C_8$ carbocycle and n is selected from 2, 3, 4, 5 and 6, and form a ring with the carbon atom to which they are attached;

$R^6$ is selected from —H and —$C_1$-$C_8$ alkyl;

$R^7$ is selected from —H, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle);

each $R^8$ is independently selected from —H, —OH, —$C_1$-$C_8$ alkyl, —$C_3$-$C_8$ carbocycle and —O—($C_1$-$C_8$ alkyl);

$R^9$ is selected from —H and —$C_1$-$C_8$ alkyl;

$R^{10}$ is selected from

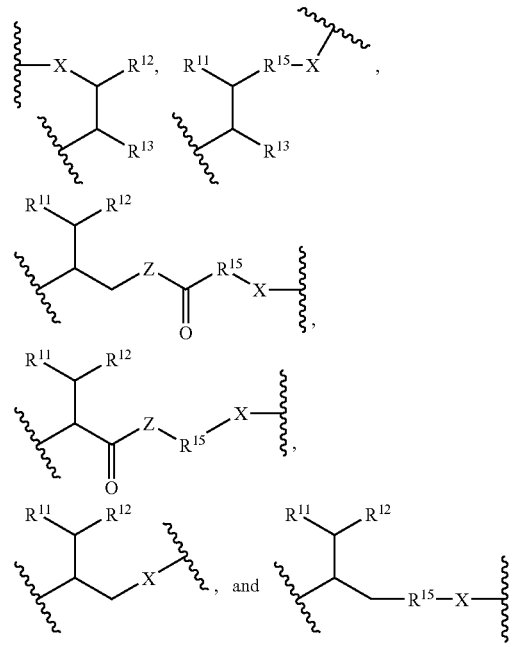

X is —O—, —S—, —NH— or —N($R^{14}$)—, where X is bonded to Y when y is 1 or 2, or X is bonded to W when y is 0;

Z is —O—, —S—, —NH— or —N($R^{14}$)—;

$R^{11}$ is selected from —H, —OH, —$NH_2$, —$NHR^{14}$, —N($R^{14}$)$_2$, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle); or $R^{11}$ is an oxygen atom which forms a carbonyl unit (C=O) with the carbon atom to which it is attached and a hydrogen atom on this carbon atom is replaced by one of the bonds in the (C=O) double bond;

each $R^{12}$ is independently selected from -aryl and —$C_3$-$C_8$ heterocycle;

$R^{13}$ is selected from —H, —OH, —$NH_2$, —$NHR^{14}$, —N($R^{14}$)$_2$, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle);

each $R^{14}$ is independently —H or —$C_1$-$C_8$ alkyl; and $R^{15}$ is -arylene-, —$C_3$-$C_8$ carbocyclo- or —$C_3$-$C_8$ heterocyclo-.

In one embodiment, when $R^1$ is —H, $R^{10}$ is selected from:

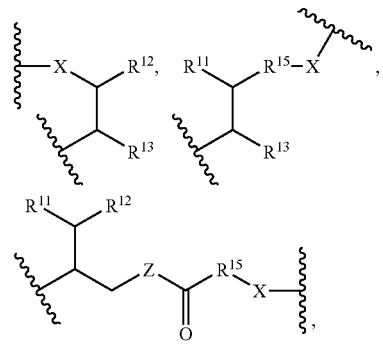

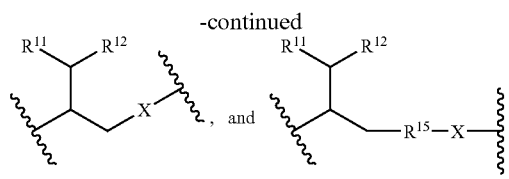

In another embodiment, w is an integer ranging from 2 to 12.

In another embodiment, p ranges from 1 to about 8.
In another embodiment, p ranges from 1 to about 3.
In another embodiment, p ranges from about 3 to about 5.
In still another embodiment, p ranges from about 7 to about 9.

In another embodiment, p is about 8.
In another embodiment, p is about 4.
In a further embodiment, p is about 2.

Illustrative classes of compounds of formula Ib have the structure:

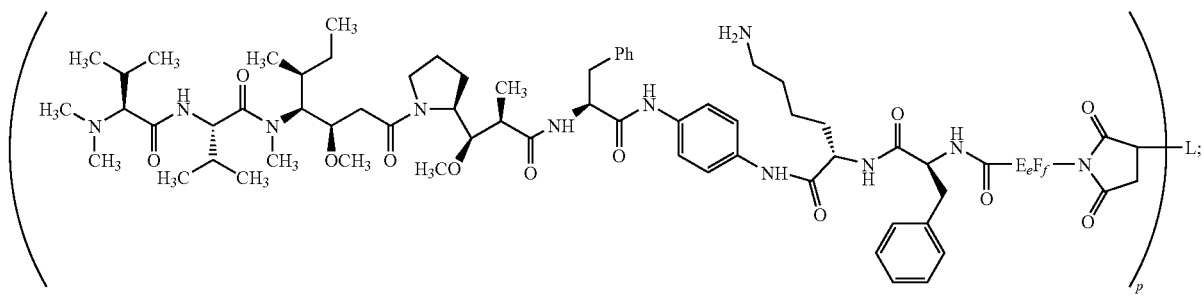

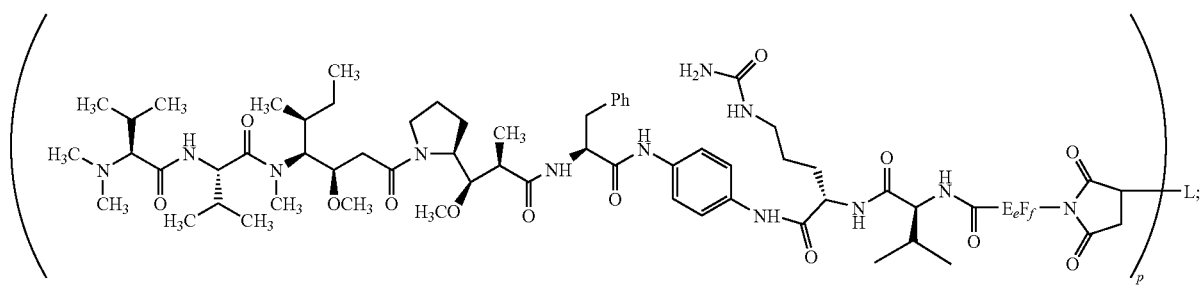

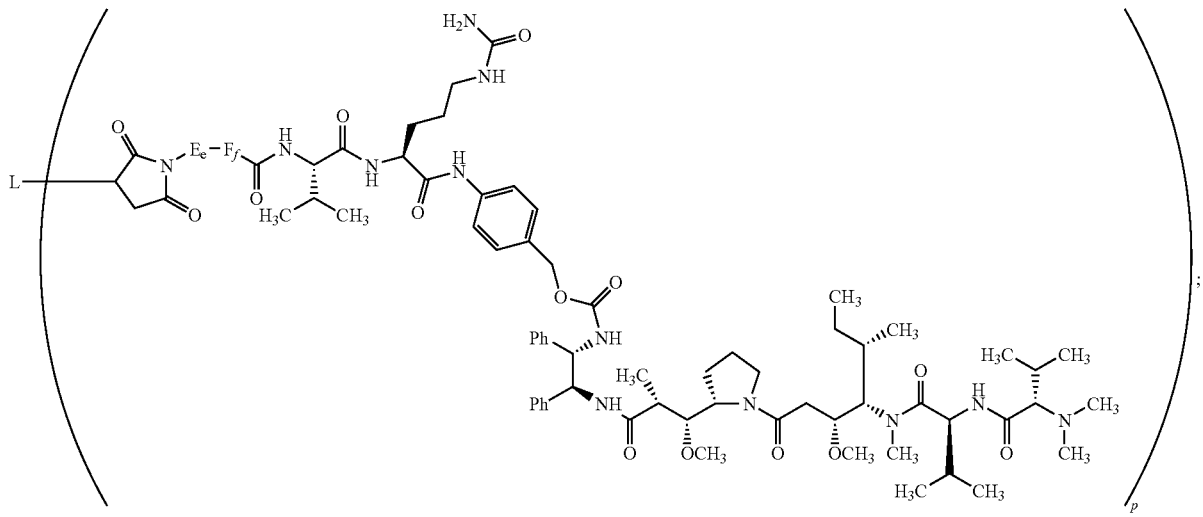

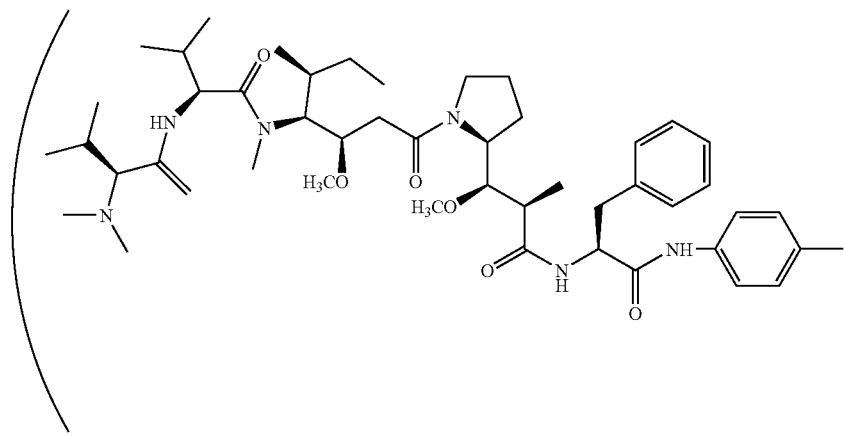
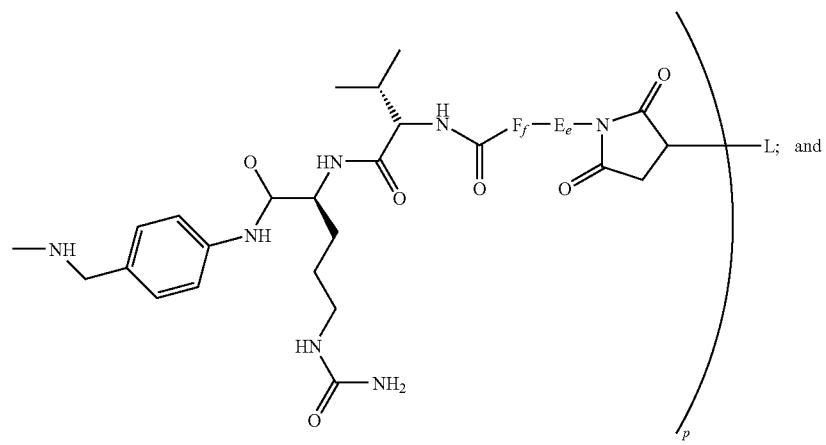
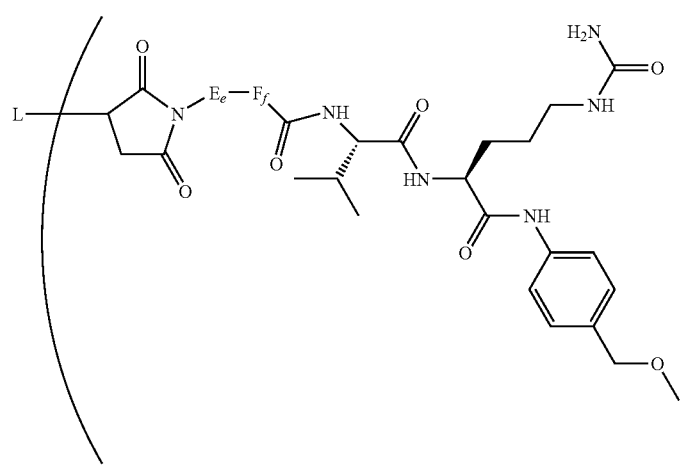

-continued

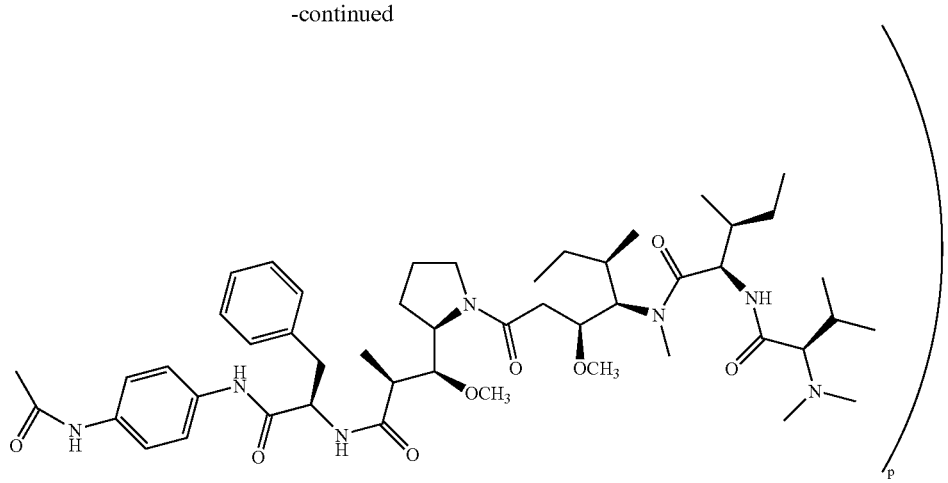

pharmaceutically acceptable salts and solvates thereof, where L- is Ligand unit, E is —$CH_2$— or —$CH_2CH_2O$—; e is an integer ranging either from 0-10 when E is —$CH_2$—, or 1-10 when E is —$CH_2CH_2$—O—; F is —$CH_2$—; f is 0 or 1; and p ranges from 1 to about 20.

In another embodiment, p ranges from 1 to about 8.
In another embodiment, p ranges from 1 to about 3.
In another embodiment, p ranges from about 3 to about 5.
In still another embodiment, p ranges from about 7 to about 9.
In another embodiment, p is about 8.
In another embodiment, p is about 4.
In a further embodiment, p is about 2.
In another embodiment L is cBR96, cAC10 or 1F6.
Illustrative compounds of formula Ib have the structure:

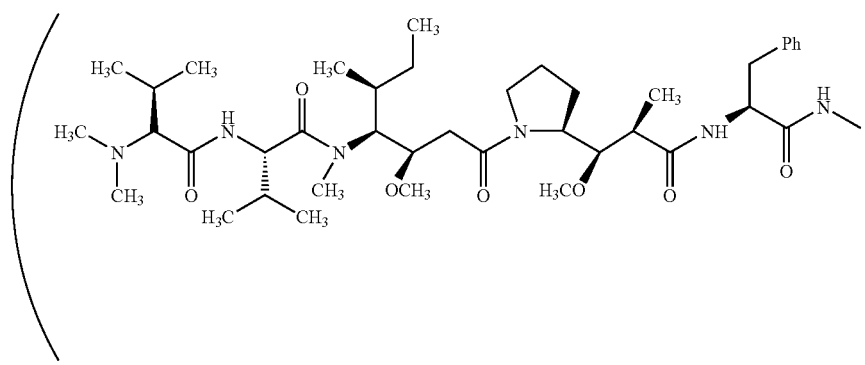

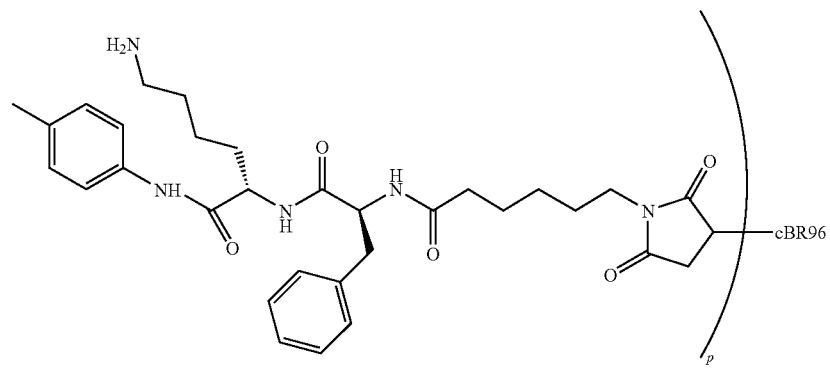

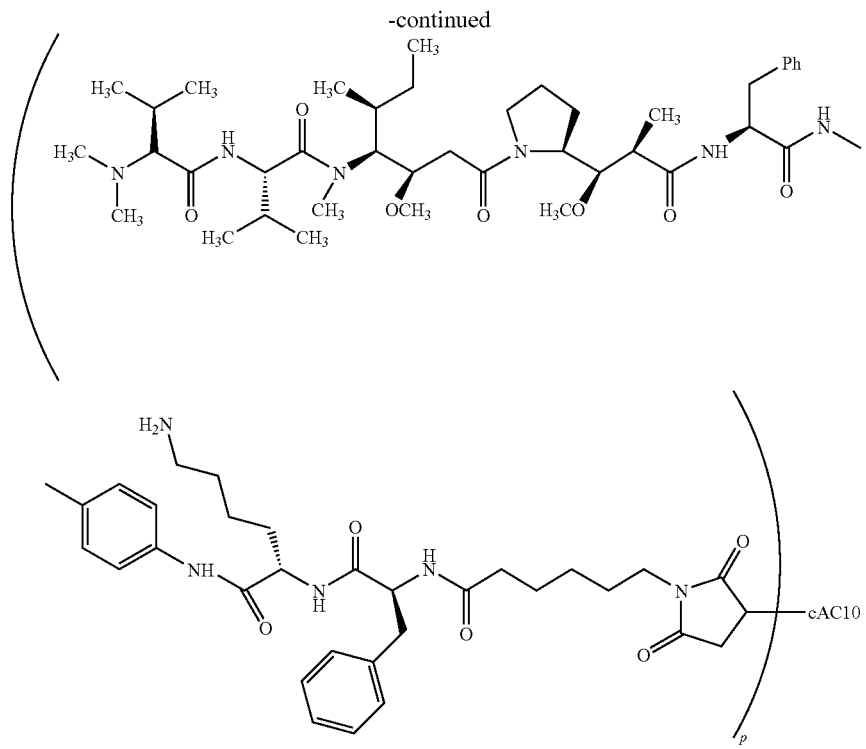

and pharmaceutically acceptable salts and solvates thereof, where p ranges from about 7 to about 9.

In one embodiment p ranges from 1 to about 3.
In another embodiment, p ranges from about 3 to about 5.
In another embodiment, p is about 8.
In yet another embodiment, p is about 4.
In a further embodiment, p is about 2.

In another aspect, the present invention provides compounds of general formula Ic:

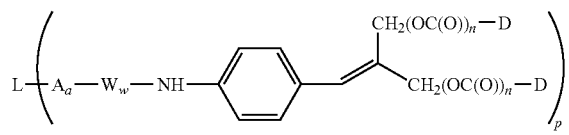

Ic

L- is a Ligand unit;
-A- is a Stretcher unit;
a is 0 or 1;
each —W— is independently an Amino Acid unit;
w is an integer ranging from 0 to 12;
each n is independently 0 or 1;
p ranges from 1 to about 20; and
each -D is independently:
(a) a Drug unit of the formula:

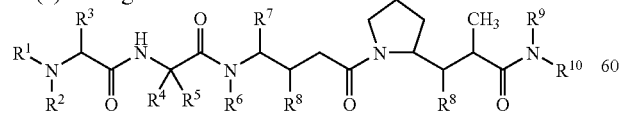

wherein, independently at each location:
$R^1$ is selected from —H, —$C_1$-$C_8$ alkyl and —$C_3$-$C_8$ carbocycle; and $R^2$ is selected from —H and —$C_1$-$C_8$ alkyl; or $R^1$ and $R^2$ join, have the formula —$(CR^aR^b)_n$— wherein $R^a$ and $R^b$ are independently selected from —H, —$C_1$-$C_8$ alkyl and —$C_3$-$C_8$ carbocycle and n is selected from 2, 3, 4, 5 and 6, and form a ring with the nitrogen atom to which they are attached;

$R^3$ is selected from —H, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle);

$R^4$ is selected from —H, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle) wherein $R^5$ is selected from —H and -methyl; or $R^4$ and $R^5$ join, have the formula —$(CR^aR^b)_n$— wherein $R^a$ and $R^b$ are independently selected from —H, —$C_1$-$C_8$ alkyl and —$C_3$-$C_8$ carbocycle and n is selected from 2, 3, 4, 5 and 6, and form a ring with the carbon atom to which they are attached;

$R^6$ is selected from —H and —$C_1$-$C_8$ alkyl;

$R^7$ is selected from —H, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle);

each $R^8$ is independently selected from —H, —OH, —$C_1$-$C_8$ alkyl, —$C_3$-$C_8$ carbocycle and —O—($C_1$-$C_8$ alkyl);

$R^9$ is selected from —H and —$C_1$-$C_8$ alkyl;

$R^{10}$ is selected from

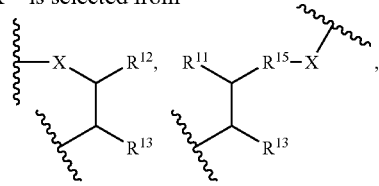

-continued

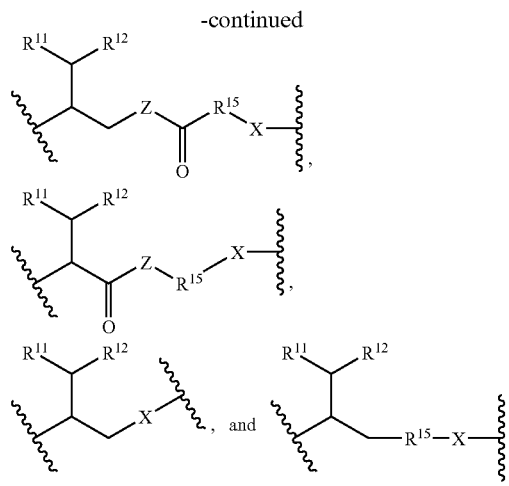

X is —O—, —S—, —NH— or —N($R^{14}$)—, where X is bonded to —C(O)— when y is 1 or 2, or X is bonded to —$CH_2$— when n is 0;

Z is —O—, —S—, —NH— or —N($R^{14}$)—;

$R^{11}$ is selected from —H, —OH, —$NH_2$, —$NHR^{14}$, —N($R^{14}$)$_2$, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle); or $R^{11}$ is an oxygen atom which forms a carbonyl unit (C=O) with the carbon atom to which it is attached and a hydrogen atom on this carbon atom is replaced by one of the bonds in the (C=O) double bond;

each $R^{12}$ is independently selected from -aryl and —$C_3$-$C_8$ heterocycle;

$R^{13}$ is selected from —H, —OH, —$NH_2$, —$NHR^{14}$, —N($R^{14}$)$_2$, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), $C_3$-$C_8$ heterocycle and —$C_1$-$C_8$ alkyl-($C_3$-$C_8$ heterocycle);

each $R^{14}$ is independently —H or —$C_1$-$C_8$ alkyl; and $R^{15}$ is -arylene-, —$C_3$-$C_8$ carbocyclo- or —$C_3$-$C_8$ heterocyclo-; or (b) a Drug unit of the formula:

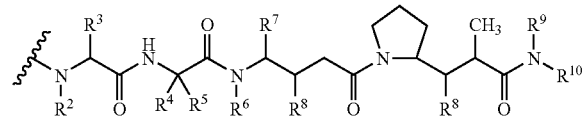

wherein, independently at each location:

$R^2$ is selected from —H and —$C_1$-$C_8$ alkyl;

$R^3$ is selected from —H, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle);

$R^4$ is selected from —H, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle) wherein $R^5$ is selected from —H and -methyl; or $R^4$ and $R^5$ join, have the formula —(C$R^aR^b$)$_n$— wherein $R^a$ and $R^b$ are independently selected from —H, —$C_1$-$C_8$ alkyl and —$C_3$-$C_8$ carbocycle and n is selected from 2, 3, 4, 5 and 6, and form a ring with the carbon atom to which they are attached;

$R^6$ is selected from —H and —$C_1$-$C_8$ alkyl;

$R^7$ is selected from —H, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle);

each $R^8$ is independently selected from —H, —OH, —$C_1$-$C_8$ alkyl, —$C_3$-$C_8$ carbocycle and —O—($C_1$-$C_8$ alkyl);

$R^9$ is selected from —H and —$C_1$-$C_8$ alkyl;

$R^{10}$ is selected from

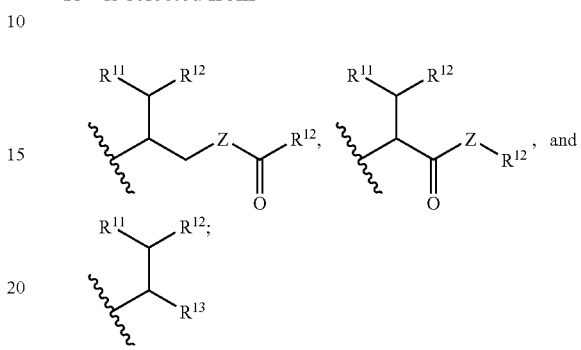

Z is —O—, —S—, —NH— or —N($R^{14}$)—;

$R^{11}$ is selected from —H, —OH, —$NH_2$, —$NHR^{14}$, —N($R^{14}$)$_2$, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle); or $R^{11}$ is an oxygen atom which forms a carbonyl unit (C=O) with the carbon atom to which it is attached and a hydrogen atom on this carbon atom is replaced by one of the bonds in the (C=O) double bond;

each $R^{12}$ is independently selected from -aryl and —$C_3$-$C_8$ heterocycle;

$R^{13}$ is selected from —H, —OH, —$NH_2$, —$NHR^{14}$, —N($R^{14}$)$_2$, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), $C_3$-$C_8$ heterocycle and —$C_1$-$C_8$ alkyl-($C_3$-$C_8$ heterocycle); and each $R^{14}$ is independently —H or —$C_1$-$C_8$ alkyl.

In one embodiment, when the drug unit has the formula:

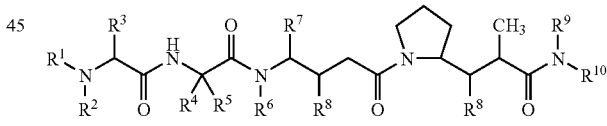

and $R^1$ is —H, $R^{10}$ is selected from

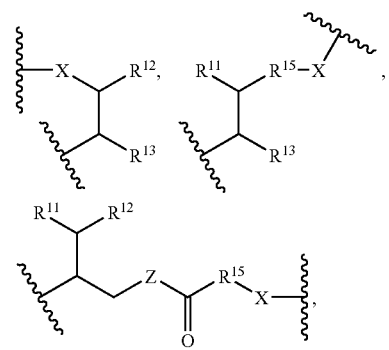

-continued

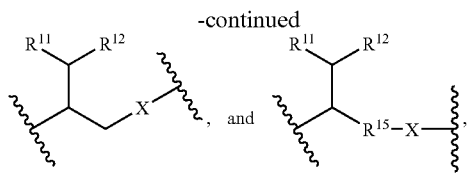

In another embodiment, when the drug unit has the formula:

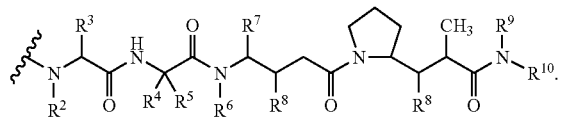

$R^{10}$ is selected from

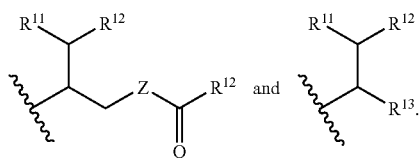

In another embodiment, w is an integer ranging from 2 to 12.

In another embodiment, p ranges from 1 to about 8.
In another embodiment, p ranges from 1 to about 3.
In another embodiment, p ranges from about 3 to about 5.
In still another embodiment, p ranges from about 7 to about 9.
In another embodiment, p is about 8.
In another embodiment, p is about 4.
In a further embodiment, p is about 2.
An illustrative compound of formula Ic has the structure:

wherein where L- is Ligand unit, E is —CH$_2$— or —CH$_2$CH$_2$O—; e is an integer ranging either from 0-10 when E is —CH$_2$—, or 1-10 when E is —CH$_2$CH$_2$—O—; F is —CH$_2$—; f is 0 or 1; and p ranges from 1 to about 20.

In another embodiment, p ranges from 1 to about 8.
In another embodiment, p ranges from 1 to about 3.
In another embodiment, p ranges from about 3 to about 5.
In still another embodiment, p ranges from about 7 to about 9.
In another embodiment, p is about 8.
In another embodiment, p is about 4.
In a further embodiment, p is about 2.
In another embodiment L is cBR96, cAC10 or 1F6.

The Drug-Linker-Ligand Conjugates are useful for treating or preventing cancer, an autoimmune disease or an infectious disease in an animal.

It is understood that p is the average number of -A$_a$-W$_w$—Y$_y$-D units per ligand in a Drug-Linker-Ligand Conjugate of formulas Ia, Ib and Ic.

In one embodiment p ranges from 1 to 15.
In another embodiment p ranges from 1 to 10.
In another embodiment, p ranges from 1 to about 8.
In a further embodiment p ranges from 1 to about 5.
In another embodiment p ranges from 1 to about 3.
In one embodiment p ranges from about 3 to about 5.
In one embodiment p ranges from about 7 to about 9.
In another embodiment p is about 8.
In yet another embodiment p is about 4.
In still another embodiment p is about 2.

The Drug-Linker-Ligand Conjugates of formulas Ia, Ib and Ic may exist as mixtures, wherein each component of a mixture has a different p value. For example, a Drug-Linker-Ligand Conjugate may exist as a mixture of two separate Conjugates, one Conjugate component wherein p is 7 and the other Conjugate component wherein p is 8.

In one embodiment, a Drug-Linker-Ligand Conjugate exists as a mixture of three separate conjugates wherein p for the three separate conjugates is 1, 2, and 3, respectively.

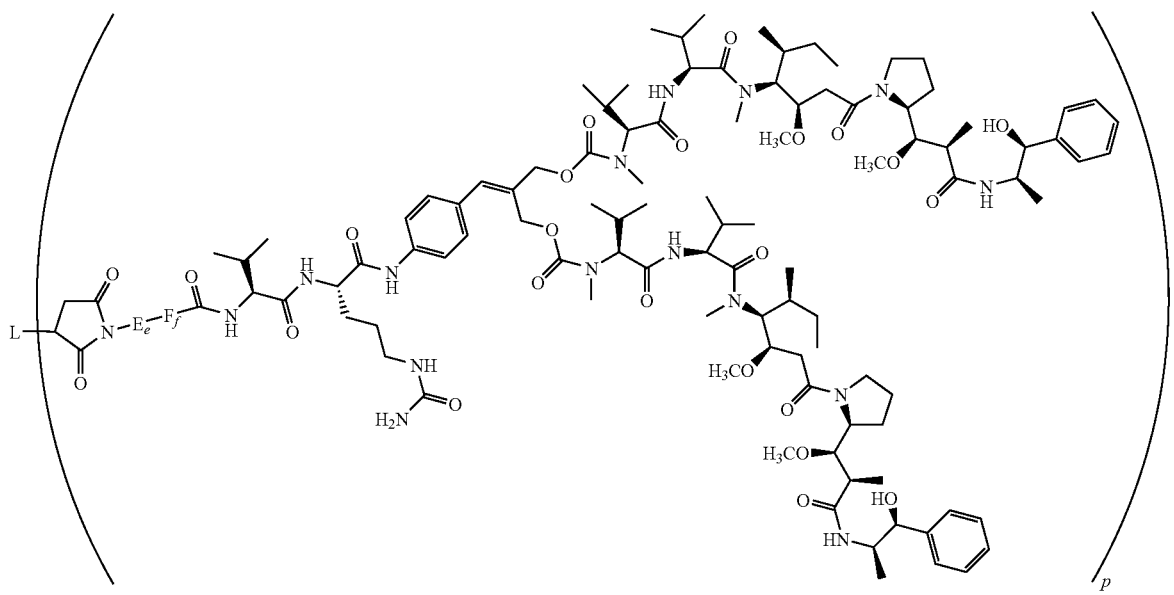

In another embodiment, a Drug-Linker-Ligand Conjugate exists as a mixture of three separate conjugates wherein p for the three separate conjugates is 3, 4, and 5, respectively.

In another embodiment, a Drug-Linker-Ligand Conjugate exists as a mixture of three separate conjugates wherein p for the three separate conjugates is 5, 6, and 7, respectively.

In still another embodiment, a Drug-Linker-Ligand Conjugate exists as a mixture of three separate conjugates wherein p for the three separate conjugates is 7, 8, and 9, respectively.

In yet another embodiment, a Drug-Linker-Ligand Conjugate exists as a mixture of three separate conjugates wherein p for the three separate conjugates is 9, 10, and 11, respectively.

In still another embodiment, a Drug-Linker-Ligand Conjugate exists as a mixture of three separate conjugates wherein p for the three separate conjugates is 11, 12, and 13, respectively.

In another embodiment, a Drug-Linker-Ligand Conjugate exists as a mixture of three separate conjugates wherein p for the three separate conjugates is 13, 14, and 15, respectively.

5.3 Drug-Linker Compounds

The present invention provides compounds of the formula IIa:

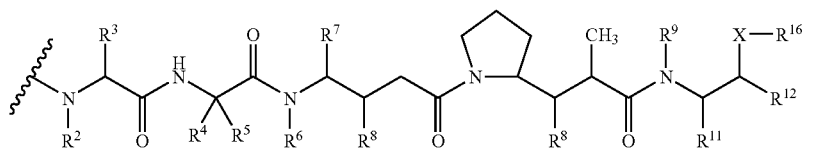

and pharmaceutically acceptable salts and solvates thereof wherein, independently at each location:

$R^1$ is selected from —H, —$C_1$-$C_8$ alkyl and —$C_3$-$C_8$ carbocycle; and $R^2$ is selected from —H and —$C_1$-$C_8$ alkyl; or $R^1$ and $R^2$ join, have the formula —$(CR^aR^b)_n$— wherein $R^a$ and $R^b$ are independently selected from —H, —$C_1$-$C_8$ alkyl and —$C_3$-$C_8$ carbocycle and n is selected from 2, 3, 4, 5 and 6, and form a ring with the nitrogen atom to which they are attached;

$R^3$ is selected from —H, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle);

$R^4$ is selected from —H, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle) wherein $R^5$ is selected from —H and -methyl; or $R^4$ and $R^5$ join, have the formula —$(CR^aR^b)_n$— wherein $R^a$ and $R^b$ are independently selected from —H, —$C_1$-$C_8$ alkyl and —$C_3$-$C_8$ carbocycle and n is selected from 2, 3, 4, 5 and 6, and form a ring with the carbon atom to which they are attached;

$R^6$ is selected from —H and —$C_1$-$C_8$ alkyl;

$R^7$ is selected from —H, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle);

each $R^8$ is independently selected from —H, —OH, —$C_1$-$C_8$ alkyl, —$C_3$-$C_8$ carbocycle and —O—($C_1$-$C_8$ alkyl);

$R^9$ is selected from —H and —$C_1$-$C_8$ alkyl;

X is —O—, —S—, —NH— or —N($R^{14}$)—, where X is bonded to Y when y is 1 or 2, or X is bonded to W when y is 0;

$R^{11}$ is selected from —H, —OH, —$NH_2$, —$NHR^{14}$, —$N(R^{14})_2$, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle); or $R^{11}$ is an oxygen atom which forms a carbonyl unit (C=O) with the carbon atom to which it is attached and a hydrogen atom on this carbon atom is replaced by one of the bonds in the (C=O) double bond;

each $R^{12}$ is independently selected from -aryl and —$C_3$-$C_8$ heterocycle;

each $R^{14}$ is independently —H or —$C_1$-$C_8$ alkyl;

$R^{16}$ is -Yy-Ww-A' wherein each —W— is independently an Amino Acid unit;

—Y— is a Spacer unit;

w is an integer ranging from 0 to 12;

y is 0, 1 or 2; and

-A' is selected from

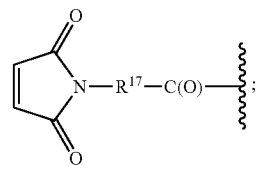

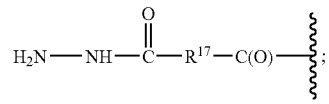

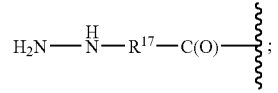

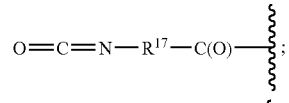

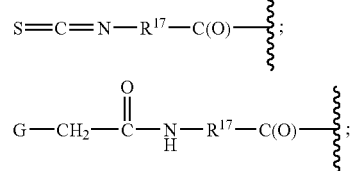

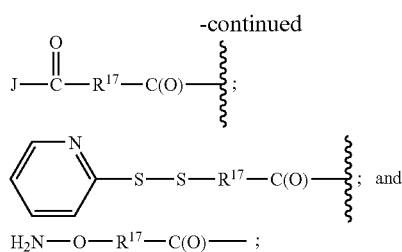

wherein
G is selected from —Cl, —Br, —I, —O-mesyl and —O-tosyl;

J is selected from —Cl, —Br, —I, —F, —OH, —O—N-succinimide, —O-(4-nitrophenyl), —O-pentafluorophenyl, —O-tetrafluorophenyl and —O—C(O)—OR$^{18}$;

R$^{17}$ is selected from —C$_1$-C$_{10}$ alkylene-, —C$_3$-C$_8$ carbocyclo-, —O—(C$_1$-C$_8$ alkyl)-, -arylene-, —C$_1$-C$_{10}$ alkylene-arylene-, -arylene-C$_1$-C$_{10}$ alkylene-, —C$_1$-C$_{10}$ alkylene-(C$_3$-C$_8$ carbocyclo)-, —(C$_3$-C$_8$ carbocyclo)-C$_1$-C$_{10}$ alkylene-, —C$_3$-C$_8$ heterocyclo-, —C$_1$-C$_{10}$ alkylene-(C$_3$-C$_8$ heterocyclo)-, —(C$_3$-C$_8$ heterocyclo)-C$_1$-C$_{10}$ alkylene-, —(CH$_2$CH$_2$O)$_r$—, and —(CH$_2$CH$_2$O)$_r$—CH$_2$—; r is an integer ranging from 1-10; and R$^{18}$ is —C$_1$-C$_8$ alkyl or -aryl.

An illustrative compound of formula IIa has the structure:

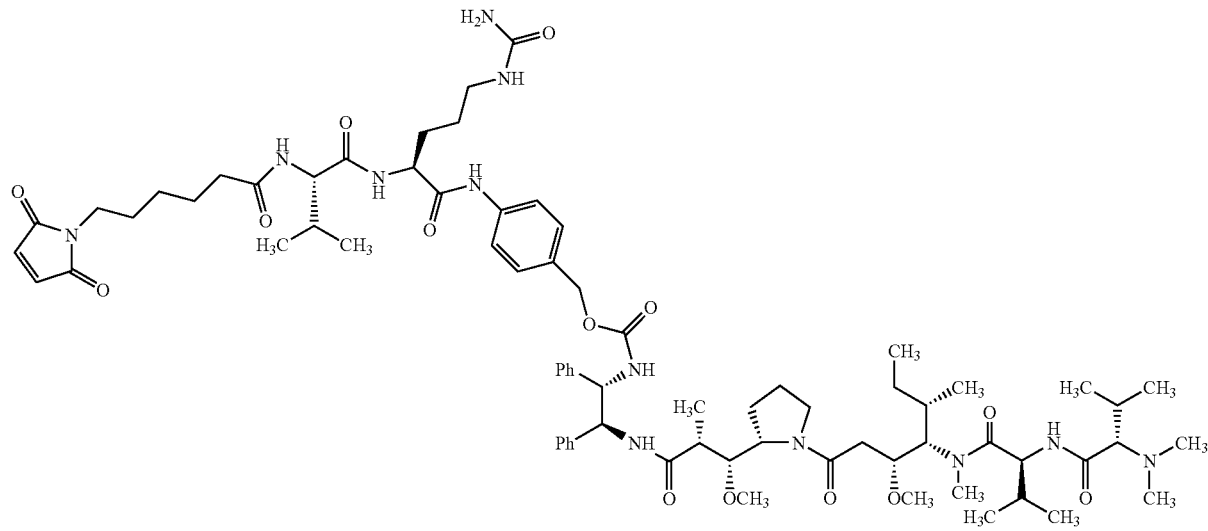

and pharmaceutically acceptable salts and solvates thereof.

In another aspect, the present invention provides compounds of the formula IIb:

and pharmaceutically acceptable salts and solvates thereof wherein, independently at each location:

R$^1$ is selected from —H, —C$_1$-C$_8$ alkyl and —C$_3$-C$_8$ carbocycle; and R$^2$ is selected from —H and —C$_1$-C$_8$ alkyl; or R$^1$ and R$^2$ join, have the formula —(CR$^a$R$^b$)$_n$— wherein R$^a$ and R$^b$ are independently selected from —H, —C$_1$-C$_8$ alkyl and —C$_3$-C$_8$ carbocycle and n is selected from 2, 3, 4, 5 and 6, and form a ring with the nitrogen atom to which they are attached;

R$^3$ is selected from —H, —C$_1$-C$_8$ alkyl, —C$_3$-C$_8$ carbocycle, —O—(C$_1$-C$_8$ alkyl), -aryl, —C$_1$-C$_8$ alkyl-aryl, —C$_1$-C$_8$ alkyl-(C$_3$-C$_8$ carbocycle), —C$_3$-C$_8$ heterocycle and —C$_1$-C$_8$ alkyl-(C$_3$-C$_8$ heterocycle);

R$^4$ is selected from —H, —C$_1$-C$_8$ alkyl, —C$_3$-C$_8$ carbocycle, —O—(C$_1$-C$_8$ alkyl), -aryl, —C$_1$-C$_8$ alkyl-aryl, —C$_1$-C$_8$ alkyl-(C$_3$-C$_8$ carbocycle), —C$_3$-C$_8$ heterocycle and —C$_1$-C$_8$ alkyl-(C$_3$-C$_8$ heterocycle) wherein R$^5$ is selected from —H and -methyl; or R$^4$ and R$^5$ join, have the formula —(CR$^a$R$^b$)$_n$— wherein R$^a$ and R$^b$ are independently selected from —H, —C$_1$-C$_8$ alkyl and —C$_3$-C$_8$ carbocycle and n is selected from 2, 3, 4, 5 and 6, and form a ring with the carbon atom to which they are attached;

R$^6$ is selected from —H and —C$_1$-C$_8$ alkyl;

R$^7$ is selected from —H, —C$_1$-C$_8$ alkyl, —C$_3$-C$_8$ carbocycle, —O—(C$_1$-C$_8$ alkyl), -aryl, —C$_1$-C$_8$ alkyl-aryl, —C$_1$-C$_8$ alkyl-(C$_3$-C$_8$ carbocycle), —C$_3$-C$_8$ heterocycle and —C$_1$-C$_8$ alkyl-(C$_3$-C$_8$ heterocycle);

each R$^8$ is independently selected from —H, —OH, —C$_1$-C$_8$ alkyl, —C$_3$-C$_8$ carbocycle and —O—(C$_1$-C$_8$ alkyl);

R$^9$ is selected from —H and —C$_1$-C$_8$ alkyl;

IIb

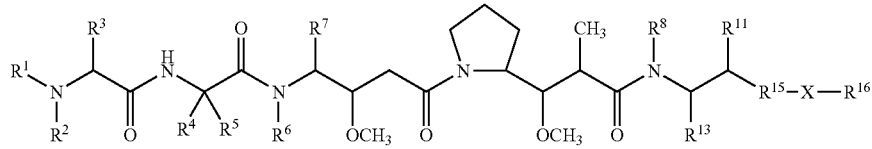

X is —O—, —S—, —NH— or —N(R$^{14}$)—;

R$^{11}$ is selected from —H, —OH, —NH$_2$, —NHR$^{14}$, —N(R$^{14}$)$_2$, —C$_1$-C$_8$ alkyl, —C$_3$-C$_8$ carbocycle, —O—(C$_1$-C$_8$ alkyl), -aryl, —C$_1$-C$_8$ alkyl-aryl, —C$_1$-C$_8$ alkyl-(C$_3$-C$_8$ carbocycle), —C$_3$-C$_8$ heterocycle and —C$_1$-C$_8$ alkyl-(C$_3$-C$_8$ heterocycle); or R$^{11}$ is an oxygen atom which forms a carbonyl unit (C=O) with the carbon atom to which it is attached and a hydrogen atom on this carbon atom is replaced by one of the bonds in the (C=O) double bond;

R$^{13}$ is selected from hydrogen, —OH, —NH$_2$, —NHR$^{14}$, —N(R$^{14}$)$_2$, C$_1$-C$_8$ alkyl, C$_3$-C$_8$ carbocycle, —O—(C$_1$-C$_8$ alkyl), -aryl, alkyl-aryl, alkyl-(C$_3$-C$_8$ carbocycle), C$_3$-C$_8$ heterocycle and alkyl-(C$_3$-C$_8$ heterocycle);

each R$^{14}$ is independently —H or —C$_1$-C$_8$ alkyl;

R$^{15}$ is -arylene-, —C$_3$-C$_8$ carbocyclo- or —C$_3$-C$_8$ heterocyclo-;

R$^{16}$ is -Y$_y$-W$_w$-A' wherein each —W— is independently an Amino Acid unit;
—Y— is a Spacer unit;
w is an integer ranging from 0 to 12;
y is 0, 1 or 2; and
-A' is selected from

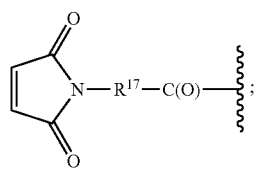

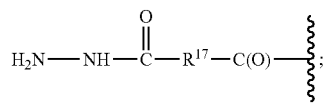

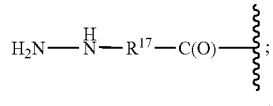

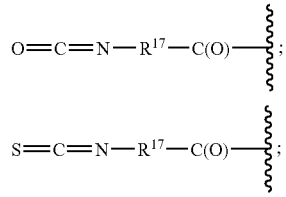

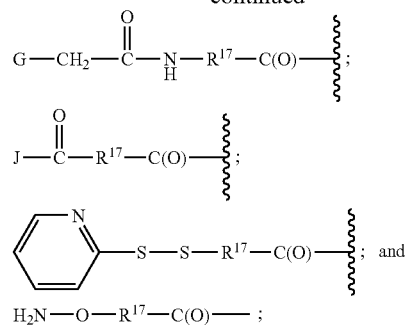

wherein

G is selected from —Cl, —Br, —I, —O-mesyl and —O-tosyl;

J is selected from —Cl, —Br, —I, —F, —OH, —O—N-succinimide, —O-(4-nitrophenyl), —O-pentafluorophenyl, —O-tetrafluorophenyl and —O—C(O)—OR$^{18}$;

R$^{17}$ is selected from —C$_1$-C$_{10}$ alkylene-, —C$_3$-C$_8$ carbocyclo-, —O—(C$_1$-C$_8$ alkyl)-, -arylene-, —C$_1$-C$_{10}$ alkylene-arylene-, -arylene-C$_1$-C$_{10}$ alkylene-, —C$_1$-C$_{10}$ alkylene-(C$_3$-C$_8$ carbocyclo)-, —(C$_3$-C$_8$ carbocyclo)-C$_1$-C$_{10}$ alkylene-, —C$_3$-C$_8$ heterocyclo-, —C$_1$-C$_{10}$ alkylene-(C$_3$-C$_8$ heterocyclo)-, —(C$_3$-C$_8$ heterocyclo)-C$_1$-C$_{10}$ alkylene-, —(CH$_2$CH$_2$O)$_r$—, and —(CH$_2$CH$_2$O)$_r$—CH$_2$—; r is an integer ranging from 1-10; and R$^{18}$ is —C$_1$-C$_8$ alkyl or -aryl.

In another aspect, the present invention provides compounds of the formula IIc:

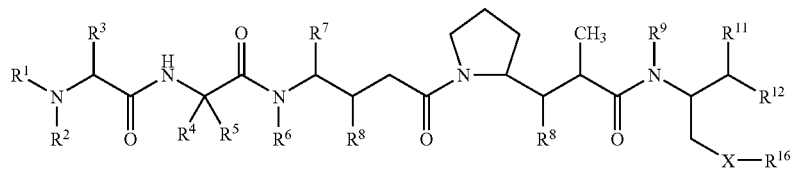

and pharmaceutically acceptable salts and solvates thereof wherein, independently at each location:

R$^1$ is selected from —H, —C$_1$-C$_8$ alkyl and —C$_3$-C$_8$ carbocycle; and R$^2$ is selected from —H and —C$_1$-C$_8$ alkyl; or R$^1$ and R$^2$ join, have the formula —(CR$^a$R$^b$)$_n$— wherein R$^a$ and R$^b$ are independently selected from —H, —C$_1$-C$_8$ alkyl and —C$_3$-C$_8$ carbocycle and n is selected from 2, 3, 4, 5 and 6, and form a ring with the nitrogen atom to which they are attached;

R$^3$ is selected from —H, —C$_1$-C$_8$ alkyl, —C$_3$-C$_8$ carbocycle, —O—(C$_1$-C$_8$ alkyl), -aryl, —C$_1$-C$_8$ alkyl-aryl, —C$_1$-C$_8$ alkyl-(C$_3$-C$_8$ carbocycle), —C$_3$-C$_8$ heterocycle and —C$_1$-C$_8$ alkyl-(C$_3$-C$_8$ heterocycle);

R$^4$ is selected from —H, —C$_1$-C$_8$ alkyl, —C$_3$-C$_8$ carbocycle, —O—(C$_1$-C$_8$ alkyl), -aryl, —C$_1$-C$_8$ alkyl-aryl, —C$_1$-C$_8$ alkyl-(C$_3$-C$_8$ carbocycle), —C$_3$-C$_8$ heterocycle and —C$_1$-C$_8$ alkyl-(C$_3$-C$_8$ heterocycle) wherein R$^5$ is selected from —H and -methyl; or R$^4$ and R$^5$ join, have the formula —(CR$^a$R$^b$)$_n$— wherein R$^a$ and R$^b$ are independently selected from —H, —C$_1$-C$_8$ alkyl and —C$_3$-C$_8$ carbocycle and n is selected from 2, 3, 4, 5 and 6, and form a ring with the carbon atom to which they are attached;

R$^6$ is selected from —H and —C$_1$-C$_8$ alkyl;

R$^7$ is selected from —H, —C$_1$-C$_8$ alkyl, —C$_3$-C$_8$ carbocycle, —O—(C$_1$-C$_8$ alkyl), -aryl, —C$_1$-C$_8$ alkyl-aryl, —C$_1$-C$_8$ alkyl-(C$_3$-C$_8$ carbocycle), —C$_3$-C$_8$ heterocycle and —C$_1$-C$_8$ alkyl-(C$_3$-C$_8$ heterocycle);

each R$^8$ is independently selected from —H, —OH, —C$_1$-C$_8$ alkyl, —C$_3$-C$_8$ carbocycle and —O—(C$_1$-C$_8$ alkyl);

R$^9$ is selected from —H and —C$_1$-C$_8$ alkyl;

X is —O—, —S—, —NH— or —N(R$^{14}$)—;

R$^{11}$ is selected from —H, —OH, —NH$_2$, —NHR$^{14}$, —N(R$^{14}$)$_2$, —C$_1$-C$_8$ alkyl, —C$_3$-C$_8$ carbocycle, —O—(C$_1$-C$_8$ alkyl), -aryl, —C$_1$-C$_8$ alkyl-aryl, —C$_1$-C$_8$ alkyl-(C$_3$-C$_8$ carbocycle), —C$_3$-C$_8$ heterocycle and —C$_1$-C$_8$ alkyl-(C$_3$-C$_8$ heterocycle); or R$^{11}$ is an oxygen atom which forms a carbonyl unit (C=O) with the carbon atom to which it is attached and a hydrogen atom on this carbon atom is replaced by one of the bonds in the (C=O) double bond;

each R$^{12}$ is independently selected from -aryl and —C$_3$-C$_8$ heterocycle;

each R$^{14}$ is independently —H or —C$_1$-C$_8$ alkyl;

R$^{16}$ is -Y$_y$-W$_w$-A' wherein each —W— is independently an Amino Acid unit;

—Y— is a Spacer unit;

w is an integer ranging from 0 to 12;

y is 0, 1 or 2; and

-A' is selected from

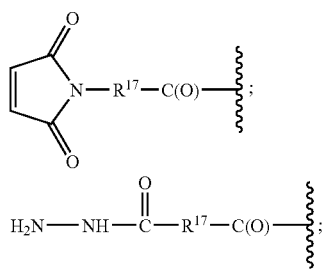

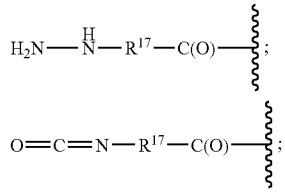

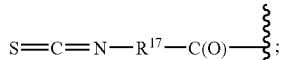

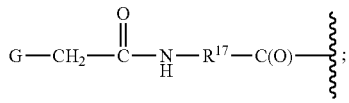

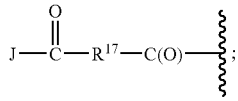

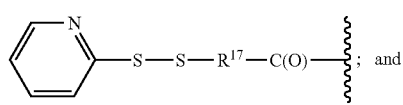

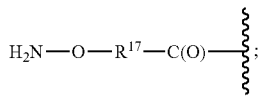

wherein

G is selected from —Cl, —Br, —I, —O-mesyl and —O-tosyl;

J is selected from —Cl, —Br, —I, —F, —OH, —O—N-succinimide, —O-(4-nitrophenyl), —O-pentafluorophenyl, —O-tetrafluorophenyl and —O—C(O)—OR$^{18}$;

R$^{17}$ is selected from —C$_1$-C$_{10}$ alkylene-, —C$_3$-C$_8$ carbocyclo-, —O—(C$_1$-C$_8$ alkyl)-, -arylene-, —C$_1$-C$_{10}$ alkylene-arylene-, -arylene-C$_1$-C$_{10}$ alkylene-, —C$_1$-C$_{10}$ alkylene-(C$_3$-C$_8$ carbocyclo)-, —(C$_3$-C$_8$ carbocyclo)-C$_1$-C$_{10}$ alkylene-, —C$_3$-C$_8$ heterocyclo-, —C$_1$-C$_{10}$ alkylene-(C$_3$-C$_8$ heterocyclo)-, —(C$_3$-C$_8$ heterocyclo)-C$_1$-C$_{10}$ alkylene-, —(CH$_2$CH$_2$O)$_r$—, and —(CH$_2$CH$_2$O)$_r$—CH$_2$—; r is an integer ranging from 1-10; and R$^{18}$ is —C$_1$-C$_8$ alkyl or -aryl.

In another aspect, the present invention provides compounds of the formula IId:

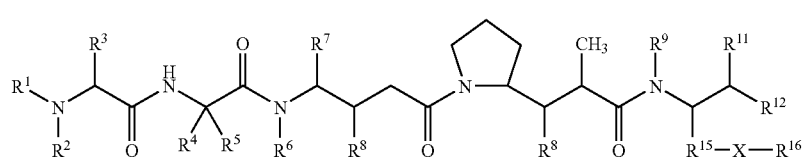

IId and pharmaceutically acceptable salts and solvates thereof wherein, independently at each location:

R$^1$ is selected from —H, —C$_1$-C$_8$ alkyl and —C$_3$-C$_8$ carbocycle; and R$^2$ is selected from —H and —C$_1$-C$_8$ alkyl; or R$^1$ and R$^2$ join, have the formula —(CR$^a$R$^b$)$_n$— wherein R$^a$ and R$^b$ are independently selected from —H, —C$_1$-C$_8$ alkyl and —C$_3$-C$_8$ carbocycle and n is selected from 2, 3, 4, 5 and 6, and form a ring with the nitrogen atom to which they are attached;

$R^3$ is selected from —H, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle);

$R^4$ is selected from —H, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle) wherein $R^5$ is selected from —H and -methyl; or $R^4$ and $R^5$ join, have the formula —$(CR^aR^b)_n$— wherein $R^a$ and $R^b$ are independently selected from —H, —$C_1$-$C_8$ alkyl and —$C_3$-$C_8$ carbocycle and n is selected from 2, 3, 4, 5 and 6, and form a ring with the carbon atom to which they are attached;

$R^6$ is selected from —H and —$C_1$-$C_8$ alkyl;

$R^7$ is selected from —H, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle);

each $R^8$ is independently selected from —H, —OH, —$C_1$-$C_8$ alkyl, —$C_3$-$C_8$ carbocycle and —O—($C_1$-$C_8$ alkyl);

$R^9$ is selected from —H and —$C_1$-$C_8$ alkyl;

X is —O—, —S—, —NH— or —N($R^{14}$)—;

$R^{11}$ is selected from —H, —OH, —$NH_2$, —$NHR^{14}$, —$N(R^{14})_2$, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle); or $R^{11}$ is an oxygen atom which forms a carbonyl unit (C=O) with the carbon atom to which it is attached and a hydrogen atom on this carbon atom is replaced by one of the bonds in the (C=O) double bond;

each $R^{12}$ is independently selected from -aryl and —$C_3$-$C_8$ heterocycle;

each $R^{14}$ is independently —H or —$C_1$-$C_8$ alkyl;

$R^{15}$ is -arylene-, —$C_3$-$C_8$ carbocyclo- or —$C_3$-$C_8$ heterocyclo-;

$R^{16}$ is -Yy-Ww-A' wherein
each —W— is independently an Amino Acid unit;
—Y— is a Spacer unit;
w is an integer ranging from 0 to 12;
y is 0, 1 or 2; and
-A' is selected from

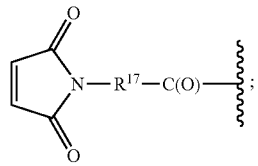

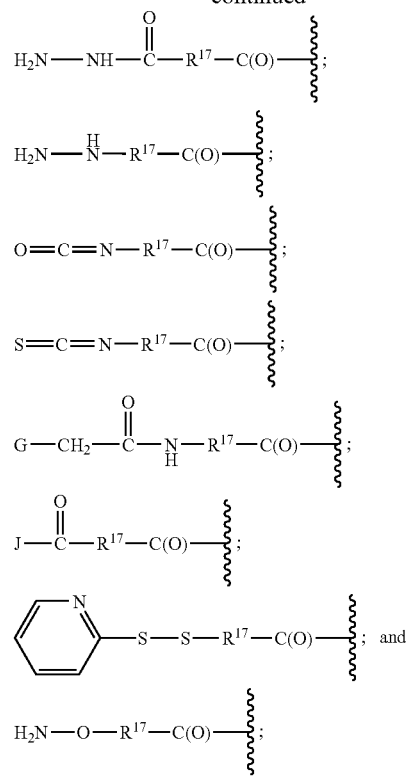

wherein
G is selected from —Cl, —Br, —I, —O-mesyl and —O-tosyl;

J is selected from —Cl, —Br, —I, —F, —OH, —O—N-succinimide, —O-(4-nitrophenyl), —O-pentafluorophenyl, —O-tetrafluorophenyl and —O—C(O)—$OR^{18}$;

$R^{17}$ is selected from —$C_1$-$C_{10}$ alkylene-, —$C_3$-$C_8$ carbocyclo-, —O—($C_1$-$C_8$ alkyl)-, -arylene-, —$C_1$-$C_{10}$ alkylene-arylene-, -arylene-$C_1$-$C_{10}$ alkylene-, —$C_1$-$C_{10}$ alkylene-($C_3$-$C_8$ carbocyclo)-, —($C_3$-$C_8$ carbocyclo)-$C_1$-$C_{10}$ alkylene-, —$C_3$-$C_8$ heterocyclo-, —$C_1$-$C_{10}$ alkylene-($C_3$-$C_8$ heterocyclo)-, —($C_3$-$C_8$ heterocyclo)-$C_1$-$C_{10}$ alkylene-, —$(CH_2CH_2O)_r$—, and —$(CH_2CH_2O)_r$—$CH_2$—; r is an integer ranging from 1-10; and $R^{18}$ is —$C_1$-$C_8$ alkyl or -aryl.

In another aspect, the present invention provides compounds of the formula IIe:

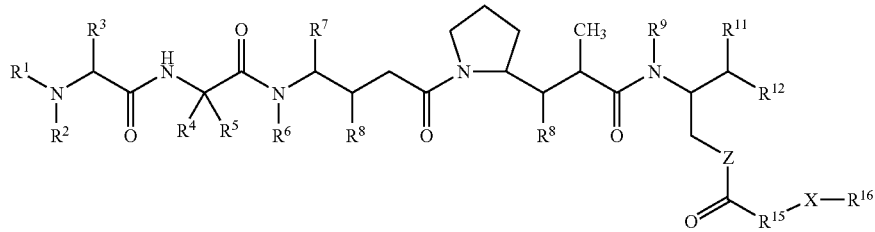

IIe and pharmaceutically acceptable salts and solvates thereof wherein, independently at each location:

$R^1$ is selected from —H, —$C_1$-$C_8$ alkyl and —$C_3$-$C_8$ carbocycle; and $R^2$ is selected from —H and —$C_1$-$C_8$ alkyl; or $R^1$ and $R^2$ join, have the formula —$(CR^aR^b)_n$— wherein $R^a$ and $R^b$ are independently selected from —H, —$C_1$-$C_8$ alkyl and —$C_3$-$C_8$ carbocycle and n is selected from 2, 3, 4, 5 and 6, and form a ring with the nitrogen atom to which they are attached;

$R^3$ is selected from —H, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle);

$R^4$ is selected from —H, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle) wherein $R^5$ is selected from —H and -methyl; or $R^4$ and $R^5$ join, have the formula —$(CR^aR^b)_n$— wherein $R^a$ and $R^b$ are independently selected from —H, —$C_1$-$C_8$ alkyl and —$C_3$-$C_8$ carbocycle and n is selected from 2, 3, 4, 5 and 6, and form a ring with the carbon atom to which they are attached;

$R^6$ is selected from —H and —$C_1$-$C_8$ alkyl;

$R^7$ is selected from —H, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle);

each $R^8$ is independently selected from —H, —OH, —$C_1$-$C_8$ alkyl, —$C_3$-$C_8$ carbocycle and —O—($C_1$-$C_8$ alkyl);

$R^9$ is selected from —H and —$C_1$-$C_8$ alkyl;

X is —O—, —S—, —NH— or —N($R^{14}$)—;

Z is —O—, —S—, —NH— or —N($R^{14}$)—;

$R^{11}$ is selected from —H, —OH, —$NH_2$, —$NHR^{14}$, —$N(R^{14})_2$, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle); or $R^{11}$ is an oxygen atom which forms a carbonyl unit (C=O) with the carbon atom to which it is attached and a hydrogen atom on this carbon atom is replaced by one of the bonds in the (C=O) double bond;

each $R^{12}$ is independently selected from -aryl and —$C_3$-$C_8$ heterocycle;

each $R^{14}$ is independently —H or —$C_1$-$C_8$ alkyl;

$R^{15}$ is -arylene-, —$C_3$-$C_8$ carbocyclo- or —$C_3$-$C_8$ heterocyclo-;

$R^{16}$ is —$Y_y$-$W_w$-A' wherein each —W— is independently an Amino Acid unit;

—Y— is a Spacer unit;

w is an integer ranging from 0 to 12;

y is 0, 1 or 2; and

-A' is selected from

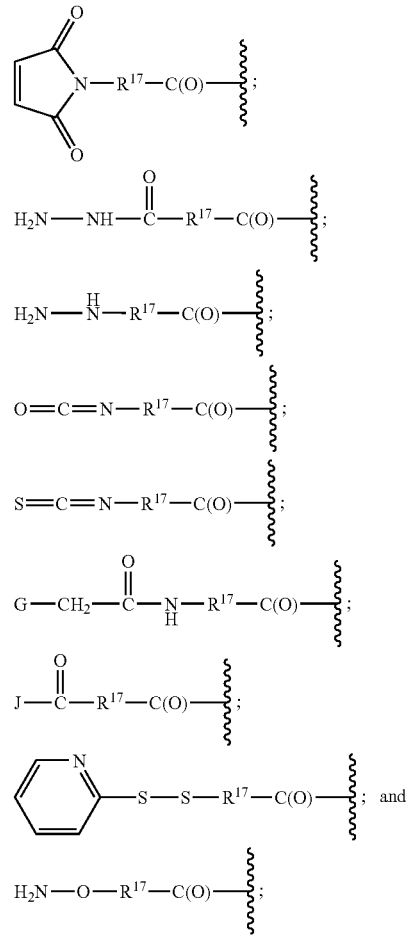

wherein

G is selected from —Cl, —Br, —I, —O-mesyl and —O-tosyl;

J is selected from —Cl, —Br, —I, —F, —OH, —O—N-succinimide, —O-(4-nitrophenyl), —O-pentafluorophenyl, —O-tetrafluorophenyl and —O—C(O)—$OR^{18}$;

$R^{17}$ is selected from —$C_1$-$C_{10}$ alkylene-, —$C_3$-$C_8$ carbocyclo-, —O—($C_1$-$C_8$ alkyl)-, -arylene-, —$C_1$-$C_{10}$ alkylene-arylene-, -arylene-$C_1$-$C_{10}$ alkylene-, —$C_1$-$C_{10}$ alkylene-($C_3$-$C_8$ carbocyclo)-, —($C_3$-$C_8$ carbocyclo)-$C_1$-$C_{10}$ alkylene-, —$C_3$-$C_8$ heterocyclo-, —$C_1$-$C_{10}$ alkylene-($C_3$-$C_8$ heterocyclo)-, —($C_3$-$C_8$ heterocyclo)-$C_1$-$C_{10}$ alkylene-, —$(CH_2CH_2O)_r$—, and —$(CH_2CH_2O)_r$—$CH_2$—; r is an integer ranging from 1-10; and $R^{18}$ is —$C_1$-$C_8$ alkyl or -aryl.

In another aspect, the present invention provides compounds of the formula IIf:

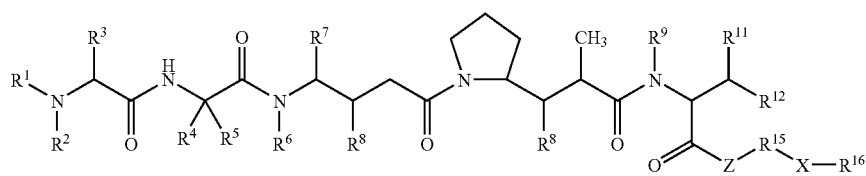

IIf and pharmaceutically acceptable salts and solvates thereof wherein, independently at each location:

$R^1$ is selected from —H, —$C_1$-$C_8$ alkyl and —$C_3$-$C_8$ carbocycle; and $R^2$ is selected from —H and —$C_1$-$C_8$ alkyl; or $R^1$ and $R^2$ join, have the formula —$(CR^aR^b)_n$— wherein $R^a$ and $R^b$ are independently selected from —H, —$C_1$-$C_8$ alkyl and —$C_3$-$C_8$ carbocycle and n is selected from 2, 3, 4, 5 and 6, and form a ring with the nitrogen atom to which they are attached;

$R^3$ is selected from —H, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle);

$R^4$ is selected from —H, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle) wherein $R^5$ is selected from —H and -methyl; or $R^4$ and $R^5$ join, have the formula —$(CR^aR^b)_n$— wherein $R^a$ and $R^b$ are independently selected from —H, —$C_1$-$C_8$ alkyl and —$C_3$-$C_8$ carbocycle and n is selected from 2, 3, 4, 5 and 6, and form a ring with the carbon atom to which they are attached;

$R^6$ is selected from —H and —$C_1$-$C_8$ alkyl;

$R^7$ is selected from —H, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle);

each $R^8$ is independently selected from —H, —OH, —$C_1$-$C_8$ alkyl, —$C_3$-$C_8$ carbocycle and —O—($C_1$-$C_8$ alkyl);

$R^9$ is selected from —H and —$C_1$-$C_8$ alkyl;

X is —O—, —S—, —NH— or —N($R^{14}$)—;

Z is —O—, —S—, —NH— or —N($R^{14}$)—;

$R^{11}$ is selected from —H, —OH, —$NH_2$, —$NHR^{14}$, —$N(R^{14})_2$, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle); or $R^{11}$ is an oxygen atom which forms a carbonyl unit (C=O) with the carbon atom to which it is attached and a hydrogen atom on this carbon atom is replaced by one of the bonds in the (C=O) double bond;

each $R^{12}$ is independently selected from -aryl and —$C_3$-$C_8$ heterocycle;

each $R^{14}$ is independently —H or —$C_1$-$C_8$ alkyl;

$R^{15}$ is -arylene-, —$C_3$-$C_8$ carbocyclo- or —$C_3$-$C_8$ heterocyclo-;

$R^{16}$ is —Yy-Ww-A' wherein each —W— is independently an Amino Acid unit;

—Y— is a Spacer unit;

w is an integer ranging from 0 to 12;

y is 0, 1 or 2; and

-A' is selected from

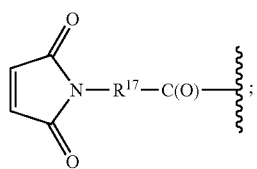

-continued

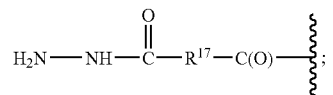

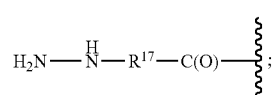

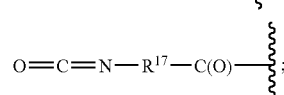

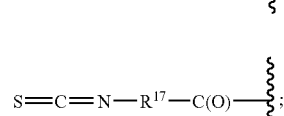

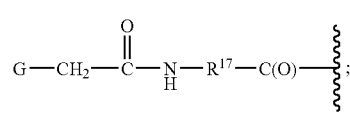

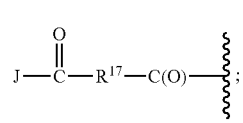

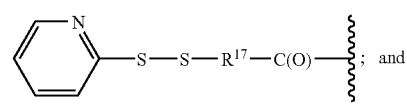

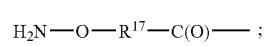

wherein

G is selected from —Cl, —Br, —I, —O-mesyl and —O-tosyl;

J is selected from —Cl, —Br, —I, —F, —OH, —O—N-succinimide, —O-(4-nitrophenyl), —O-pentafluorophenyl, —O-tetrafluorophenyl and —O—C(O)—$OR^{18}$;

$R^{17}$ is selected from —$C_1$-$C_{10}$ alkylene-, —$C_3$-$C_8$ carbocyclo-, —O—($C_1$-$C_8$ alkyl)-, -arylene-, —$C_1$-$C_{10}$ alkylene-arylene-, -arylene-$C_1$-$C_{10}$ alkylene-, —$C_1$-$C_{10}$ alkylene-($C_3$-$C_8$ carbocyclo)-, —($C_3$-$C_8$ carbocyclo)-$C_1$-$C_{10}$ alkylene-, —$C_3$-$C_8$ heterocyclo-, —$C_1$-$C_{10}$ alkylene-($C_3$-$C_8$ heterocyclo)-, —($C_3$-$C_8$ heterocyclo)-$C_1$-$C_{10}$ alkylene-, —$(CH_2CH_2O)_r$—, and —$(CH_2CH_2O)_r$—$CH_2$—; r is an integer ranging from 1-10; and $R^{18}$ is —$C_1$-$C_8$ alkyl or -aryl.

In one embodiment $R^1$ is selected from —$C_1$-$C_8$ alkyl and —$C_3$-$C_8$ carbocycle; and $R^2$ is selected from —H and —$C_1$-$C_8$ alkyl; or $R^1$ and $R^2$ join, have the formula —$(CR^aR^b)_n$— wherein $R^a$ and $R^b$ are independently selected from —H, —$C_1$-$C_8$ alkyl and —$C_3$-$C_8$ carbocycle and n is selected from 2, 3, 4, 5 and 6, and form a ring with the nitrogen atom to which they are attached Illustrative compounds of formula IIf have the structure:
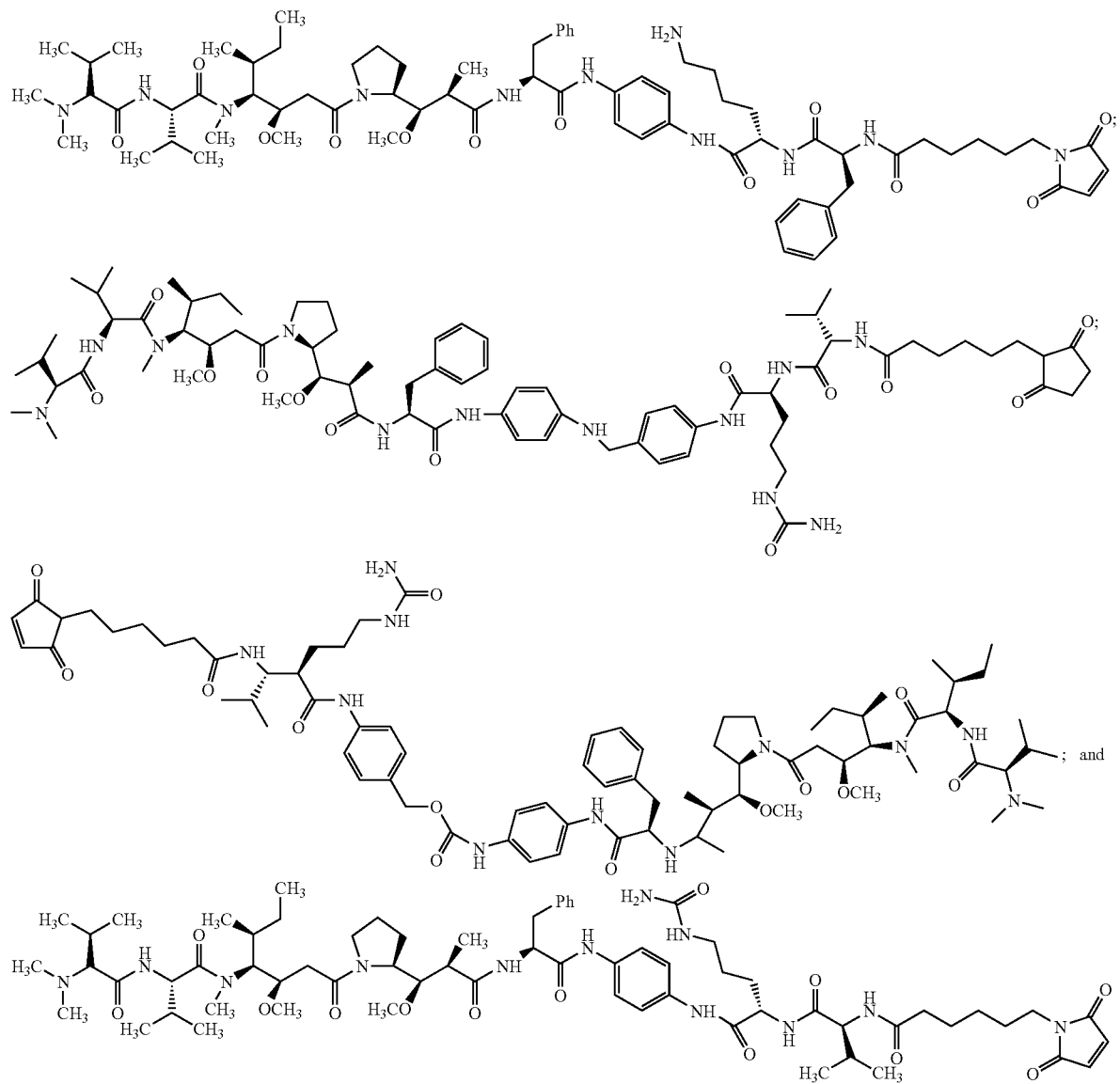
and pharmaceutically acceptable salts and solvates thereof.
In another aspect, the present invention provides compounds of the formula IIg:
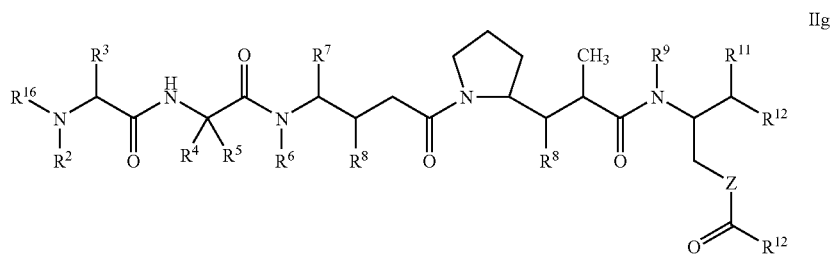
IIg and pharmaceutically acceptable salts and solvates thereof wherein, independently at each location:

$R^2$ is selected from —H and —$C_1$-$C_8$ alkyl;

$R^3$ is selected from —H, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle);

$R^4$ is selected from —H, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle) wherein $R^5$ is selected from —H and -methyl; or $R^4$ and $R^5$ join, have the formula —$(CR^aR^b)_n$— wherein $R^a$ and $R^b$ are independently selected from —H, —$C_1$-$C_8$ alkyl and —$C_3$-$C_8$ carbocycle and n is selected from 2, 3, 4, 5 and 6, and form a ring with the carbon atom to which they are attached;

$R^6$ is selected from —H and —$C_1$-$C_8$ alkyl;

$R^7$ is selected from —H, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle);

each $R^8$ is independently selected from —H, —OH, —$C_1$-$C_8$ alkyl, —$C_3$-$C_8$ carbocycle and —O—($C_1$-$C_8$ alkyl);

$R^9$ is selected from —H and —$C_1$-$C_8$ alkyl;

Z is —O—, —S—, —NH— or —N($R^{14}$)—;

$R^{11}$ is selected from —H, —OH, —$NH_2$, —$NHR^{14}$, —N($R^{14}$)$_2$, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle); or $R^{11}$ is an oxygen atom which forms a carbonyl unit (C=O) with the carbon atom to which it is attached and a hydrogen atom on this carbon atom is replaced by one of the bonds in the (C=O) double bond;

each $R^{12}$ is independently selected from -aryl and —$C_3$-$C_8$ heterocycle;

each $R^{14}$ is independently —H or —$C_1$-$C_8$ alkyl;

$R^{16}$ is —Yy-Ww-A' wherein each —W— is independently an Amino Acid unit;

—Y— is a Spacer unit;

w is an integer ranging from 0 to 12;

y is 0, 1 or 2; and

-A' is selected from

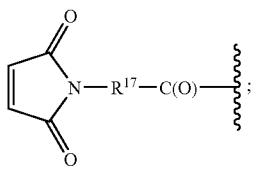

-continued

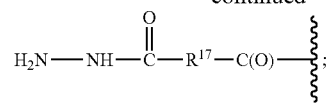

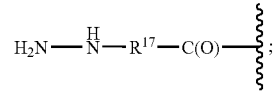

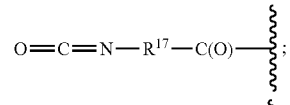

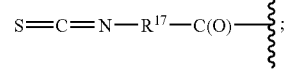

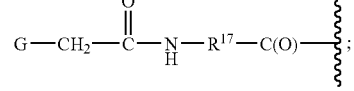

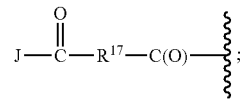

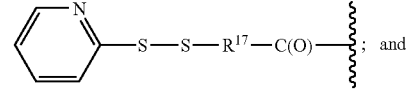; and

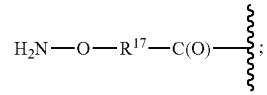

wherein

G is selected from —Cl, —Br, —I, —O-mesyl and —O-tosyl;

J is selected from —Cl, —Br, —I, —F, —OH, —O—N-succinimide, —O-(4-nitrophenyl), —O-pentafluorophenyl, —O-tetrafluorophenyl and —O—C(O)—$OR^{18}$;

$R^{17}$ is selected from —$C_1$-$C_{10}$ alkylene-, —$C_3$-$C_8$ carbocyclo-, —O—($C_1$-$C_8$ alkyl)-, -arylene-, —$C_1$-$C_{10}$ alkylene-arylene-, -arylene-$C_1$-$C_{10}$ alkylene-, —$C_1$-$C_{10}$ alkylene-($C_3$-$C_8$ carbocyclo)-, —($C_3$-$C_8$ carbocyclo)-$C_1$-$C_{10}$ alkylene-, —$C_3$-$C_8$ heterocyclo-, —$C_1$-$C_{10}$ alkylene-($C_3$-$C_8$ heterocyclo)-, —($C_3$-$C_8$ heterocyclo)-$C_1$-$C_{10}$ alkylene-, —$(CH_2CH_2O)_r$—, and —$(CH_2CH_2O)_r$—$CH_2$—; r is an integer ranging from 1-10; and $R^{18}$ is —$C_1$-$C_8$ alkyl or -aryl.

In another aspect, the present invention provides compounds of the formula IIh:

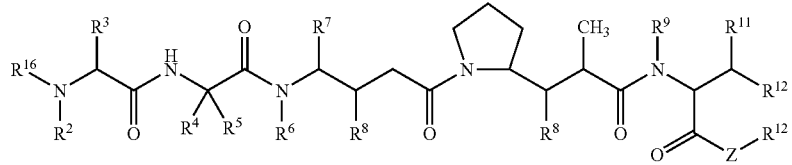

IIh and pharmaceutically acceptable salts and solvates thereof wherein, independently at each location:

$R^2$ is selected from —H and —$C_1$-$C_8$ alkyl;

$R^3$ is selected from —H, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle);

$R^4$ is selected from —H, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle) wherein $R^5$ is selected from —H and -methyl; or $R^4$ and $R^5$ join, have the formula —$(CR^aR^b)_n$— wherein $R^a$ and $R^b$ are independently selected from —H, —$C_1$-$C_8$ alkyl and —$C_3$-$C_8$ carbocycle and n is selected from 2, 3, 4, 5 and 6, and form a ring with the carbon atom to which they are attached;

$R^6$ is selected from —H and —$C_1$-$C_8$ alkyl;

$R^7$ is selected from —H, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle);

each $R^8$ is independently selected from —H, —OH, —$C_1$-$C_8$ alkyl, —$C_3$-$C_8$ carbocycle and —O—($C_1$-$C_8$ alkyl);

$R^9$ is selected from —H and —$C_1$-$C_8$ alkyl;

Z is —O—, —S—, —NH— or —N($R^{14}$)—;

$R^{11}$ is selected from —H, —OH, —$NH_2$, —$NHR^{14}$, —$N(R^{14})_2$, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle); or $R^{11}$ is an oxygen atom which forms a carbonyl unit (C=O) with the carbon atom to which it is attached and a hydrogen atom on this carbon atom is replaced by one of the bonds in the (C=O) double bond;

each $R^{12}$ is independently selected from -aryl and —$C_3$-$C_8$ heterocycle;

each $R^{14}$ is independently —H or —$C_1$-$C_8$ alkyl;

$R^{16}$ is —Yy-Ww-A' wherein each —W— is independently an Amino Acid unit;

—Y— is a Spacer unit;

w is an integer ranging from 0 to 12;

y is 0, 1 or 2; and

-A' is selected from

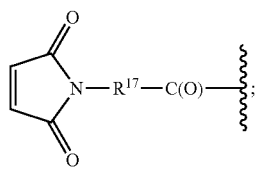

-continued

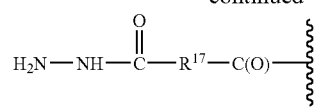
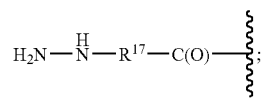
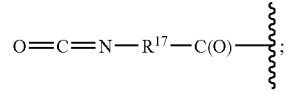
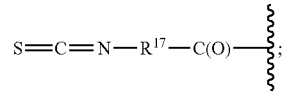
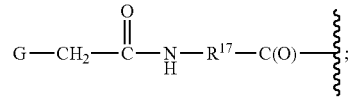
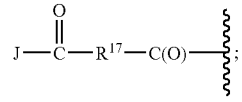
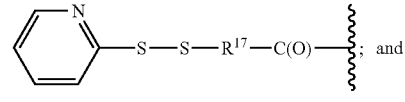
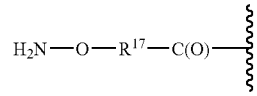

wherein

G is selected from —Cl, —Br, —I, —O-mesyl and —O-tosyl;

J is selected from —Cl, —Br, —I, —F, —OH, —O—N-succinimide, —O-(4-nitrophenyl), —O-pentafluorophenyl, —O-tetrafluorophenyl and —O—C(O)—$OR^{18}$;

$R^{17}$ is selected from —$C_1$-$C_{10}$ alkylene-, —$C_3$-$C_8$ carbocyclo-, —O—($C_1$-$C_8$ alkyl)-, -arylene-, —$C_1$-$C_{10}$ alkylene-arylene-, -arylene-$C_1$-$C_{10}$ alkylene-, —$C_1$-$C_{10}$ alkylene-($C_3$-$C_8$ carbocyclo)-, —($C_3$-$C_8$ carbocyclo)-$C_1$-$C_{10}$ alkylene-, —$C_3$-$C_8$ heterocyclo-, —$C_1$-$C_{10}$ alkylene-($C_3$-$C_8$ heterocyclo)-, —($C_3$-$C_8$ heterocyclo)-$C_1$-$C_{10}$ alkylene-, —$(CH_2CH_2O)_r$—, and —$(CH_2CH_2O)_r$—$CH_2$—; r is an integer ranging from 1-10; and $R^{18}$ is —$C_1$-$C_8$ alkyl or -aryl.

In another aspect, the present invention provides compounds of the formula IIi:

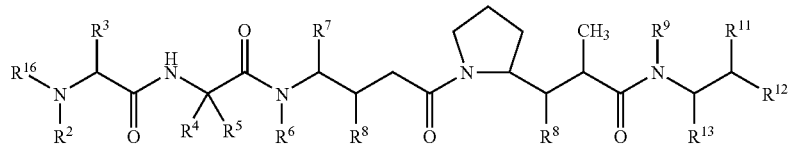

IIi and pharmaceutically acceptable salts and solvates thereof wherein, independently at each location:

$R^2$ is selected from —H and —$C_1$-$C_8$ alkyl;

$R^3$ is selected from —H, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle);

$R^4$ is selected from —H, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle) wherein $R^5$ is selected from —H and -methyl; or $R^4$ and $R^5$ join, have the formula —$(CR^aR^b)_n$— wherein $R^a$ and $R^b$ are independently selected from —H, —$C_1$-$C_8$ alkyl and —$C_3$-$C_8$ carbocycle and n is selected from 2, 3, 4, 5 and 6, and form a ring with the carbon atom to which they are attached;

$R^6$ is selected from —H and —$C_1$-$C_8$ alkyl;

$R^7$ is selected from —H, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle);

each $R^8$ is independently selected from —H, —OH, —$C_1$-$C_8$ alkyl, —$C_3$-$C_8$ carbocycle and —O—($C_1$-$C_8$ alkyl);

$R^9$ is selected from —H and —$C_1$-$C_8$ alkyl;

$R^{11}$ is selected from —H, —OH, —$NH_2$, —$NHR^{14}$, —$N(R^{14})_2$, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle); or $R^{11}$ is an oxygen atom which forms a carbonyl unit (C=O) with the carbon atom to which it is attached and a hydrogen atom on this carbon atom is replaced by one of the bonds in the (C=O) double bond;

each $R^{12}$ is independently selected from -aryl and —$C_3$-$C_8$ heterocycle;

$R^{13}$ is selected from hydrogen, —OH, —$NH_2$, —$NHR^{14}$, —$N(R^{14})_2$, $C_1$-$C_8$ alkyl, $C_3$-$C_8$ carbocycle, —O—($C_1$-$C_8$ alkyl), -aryl, alkyl-aryl, alkyl-($C_3$-$C_8$ carbocycle), $C_3$-$C_8$ heterocycle and alkyl-($C_3$-$C_8$ heterocycle);

each $R^{14}$ is independently —H or —$C_1$-$C_8$ alkyl;

$R^{16}$ is —Yy-Ww-A' wherein each —W— is independently an Amino Acid unit;

—Y— is a Spacer unit;

w is an integer ranging from 0 to 12;

y is 0, 1 or 2; and

-A' is selected from

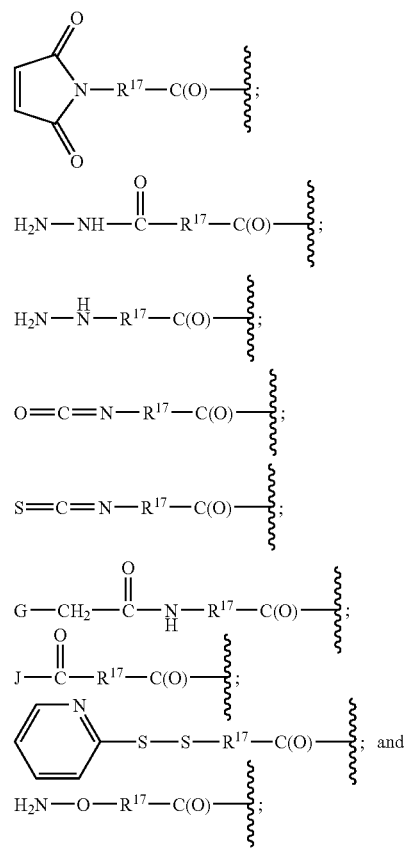

wherein

G is selected from —Cl, —Br, —I, —O-mesyl and —O-tosyl;

J is selected from —Cl, —Br, —I, —F, —OH, —O—N-succinimide, —O-(4-nitrophenyl), —O-pentafluorophenyl, —O-tetrafluorophenyl and —O—C(O)—$OR^{18}$;

$R^{17}$ is selected from —$C_1$-$C_{10}$ alkylene-, —$C_3$-$C_8$ carbocyclo-, —O—($C_1$-$C_8$ alkyl)-, -arylene-, —$C_1$-$C_{10}$ alkylene-arylene-, -arylene-$C_1$-$C_{10}$ alkylene-, —$C_1$-$C_{10}$ alkylene-($C_3$-$C_8$ carbocyclo)-, —($C_3$-$C_8$ carbocyclo)-$C_1$-$C_{10}$ alkylene-, —$C_3$-$C_8$ heterocyclo-, —$C_1$-$C_{10}$ alkylene-($C_3$-$C_8$ heterocyclo)-, —($C_3$-$C_8$ heterocyclo)-$C_1$-$C_{10}$ alkylene-, —$(CH_2CH_2O)_r$—, and —$(CH_2CH_2O)_r$—$CH_2$—; r is an integer ranging from 1-10; and $R^{18}$ is —$C_1$-$C_8$ alkyl or -aryl.

Illustrative compounds of formula III have the structures:

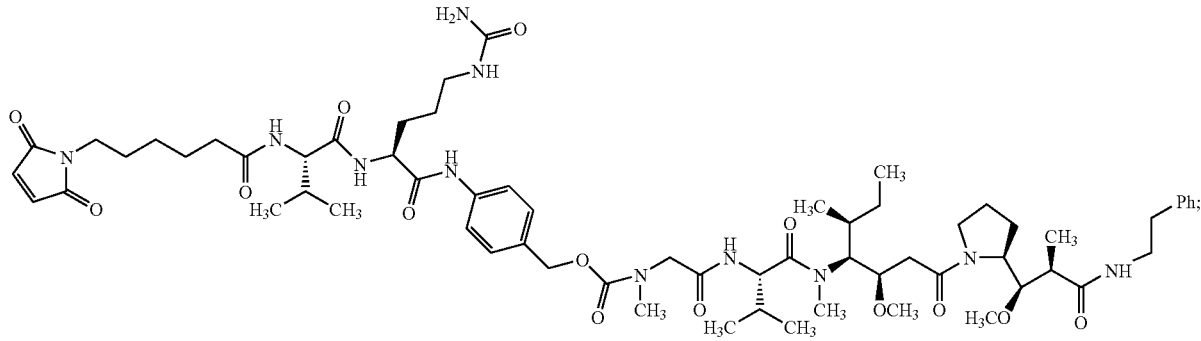

-continued
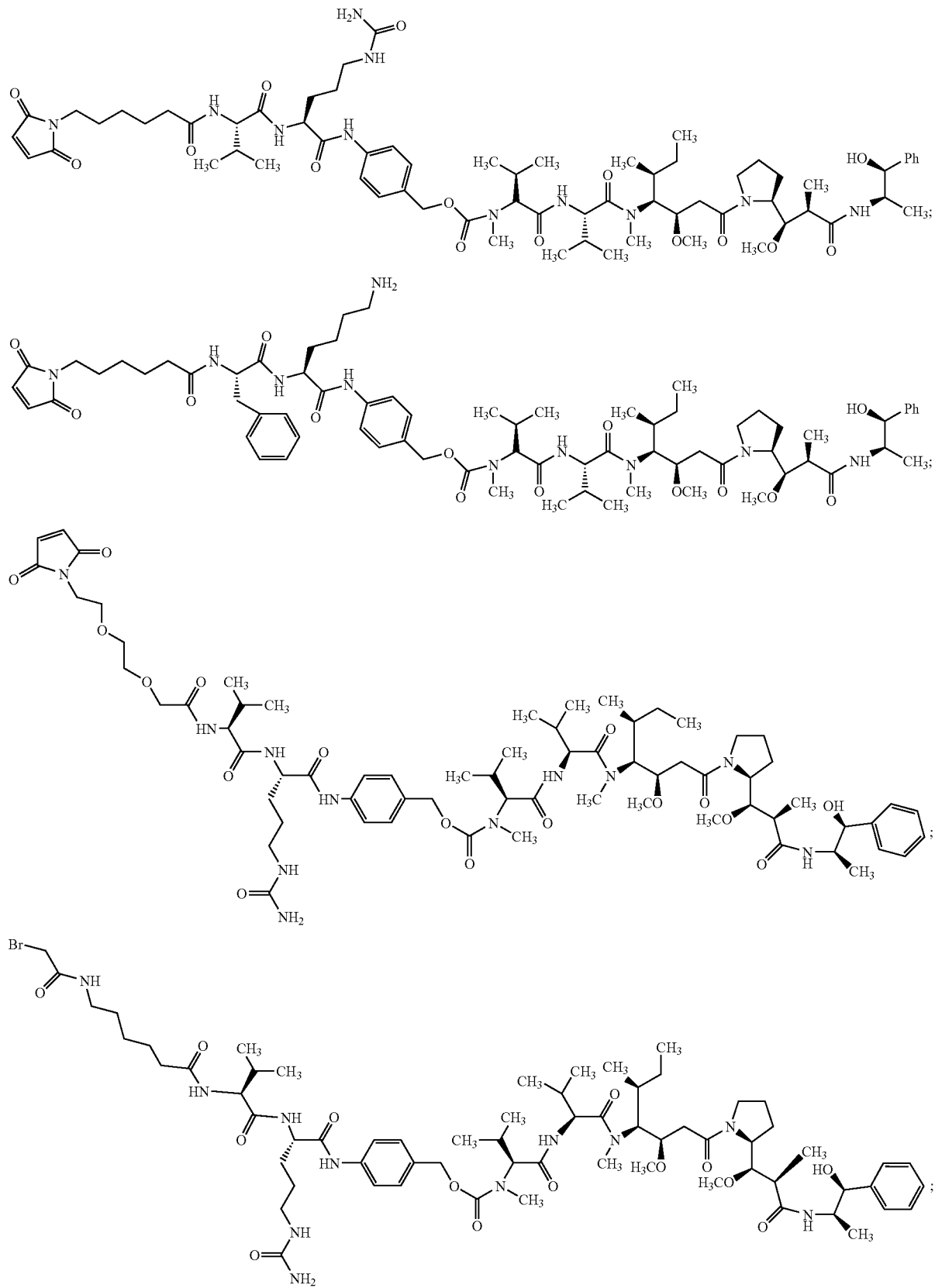

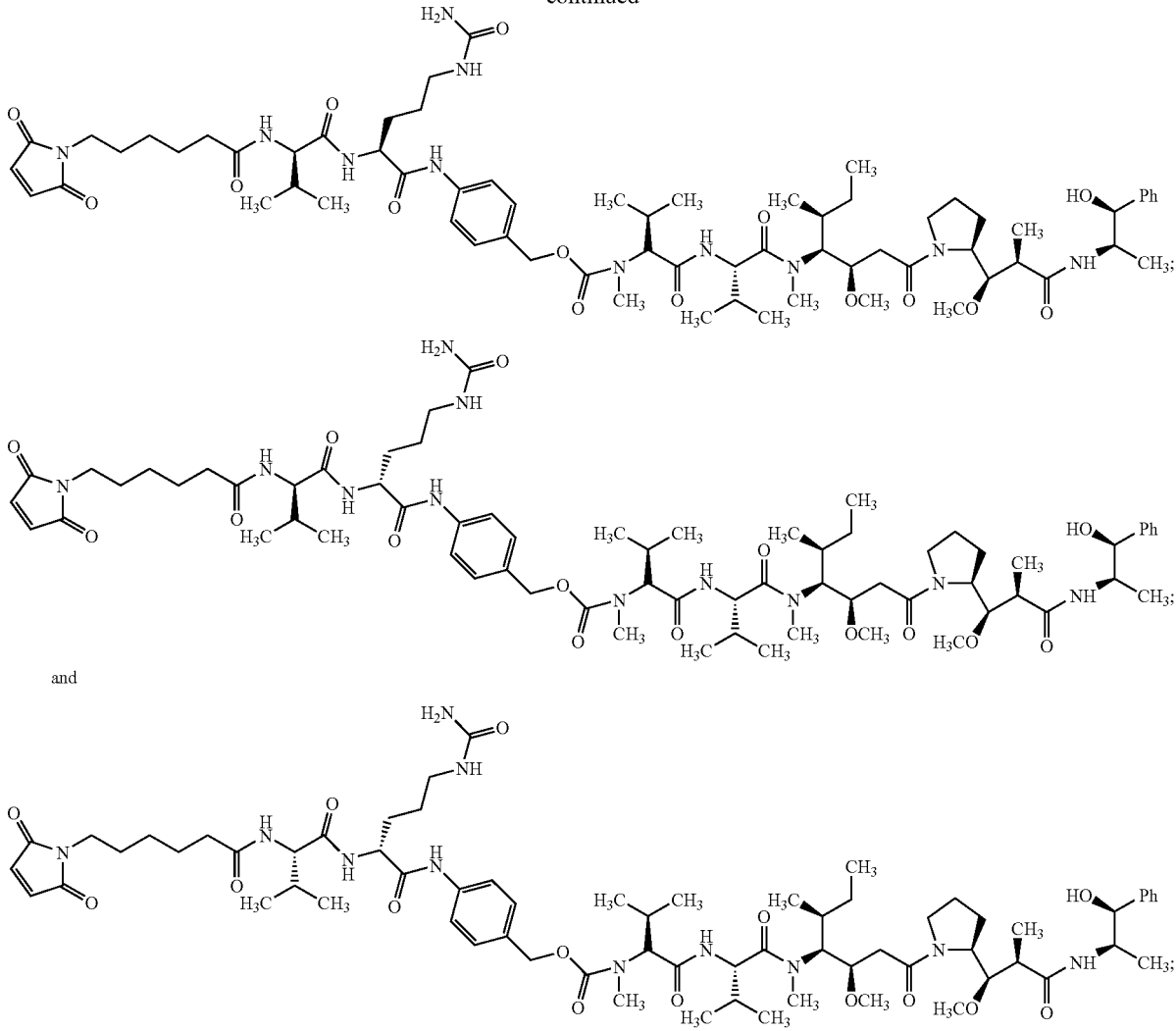

and pharmaceutically acceptable salts and solvates thereof.

The compounds of formulas IIa-i are useful for treating or preventing cancer, an autoimmune disease or an infectious disease in an animal.

5.4 The Linker Unit

The Linker unit of the Drug-Linker-Ligand Conjugate links the Drug unit and the Ligand unit and has the formula:

$$-A_a\text{-}W_w\text{-}Y_y-$$

wherein:
-A- is a Stretcher unit;
a is 0 or 1;
each —W— is independently an Amino Acid unit;
w is independently an integer ranging from 0 to 12;
—Y— is a Spacer unit; and
y is 0, 1 or 2.

5.4.1 The Stretcher Unit

The Stretcher unit (-A-), when present, links a Ligand unit to an amino acid unit (—W—). In this regard a Ligand (L) has a functional group that can form a bond with a functional group of a Stretcher. Useful functional groups that can be present on a ligand, either naturally or via chemical manipulation include, but are not limited to, sulfhydryl (—SH), amino, hydroxyl, carboxy, the anomeric hydroxyl group of a carbohydrate, and carboxyl. Preferred Ligand functional groups are sulfhydryl and amino. Sulfhydryl groups can be generated by reduction of an intramolecular disulfide bond of a Ligand. Alternatively, sulfhydryl groups can be generated by reaction of an amino group of a lysine moiety of a Ligand using 2-iminothiolane (Traut's reagent) or another sulfhydryl generating reagent.

In one embodiment, the Stretcher unit forms a bond with a sulfur atom of the Ligand unit. The sulfur atom can be derived from a sulfhydryl group of a Ligand. Representative Stretcher units of this embodiment are depicted within the square brackets of Formulas (IIIa) and (IIIb), wherein L-, —W—, —Y—, -D, w and y are as defined above and $R^{17}$ is selected from —$C_1$-$C_{10}$ alkylene-, —$C_3$-$C_8$ carbocyclo-, —O—($C_1$-$C_8$ alkyl)-, -arylene-, —$C_1$-$C_{10}$ alkylene-arylene-, -arylene-$C_1$-$C_{10}$ alkylene-, —$C_1$-$C_{10}$ alkylene-($C_3$-$C_8$ carbocyclo)-, —($C_3$-$C_8$ carbocyclo)-$C_1$-$C_{10}$ alkylene-, —$C_3$-$C_8$ heterocyclo-, —$C_1$-$C_{10}$ alkylene-($C_3$-$C_8$ heterocyclo)-, —($C_3$-$C_8$ heterocyclo)-$C_1$-$C_{10}$ alkylene-, —$(CH_2CH_2O)_r$—, and —$(CH_2CH_2O)_r$—$CH_2$—; and r is an integer ranging from 1-10.

(IIIa)

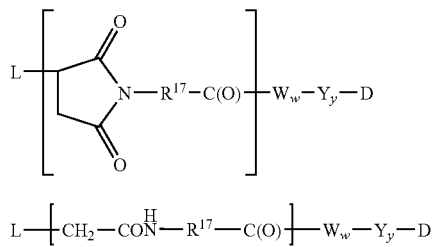

(IIIb)

An illustrative Stretcher unit is that of formula (IIIa) where $R^{17}$ is —$(CH_2)_5$—:

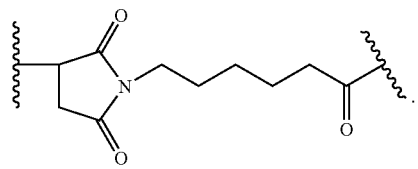

Another illustrative Stretcher unit is that of formula (IIIa) where $R^{17}$ is —$(CH_2CH_2O)_r$—$CH_2$—; and r is 2:

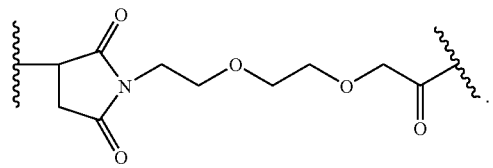

Still another illustrative Stretcher unit is that of formula (IIIb) where $R^{17}$ is —$(CH_2)_5$—:

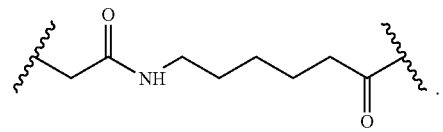

In another embodiment, the Stretcher unit is linked to the Ligand unit via a disulfide bond between a sulfur atom of the Ligand unit and a sulfur atom of the Stretcher unit. A representative Stretcher unit of this embodiment is depicted within the square brackets of Formula (IV), wherein $R^{17}$, L-, —W—, —Y—, -D, w and y are as defined above.

(IV)

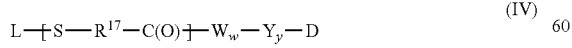

In yet another embodiment, the reactive group of the Stretcher contains a reactive site that can form a bond with a primary or secondary amino group of a Ligand. Example of these reactive sites include, but are not limited to, activated esters such as succinimide esters, 4-nitrophenyl esters, pentafluorophenyl esters, tetrafluorophenyl esters, anhydrides, acid chlorides, sulfonyl chlorides, isocyanates and isothiocyanates. Representative Stretcher units of this embodiment are depicted within the square brackets of Formulas (Va) and (Vb), wherein —$R^{17}$—, L-, —W—, —Y—, -D, w and y are as defined above;

(Va)

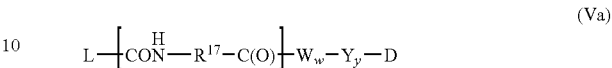

(Vb)

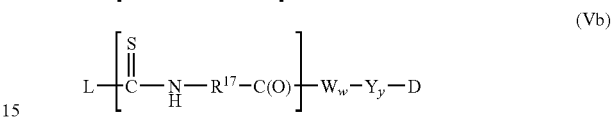

In yet another aspect of the invention, the reactive group of the Stretcher contains a reactive site that is reactive to a carbohydrate's (—CHO) group that can be present on a Ligand. For example, a carbohydrate can be mildly oxidized using a reagent such as sodium periodate and the resulting (—CHO) unit of the oxidized carbohydrate can be condensed with a Stretcher that contains a functionality such as a hydrazide, an oxime, a primary or secondary amine, a hydrazine, a thiosemicarbazone, a hydrazine carboxylate, and an arylhydrazide such as those described by Kaneko, T. et al. *Bioconjugate Chem* 1991, 2, 133-41. Representative Stretcher units of this embodiment are depicted within the square brackets of Formulas (VIa)-(VIc), wherein —$R^{17}$—, L-, —W—, —Y—, -D, w and y are as defined above.

(VIa)

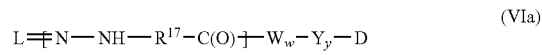

(VIb)

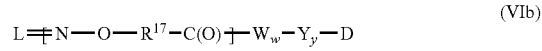

(VIc)

5.4.2 The Amino Acid Unit

The Amino Acid unit (—W—), when present, links the Stretcher unit to the Spacer unit if the Spacer unit is present, links the Stretcher unit to the Drug unit if the Spacer unit is absent, and links the Ligand unit to the Drug unit if the Stretcher unit and Spacer unit are absent.

—$W_w$— is a dipeptide, tripeptide, tetrapeptide, pentapeptide, hexapeptide, heptapeptide, octapeptide, nonapeptide, decapeptide, undecapeptide or dodecapeptide unit. Each —W— unit independently has the formula denoted below in the square brackets, and w is an integer ranging from 0 to 12:

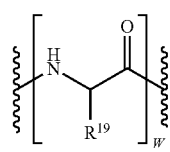

wherein $R^{19}$ is hydrogen, methyl, isopropyl, isobutyl, sec-butyl, benzyl, p-hydroxybenzyl, —$CH_2OH$, —$CH(OH)CH_3$, —$CH_2CH_2SCH_3$, —$CH_2CONH_2$, —$CH_2COOH$, —CH$_2$CH$_2$CONH$_2$, —CH$_2$CH$_2$COOH, —(CH$_2$)$_3$NHC(=NH)NH$_2$, —(CH$_2$)$_3$NH$_2$, —(CH$_2$)$_3$NHCOCH$_3$, —(CH$_2$)$_3$NHCHO, —(CH$_2$)$_4$NHC(=NH)NH$_2$, —(CH$_2$)$_4$NH$_2$, —(CH$_2$)$_4$NHCOCH$_3$, —(CH$_2$)$_4$NHCHO, —(CH$_2$)$_3$NHCONH$_2$, —(CH$_2$)$_4$NHCONH$_2$, —CH$_2$CH$_2$CH(OH)CH$_2$NH$_2$, 2-pyridylmethyl-, 3-pyridylmethyl-, 4-pyridylmethyl-, phenyl, cyclohexyl,

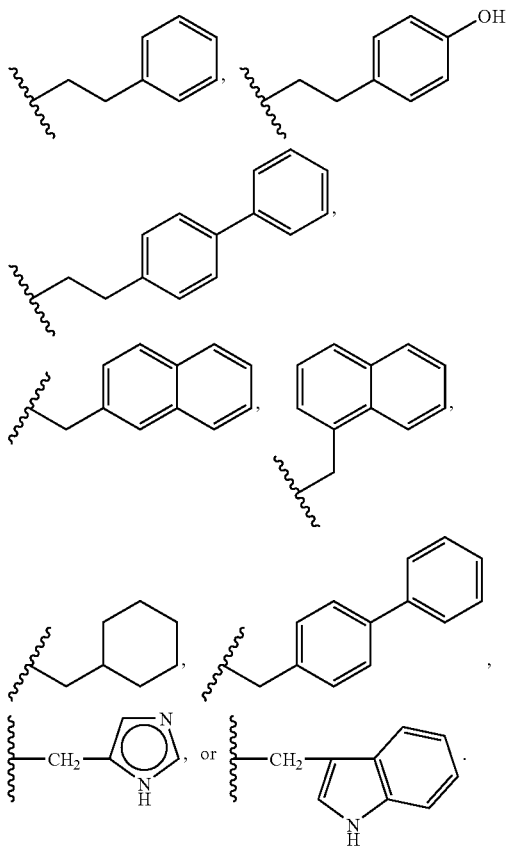

The Amino Acid unit of the Compounds of the Invention can be enzymatically cleaved by one or more enzymes, including a tumor-associated protease, to liberate the Drug unit (-D), which in one embodiment is protonated in vivo upon release to provide a Drug (D).

Illustrative $W_w$ units are represented by formulas (VII)-(IX):

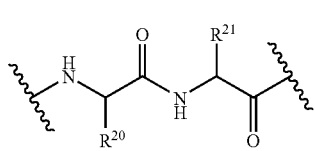 (VII)

wherein $R^{20}$ and $R^{21}$ are as follows:

| $R^{20}$ | $R^{21}$ |
|---|---|
| benzyl | (CH$_2$)$_4$NH$_2$; |
| methyl | (CH$_2$)$_4$NH$_2$; |

-continued

| $R^{20}$ | $R^{21}$ |
|---|---|
| isopropyl | (CH$_2$)$_4$NH$_2$; |
| isopropyl | (CH$_2$)$_3$NHCONH$_2$; |
| benzyl | (CH$_2$)$_3$NHCONH$_2$; |
| isobutyl | (CH$_2$)$_3$NHCONH$_2$; |
| sec-butyl | (CH$_2$)$_3$NHCONH$_2$; |
| 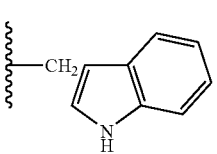 | (CH$_2$)$_3$NHCONH$_2$; |
| benzyl | methyl; and |
| benzyl | (CH$_2$)$_3$NHC(=NH)NH$_2$; |

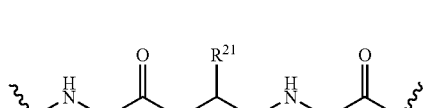 (VIII)

wherein $R^{20}$, $R^{21}$ and $R^{22}$ are as follows:

| $R^{20}$ | $R^{21}$ | $R^{22}$ |
|---|---|---|
| benzyl | benzyl | (CH$_2$)$_4$NH$_2$; |
| isopropyl | benzyl | (CH$_2$)$_4$NH$_2$; and |
| H | benzyl | (CH$_2$)$_4$NH$_2$; |

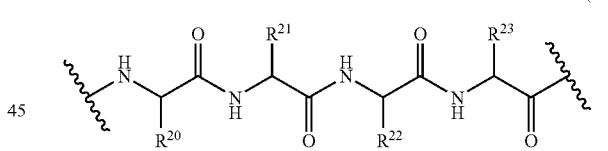 (IX)

wherein $R^{20}$, $R^{21}$, $R^{22}$ and $R^{23}$ are as follows:

| $R^{20}$ | $R^{21}$ | $R^{22}$ | $R^{23}$ |
|---|---|---|---|
| H | benzyl | isobutyl | H; and |
| methyl | isobutyl | methyl | isobutyl. |

Preferred Amino Acid units include, but are not limited to, units of formula (VII) where: $R^{20}$ is benzyl and $R^{21}$ is —(CH$_2$)$_4$NH$_2$; $R^{20}$ isopropyl and $R^{21}$ is —(CH$_2$)$_4$NH$_2$; $R^{20}$ isopropyl and $R^{21}$ is —(CH$_2$)$_3$NHCONH$_2$. Another preferred Amino Acid unit is a unit of formula (VIII) where $R^{20}$ is benzyl, $R^{21}$ is benzyl, and $R^{22}$ is —(CH$_2$)$_4$NH$_2$.

—$W_w$— units useful in the present invention can be designed and optimized in their selectivity for enzymatic cleavage by a particular enzymes, for example, a tumor-associated protease. In one embodiment, a —$W_w$— unit is that whose cleavage is catalyzed by cathepsin B, C and D, or a plasmin protease.

In one embodiment, —$W_w$— is a dipeptide, tripeptide or pentapeptide.

Where $R^{19}$, $R^{20}$, $R^{21}$, $R^{22}$ or $R^{23}$ is other than hydrogen, the carbon atom to which $R^{19}$, $R^{20}$, $R^{21}$, $R^{22}$ or $R^{23}$ is attached is chiral.

Each carbon atom to which $R^{19}$, $R^{20}$, $R^{21}$, $R^{22}$ or $R^{23}$ is attached is independently in the (S) or (R) configuration.

5.4.3 The Spacer Unit

The Spacer unit (—Y—), when present, links an Amino Acid unit to the Drug unit when an Amino Acid unit is present. Alternately, the Spacer unit links the Stretcher unit to the Drug unit when the Amino Acid unit is absent. The Spacer unit also links the Drug unit to the ligand unit when both the Amino Acid unit and Stretcher unit are absent. Spacer units are of two general types: self-immolative and non self-immolative. A non self-immolative Spacer unit is one in which part or all of the Spacer unit remains bound to the Drug unit after cleavage, particularly enzymatic, of an Amino Acid unit from the Drug-Linker-Ligand Conjugate or the Drug-Linker Compound. Examples of a non self-immolative Spacer unit include, but are not limited to a (glycine-glycine) Spacer unit and a glycine Spacer unit (both depicted in Scheme 1). When a Compound of the Invention containing a glycine-glycine Spacer unit or a glycine Spacer unit undergoes enzymatic cleavage via a tumor-cell associated-protease, a cancer-cell-associated protease or a lymphocyte-associated protease, a glycine-glycine-Drug moiety or a glycine-Drug moiety is cleaved from L-$A_a$-$W_w$—. In one embodiment, an independent hydrolysis reaction takes place within the target cell, cleaving the glycine-Drug unit bond and liberating the Drug.

In a preferred embodiment, —$Y_y$— is a p-aminobenzyl alcohol (PAB) unit (see Schemes 2 and 3) whose phenylene portion is substituted with $Q_m$ where Q is —$C_1$-$C_8$ alkyl, —O—($C_1$-$C_8$ alkyl), -halogen, -nitro or -cyano; and m is an integer ranging from 0-4.

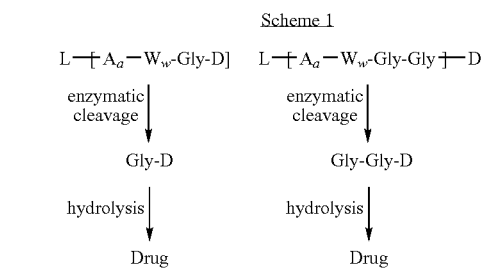

In one embodiment, a non self-immolative Spacer unit (—Y—) is -Gly-Gly-.

In another embodiment, a non self-immolative the Spacer unit (—Y—) is -Gly-.

In one embodiment, the invention provides a Drug-Linker Compound or a Drug-Linker Ligand Conjugate in which the Spacer unit is absent (y=0), or a pharmaceutically acceptable salt or solvate thereof.

Alternatively, a Compound of the Invention containing a self-immolative Spacer unit can release -D without the need for a separate hydrolysis step. In this embodiment, —Y— is a PAB group that is linked to —$W_w$— via the amino nitrogen atom of the PAB group, and connected directly to -D via a carbonate, carbamate or ether group. Without being bound by theory, Scheme 2 depicts a possible mechanism of Drug release of a PAB group which is attached directly to -D via a carbamate or carbonate group.

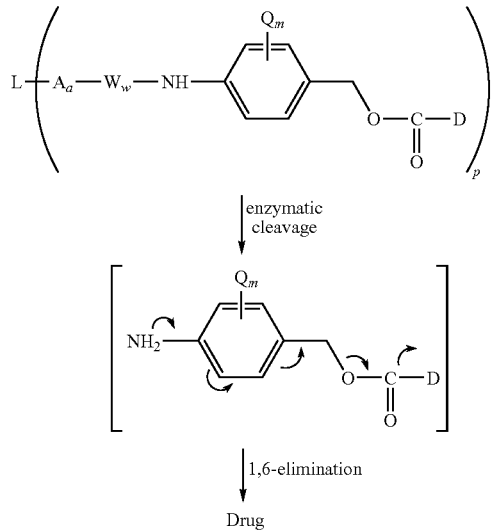

where Q is —$C_1$-$C_8$ alkyl, —O—($C_1$-$C_8$ alkyl), -halogen, -nitro or -cyano; m is an integer ranging from 0-4; and p ranges from 1 to about 20.

Without being bound by theory, Scheme 3 depicts a possible mechanism of Drug release of a PAB group which is attached directly to -D via an ether or amine linkage.

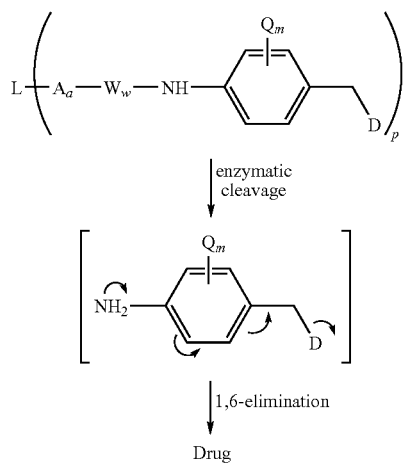

where Q is —$C_1$-$C_8$ alkyl, —O—($C_1$-$C_8$ alkyl), -halogen, -nitro or -cyano; m is an integer ranging from 0-4; and p ranges from 1 to about 20.

Other examples of self-immolative spacers include, but are not limited to, aromatic compounds that are electronically similar to the PAB group such as 2-aminoimidazol-5-methanol derivatives (see Hay et al., *Bioorg. Med. Chem. Lett.*, 1999, 9, 2237) and ortho or para-aminobenzylacetals. Spacers can be used that undergo cyclization upon amide bond hydrolysis, such as substituted and unsubstituted 4-aminobutyric acid amides (Rodrigues et al., *Chemistry Biology*, 1995, 2, 223), appropriately substituted bicyclo[2.2.1] and bicyclo [2.2.2] ring systems (Storm, et al., *J. Amer. Chem. Soc.*, 1972, 94, 5815) and 2-aminophenylpropionic acid amides (Amsberry, et al., *J. Org. Chem.*, 1990, 55, 5867). Elimination of amine-containing drugs that are substituted at the a-position of glycine (Kingsbury, et al., *J. Med. Chem.*, 1984, 27, 1447) are also examples of self-immolative spacer useful in the Compounds of the Invention.

In a preferred embodiment, the Spacer unit is a branched bis(hydroxymethyl)styrene (BHMS) unit as depicted in Scheme 4, which can be used to incorporate and release multiple drugs.

Scheme 4

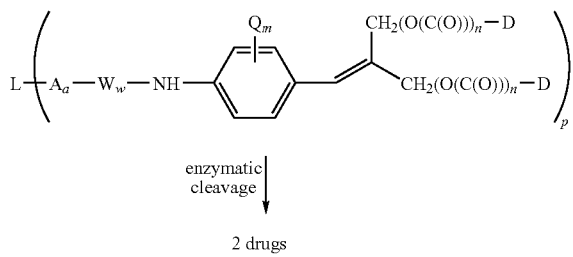

enzymatic cleavage 2 drugs where Q is —$C_1$-$C_8$ alkyl, —O—($C_1$-$C_8$ alkyl), -halogen, -nitro or -cyano; m is an integer ranging from 0-4; n is 0 or 1; and p ranges raging from 1 to about 20.

In one embodiment, the -D moieties are the same.

In another embodiment, the -D moieties are different.

Preferred Spacer units (—$Y_y$—) are represented by Formulas (X)-(XII):

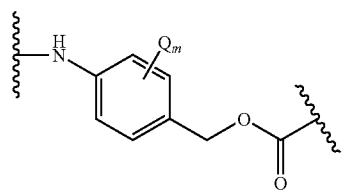

(X)

where Q is —$C_1$-$C_8$ alkyl, —O—($C_1$-$C_8$ alkyl), -halogen, -nitro or -cyano; and m is an integer ranging from 0-4;

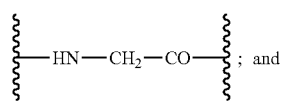

(XI)

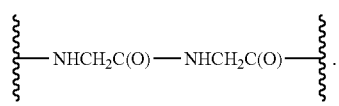

(XII)

5.5 The Drug Unit

-D is a Drug unit having a nitrogen or oxygen atom that can form a bond with the Spacer unit when y=1 or 2 or with the C-terminal carbonyl group of an Amino Acid unit when y=0.

In one embodiment, -D is represented by the formula:

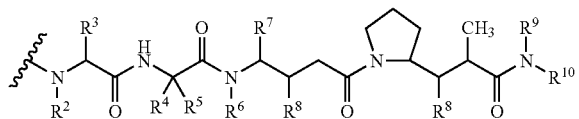

wherein, independently at each location:

$R^2$ is selected from —H and —$C_1$-$C_8$ alkyl;

$R^3$ is selected from —H, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle);

$R^4$ is selected from —H, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle) wherein $R^5$ is selected from —H and -methyl; or $R^4$ and $R^5$ join, have the formula —$(CR^aR^b)_n$— wherein $R^a$ and $R^b$ are independently selected from —H, —$C_1$-$C_8$ alkyl and —$C_3$-$C_8$ carbocycle and n is selected from 2, 3, 4, 5 and 6, and form a ring with the carbon atom to which they are attached;

$R^6$ is selected from —H and —$C_1$-$C_8$ alkyl;

$R^7$ is selected from —H, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle);

each $R^8$ is independently selected from —H, —OH, —$C_1$-$C_8$ alkyl, —$C_3$-$C_8$ carbocycle and —O—($C_1$-$C_8$ alkyl);

$R^9$ is selected from —H and —$C_1$-$C_8$ alkyl;

$R^{10}$ is selected from

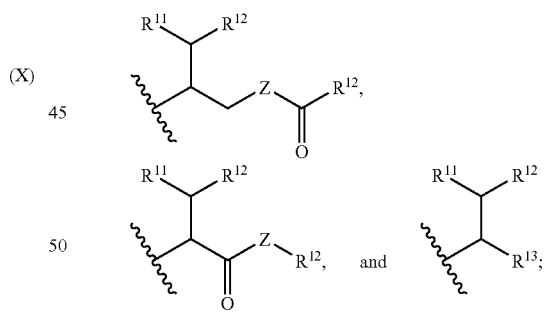

Z is —O—, —S—, —NH— or —N($R^{14}$)—;

$R^{11}$ is selected from —H, —OH, —$NH_2$, —$NHR^{14}$, —N($R^{14}$)$_2$, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle); or $R^{11}$ is an oxygen atom which forms a carbonyl unit (C=O) with the carbon atom to which it is attached and a hydrogen atom on this carbon atom is replaced by one of the bonds in the (C=O) double bond;

each $R^{12}$ is independently selected from -aryl and —$C_3$-$C_8$ heterocycle;

$R^{13}$ is selected from —H, —OH, —$NH_2$, —$NHR^{14}$, —N($R^{14}$)$_2$, —$C_1$-$C_8$ alkyl, —$C_3$-$C_8$ carbocycle, —O—($C_1$-

$C_8$ alkyl), -aryl, —$C_1$-$C_8$ alkyl-aryl, —$C_1$-$C_8$ alkyl-($C_3$-$C_8$ carbocycle), $C_3$-$C_8$ heterocycle and —$C_1$-$C_8$ alkyl-($C_3$-$C_8$ heterocycle); and each $R^{14}$ is independently —H or —$C_1$-$C_8$ alkyl.

In one embodiment, $R^{10}$ is selected from

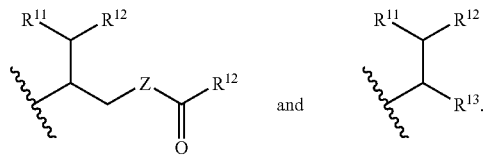

In a preferred embodiment, -D has the formula

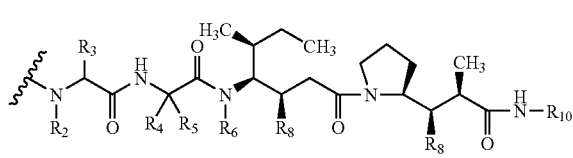

or a pharmaceutically acceptable salt or solvate thereof, wherein, independently at each location:

$R^2$ is selected from —H and -methyl;

$R^3$ is selected from —H, -methyl, and -isopropyl;

$R^4$ is selected from —H and -methyl; $R^5$ is selected from -isopropyl, -isobutyl, -sec-butyl, -methyl and -t-butyl; or $R^4$ and $R^5$ join, have the formula —$(CR^aR^b)_n$— where $R^a$ and $R^b$ are independently selected from —H, —$C_1$-$C_8$ alkyl, and —$C_3$-$C_8$ carbocycle, and n is selected from 2, 3, 4, 5 and 6, and form a ring with the carbon atom to which they are attached;

$R^6$ is selected from —H and -methyl;

each $R^5$ is independently selected from —OH, -methoxy and -ethoxy;

$R^{10}$ is selected from

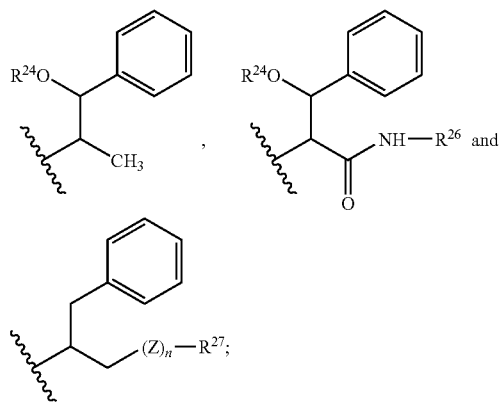

$R^{24}$ is selected from H and —C(O)$R^{25}$; wherein $R^{25}$ is selected from —$C_1$-$C_8$ alkyl, —$C_3$-$C_8$ carbocycle, -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle);

$R^{26}$ is selected from —$C_1$-$C_8$ alkyl, —$C_3$-$C_8$ carbocycle, -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle);

Z is —O—, —NH—, —OC(O)—, —NHC(O)—, —N($R^{28}$)C(O)—; where $R^2$ is selected from —H and —$C_1$-$C_8$ alkyl;

n is 0 or 1; and $R^{27}$ is selected from —H, —$N_3$, —$C_1$-$C_8$ alkyl, —$C_3$-$C_8$ carbocycle, -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle) when n is 0; and $R^{27}$ is selected from —H, —$C_1$-$C_8$ alkyl, —$C_3$-$C_8$ carbocycle, -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle) when n is 1.

In one embodiment, $R^{10}$ is selected from

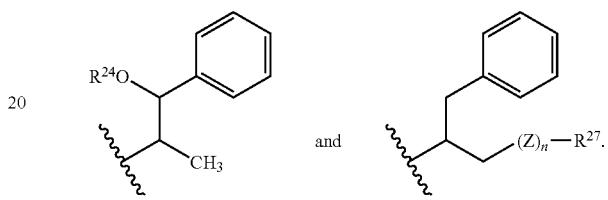

In another embodiment, -D is represented by the formula:

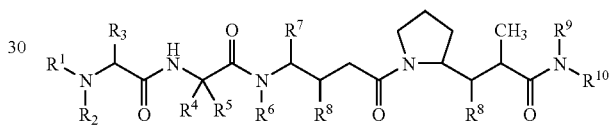

wherein, independently at each location:

$R^1$ is selected from —H, —$C_1$-$C_8$ alkyl and —$C_3$-$C_8$ carbocycle; and $R^2$ is selected from —H and —$C_1$-$C_8$ alkyl; or $R^1$ and $R^2$ join, have the formula —$(CR^aR^b)_n$— wherein $R^a$ and $R^b$ are independently selected from —H, —$C_1$-$C_8$ alkyl and —$C_3$-$C_8$ carbocycle and n is selected from 2, 3, 4, 5 and 6, and form a ring with the nitrogen atom to which they are attached;

$R^3$ is selected from —H, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle);

$R^4$ is selected from —H, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle) wherein $R^5$ is selected from —H and -methyl; or $R^4$ and $R^5$ join, have the formula —$(CR^aR^b)_n$— wherein $R^a$ and $R^b$ are independently selected from —H, —$C_1$-$C_8$ alkyl and —$C_3$-$C_8$ carbocycle and n is selected from 2, 3, 4, 5 and 6, and form a ring with the carbon atom to which they are attached;

$R^6$ is selected from —H and —$C_1$-$C_8$ alkyl;

$R^7$ is selected from —H, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle);

each $R^8$ is independently selected from —H, —OH, —$C_1$-$C_8$ alkyl, —$C_3$-$C_8$ carbocycle and —O—($C_1$-$C_8$ alkyl);

$R^9$ is selected from —H and —$C_1$-$C_8$ alkyl;
$R^{10}$ is selected from

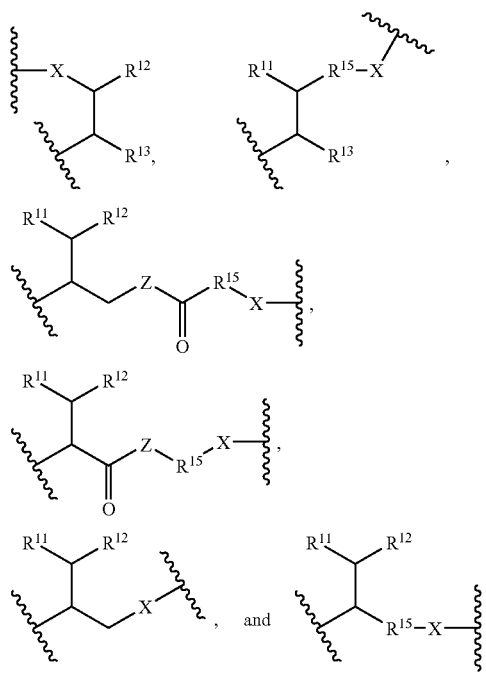

X is —O—, —S—, —NH— or —N($R^{14}$)—, where X forms a bond with a Linker unit;

Z is —O—, —S—, —NH— or —N($R^{14}$)—;

$R^{11}$ is selected from —H, —OH, —$NH_2$, —$NHR^{14}$, —N($R^{14}$)$_2$, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle); or $R^{11}$ is an oxygen atom which forms a carbonyl unit (C=O) with the carbon atom to which it is attached and a hydrogen atom on this carbon atom is replaced by one of the bonds in the (C=O) double bond;

each $R^{12}$ is independently selected from -aryl and —$C_3$-$C_8$ heterocycle;

$R^{13}$ is selected from —H, —OH, —$NH_2$, —$NHR^{14}$, —N($R^{14}$)$_2$, —O—($C_1$-$C_8$ alkyl), —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), $C_3$-$C_8$ heterocycle and —$C_1$-$C_8$ alkyl-($C_3$-$C_8$ heterocycle);

each $R^{14}$ is independently —H or —$C_1$-$C_8$ alkyl; and $R^{15}$ is -arylene-, —$C_3$-$C_8$ carbocyclo- or —$C_3$-$C_8$ heterocyclo-.

In one embodiment, when $R^1$ is —H, $R^{10}$ is selected from:

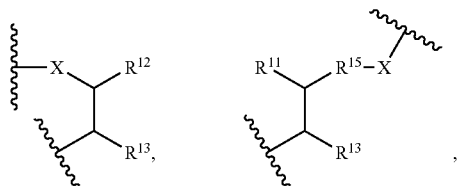

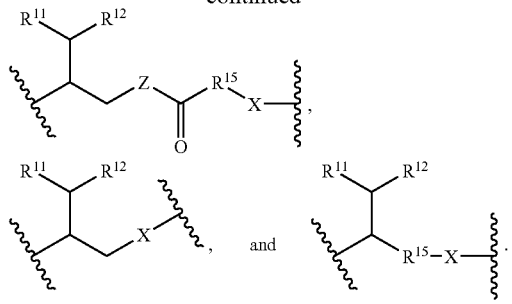

In a preferred embodiment, -D has the formula

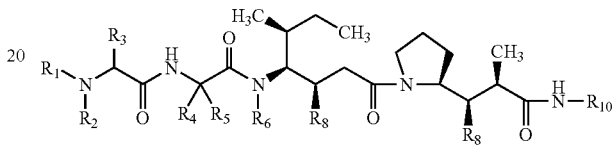

or a pharmaceutically acceptable salt or solvate thereof, wherein, independently at each location:

$R^1$ is selected from —H and -methyl;
$R^2$ is selected from —H and -methyl;
$R^3$ is selected from —H, -methyl, and -isopropyl;
$R^4$ is selected from —H and -methyl; $R^5$ is selected from -isopropyl, -isobutyl, -sec-butyl, -methyl and -t-butyl; or $R^4$ and $R^5$ join, have the formula —(CR$^a$R$^b$), where R$^a$ and R$^b$ are independently selected from —H, —$C_1$-$C_8$ alkyl, and —$C_3$-$C_8$ carbocycle, and N is selected from 2, 3, 4, 5 and 6, and form a ring with the carbon atom to which they are attached;

$R^6$ is selected from —H and -methyl;
each $R^8$ is independently selected from —OH, -methoxy and -ethoxy; $R^{10}$ is selected from

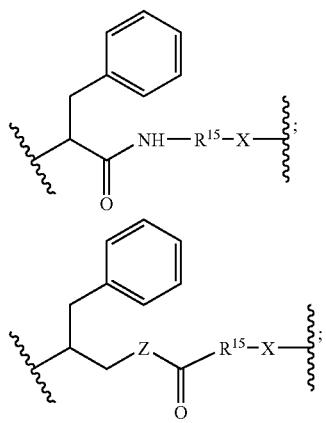

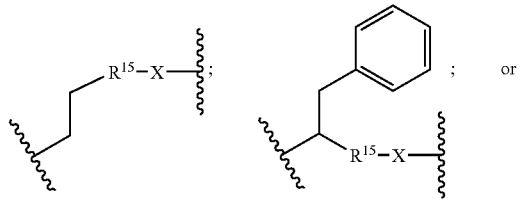

-continued

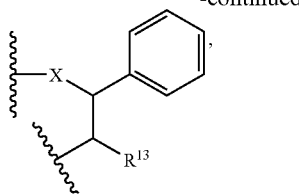

where X is —O—, —NH— or —N(R$^{14}$)— and forms a bond with Y when y is 1 or 2, with W when y is 0, and with A when w and y are both 0;
Z is —O—, —NH— or —N(R$^{14}$)—;
R$^{13}$ is —H or -methyl;
R$^{14}$ is C$_1$-C$_8$ alkyl; and
R$^{15}$ is -arylene-, —C$_3$-C$_8$ carbocyclo or —C$_3$-C$_8$ heterocyclo-, In one embodiment, when R$^1$ is -methyl, R$^{10}$ is selected from

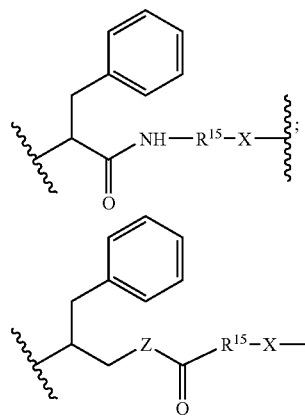

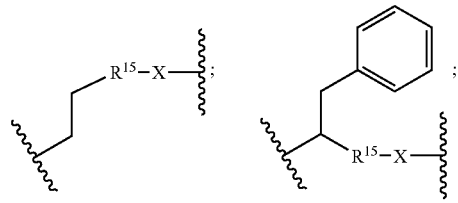

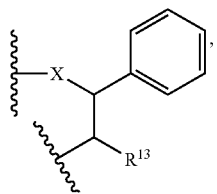

where X is —O—, —NH— or —N(R$^{14}$)— and forms a bond with Y when y is 1 or 2, and with W when y is 0;
Z is —O—, —NH— or —N(R$^{14}$)—;
R$^{13}$ is —H or -methyl;
R$^{14}$ is C$_1$-C$_8$ alkyl; and
R$^{15}$ is -arylene-, —C$_3$-C$_8$ carbocyclo or —C$_3$-C$_8$ heterocyclo-.

In another embodiment, when R$^1$ is —H, R$^{10}$ is selected from:

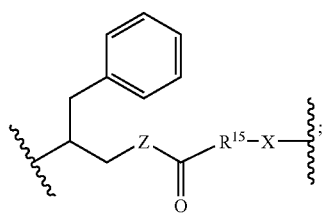

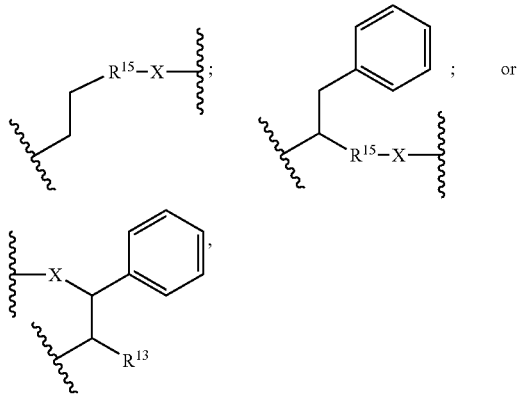

where X is —O—, —NH— or —N(R$^{14}$)— and forms a bond with Y when y is 1 or 2, and with W when y is 0;
Z is —O—, —NH— or —N(R$^{14}$)—;
R$^{13}$ is —H or -methyl;
R$^{14}$ is C$_1$-C$_8$ alkyl; and
R$^{15}$ is -arylene-, —C$_3$-C$_8$ carbocyclo or —C$_3$-C$_8$ heterocyclo-.

A Drug unit can form a bond with a Linker unit via a nitrogen atom of a Drug's primary or secondary amino group, via an oxygen atom of a Drug's hydroxyl group, or via a sulfur atom of a Drug's sulfhydryl group to form a Drug-Linker Compound.

In a preferred embodiment, Drug units have the formula

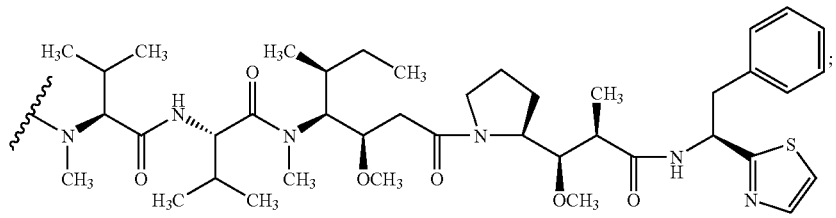

-continued
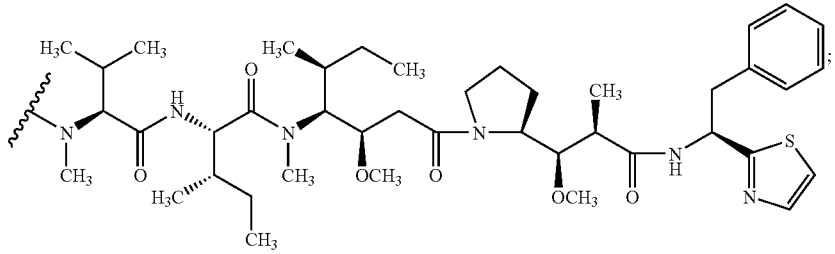
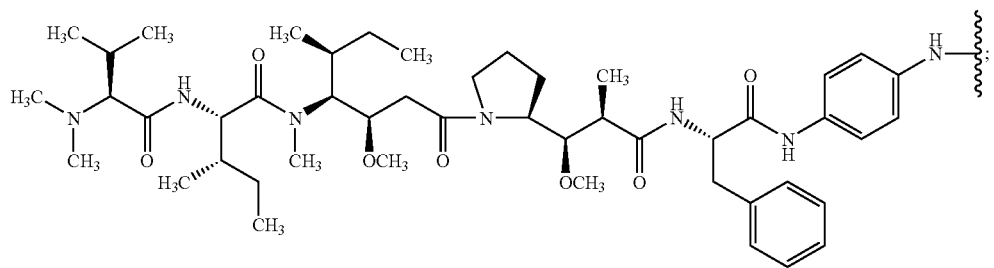
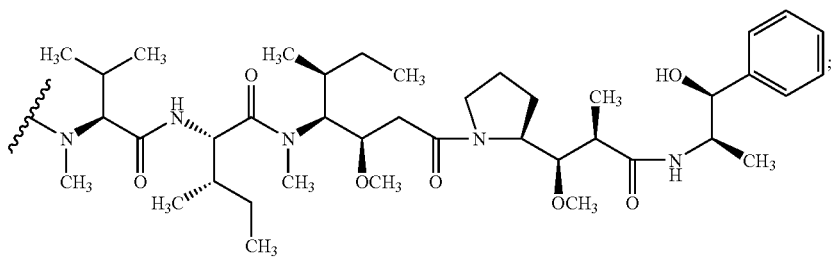
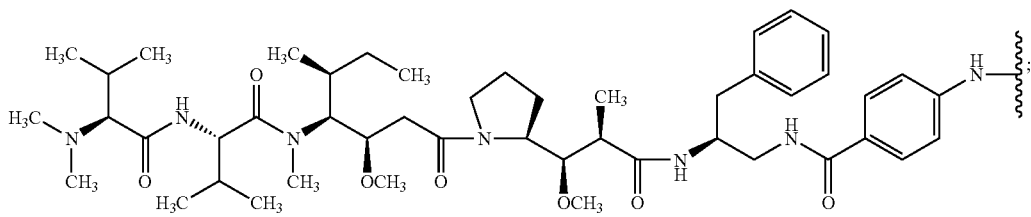
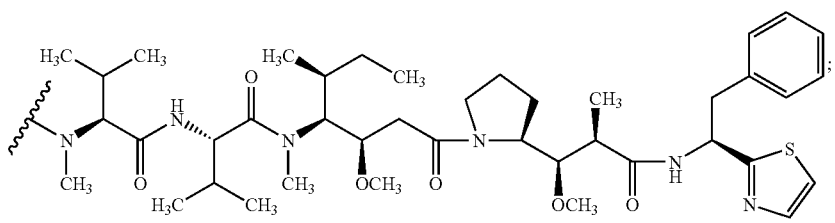
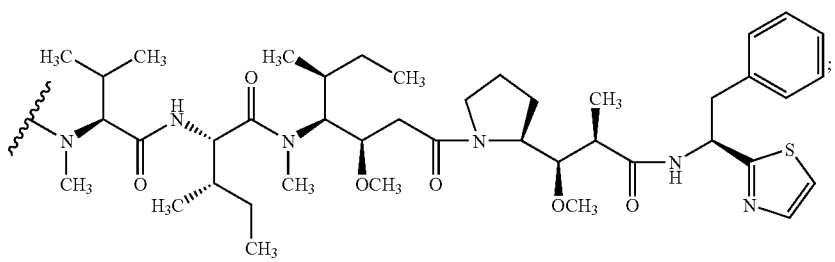

-continued

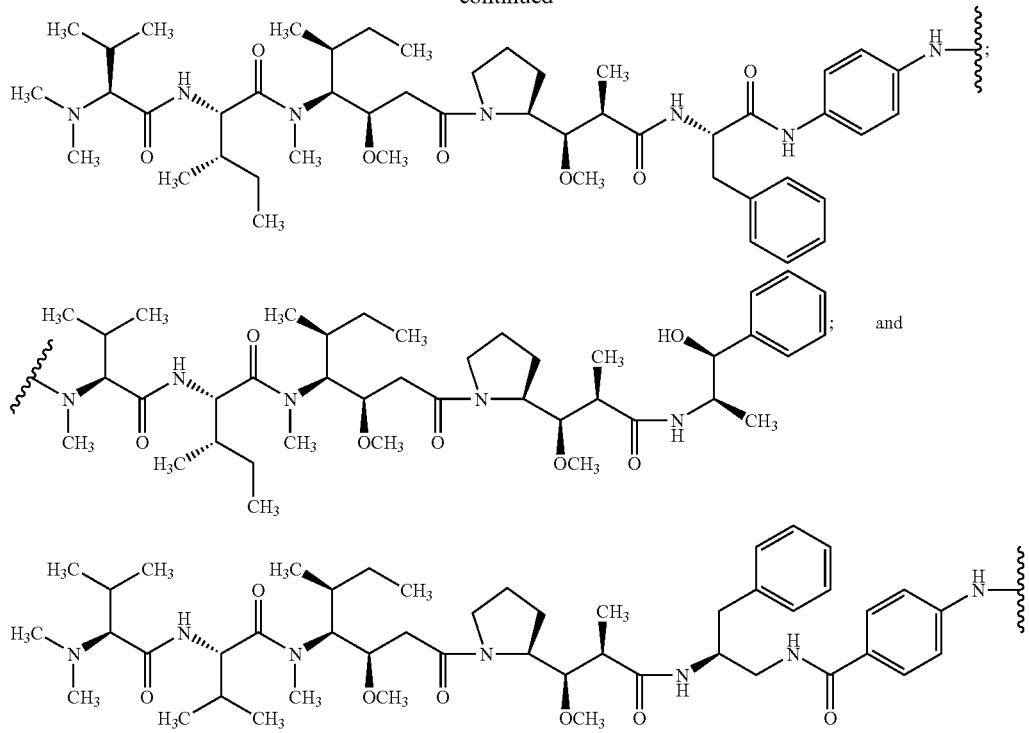

5.6 The Ligand Unit

The Ligand unit (L-) includes within its scope any unit of a Ligand (L) that binds or reactively associates or complexes with a receptor, antigen or other receptive moiety associated with a given target-cell population. A Ligand can be any molecule that binds to, complexes with or reacts with a moiety of a cell population sought to be therapeutically or otherwise biologically modified. The Ligand unit acts to deliver the Drug unit to the particular target cell population with which the Ligand unit reacts. Such Ligands include, but are not limited to, large molecular weight proteins such as, for example, full-length antibodies, antibody fragments, smaller molecular weight proteins, polypeptide or peptides, and lectins.

A Ligand unit can form a bond to either a Stretcher unit or an Amino Acid unit of a Linker. A Ligand unit can form a bond to a Linker unit via a heteroatom of the Ligand. Heteroatoms that may be present on a Ligand unit include sulfur (in one embodiment, from a sulfhydryl group of a Ligand), oxygen (in one embodiment, from a carbonyl, carboxyl or hydroxyl group of a Ligand) and nitrogen (in one embodiment, from a primary or secondary amino group of a Ligand). These heteroatoms can be present on the Ligand in the Ligand's natural state, for example a naturally occurring antibody, or can be introduced into the Ligand via chemical modification.

In a preferred embodiment, a Ligand has a sulfhydryl group and the Ligand bonds to the Linker unit via the sulfhydryl group's sulfur atom.

In another embodiment, the Ligand can have one or more carbohydrate groups that can be chemically modified to have one or more sulfhydryl groups. The Ligand unit bonds to the Stretcher unit via the sulfhydryl group's sulfur atom.

In yet another embodiment, the Ligand can have one or more carbohydrate groups that can be oxidized to provide an aldehyde (—CHO) group (see Laguzza, et al., *J. Med. Chem.* 1989, 32(3), 548-55). The corresponding aldehyde can form a bond with a Reactive Site on a Stretcher. Reactive sites on a Stretcher that can react with a carbonyl group on a Ligand include, but are not limited to, hydrazine and hydroxylamine.

Useful non-immunoreactive protein, polypeptide, or peptide Ligands include, but are not limited to, transferrin, epidermal growth factors ("EGF"), bombesin, gastrin, gastrin-releasing peptide, platelet-derived growth factor, IL-2, IL-6, transforming growth factors ("TGF"), such as TGF-α and TGF-β, vaccinia growth factor ("VGF"), insulin and insulin-like growth factors I and II, lectins and apoprotein from low density lipoprotein.

Useful Polyclonal antibody Ligands are heterogeneous populations of antibody molecules derived from the sera of immunized animals. Various procedures well known in the art may be used for the production of polyclonal antibodies to an antigen-of-interest. For example, for the production of polyclonal antibodies, various host animals can be immunized by injection with an antigen of interest or derivative thereof, including but not limited to rabbits, mice, rats, and guinea pigs. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants are also well known in the art.

Useful monoclonal antibody Ligands are homogeneous populations of antibodies to a particular antigen (e.g., a cancer cell antigen, a viral antigen, a microbial antigen covalently linked to a second molecule). A monoclonal antibody (mAb) to an antigen-of-interest can be prepared by using any technique known in the art which provides for the production of antibody molecules by continuous cell lines in culture. These include, but are not limited to, the hybridoma technique originally described by Kohler and Milstein (1975, *Nature* 256, 495-497), the human B cell hybridoma technique (Kozbor et al., 1983, *Immunology Today* 4: 72), and the EBV-hybridoma technique (Cole et al., 1985, *Monoclonal Antibodies and Cancer Therapy*, Alan R. Liss, Inc., pp. 77-96). Such antibodies may be of any immunoglobulin class including IgG, IgM, IgE, IgA, and IgD and any subclass thereof. The hybridoma producing the mAbs of use in this invention may be cultivated in vitro or in vivo.

Useful monoclonal antibody Ligands include, but are not limited to, human monoclonal antibodies or chimeric human-mouse (or other species) monoclonal antibodies. Human monoclonal antibodies may be made by any of numerous techniques known in the art (e.g., Teng et al., 1983, *Proc. Natl. Acad. Sci. U.S.A.* 80, 7308-7312; Kozbor et al., 1983, *Immunology Today* 4, 72-79; and Olsson et al., 1982, *Meth. Enzymol.* 92, 3-16).

The Ligand can also be a bispecific antibody. Methods for making bispecific antibodies are known in the art. Traditional production of full-length bispecific antibodies is based on the coexpression of two immunoglobulin heavy chain-light chain pairs, where the two chains have different specificities (Milstein et al., 1983, *Nature* 305:537-539). Because of the random assortment of immunoglobulin heavy and light chains, these hybridomas (quadromas) produce a potential mixture of 10 different antibody molecules, of which only one has the correct bispecific structure. Purification of the correct molecule, which is usually performed using affinity chromatography steps, is rather cumbersome, and the product yields are low. Similar procedures are disclosed in International Publication No. WO 93/08829, and in Traunecker et al., *EMBO J.* 10:3655-3659 (1991).

According to a different and more preferred approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies have a hybrid immunoglobulin heavy chain with a first binding specificity in one arm, and a hybrid immunoglobulin heavy chain-light chain pair (providing a second binding specificity) in the other arm. This asymmetric structure facilitates the separation of the desired bispecific compound from unwanted immunoglobulin chain combinations, as the presence of an immunoglobulin light chain in only one half of the bispecific molecule provides for a facile way of separation (International Publication No. WO 94/04690) which is incorporated herein by reference in its entirety.

For further details of generating bispecific antibodies see, for example, Suresh et al., *Methods in Enzymology*, 1986, 121:210. Using such techniques, bispecific antibody Ligands can be prepared for use in the treatment or prevention of disease as defined herein.

Bifunctional antibodies are also described, in European Patent Publication No. EPA 0 105 360. As disclosed in this reference, hybrid or bifunctional antibodies can be derived either biologically, i.e., by cell fusion techniques, or chemically, especially with cross-linking agents or disulfide-bridge forming reagents, and may comprise whole antibodies or fragments thereof. Methods for obtaining such hybrid antibodies are disclosed for example, in International Publication WO 83/03679, and European Patent Publication No. EPA 0 217 577, both of which are incorporated herein by reference.

The Ligand can be a functionally active fragment, derivative or analog of an antibody that immunospecifically binds to cancer cell antigens, viral antigens, or microbial antigens. In this regard, "Functionally active" means that the fragment, derivative or analog is able to elicit anti-anti-idiotype antibodies that recognize the same antigen that the antibody from which the fragment, derivative or analog is derived recognized. Specifically, in a preferred embodiment the antigenicity of the idiotype of the immunoglobulin molecule can be enhanced by deletion of framework and CDR sequences that are C-terminal to the CDR sequence that specifically recognizes the antigen. To determine which CDR sequences bind the antigen, synthetic peptides containing the CDR sequences can be used in binding assays with the antigen by any binding assay method known in the art (e.g., the BIA core assay)

Other useful Ligands include fragments of antibodies such as, but not limited to, F(ab')2 fragments, which contain the variable region, the light chain constant region and the CH1 domain of the heavy chain can be produced by pepsin digestion of the antibody molecule, and Fab fragments, which can be generated by reducing the disulfide bridges of the F(ab')2 fragments. Other useful Ligands are heavy chain and light chain dimers of antibodies, or any minimal fragment thereof such as Fvs or single chain antibodies (SCAs) (e.g., as described in U.S. Pat. No. 4,946,778; Bird, 1988, *Science* 242:423-42; Huston et al., 1988, *Proc. Natl. Acad. Sci. USA* 85:5879-5883; and Ward et al., 1989, *Nature* 334:544-54), or any other molecule with the same specificity as the antibody.

Additionally, recombinant antibodies, such as chimeric and humanized monoclonal antibodies, comprising both human and non-human portions, which can be made using standard recombinant DNA techniques, are useful Ligands. A chimeric antibody is a molecule in which different portions are derived from different animal species, such as those having a variable region derived from a murine monoclonal and a human immunoglobulin constant region. (See, e.g., Cabilly et al., U.S. Pat. No. 4,816,567; and Boss et al., U.S. Pat. No. 4,816,397, which are incorporated herein by reference in their entirety.) Humanized antibodies are antibody molecules from non-human species having one or more complementarity determining regions (CDRs) from the non-human species and a framework region from a human immunoglobulin molecule. (See, e.g., Queen, U.S. Pat. No. 5,585,089, which is incorporated herein by reference in its entirety.) Such chimeric and humanized monoclonal antibodies can be produced by recombinant DNA techniques known in the art, for example using methods described in International Publication No. WO 87/02671; European Patent Publication No. 184,187; European Patent Publication No. 171,496; European Patent Publication No. 173,494; International Publication No. WO 86/01533; U.S. Pat. No. 4,816,567; European Patent Publication No. 125,023; Berter et al., 1988, *Science* 240:1041-1043; Liu et al., 1987, *Proc. Natl. Acad. Sci. USA* 84:3439-3443; Liu et al., 1987, *J. Immunol.* 139:3521-3526; Sun et al., 1987, *Proc. Natl. Acad. Sci. USA* 84:214-218; Nishimura et al., 1987, *Canc. Res.* 47:999-1005; Wood et al., 1985, *Nature* 314:446-449; and Shaw et al., 1988, *J. Natl. Cancer Inst.* 80:1553-1559; Morrison, 1985, *Science* 229:1202-1207; Oi et al., 1986, *BioTechniques* 4:214; U.S. Pat. No. 5,225,539; Jones et al., 1986, *Nature* 321:552-525; Verhoeyan et al. (1988) *Science* 239:1534; and Beidler et al., 1988, *J. Immunol.* 141:4053-4060; each of which is incorporated herein by reference in its entirety.

Completely human antibodies are particularly desirable for Ligands. Such antibodies can be produced using transgenic mice that are incapable of expressing endogenous immunoglobulin heavy and light chains genes, but which can express human heavy and light chain genes. The transgenic mice are immunized in the normal fashion with a selected antigen, e.g., all or a portion of a polypeptide of the invention. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, *Int. Rev. Immunol.* 13:65-93). For a detailed discussion of this technology for producing human antibodies and human monoclonal antibodies and protocols for producing such antibodies, see, e.g., U.S. Pat. No. 5,625,126; U.S. Pat. No. 5,633,425; U.S. Pat. No. 5,569,825; U.S. Pat. No. 5,661,016; and U.S. Pat. No. 5,545,806; each of which is incorporated herein by reference in its entirety. Other human antibodies can be obtained commercially from, for example, Abgenix, Inc. (Freemont, Calif.) and Genpharm (San Jose, Calif.).

Completely human antibodies that recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al. (1994) *Biotechnology* 12:899-903).

In other embodiments, the Ligand is a fusion protein of an antibody, or a functionally active fragment thereof, for example in which the antibody is fused via a covalent bond (e.g., a peptide bond), at either the N-terminus or the C-terminus to an amino acid sequence of another protein (or portion thereof, preferably at least 10, 20 or 50 amino acid portion of the protein) that is not the antibody. Preferably, the antibody or fragment thereof is covalently linked to the other protein at the N-terminus of the constant domain.

The Ligand antibodies include analogs and derivatives that are either modified, i.e, by the covalent attachment of any type of molecule as long as such covalent attachment permits the antibody to retain its antigen binding immunospecificity. For example, but not by way of limitation, the derivatives and analogs of the antibodies include those that have been further modified, e.g., by glycosylation, acetylation, pegylation, phosphorylation, amidation, derivatization by known protecting/blocking groups, proteolytic cleavage, linkage to a cellular Ligand unit or other protein, etc. Any of numerous chemical modifications can be carried out by known techniques, including, but not limited to specific chemical cleavage, acetylation, formylation, metabolic synthesis of tunicamycin, etc. Additionally, the analog or derivative can contain one or more unnaturalamino acids.

The Ligand antibodies include antibodies having modifications (e.g., substitutions, deletions or additions) in amino acid residues that interact with Fc receptors. In particular, the Ligand antibodies include antibodies having modifications in amino acid residues identified as involved in the interaction between the Fc domain and the FcRn receptor (see, e.g., International Publication No. WO 97/34631, which is incorporated herein by reference in its entirety). Antibodies immunospecific for a cancer cell antigen can be obtained commercially, for example, from Genentech (San Francisco, Calif.) or produced by any method known to one of skill in the art such as, e.g., chemical synthesis or recombinant expression techniques. The nucleotide sequence encoding antibodies immunospecific for a cancer cell antigen can be obtained, e.g., from the GenBank database or a database like it, the literature publications, or by routine cloning and sequencing.

In a specific embodiment, known antibodies for the treatment or prevention of cancer are used in accordance with the compositions and methods of the invention. Antibodies immunospecific for a cancer cell antigen can be obtained commercially or produced by any method known to one of skill in the art such as, e.g., chemical synthesis or recombinant expression techniques. The nucleotide sequence encoding antibodies immunospecific for a cancer cell antigen can be obtained, e.g., from the GenBank database or a database like it, the literature publications, or by routine cloning and sequencing. Examples of antibodies available for the treatment of cancer include, but are not limited to, HERCEPTIN (Trastuzumab; Genentech, Calif.) which is a humanized anti-HER2 monoclonal antibody for the treatment of patients with metastatic breast cancer (Stebbing, J., Copson, E., and O'Reilly, S. "Herceptin (trastuzamab) in advanced breast cancer" Cancer Treat Rev. 26, 287-90, 2000); RITUXAN (rituximab; Genentech) which is a chimeric anti-CD20 monoclonal antibody for the treatment of patients with non-Hodgkin's lymphoma; OvaRex (AltaRex Corporation, MA) which is a murine antibody for the treatment of ovarian cancer; Panorex (Glaxo Wellcome, NC) which is a murine $IgG_{2a}$ antibody for the treatment of colorectal cancer; BEC2 (ImClone Systems Inc., NY) which is murine IgG antibody for the treatment of lung cancer; IMC-C225 (Imclone Systems Inc., NY) which is a chimeric IgG antibody for the treatment of head and neck cancer; Vitaxin (MedImmune, Inc., MD) which is a humanized antibody for the treatment of sarcoma; Campath I/H (Leukosite, Mass.) which is a humanized $IgG_1$ antibody for the treatment of chronic lymphocytic leukemia (CLL); Smart M195 (Protein Design Labs, Inc., CA) which is a humanized IgG antibody for the treatment of acute myeloid leukemia (AML); LymphoCide (Immunomedics, Inc., NJ) which is a humanized IgG antibody for the treatment of non-Hodgkin's lymphoma; Smart ID10 (Protein Design Labs, Inc., CA) which is a humanized antibody for the treatment of non-Hodgkin's lymphoma; Oncolym (Techniclone, Inc., CA) which is a murine antibody for the treatment of non-Hodgkin's lymphoma; Allomune (BioTransplant, CA) which is a humanized anti-CD2 mAb for the treatment of Hodgkin's Disease or non-Hodgkin's lymphoma; anti-VEGF (Genentech, Inc., CA) which is humanized antibody for the treatment of lung and colorectal cancers; CEAcide (Immunomedics, NJ) which is a humanized anti-CEA antibody for the treatment of colorectal cancer; IMC-1C11 (ImClone Systems, NJ) which is an anti-KDR chimeric antibody for the treatment of colorectal cancer, lung cancers, and melanoma; and Cetuximab (ImClone, NJ) which is an anti-EGFR chimeric antibody for the treatment of epidermal growth factor positive cancers.

Other antibodies useful in the treatment of cancer include, but are not limited to, antibodies against the following antigens: CA125 (ovarian), CA15-3 (carcinomas), CA19-9 (carcinomas), L6 (carcinomas), Lewis Y (carcinomas), Lewis X (carcinomas), alpha fetoprotein (carcinomas), CA 242 (colorectal), placental alkaline phosphatase (carcinomas), prostate specific antigen (prostate), prostatic acid phosphatase (prostate), epidermal growth factor (carcinomas), MAGE-1 (carcinomas), MAGE-2 (carcinomas), MAGE-3 (carcinomas), MAGE -4 (carcinomas), anti-transferrin receptor (carcinomas), p97 (melanoma), MUC1-KLH (breast cancer), CEA (colorectal), gp 00 (melanoma), MART1 (melanoma), PSA (prostate), IL-2 receptor (T-cell leukemia and lymphomas), CD20 (non-Hodgkin's lymphoma), CD52 (leukemia), CD33 (leukemia), CD22 (lymphoma), human chorionic gonadotropin (carcinoma), CD38 (multiple myeloma), CD40 (lymphoma), mucin (carcinomas), P21 (carcinomas), MPG (melanoma), and Neu oncogene product (carcinomas). Some specific useful antibodies include, but are not limited to, BR96 mAb (Trail, P. A., Willner, D., Lasch, S. J., Henderson, A. J., Hofstead, S. J., Casazza, A. M., Firestone, R. A., Hellström, I., Hellström, K. E., "Cure of Xenografted Human Carcinomas by BR96-Doxorubicin Immunoconjugates" *Science* 1993, 261, 212-215), BR64 (Trail, P A, Willner, D, Knipe, J., Henderson, A. J., Lasch, S. J., Zoeckler, M. E., Trailsmith, M. D., Doyle, T. W., King, H. D., Casazza, A. M., Braslawsky, G. R., Brown, J. P., Hofstead, S. J., (Greenfield, R. S., Firestone, R. A., Mosure, K., Kadow, D. F., Yang, M. B., Hellstrom, K. E., and Hellstrom, I. "Effect of Linker Variation on the Stability, Potency, and Efficacy of Carcinoma-reactive BR64-Doxorubicin Immunoconjugates" *Cancer Research* 1997, 57, 100-105, mAbs against the CD40 antigen, such as S2C6 mAb (Francisco, J. A., Donaldson, K. L., Chace, D., Siegall, C. B., and Wahl, A. F. "Agonistic properties and in vivo antitumor activity of the anti-CD-40 antibody, SGN-14" Cancer Res. 2000, 60, 3225-3231), mAbs against the CD70 antigen, such as 1F6 mAb, and mAbs against the CD30 antigen, such as AC10 (Bowen, M. A., Olsen, K. J., Cheng, L., Avila, D., and Podack, E. R. "Functional effects of CD30 on a large granular lymphoma cell line YT" *J. Immunol.*, 151, 5896-5906, 1993). Many other internalizing antibodies that bind to tumor associated antigens can be used in this invention, and have been reviewed (Franke, A. E., Sievers, E. L., and Scheinberg, D. A., "Cell surface receptor-targeted therapy of acute myeloid leukemia: areview" *Cancer Biother Radiopharm.* 2000, 15, 459-76; Murray, J. L., "Monoclonal antibody treatment of solid tumors: a coming of age" *Semin Oncol.* 2000, 27, 64-70; Breitling, F., and Dubel, S., *Recombinant Antibodies*, John Wiley, and Sons, New York, 1998).

In another specific embodiment, known antibodies for the treatment or prevention of an autoimmune disease are used in accordance with the compositions and methods of the invention. Antibodies immunospecific for an antigen of a cell that is responsible for producing autoimmune antibodies can be obtained from any organization (e.g., a university scientist or a company such as Genentech) or produced by any method known to one of skill in the art such as, e.g., chemical synthesis or recombinant expression techniques. In another embodiment, useful Ligand antibodies that are immunospecific for the treatment of autoimmune diseases include, but are not limited to, Anti-Nuclear Antibody; Anti ds DNA; Anti ss DNA, Anti Cardiolipin Antibody IgM, IgG; Anti Phospholipid Antibody IgM, IgG; Anti SM Antibody; Anti Mitochondrial Antibody; Thyroid Antibody; Microsomal Antibody; Thyroglobulin Antibody; Anti SCL-70; Anti-Jo; Anti-$U_1$RNP; Anti-La/SSB; Anti SSA; Anti SSB; Anti Perital Cells Antibody; Anti Histones; Anti RNP; C-ANCA; P-ANCA; Anti centromere; Anti-Fibrillarin, and Anti GBM Antibody.

In certain preferred embodiments, antibodies useful in the present methods, can bind to both a receptor or a receptor complex expressed on an activated lymphocyte. The receptor or receptor complex can comprise an immunoglobulin gene superfamily member, a TNF receptor superfamily member, an integrin, a cytokine receptor, a chemokine receptor, a major histocompatibility protein, a lectin, or a complement control protein. Non-limiting examples of suitable immunoglobulin superfamily members are CD2, CD3, CD4, CD8, CD19, CD22, CD28, CD79, CD90, CD152/CTLA-4, PD-1, and ICOS. Non-limiting examples of suitable TNF receptor superfamily members are CD27, CD40, CD95/Fas, CD134/OX40, CD137/4-IBB, TNF-R1, TNFR-2, RANK, TACI, BCMA, osteoprotegerin, Apo2/TRAIL-R1, TRAIL-R2, TRAIL-R3, TRAIL-R4, and APO-3. Non-limiting examples of suitable integrins are CD11a, CD11b, CD11c, CD18, CD29, CD41, CD49a, CD49b, CD49c, CD49d, CD49e, CD49f, CD103, and CD104. Non-limiting examples of suitable lectins are C-type, S-type, and I-type lectin.

In one embodiment, the Ligand is an antibody that binds to an activated lymphocyte that is associated with an autoimmune disease.

In another specific embodiment, useful Ligand antibodies that are immunospecific for a viral or a microbial antigen are monoclonal antibodies. Preferably, Ligand antibodies that are immunospecific for a viral antigen or microbial antigen are humanized or human monoclonal antibodies. As used herein, the term "viral antigen" includes, but is not limited to, any viral peptide, polypeptide protein (e.g., HIV gp120, HIV nef, RSV F glycoprotein, influenza virus neuraminidase, influenza virus hemagglutinin, HTLV tax, herpes simplex virus glycoprotein (e.g., gB, gC, gD, and gE) and hepatitis B surface antigen) that is capable of eliciting an immune response. As used herein, the term "microbial antigen" includes, but is not limited to, any microbial peptide, polypeptide, protein, saccharide, polysaccharide, or lipid molecule (e.g., a bacterial, fungi, pathogenic protozoa, or yeast polypeptide including, e.g., LPS and capsular polysaccharide 5/8) that is capable of eliciting an immune response.

Antibodies immunospecific for a viral or microbial antigen can be obtained commercially, for example, from Genentech (San Francisco, Calif.) or produced by any method known to one of skill in the art such as, e.g., chemical synthesis or recombinant expression techniques. The nucleotide sequence encoding antibodies that are immunospecific for a viral or microbial antigen can be obtained, e.g., from the GenBank database or a database like it, the literature publications, or by routine cloning and sequencing.

In a specific embodiment, useful Ligand antibodies are those that are useful for the treatment or prevention of viral or microbial infection in accordance with the methods of the invention. Examples of antibodies available useful for the treatment of viral infection or microbial infection include, but are not limited to, SYNAGIS (MedImmune, Inc., MD) which is a humanized anti-respiratory syncytial virus (RSV) monoclonal antibody useful for the treatment of patients with RSV infection; PRO542 (Progenics) which is a CD4 fusion antibody useful for the treatment of HIV infection; OSTAVIR (Protein Design Labs, Inc., CA) which is a human antibody useful for the treatment of hepatitis B virus; PROTOVIR (Protein Design Labs, Inc., CA) which is a humanized IgG$_1$ antibody useful for the treatment of cytomegalovirus (CMV); and anti-LPS antibodies.

Other antibodies useful in the treatment of infectious diseases include, but are not limited to, antibodies against the antigens from pathogenic strains of bacteria (*Streptococcus pyogenes, Streptococcus pneumoniae, Neisseria gonorrheae, Neisseria meningitidis, Corynebacterium diphtheriae, Clostridium botulinum, Clostridium perfringens, Clostridium tetani, Hemophilus influenzae, Klebsiella pneumoniae, Klebsiella ozaenas, Klebsiella rhinoscleromotis, Staphylococcus aureus, Vibrio colerae, Escherichia coli, Pseudomonas aeruginosa, Campylobacter* (*Vibrio*) *fetus, Aeromonas hydrophila, Bacillus cereus, Edwardsiella tarda, Yersinia enterocolitica, Yersinia pestis, Yersinia pseudotuberculosis, Shigella dysenteriae, Shigella flexneri, Shigella sonnei, Salmonella typhimurium, Treponema pallidum, Treponema pertenue, Treponema carateneum, Borrelia vincentii, Borrelia burgdorferi, Leptospira icterohemorrhagiae, Mycobacterium tuberculosis, Pneumocystis carinii, Francisella tularensis, Brucella abortus, Brucella suis, Brucella melitensis, Mycoplasma* spp., *Rickettsia prowazeki, Rickettsia tsutsugumushi, Chlamydia* spp.); pathogenic fungi (*Coccidioides immitis, Aspergillus fumigatus, Candida albicans, Blastomyces dermatitidis, Cryptococcus neoformans, Histoplasma capsulatum*); protozoa (*Entomoeba histolytica, Toxoplasma gondii, Trichomonas tenas, Trichomonas hominis, Trichomonas vaginalis, Tryoanosoma gambiense, Trypanosoma rhodesiense, Trypanosoma cruzi, Leishmania donovani, Leishmania tropica, Leishmania braziliensis, Pneumocystis pneumonia, Plasmodium vivax, Plasmodium falciparum, Plasmodium malaria*); or Helminiths (*Enterobius vermicularis, Trichuris trichiura, Ascaris lumbricoides, Trichinella spiralis, Strongyloides stercoralis, Schistosoma japonicum, Schistosoma mansoni, Schistosoma haematobium,* and hookworms).

Other antibodies useful in this invention for treatment of viral disease include, but are not limited to, antibodies against antigens of pathogenic viruses, including as examples and not by limitation: Poxyiridae, Herpesviridae, Herpes Simplex virus 1, Herpes Simplex virus 2, Adenoviridae, Papovaviridae, Enteroviridae, Picornaviridae, Parvoviridae, Reoviridae, Retroviridae, influenza viruses, parainfluenza viruses, mumps, measles, respiratory syncytial virus, rubella, Arboviridae, Rhabdoviridae, Arenaviridae, Hepatitis A virus, Hepatitis B virus, Hepatitis C virus, Hepatitis E virus, Non-A/Non-B Hepatitis virus, Rhinoviridae, Coronaviridae, Rotoviridae, and Human Immunodeficiency Virus.

The antibodies suitable for use in the invention can be produced by any method known in the art for the synthesis of antibodies, in particular, by chemical synthesis or by recombinant expression, and are preferably produced by recombinant expression techniques.

5.6.1 Production of Recombinant Antibodies

Ligand antibodies of the invention can be produced using any method known in the art to be useful for the synthesis of antibodies, in particular, by chemical synthesis or by recombinant expression, and are preferably produced by recombinant expression techniques.

Recombinant expression of the Ligand antibodies, or fragment, derivative or analog thereof, requires construction of a nucleic acid that encodes the antibody. If the nucleotide sequence of the antibody is known, a nucleic acid encoding the antibody may be assembled from chemically synthesized oligonucleotides (e.g., as described in Kutmeier et al., 1994, *BioTechniques* 17:242), which involves the synthesis of overlapping oligonucleotides containing portions of the sequence encoding the antibody, annealing and ligation of those oligonucleotides, and then amplification of the ligated oligonucleotides by PCR.

Alternatively, a nucleic acid molecule encoding an antibody can be generated from a suitable source. If a clone containing the nucleic acid encoding the particular antibody is not available, but the sequence of the antibody is known, a nucleic acid encoding the antibody can be obtained from a suitable source (e.g., an antibody cDNA library, or cDNA library generated from any tissue or cells expressing the immunoglobulin) by PCR amplification using synthetic primers hybridizable to the 3' and 5' ends of the sequence or by cloning using an oligonucleotide probe specific for the particular gene sequence.

If an antibody that specifically recognizes a particular antigen is not commercially available (or a source for a cDNA library for cloning a nucleic acid encoding such an immunoglobulin), antibodies specific for a particular antigen can be generated by any method known in the art, for example, by immunizing an animal, such as a rabbit, to generate polyclonal antibodies or, more preferably, by generating monoclonal antibodies, e.g., as described by Kohler and Milstein (1975, *Nature* 256:495-497) or, as described by Kozbor et al. (1983, *Immunology Today* 4:72) or Cole et al. (1985 in *Monoclonal Antibodies and Cancer Therapy*, Alan R. Liss, Inc., pp. 77-96). Alternatively, a clone encoding at least the Fab portion of the antibody can be obtained by screening Fab expression libraries (e.g., as described in Huse et al., 1989, *Science* 246:1275-1281) for clones of Fab fragments that bind the specific antigen or by screening antibody libraries (See, e.g., Clackson et al., 1991, *Nature* 352:624; Hane et al., 1997 *Proc. Natl. Acad. Sci. USA* 94:4937).

Once a nucleic acid sequence encoding at least the variable domain of the antibody is obtained, it can be introduced into a vector containing the nucleotide sequence encoding the constant regions of the antibody (see, e.g., International Publication No. WO 86/05807; International Publication No. WO 89/01036; and U.S. Pat. No. 5,122,464). Vectors containing the complete light or heavy chain that allow for the expression of a complete antibody molecule are available. Then, the nucleic acid encoding the antibody can be used to introduce the nucleotide substitutions or deletion necessary to substitute (or delete) the one or more variable region cysteine residues participating in an intrachain disulfide bond with an amino acid residue that does not contain a sulfhydryl group. Such modifications can be carried out by any method known in the art for the introduction of specific mutations or deletions in a nucleotide sequence, for example, but not limited to, chemical mutagenesis and in vitro site directed mutagenesis (Hutchinson et al., 1978, *J. Biol. Chem.* 253:6551).

In addition, techniques developed for the production of "chimeric antibodies" (Morrison et al., 1984, *Proc. Natl. Acad. Sci.* 81:851-855; Neuberger et al., 1984, *Nature* 312: 604-608; Takeda et al., 1985, *Nature* 314:452-454) by splicing genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine monoclonal antibody and a human immunoglobulin constant region, e.g., humanized antibodies.

Alternatively, techniques described for the production of single chain antibodies (U.S. Pat. No. 4,694,778; Bird, 1988, *Science* 242:423-42; Huston et al., 1988, *Proc. Natl. Acad. Sci. USA* 85:5879-5883; and Ward et al., 1989, *Nature* 334: 544-54) can be adapted to produce single chain antibodies.

Single chain antibodies are formed by linking the heavy and light chain fragments of the Fv region via an amino acid bridge, resulting in a single chain polypeptide. Techniques for the assembly of functional Fv fragments in *E. coli* may also be used (Skerra et al., 1988, *Science* 242:1038-1041).

Antibody fragments that recognize specific epitopes can be generated by known techniques. For example, such fragments include, but are not limited to, the F(ab')2 fragments that can be produced by pepsin digestion of the antibody molecule and the Fab fragments that can be generated by reducing the disulfide bridges of the F(ab')2 fragments.

Once a nucleic acid sequence encoding a Ligand antibody has been obtained, the vector for the production of the antibody can be produced by recombinant DNA technology using techniques well known in the art. Methods that are well known to those skilled in the art can be used to construct expression vectors containing the antibody coding sequences and appropriate transcriptional and translational control signals. These methods include, for example, in vitro recombinant DNA techniques, synthetic techniques, and in vivo genetic recombination. See, for example, the techniques described in Sambrook et al. (1990, *Molecular Cloning, A Laboratory Manual*, $2^{nd}$ Ed., Cold Spring Harbor Laboratory, Cold Spring Harbor, N.Y.) and Ausubel et al. (eds., 1998, *Current Protocols in Molecular Biology*, John Wiley & Sons, NY).

An expression vector comprising the nucleotide sequence of an antibody or the nucleotide sequence of an antibody can be transferred to a host cell by conventional techniques (e.g., electroporation, liposomal transfection, and calcium phosphate precipitation), and the transfected cells are then cultured by conventional techniques to produce the antibody. In specific embodiments, the expression of the antibody is regulated by a constitutive, an inducible or a tissue, specific promoter.

The host cells used to express the recombinant Ligand antibody can be either bacterial cells such as *Escherichia coli*, or, preferably, eukaryotic cells, especially for the expression of whole recombinant immunoglobulin molecule. In particular, mammalian cells such as Chinese hamster ovary cells (CHO), in conjunction with a vector such as the major intermediate early gene promoter element from human cytomegalovirus is an effective expression system for immunoglobulins (Foecking et al., 198, *Gene* 45:101; Cockett et al., 1990, *BioTechnology* 8:2).

A variety of host-expression vector systems can be utilized to express the immunoglobulin Ligands. Such host-expression systems represent vehicles by which the coding sequences of the antibody can be produced and subsequently purified, but also represent cells that can, when transformed or transfected with the appropriate nucleotide coding sequences, express a Ligand immunoglobulin molecule in situ. These include, but are not limited to, microorganisms such as bacteria (e.g., *E. coli* and *B. subtilis*) transformed with recombinant bacteriophage DNA, plasmid DNA or cosmid DNA expression vectors containing immunoglobulin coding sequences; yeast (e.g., *Saccharomyces Pichia*) transformed with recombinant yeast expression vectors containing immunoglobulin coding sequences; insect cell systems infected with recombinant virus expression vectors (e.g., baculovirus) containing the immunoglobulin coding sequences; plant cell systems infected with recombinant virus expression vectors (e.g., cauliflower mosaic virus (CaMV) and tobacco mosaic virus (TMV)) or transformed with recombinant plasmid expression vectors (e.g., Ti plasmid) containing immunoglobulin coding sequences; or mammalian cell systems (e.g., COS, CHO, BH, 293, 293T, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors can be advantageously selected depending upon the use intended for the antibody being expressed. For example, when a large quantity of such a protein is to be produced, vectors that direct the expression of high levels of fusion protein products that are readily purified might be desirable. Such vectors include, but are not limited, to the *E. coli* expression vector pUR278 (Ruther et al., 1983, *EMBO J.* 2:1791), in which the antibody coding sequence may be ligated individually into the vector in frame with the lac Z coding region so that a fusion protein is produced; pIN vectors (Inouye & Inouye, 1985, *Nucleic Acids Res.* 13:3101-3109; Van Heeke & Schuster, 1989, *J. Biol. Chem.* 24:5503-5509); and the like. pGEX vectors can also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) or the analogous virus from *Drosophila Melanogaster* is used as a vector to express foreign genes. The virus grows in *Spodoptera frugiperda* cells. The antibody coding sequence can be cloned individually into non-essential regions (for example the polyhedrin gene) of the virus and placed under control of an AcNPV promoter (for example the polyhedrin promoter).

In mammalian host cells, a number of viral-based expression systems can be utilized. In cases where an adenovirus is used as an expression vector, the antibody coding sequence of interest can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) results in a recombinant virus that is viable and capable of expressing the immunoglobulin molecule in infected hosts. (e.g., see Logan & Shenk, 1984, *Proc. Natl. Acad. Sci. USA* 81:355-359). Specific initiation signals can also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (see Bittner et al., 1987, *Methods in Enzymol.* 153:51-544).

In addition, a host cell strain can be chosen to modulate the expression of the inserted sequences, or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins and gene products. Appropriate cell lines or host systems can be chosen to ensure the correct modification and processing of the foreign protein expressed.

To this end, eukaryotic host cells that possess the cellular machinery for proper processing of the primary transcript, glycosylation, and phosphorylation of the gene product can be used. Such mammalian host cells include, but are not limited to, CHO, VERY, BH, Hela, COS, MDCK, 293, 293T, 3T3, W138, BT483, Hs578T, HTB2, BT20 and T47D, CRL7030 and Hs578Bst.

For long-term, high-yield production of recombinant proteins, stable expression is preferred. For example, cell lines that stably express an antibody can be engineered. Rather than using expression vectors that contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells can be allowed to grow for 1-2 days in an enriched media, and then are switched to a selective media. The selectable marker in the recombinant plasmid confers resistance to the selection and allows cells to stably integrate the plasmid into their chromosomes and grow to form foci that in turn can be cloned and expanded into cell lines. This method can advantageously be used to engineer cell lines which express the antibody Such engineered cell lines can be particularly useful in screening and evaluation of tumor antigens that interact directly or indirectly with the antibody Ligand.

A number of selection systems can be used, including but not limited to the herpes simplex virus thymidine kinase (Wigler et al., 1977, *Cell* 11:223), hypoxanthine-guanine phosphoribosyltransferase (Szybalska & Szybalski, 192, *Proc. Natl. Acad. Sci. USA* 48:202), and adenine phosphoribosyltransferase (Lowy et al., 1980, *Cell* 22:817) genes can be employed in tk-, hgprt- or aprt-cells, respectively. Also, antimetabolite resistance can be used as the basis of selection for the following genes: dhfr, which confers resistance to methotrexate (Wigler et al., 1980, *Proc. Natl. Acad. Sci. USA* 77:357; O'Hare et al., 1981, *Proc. Natl. Acad. Sci. USA* 78:1527); gpt, which confers resistance to mycophenolic acid (Mulligan & Berg, 1981, *Proc. Natl. Acad. Sci. USA* 78:2072); neo, which confers resistance to the aminoglycoside G-418 (*Clinical Pharmacy* 12:488-505; Wu and Wu, 1991, *Biotherapy* 3:87-95; Tolstoshev, 1993, *Ann. Rev. Pharmacol. Toxicol.* 32:573-596; Mulligan, 1993, *Science* 260: 926-932; and Morgan and Anderson, 1993, *Ann. Rev. Biochem.* 62:191-217; May, 1993, *TIB TECH* 11(5):155-215) and hygro, which confers resistance to hygromycin (Santerre et al., 1984, *Gene* 30:147). Methods commonly known in the art of recombinant DNA technology which can be used are described in Ausubel et al. (eds., 1993, *Current Protocols in Molecular Biology*, John Wiley & Sons, NY; Kriegler, 1990, *Gene Transfer and Expression, A Laboratory Manual*, Stockton Press, NY; and in Chapters 12 and 13, Dracopoli et al. (eds), 1994, *Current Protocols in Human Genetics*, John Wiley & Sons, NY.; Colberre-Garapin et al., 1981, *J. Mol. Biol.* 150:1).

The expression levels of an antibody can be increased by vector amplification (for a review, see Bebbington and Hentschel, *The use of vectors based on gene amplification for the expression of cloned genes in mammalian cells in DNA cloning*, Vol. 3. (Academic Press, New York, 1987)). When a marker in the vector system expressing an antibody is amplifiable, an increase in the level of inhibitor present in culture of host cell will increase the number of copies of the marker gene. Since the amplified region is associated with the nucleotide sequence of the antibody, production of the antibody will also increase (Crouse et al., 1983, *Mol. Cell. Biol.* 3:257).

The host cell can be co-transfected with two expression vectors of the invention, the first vector encoding a heavy chain derived polypeptide and the second vector encoding a light chain derived polypeptide. The two vectors can contain identical selectable markers that enable equal expression of heavy and light chain polypeptides. Alternatively, a single vector can be used to encode both heavy and light chain polypeptides. In such situations, the light chain should be placed before the heavy chain to avoid an excess of toxic free heavy chain (Proudfoot, 1986, *Nature* 322:52; Kohler, 1980, *Proc. Natl. Acad. Sci. USA* 77:2197). The coding sequences for the heavy and light chains can comprise cDNA or genomic DNA.

Once the antibody has been recombinantly expressed, it can be purified using any method known in the art for purification of an antibody, for example, by chromatography (e.g., ion exchange, affinity, particularly by affinity for the specific antigen after Protein A, and sizing column chromatography), centrifugation, differential solubility, or by any other standard technique for the purification of proteins.

In a preferred embodiment, the Ligand is an antibody.

In a more preferred embodiment, the Ligand is a monoclonal antibody.

In any case, the hybrid antibodies have a dual specificity, preferably with one or more binding sites specific for the hapten of choice or one or more binding sites specific for a target antigen, for example, an antigen associated with a tumor, an autoimmune disease, an infectious organism, or other disease state.

5.7 Synthesis of the Compounds of the Invention

As described in more detail below, the Compounds of the Invention are conveniently prepared using a Linker having two or more Reactive Sites for binding to the Drug and Ligand. In one aspect of the invention, a Linker has a Reactive site which has an electrophilic group that is reactive to a nucleophilic group present on a Ligand. Useful nucleophilic groups on a Ligand include but are not limited to, sulfhydryl, hydroxyl and amino groups. The heteroatom of the nucleophilic group of a Ligand is reactive to an electrophilic group on a Linker and forms a covalent bond to a Linker unit. Useful electrophilic groups include, but are not limited to, maleimide and haloacetamide groups. The electrophilic group provides a convenient site for Ligand attachment.

In another embodiment, a Linker has a Reactive site which has a nucleophilic group that is reactive to an electrophilic group present on a Ligand. Useful electrophilic groups on a Ligand include, but are not limited to, aldehyde and ketone carbonyl groups. The heteroatom of a nucleophilic group of a Linker can react with an electrophilic group on a Ligand and form a covalent bond to a Ligand unit. Useful nucleophilic groups on a Linker include, but are not limited to, hydrazide, oxime, amino, hydrazine, thiosemicarbazone, hydrazine carboxylate, and arylhydrazide. The electrophilic group on a Ligand provides a convenient site for attachment to a Linker.

Carboxylic acid functional groups and chloroformate functional groups are also useful reactive sites for a Linker because they can react with primary or secondary amino groups of a Drug to form an amide linkage. Also useful as a reactive site is a carbonate functional group on a Linker which can react with an amino group or hydroxyl group of a Drug to form a carbamate linkage or carbonate linkage, respectively. Similarly, a Drug's phenol moiety can react with the Linker, existing as an alcohol, under Mitsunobu conditions.

Typically, peptide-based Drugs can be prepared by forming a peptide bond between two or more amino acids and/or peptide fragments. Such peptide bonds can be prepared, for example, according to the liquid phase synthesis method (see E. Schröder and K. Lübke, "The Peptides", volume 1, pp 76-136, 1965, Academic Press) that is well known in the field of peptide chemistry.

In one embodiment, a Drug is prepared by combining about a stoichiometric equivalent of a dipeptide and a tripeptide, preferably in a one-pot reaction under suitable condensation conditions. This approach is illustrated in the following Schemes 5-7. Thus, the tripeptide 6 can be prepared as shown in Scheme 5, and the dipeptide 9 can be prepared as shown in Scheme 6. The two fragments 6 and 9 can be condensed to provide a Drug 10 as shown in Scheme 7.

The synthesis of an illustrative Stretcher having an electrophilic maleimide group is illustrated in Schemes 8-9. General synthetic methods useful for the synthesis of a Linker are described in Scheme 10. Scheme 11 shows the construction of a Linker unit having a val-cit group, an electrophilic maleimide group and a PAB self-immolative Spacer group. Scheme 12 depicts the synthesis of a Linker having a phe-lys group, an electrophilic maleimide group, with and without the PAB self-immolative Spacer group. Scheme 13 presents a general outline for the synthesis of a Drug-Linker Compound, while Scheme 14 presents an alternate route for preparing a Drug-Linker Compound. Scheme 15 depicts the synthesis of a branched linker containing a BHMS group. Scheme 16 outlines the attachment of a Ligand to a Drug-Linker Compound to form a Drug-Linker-Ligand Conjugate, and Scheme 17 illustrates the synthesis of Drug-Linker-Ligand Conjugates having 2 or 4 drugs per Ligand.

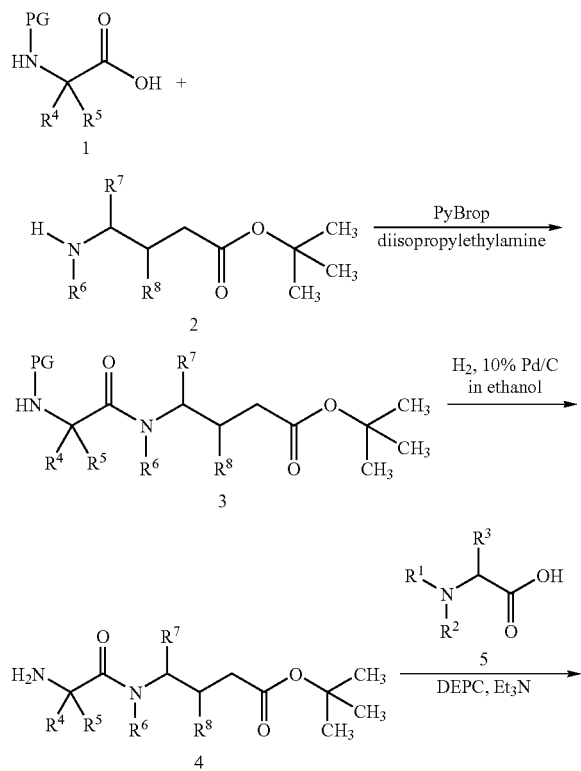

-continued

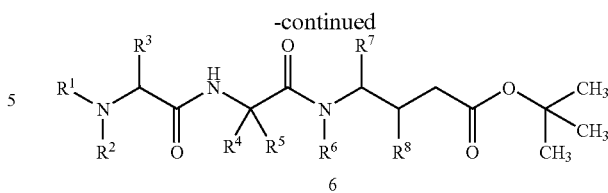

As illustrated in Scheme 5, a protected amino acid 1 (where PG represents an amine protecting group, $R^4$ is selected from hydrogen, $C_1$-$C_8$ alkyl, $C_3$-$C_8$ carbocycle, —O—($C_1$-$C_8$ alkyl), -aryl, alkyl-aryl, alkyl-($C_3$-$C_8$ carbocycle), $C_3$-$C_8$ heterocycle, alkyl-($C_3$-$C_8$ heterocycle) wherein $R^5$ is selected from H and methyl; or $R^4$ and $R^5$ join, have the formula $(CR^aR^b)_n$— wherein $R^a$ and $R^b$ are independently selected from hydrogen, $C_1$-$C_8$ alkyl and $C_3$-$C_8$ carbocycle and n is selected from 2, 3, 4, 5 and 6, and form a ring with the carbon atom to which they are attached) is coupled to t-butyl ester 2 (where $R^6$ is selected from —H and —$C_1$-$C_8$ alkyl; and $R^7$ is selected from hydrogen, $C_1$-$C_8$ alkyl, $C_3$-$C_8$ carbocycle, —O—($C_1$-$C_8$ alkyl), -aryl, alkyl-aryl, alkyl-($C_3$-$C_8$ carbocycle), $C_3$-$C_8$ heterocycle and alkyl-($C_3$-$C_8$ heterocycle)) under suitable coupling conditions, e.g., in the presence of PyBrop and diisopropylethylamine, or using DCC (see, for example, Miyazaki, K. et. al. *Chem. Pharm. Bull* 1995, 43(10), 1706-1718).

Suitable protecting groups PG, and suitable synthetic methods to protect an amino group with a protecting group are well known in the art. See, e.g., Greene, T. W. and Wuts, P.G.M., Protective Groups in Organic Synthesis, 2nd Edition, 1991, John Wiley & Sons. Preferred protected amino acids 1 are PG-Ile and, particularly, PG-Val, while other suitable protected amino acids include, without limitation: PG-cyclohexylglycine, PG-cyclohexylalanine, PG-aminocyclopropane-1-carboxylic acid, PG-aminoisobutyric acid, PG-phenylalanine, PG-phenylglycine, and PG-tert-butylglycine. Z is a preferred protecting group. Fmoc is another preferred protecting group. A preferred t-butyl ester 2 is dolaisoleuine t-butyl ester.

The dipeptide 3 can be purified, e.g., using chromatography, and subsequently deprotected, e.g., using $H_2$ and 10% Pd—C in ethanol when PG is benzyloxycarbonyl, or using diethylamine for removal of an Fmoc protecting group. The resulting amine 4 readily forms a peptide bond with an amino acid 5 (where $R^1$ is selected from —H, —$C_1$-$C_8$ alkyl and —$C_3$-$C_8$ carbocycle; and $R^2$ is selected from —H and —$C_1$-$C_8$ alkyl; or $R^1$ and $R^2$ join, have the formula —$(CR^aR^b)_n$— wherein $R^a$ and $R^b$ are independently selected from —H, —$C_1$-$C_8$ alkyl and —$C_3$-$C_8$ carbocycle and n is selected from 2, 3, 4, 5 and 6, and form a ring with the nitrogen atom to which they are attached; and $R^3$ is selected from hydrogen, $C_1$-$C_8$ alkyl, $C_3$-$C_8$ carbocycle, —O—($C_1$-$C_8$ alkyl), -aryl, alkyl-aryl, alkyl-($C_3$-$C_8$ carbocycle), $C_3$-$C_8$ heterocycle and alkyl-($C_3$-$C_8$ heterocycle)). N,N-Dialkyl amino acids are preferred amino acids 5, such as commercially available N,N-dimethyl valine. Other N,N-dialkyl amino acids can be prepared by reductive bis-alkylation using known procedures (see, e.g., Bowman, R. E, Stroud, H. H *J. Chem. Soc.*, 1950, 1342-1340). Fmoc-Me-L-Val and Fmoc-Me-L-glycine are two preferred amino acids 5 useful for the synthesis of N-monoalkyl derivatives. The amine 4 and the amino acid 5 react to provide the tripeptide 6 using coupling reagent DEPC with triethylamine as the base.

Illustrative DEPC coupling methodology and the PyBrop coupling methodology shown in Scheme 5 are outlined below in General Procedure A and General Procedure B, respectively. Illustrative methodology for the deprotection of a Z-protected amine via catalytic hydrogenation is outlined below in General Procedure C.

General Procedure A: Peptide synthesis using DEPC. The N-protected or N,N-disubstituted amino acid or peptide 4 (1.0 eq.) and an amine 5 (1.1 eq.) are diluted with an aprotic organic solvent, such as dichloromethane (0.1 to 0.5 M). An organic base such as triethylamine or diisopropylethylamine (1.5 eq.) is then added, followed by DEPC (1.1 eq.). The resulting solution is stirred, preferably under argon, for up to 12 hours while being monitored by HPLC or TLC. The solvent is removed in vacuo at room temperature, and the crude product is purified using, for example, HPLC or flash column chromatography (silica gel column). Relevant fractions are combined and concentrated in vacuo to afford tripeptide 6 which is dried under vacuum overnight.

General procedure B: Peptide synthesis using PyBrop. The amino acid 2 (1.0 eq.), optionally having a carboxyl protecting group, is diluted with an aprotic organic solvent such as dichloromethane or DME to provide a solution of a concentration between 0.5 and 1.0 mM, then diisopropylethylamine (1.5 eq.) is added. Fmoc-, or Z-protected amino acid 1 (1.1 eq.) is added as a solid in one portion, then PyBrop (1.2 eq.) is added to the resulting mixture. The reaction is monitored by TLC or HPLC, followed by a workup procedure similar to that described in General Procedure A.

General procedure C: Z-removal via catalytic hydrogenation. Z-protected amino acid or peptide 3 is diluted with ethanol to provide a solution of a concentration between 0.5 and 1.0 mM in a suitable vessel, such as a thick-walled round bottom flask. 10% palladium on carbon is added (5-10% w/w) and the reaction mixture is placed under a hydrogen atmosphere. Reaction progress is monitored using HPLC and is generally complete within 1-2 h. The reaction mixture is filtered through a pre-washed pad of celite and the celite is again washed with a polar organic solvent, such as methanol after filtration. The eluent solution is concentrated in vacuo to afford a residue which is diluted with an organic solvent, preferably toluene. The organic solvent is then removed in vacuo to afford the deprotected amine 4.

Table 1 lists representative examples of tripeptide intermediates (compounds 39-43) that were prepared according to Scheme 5.

TABLE 1

| Compound | $X^1$ | $X^2$ |
|---|---|---|
| 39 | Fmoc-N-Me-L-val | L-val |
| 40 | Fmoc-N-Me-L-val | L-ile |
| 41 | Fmoc-N-Me-gly | L-ile |
| 42 | dov | L-val |
| 43 | dov | L-ile |

$^a$dov = N,N-dimethyl-L-valine

The dipeptide 9 can be readily prepared by condensation of the modified amino acid Boc-Dolaproine 7 (see, for example, Pettit, G. R., et al. *Synthesis*, 1996, 719-725), with (1S,2R)-norephedrine, L- or D-phenylalaminol, or with synthetic p-acetylphenethylamine 8 (U.S. Pat. No. 3,445,518 to Shavel et al.) using condensing agents well known for peptide chemistry, such as, for example, DEPC in the presence of triethylamine, as shown in Scheme 6. Compound 7 may also be condensed with commercially available compounds in this manner to form dipeptides of formula 9. Examples of commercially available compounds useful for this purpose include, but are not limited to, norephedrine, ephedrine, and stereoisomers thereof (Sigma-Sigma-Aldrich), L- or D-phenylalaminol (Sigma-Aldrich), 2-phenylethylamine (Sigma-Aldrich), 2-(4-aminophenyl)ethylamine (Sigma-Aldrich), 1,2-ethanediamine-1,2-diphenyl (Sigma-Aldrich), or 4-(2-aminoethyl)phenol (Sigma-Aldrich), or with synthetically prepared p-acetylphenethylamine, aryl- and heterocycloamides of L-phenylalanine, 1-azidomethyl-2-phenylethylamine (prepared from phenylalaninol according to a general procedure described in *J. Chem. Research* (S), 1992, 391), and 1-(4-hydroxyphenyl)-2-phenylethylamine (European Patent Publication No. 0356035 A2) among others.

Scheme 6

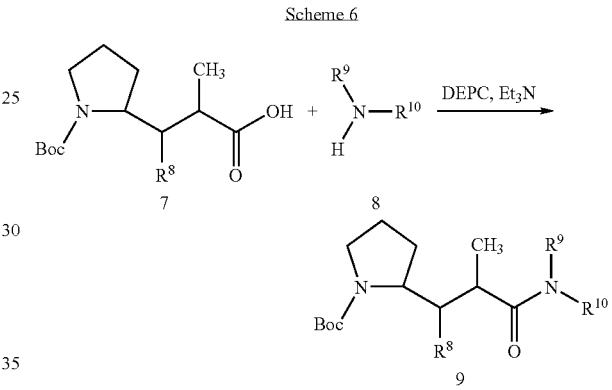

where $R^8$ is independently selected from —H, —OH, —$C_1$-$C_8$ alkyl, —$C_3$-$C_8$ carbocycle and —O—($C_1$-$C_8$ alkyl); $R^9$ is selected from —H and —$C_1$-$C_8$ alkyl; and $R^{10}$ is selected from:

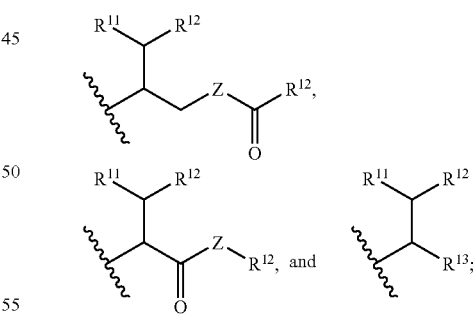

where Z is —O—, —S—, —NH— or —N($R^{14}$)—; $R^{11}$ is selected from —H, —OH, —$NH_2$, —$NHR^{14}$, —N($R^{14}$)$_2$, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle); or $R^{11}$ is an oxygen atom which forms a carbonyl unit (C=O) with the carbon atom to which it is attached and a hydrogen atom on this carbon atom is replaced by one of the bonds in the (C=O) double bond; each $R^{12}$ is independently selected from -aryl and —$C_3$-$C_8$ heterocycle; $R^{13}$ is selected from —H, —OH, —NH$_2$, —NHR$^{14}$, —N(R$^{14}$)$_2$, —C$_1$-C$_8$ alkyl, —C$_3$-C$_8$ carbocycle, —O—(C$_1$-C$_8$ alkyl), -aryl, —C$_1$-C$_8$ alkyl-aryl, —C$_1$-C$_8$ alkyl-(C$_3$-C$_8$ carbocycle), —C$_3$-C$_8$ heterocycle and —C$_1$-C$_8$ alkyl-(C$_3$-C$_8$ heterocycle); and each R$^{14}$ is independently —H or —C$_1$-C$_8$ alkyl.

Table 2 lists representative examples of dipeptides (Compounds 44-48) that were prepared according to Scheme 6.

Scheme 7 illustrates a procedure useful for coupling tripeptide 6 and dipeptide 9 to form Drug 10. The coupling of 6 and 9 can be accomplished using a strong acid, e.g. TFA, to facilitate Boc and t-butyl ester cleavage, from dipeptide 9 and tripeptide 6, respectively, followed by condensation conditions, e.g., utilizing DEPC, or similar coupling reagent, in the presence of excess base (triethylamine or equivalent) to provide Drug 10.

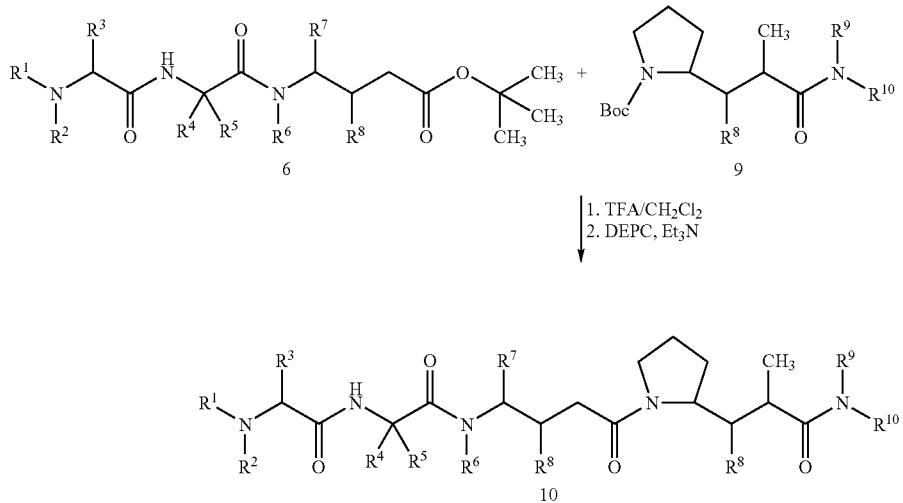

An illustrative procedure for the synthesis of Drug 10 as depicted in Scheme 7 is outlined below in General Procedure D.

The $R^{10}$ group of a Drug of general formula 10 can be further modified, if desired, to include a functional group that allows the drug to be attached to a Linker. Examples of useful modifications to the $R^{10}$ group of a Drug 10, include, but are not limited to the chemical transformations described below.

When $R^{10}$ is

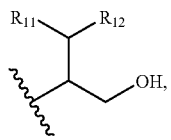

the hydroxyl group of $R^{10}$ can be reacted with commercially available or synthetically derived carboxylic acids or carboxylic acid derivatives, including but not limited to, carboxylic esters, acid chlorides, anhydrides and carbonates to provide the corresponding esters according to well known methods in the art. Coupling reagents, including, but not limited to DCC/DMAP and EDCI/HOBt, can be useful in such coupling reactions between alcohols and carboxylic acids or carboxylic acid derivatives. In a preferred embodiment carboxylic acids are substituted or unsubstituted arylcarboxylic acids, for example, 4-aminobenzoic acid. Thus, condensation of a hydroxyl group of the $R^{10}$ group shown above with carboxylic acids provides drugs of the general structure 10 where $R^{10}$ is

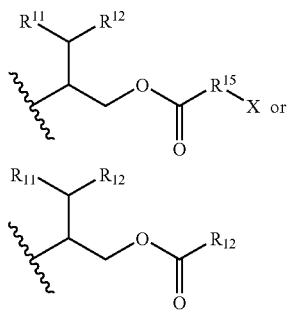

and where $R^{11}$, $R^{12}$, $R^{14}$ and $R^{15}$ are as previously described herein and X is selected from —OH, —NH$_2$ and —NHR$^{14}$ When $R^{10}$ is

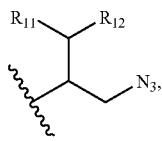

the azido group of the drug can be reduced (for an example see J. Chem. Research (S), 1992, 391) to provide the corresponding amino derivative wherein $R^{10}$ is

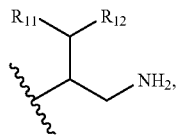

the amino group of which can be reacted with the carboxyl group of a carboxylic acid under general peptide coupling conditions to provide drugs of general structure 10, where $R^{10}$ is

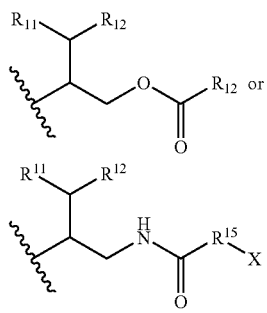

and where $R^{11}$, $R^{12}$, $R^{14}$ and $R^{15}$ are as previously described herein and X is selected from —OH, —NH$_2$ and —NHR$^{14}$Carboxylic acids useful in the above regard include, but are not limited to, 4-aminobenzoic acid, p-acetylbenzoic acid and 2-amino-4-thiazolecarboxylic acid (Tyger Scientific, Inc., Ewing, N.J.).

An Fmoc-protected amino group may be present on an amine-containing $R^{10}$ group of Drug 10 (e.g., as depicted in Table 2). The Fmoc group is removable from the protected amine using diethylamine (see General Procedure E as an illustrative example described below).

General procedure D: Drug synthesis. A mixture of dipeptide 9 (1.0 eq.) and tripeptide 6 (1 eq.) is diluted with an aprotic organic solvent, such as dichloromethane, to form a 0.1M solution, then a strong acid, such as trifluoroacetic acid (½ v/v) is added and the resulting mixture is stirred under a nitrogen atmosphere for two hours at 0° C. The reaction can be monitored using TLC or, preferably, HPLC. The solvent is removed in vacuo and the resulting residue is azeotropically dried twice, preferably using toluene. The resulting residue is dried under high vacuum for 12 h and then diluted with and aprotic organic solvent, such as dichloromethane. An organic base such as triethylamine or diisopropylethylamine (1.5 eq.) is then added, followed by either PyBrop (1.2 eq.) or DEPC (1.2 eq.) depending on the chemical functionality on the residue. The reaction mixture is monitored by either TLC or HPLC and upon completion, the reaction is subjected to a workup procedure similar or identical to that described in General Procedure A.

General procedure E: Fmoc-removal using diethylamine. An Fmoc-protected Drug 10 is diluted with an aprotic organic solvent such as dichloromethane and to the resulting solution is added diethylamine (½ v/v). Reaction progress is monitored by TLC or HPLC and is typically complete within 2 h. The reaction mixture is concentrated in vacuo and the resulting residue is azeotropically dried, preferably using toluene, then dried under high vacuum to afford Drug 10 having a deprotected amino group.

Thus, the above methods are useful for making Drugs that can be used in the present invention.

To prepare a Drug-Linker Compound of the present invention, the Drug is reacted with a reactive site on the Linker. In general, the Linker can have the structure:

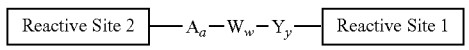

when both a Spacer unit (—Y—) and a Stretcher unit (-A-) are present. Alternately, the Linker can have the structure:

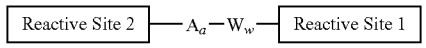

when the Spacer unit (—Y—) is absent.

The Linker can also have the structure:

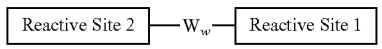

when both the Stretcher unit (-A-) and the Spacer unit (—Y—) are absent.

In general, a suitable Linker has an Amino Acid unit linked to an optional Stretcher Unit and an optional Spacer Unit. Reactive Site 1 is present at the terminus of the Spacer and Reactive site 2 is present at the terminus of the Stretcher. If a Spacer unit is not present, then Reactive site 1 is present at the C-terminus of the Amino Acid unit.

In one embodiment of the invention, Reactive Site No. 1 is reactive to a nitrogen atom of the Drug, and Reactive Site No. 2 is reactive to a sulfhydryl group on the Ligand. Reactive Sites 1 and 2 can be reactive to different functional groups.

In one aspect of the invention, Reactive Site No. 1 is

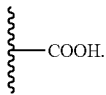

In another aspect of the invention, Reactive Site No. 1 is

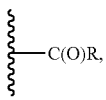

wherein R is —Br, —Cl, —O-Su or —O-(4-nitrophenyl).

In one embodiment, Reactive Site No. 1 is

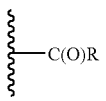

wherein R is —Br, —Cl, —O-Su or —O-(4-nitrophenyl), when a Spacer unit (—Y—) is absent.

Linkers having

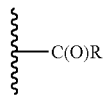

at Reactive Site No. 1 where R is —Br or —Cl can be prepared from Linkers having

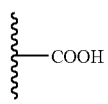

at Reactive Site No. 1 by reacting the —COOH group with $PX_3$ or $PX_5$, where X is —Br or —Cl. Alternatively, linkers having

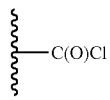

at Reactive Site No. 1 can be prepared from Linkers having

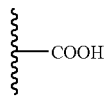

at Reactive Site No. 1 by reacting the —COOH group with thionyl chloride. For a general discussion of the conversion of carboxylic acids to acyl halides, see March, Advanced Organic Chemistry—Reactions, Mechanisms and Structure, 4th Ed., 1992, John Wiley and Sons, New York, p. 437-438.

In another aspect of the invention, Reactive Site No. 1 is

In still another aspect of the invention, Reactive Site No. 1 is

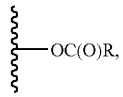

wherein R is —Cl, —O—CH(Cl)CCl$_3$ or —O-(4-nitrophenyl).

Linkers having

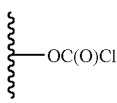

at Reactive Site No. 1 can be prepared from Linkers having

at Reactive Site No. 1 by reacting the —OH group with phosgene or triphosgene to form the corresponding chloroformate. Linkers having

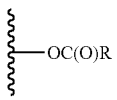

at Reactive Site No. 1 where R is —O—CH(Cl)CCl$_3$ or —O-(4-nitrophenyl) can be prepared from Linkers having

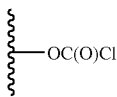

at Reactive Site No. 1 by reacting the —OC(O)Cl group with HO—CH(Cl)CCl$_3$ or HO-(4-nitrophenyl), respectively. For a discussion of this chemistry, see March, Advanced Organic Chemistry—Reactions, Mechanisms and Structure, 4th Ed., 1992, John Wiley and Sons, New York, p. 392.

In a further aspect of the invention, Reactive Site No. 1 is

wherein X is —F, —Cl, —Br, —I, or a leaving group such as —O-mesyl, —O-tosyl or —O-triflate.

Linkers having

at Reactive Site No. 1 where X is —O-mesyl, —O-tosyl and O-triflate can be prepared from Linkers having

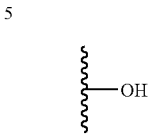

at Reactive Site No. 1 by reacting the —OH group with various reagents, including HCl, SOCl$_2$, PCl$_5$, PCl$_3$ and POCl$_3$ (where X is Cl); HBr, PBr$_3$, PBr$_5$ and SOBr$_2$ (where X is Br); HI (where X is I); and CH$_3$CH$_2$NSF$_3$ (DAST), SF$_4$, SeF$_4$ and p-toluenesulfonyl fluoride (where X is F). For a general discussion on the conversion of alcohols to alkyl halides, see March, Advanced Organic Chemistry—Reactions, Mechanisms and Structure, 4th Ed., 1992, John Wiley and Sons, New York, p. 431-433.

Linkers having

at Reactive Site No. 1 where X is —O-mesyl, —O-tosyl and —O-triflate, can be prepared from Linkers having

at Reactive Site No. 1 by reacting the —OH group with various mesylating, tosylating and triflating reagents, respectively. Such reagents and methods for their use will be well known to one of ordinary skill in the art of organic synthesis. For a general discussion of mesyl, tosyl and triflates as leaving groups, see March, Advanced Organic Chemistry-Reactions, Mechanisms and Structure, 4th Ed., 1992, John Wiley and Sons, New York, p. 353-354.

In one embodiment, when a Spacer unit (—Y—) is present, Reactive Site No. 1 is

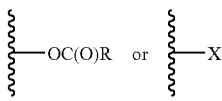

wherein R is —Cl, —O—CH(Cl)CCl$_3$ or —O-(4-nitrophenyl) and X is —F, —Cl, —Br, —I, or a leaving group such as —O-mesyl, —O-tosyl or —O-triflate.

In another aspect of the invention, Reactive Site No. 1 is

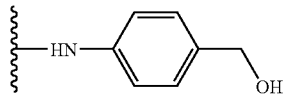

In still another aspect of the invention, Reactive Site No. 1 is a p-nitrophenyl carbonate having the formula

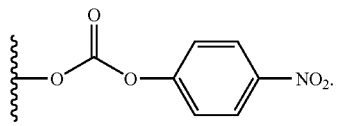

In one aspect of the invention, Reactive Site No. 2 is a thiol-accepting group. Suitable thiol-accepting groups include haloacetamide groups having the formula

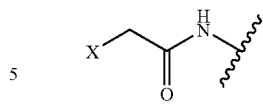

where X represents a leaving group, preferably O-mesyl, O-tosyl, —Cl, —Br, or —I; or a maleimide group having the formula

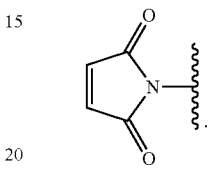

Useful Linkers can be obtained via commercial sources, such as Molecular Biosciences Inc. (Boulder, Colo.), or synthesized in accordance with procedures described in U.S. Pat. No. 6,214,345 to Firestone et al., summarized in Schemes 8-10 below.

Scheme 8

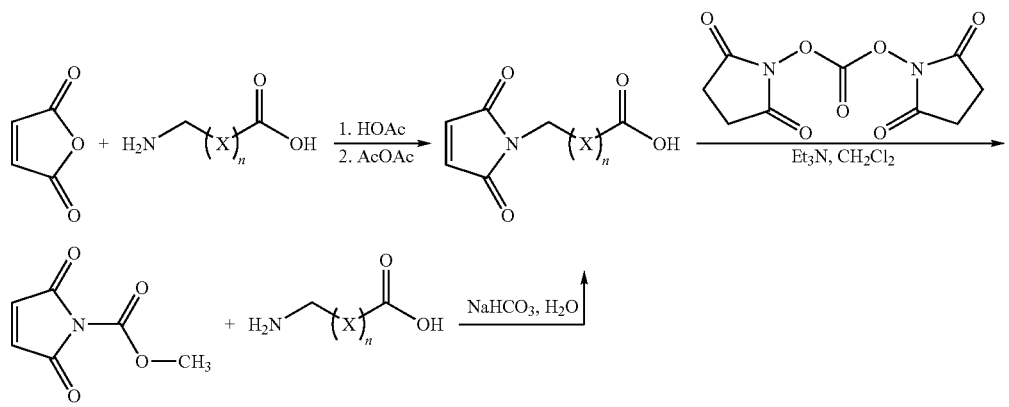

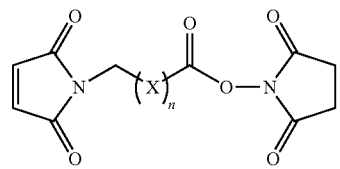

11 where X is —CH$_2$— or —CH$_2$OCH$_2$—; and n is an integer ranging either from 0-10 when X is —CH$_2$—; or 1-10 when X is —CH$_2$OCH$_2$—.

The method shown in Scheme 9 combines maleimide with a glycol under Mitsunobu conditions to make a polyethylene glycol maleimide Stretcher (see for example, Walker, M. A. *J. Org. Chem.* 1995, 60, 5352-5), followed by installation of a p-nitrophenyl carbonate Reactive Site group.

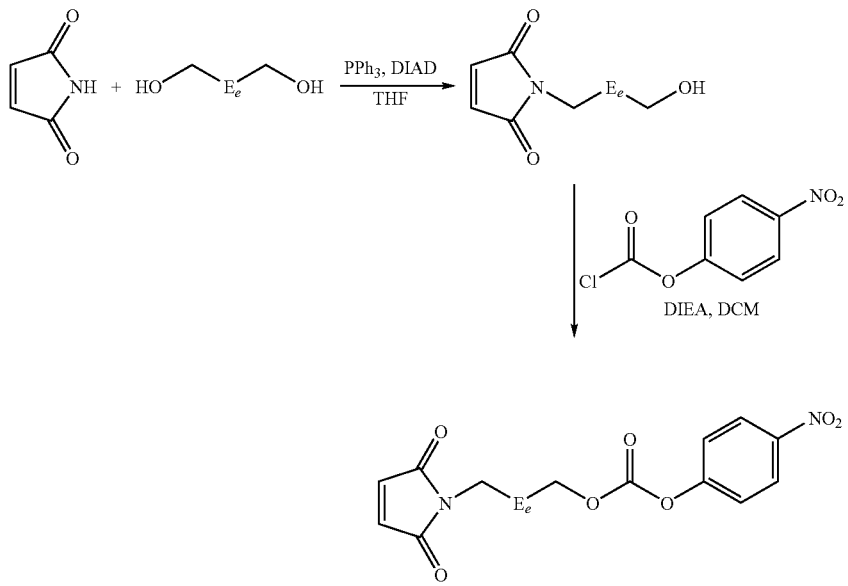

where E is —CH$_2$— or —CH$_2$OCH$_2$—; and e is an integer ranging from 0-8;

Alternatively, PEG-maleimide and PEG-haloacetamide stretchers can be prepared as described by Frisch, et al., *Bioconjugate Chem.* 1996, 7, 180-186.

Scheme 10 illustrates a general synthesis of an illustrative Linker unit containing a maleimide Stretcher group and optionally a p-aminobenzyl ether self-immolative Spacer.

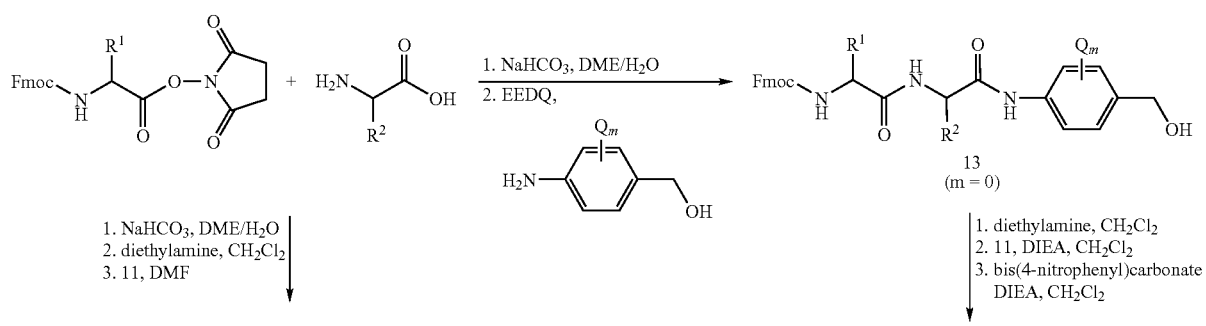

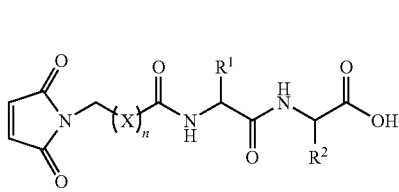

R$^1$ = benzyl; R$^2$ = (CH$_2$)$_4$NHMtr (15)
R$^1$ = isopropyl; R$^2$ = (CH$_2$)$_3$NHCONH$_2$ (16)

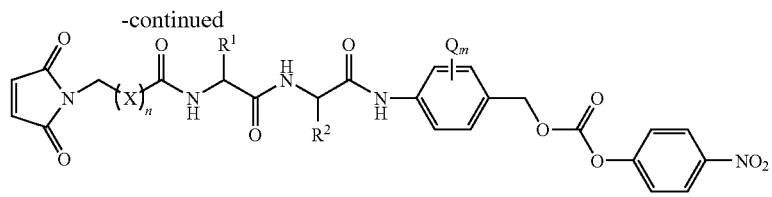

14
(m = 0)

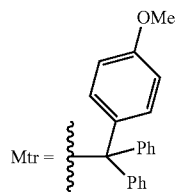

where Q is —C$_1$-C$_8$ alkyl, —O—(C$_1$-C$_8$ alkyl), -halogen, -nitro or -cyano; m is an integer ranging from 0-4; and n is an integer ranging from 0-10.

Useful Stretchers may be incorporated into a Linker using the commercially available intermediates from Molecular Biosciences (Boulder, Colo.) described below by utilizing known techniques of organic synthesis.

Stretchers of formula (IIIa) can be introduced into a Linker by reacting the following intermediates with the N-terminus of an Amino Acid unit as depicted in Schemes 11 and 12:

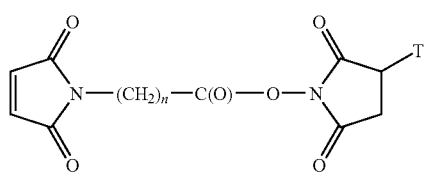

where n is an integer ranging from 1-10 and T is —H or —SO$_3$Na;

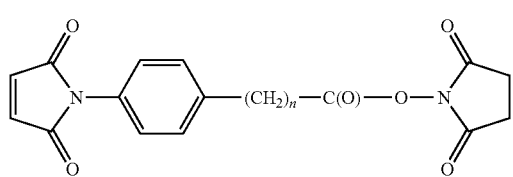

where n is an integer ranging from 0-3;

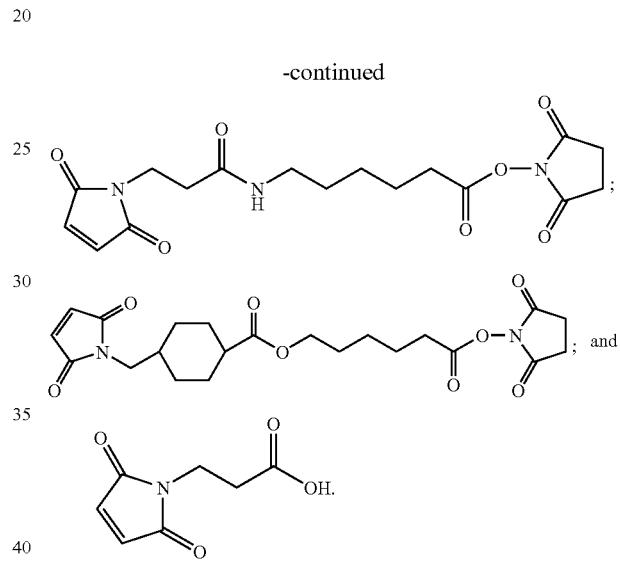

Stretcher units of formula (IIIb) can be introduced into a Linker by reacting the following intermediates with the N-terminus of an Amino Acid unit:

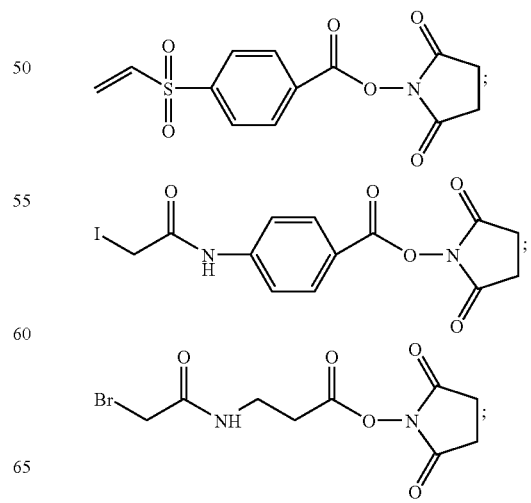

-continued

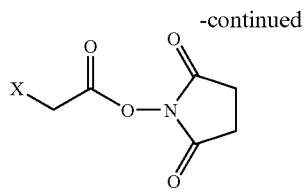

where X is —Br or —I; and

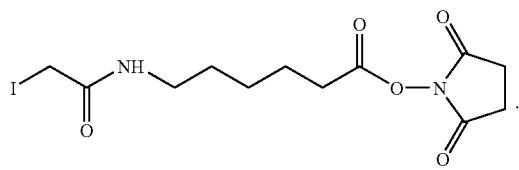

Stretcher units of formula (IV) can be introduced into a Linker by reacting the following intermediates with the N-terminus of an Amino Acid unit:

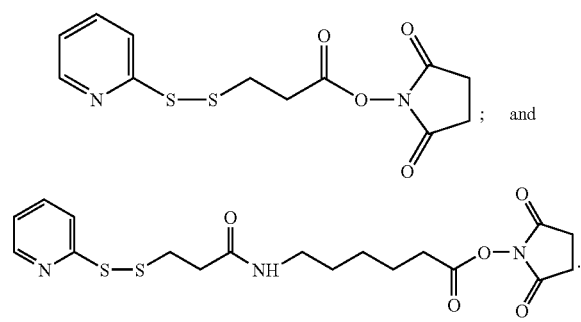
; and

Stretcher units of formula (Va) can be introduced into a Linker by reacting the following intermediates with the N-terminus of an Amino Acid unit:

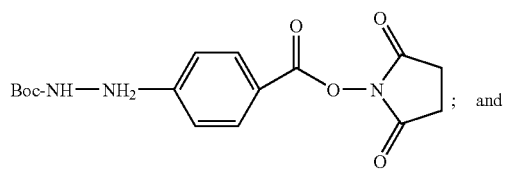
; and

-continued

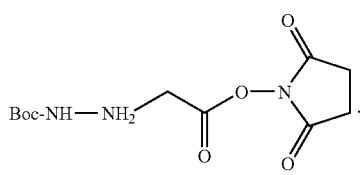

Other Stretchers useful in the invention may be synthesized according to known procedures. Aminooxy Stretchers of the formula shown below can be prepared by treating alkyl halides with N-Boc-hydroxylamine according to procedures described in Jones, D. S. et al., *Tetrahedron Letters*, 2000, 41(10), 1531-1533; and Gilon, C. et al., *Tetrahedron*, 1967, 23(11), 4441-4447.

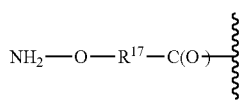

where —$R^{17}$— is selected from —$C_1$-$C_{10}$ alkylene-, —$C_3$-$C_8$ carbocyclo-, —O—($C_1$-$C_8$ alkyl)-, -arylene-, —$C_1$-$C_{10}$ alkylene-arylene-, -arylene-$C_1$-$C_{10}$ alkylene-, —$C_1$-$C_{10}$ alkylene-($C_3$-$C_8$ carbocyclo)-, —($C_3$-$C_8$ carbocyclo)-$C_1$-$C_{10}$ alkylene-, —$C_3$-$C_8$ heterocyclo-, —$C_1$-$C_{10}$ alkylene-($C_3$-$C_8$ heterocyclo)-, —($C_3$-$C_8$ heterocyclo)-$C_1$-$C_{10}$ alkylene-, —($CH_2CH_2O)_n$—, —($CH_2CH_2O)_r$—$CH_2$—; and r is an integer ranging from 1-10;

Isothiocyanate Stretchers of the formula shown below may be prepared from isothiocyanatocarboxylic acid chlorides as described in *Angew. Chem.*, 1975, 87(14), 517.

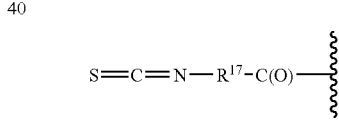

where —$R^{17}$— is as described herein.

Scheme 11 shows a method for obtaining of a val-cit dipeptide Linker having a maleimide Stretcher and optionally a p-aminobenzyl self-immolative Spacer.

Scheme 11

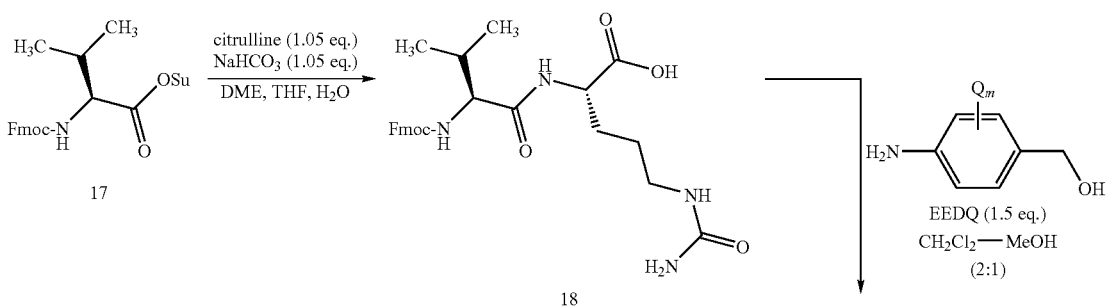

-continued

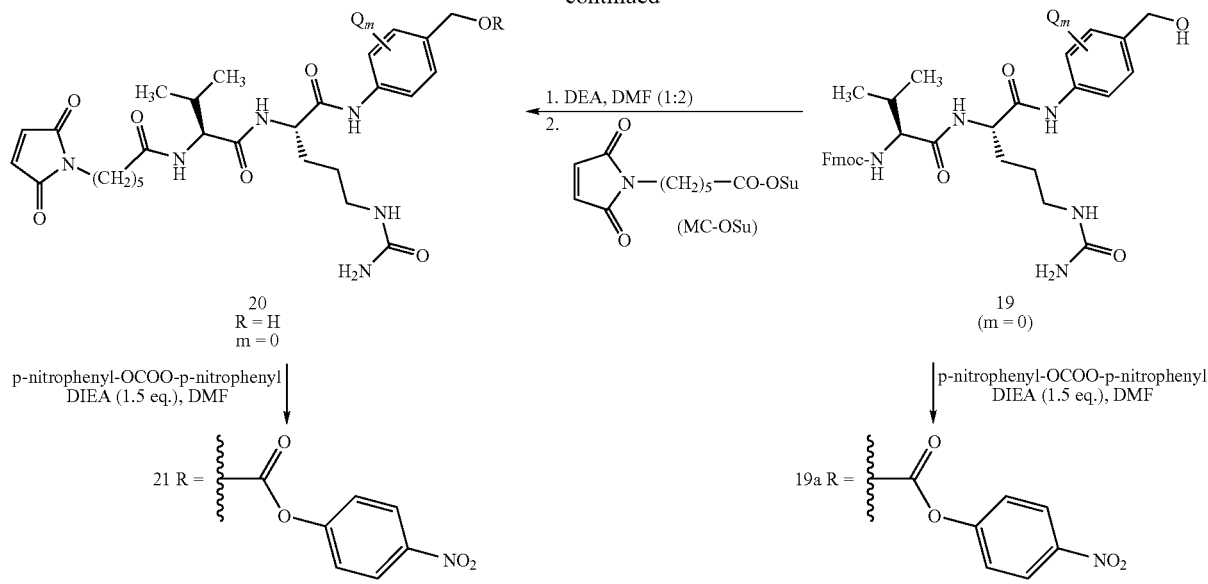

where Q is —$C_1$-$C_8$ alkyl, —O—($C_1$-$C_8$ alkyl), -halogen, -nitro or -cyano; and m is an integer ranging from 0-4.

Scheme 12 illustrates the synthesis of a phe-lys(Mtr) dipeptide Linker unit having a maleimide Stretcher unit and a p-aminobenzyl self-immolative Spacer unit. Starting material 23 (lys(Mtr)) is commercially available (Bachem, Torrance, Calif.) or can be prepared according to Dubowchik, et al. *Tetrahedrom Letters* 1997, 38, 5257-60.

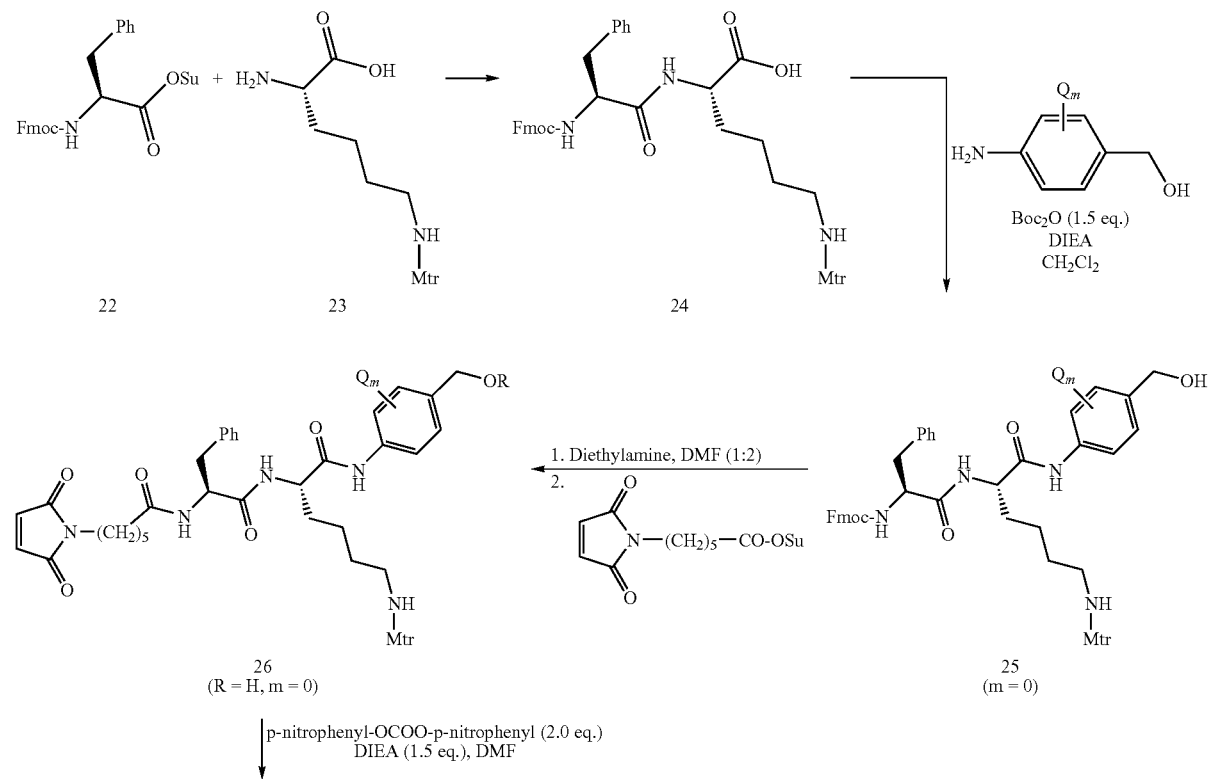

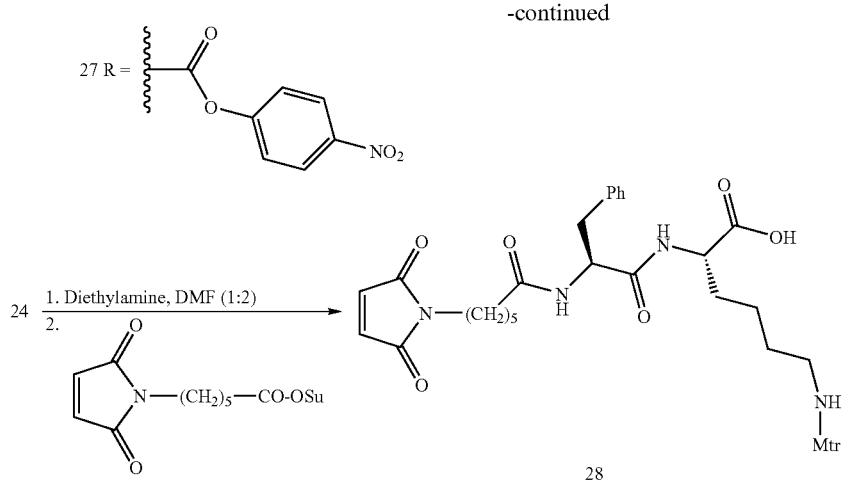

where Q is —$C_1$-$C_8$ alkyl, —O—($C_1$-$C_8$ alkyl), -halogen, -nitro or -cyano; and m is an integer ranging from 0-4.

As shown in Scheme 13, a Linker can be reacted with an amino group of a Drug 10 to form a Drug-Linker Compound that contains an amide or carbamate group, linking the Drug unit to the Linker unit. When Reactive Site No. 1 is a carboxylic acid group, as in Linker 29, the coupling reaction can be performed using HATU or PyBrop and an appropriate amine base, resulting in a Drug-Linker Compound 30, containing a amide bond between the Drug unit and the Linker unit. When Reactive Site No. 1 is a carbonate, as in Linker 31, the Linker can be coupled to the Drug using HOBt in a mixture of DMF/pyridine to provide a Drug-Linker Compound 32, containing a carbamate bond between the Drug unit and the Linker unit.

When Reactive Site No. 1 is an hydroxyl group, such as Linker 33, the Linker can be coupled with a phenol group of a Drug using Mitsunobu chemistry to provide a Drug-Linker Compound 34 having an ether linkage between the Drug unit and the Linker unit.

Alternately, when Reactive Site No. 1 is a good leaving group, such as in Linker 70, the Linker can be coupled with a hydroxyl group or an amine group of a Drug via a nucleophilic substitution process to provide a Drug-Linker Compound having an ether linkage (34) or an amine linkage (71) between the Drug unit and the Linker unit.

Illustrative methods useful for linking a Drug to a Ligand to form a Drug-Linker Compound are depicted in Scheme 13 and are outlined in General Procedures G-J.

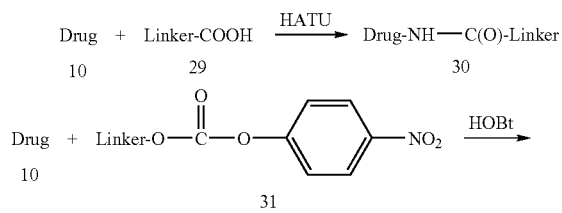

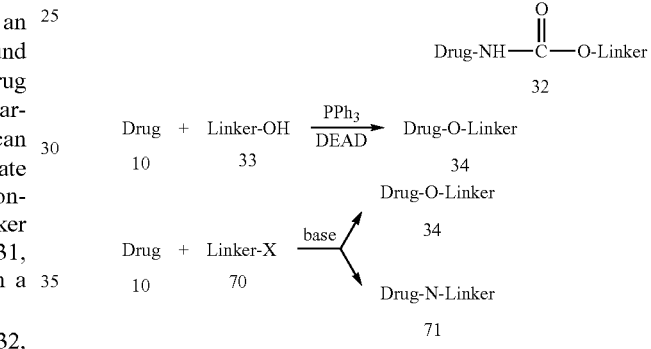

General Procedure G: Amide formation using HATU. A Drug 10 (1.0 eq.) and an N-protected Linker containing a carboxylic acid Reactive site (1.0 eq.) are diluted with a suitable organic solvent, such as dichloromethane, and the resulting solution is treated with HATU (1.5 eq.) and an organic base, preferably pyridine (1.5 eq.). The reaction mixture is allowed to stir under an inert atmosphere, preferably argon, for 6 h, during which time the reaction mixture is monitored using HPLC. The reaction mixture is concentrated and the resulting residue is purified using HPLC to yield the amide 30.

General Procedure H: Carbamate formation using HOBt. A mixture of a Linker 31 having a p-nitrophenyl carbonate Reactive site (1.1 eq.) and Drug 10 (1.0 eq.) are diluted with an aprotic organic solvent, such as DMF, to provide a solution having a concentration of 50-100 mM, and the resulting solution is treated with HOBt (2.0 eq.) and placed under an inert atmosphere, preferably argon. The reaction mixture is allowed to stir for 15 min, then an organic base, such as pyridine (¼ v/v), is added and the reaction progress is monitored using HPLC. The Linker is typically consumed within 16 h. The reaction mixture is then concentrated in vacuo and the resulting residue is purified using, for example, HPLC to yield the carbamate 32.

General Procedure I: Ether formation using Mitsunobu chemistry. A Drug of general formula 10, which contains a free hydroxyl group, is diluted with THF to make a 1.0 M solution and to this solution is added a Linker (1.0 eq) containing an hydroxy group at Reactive site No. 1 (33), followed by triphenylphosphine (1.5 eq.). The reaction mixture is put under an argon atmosphere and cooled to 0° C. DEAD (1.5 eq.) is then added dropwise via syringe and the reaction is allowed to stir at room temperature while being monitored using HPLC. The reaction is typically complete in 0.5-12 h, depending on the substrates. The reaction mixture is diluted with water (in volume equal to that of the THF) and the reaction mixture is extracted into EtOAc. The EtOAc layer is washed sequentially with water and brine, then dried over $MgSO_4$ and concentrated. The resulting residue is purified via flash column chromatography using a suitable eluent to provide ether 34.

General Procedure J: Ether/amine Formation via Nucleophilic Substitution. A Drug of general formula 10, which contains a free hydroxyl group or a free amine group, is diluted with a polar aprotic solvent, such as THF, DMF or DMSO, to make a 1.0 M solution and to this solution is added a non-nucleophilic base (about 1.5 eq), such as pyridine, diisopropylethylamine or triethylamine. The reaction mixture is allowed to stir for about 1 hour, and to the resulting solution is added an approximately 1.0M solution of Linker 70 in a polar aprotic solvent, such as THF, DMF or DMSO.

The resulting reaction is stirred under an inert atmosphere while being monitored using TLC or HPLC. The reaction is typically complete in 0.5-12 h, depending on the substrates. The reaction mixture is diluted with water (in volume equal to that of the reaction volume) and extracted into EtOAc. The EtOAc layer is washed sequentially with water, 1N HCl, water, and brine, then dried over $MgSO_4$ and concentrated. The resulting residue is purified via flash column chromatography using a suitable eluent to provide an ether of formula 34 or an amine of formula 71, depending on whether the drug 10 contained a free hydroxyl group or a free amine group.

An alternate method of preparing Drug-Linker Compounds of the invention is outlined in Scheme 14. Using the method of Scheme 14, the Drug is attached to a partial Linker unit (19a, for example), which does not have a Stretcher unit attached. This provides intermediate 35, which has an Amino Acid unit having an Fmoc-protected N-terminus. The Fmoc group is then removed and the resulting amine intermediate 36 is then attached to a Stretcher unit via a coupling reaction catalyzed using PyBrop or DEPC. The construction of Drug-Linker Compounds containing either a bromoacetamide Stretcher 39 or a PEG maleimide Stretcher 38 is illustrated in Scheme 14.

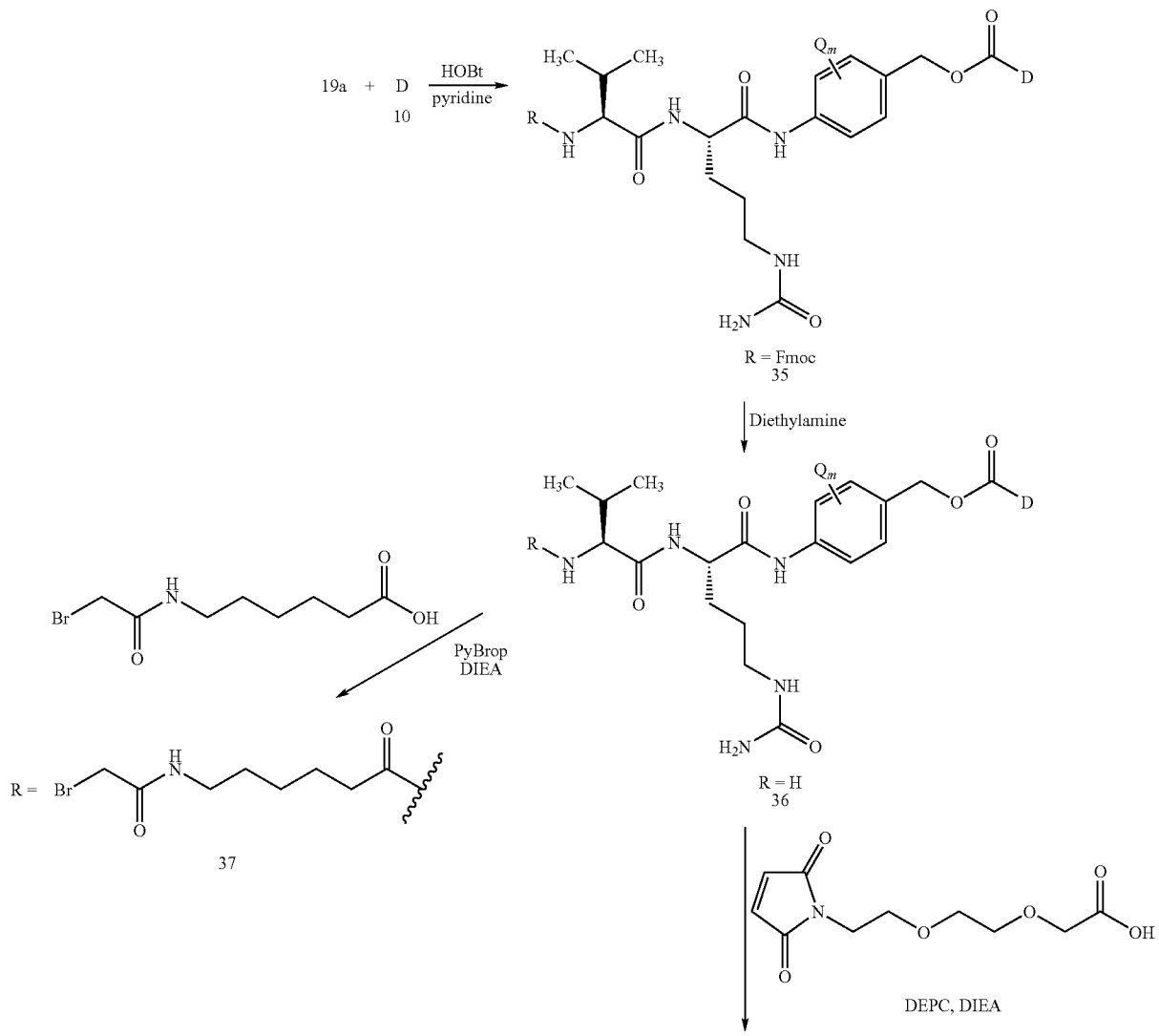

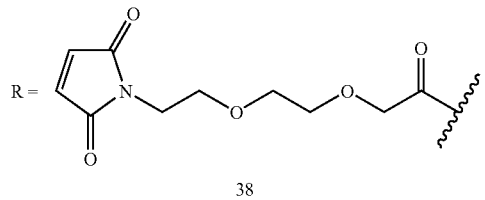
where Q is —$C_1$-$C_8$ alkyl, —O—($C_1$-$C_8$ alkyl), -halogen, -nitro or -cyano; and m is an integer ranging from 0-4.
Methodology useful for the preparation of a Linker unit containing a branched spacer is shown in Scheme 15.
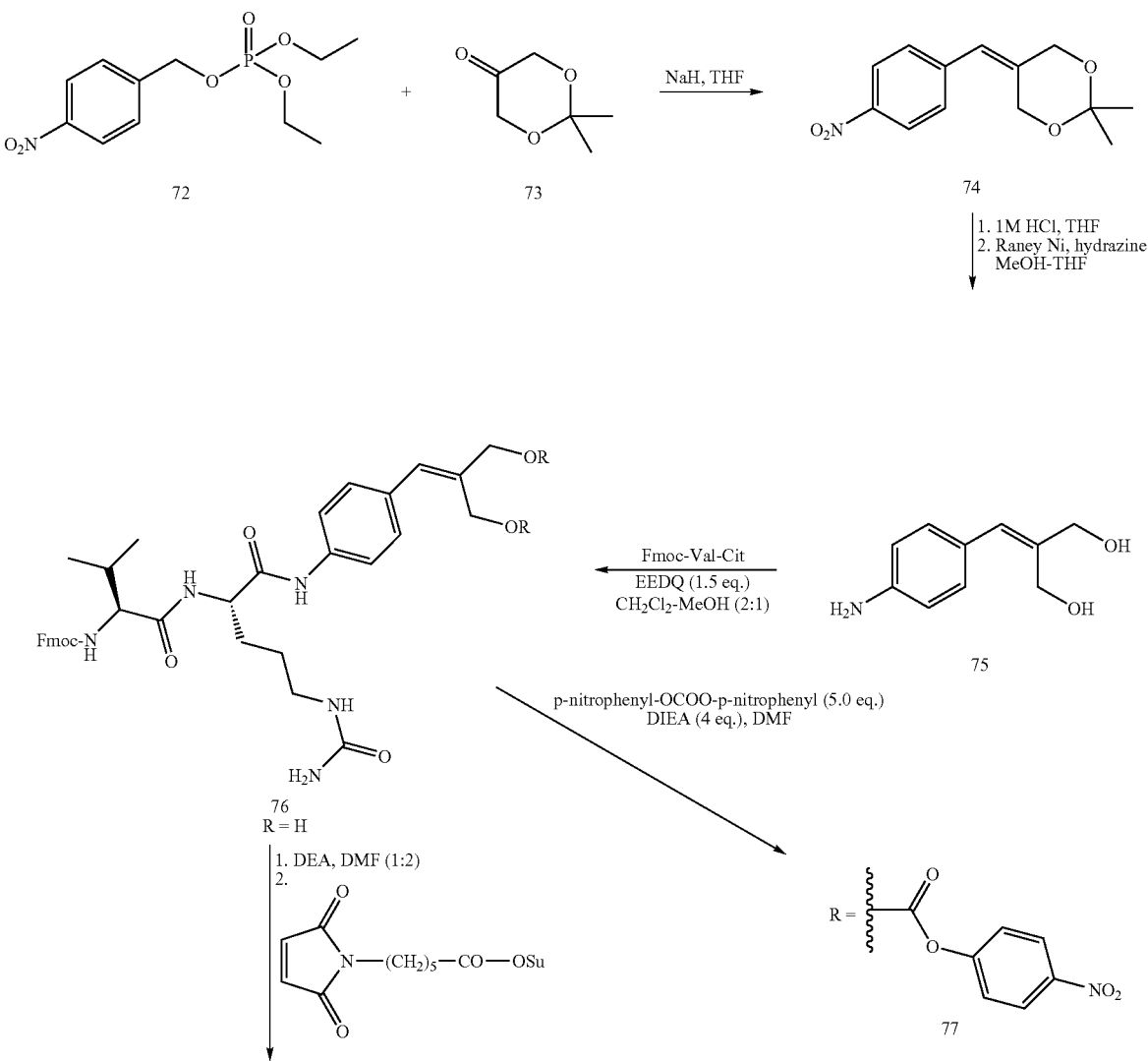

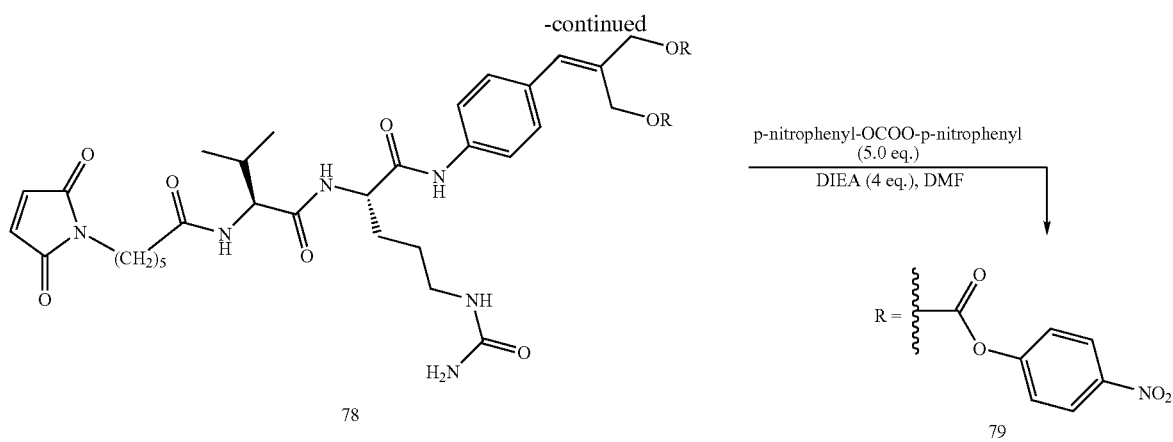

Scheme 15 illustrates the synthesis of a val-cit dipeptide linker having a maleimide Stretcher unit and a bis(4-hydroxymethyl)styrene (BHMS) unit. The synthesis of the BHMS intermediate (75) has been improved from previous literature procedures (see International Publication No, WO 9813059 to Firestone et al., and Crozet, M. P.; Archaimbault, G.; Vanelle, P.; Nouguier, R. *Tetrahedron Lett.* 1985, 26, 5133-5134) and utilizes as starting materials, commercially available diethyl (4-nitrobenzyl)phosphonate (72) and commercially available 2,2-dimethyl-1,3-dioxan-5-one (73). Linkers 77 and 79 can be prepared from intermediate 75 using the methodology described in Scheme 11.

Scheme 16 illustrates methodology useful for making Drug-Linker-Ligand conjugates of the invention having about 2 to about 4 drugs per antibody.

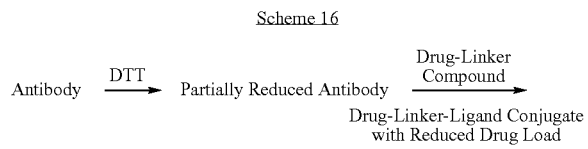

General Procedure K: Preparation of Conjugates Having about 2 to about 4 Drugs Per Antibody.

Partial Reduction of the Antibody

In general, to prepare conjugates having 2 drugs per antibody, the relevant antibody is reduced using a reducing agent such as dithiothreitol (DTT) or tricarbonyl ethylphosphine (TCEP) (about 1.8 equivalents) in PBS with 1 mM DTPA, adjusted to pH 8 with 50 mM borate. The solution is incubated at 37° C. for 1 hour, purified using a 50 ml G25 desalting column equilibrated in PBS/1 mM DTPA at 4° C. The thiol concentration can be determined according to General Procedure M, the protein concentration can be determined by dividing the A280 value by 1.58 extinction coefficient (mg/ml), and the ratio of thiol to antibody can be determined according to General Procedure N.

Conjugates having 4 drugs per antibody can be made using the same methodology, using about 4.2 equivalents of a suitable reducing agent to partially reduce the antibody.

Conjugation of Drug-Linker to Partially Reduced Antibody

The partially reduced antibody samples can be conjugated to a corresponding Drug-Linker compound using about 2.4 and about 4.6 molar equivalents of Drug-Linker compound per antibody to prepare the 2 and 4 drug per antibody conjugates, respectively. The conjugation reactions are incubated on ice for 1 hour, quenched with about 20-fold excess of cysteine to drug, and purified by elution over a G25 desalting column at about 4° C. The resulting Drug-Linker-Ligand conjugates are concentrated to about 3 mg/ml, sterile filtered, aliquoted and stored frozen.

Scheme 17 depicts the construction of a Drug-Linker-Ligand Conjugate by reacting the sulfhydryl group of a Ligand with a thiol-acceptor group on the Linker group of a Drug-Linker Compound.

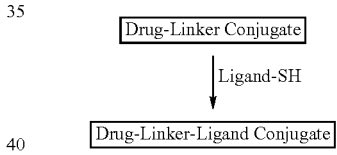

Illustrative methods for attaching a Ligand antibody to a Drug-Linker Compound are outlined below in General Procedures L-R.

General Procedure L: Attachment of an Antibody Ligand to a Drug-Linker Compound. All reaction steps are typically carried out at 4° C. Where the Ligand is a monoclonal antibody having one or more disulfide bonds, solutions of the monoclonal antibody (5-20 mg/mL) in phosphate buffered saline, pH 7.2, are reduced with dithiothreitol (10 mM final) at 37° C. for 30 minutes (See General Procedure M) and separation of low molecular weight agents is achieved by size exclusion chromatography on Sephadex G25 columns in PBS containing 1 mM diethylenetriaminepentaacetic acid.

The sulfhydryl content in the Ligand can be determined using 5,5'-dithiobis(2-nitrobenzoic acid) (DTNB) as described in General Procedure M (see Riddles, P. W., Blakeley, R. L., and Zerner, B. (1979) Anal. Biochem. 94, 75-81). To a PBS solution of Ligand reduced according to General Procedure L, a Drug-Linker Compound in MeCN is added so that the solution is 20% MeCN/PBS (vol/vol). The amount of Drug-Linker Compound is approximately 10% more than the total number of sulfhydryl groups on a Ligand. After 60 min at 4° C., cysteine is added (20-fold excess over concentration of the Drug-Linker Compound), the solution is concentrated by ultrafiltration, and any low molecular weight agents are removed by gel filtration. The number of Drug-Linker Compounds per antibody is determined by uv/vis spectroscopy using formulas derived from the relative extinction coefficients of the Ligands and Drug-Linker Compounds as described in General Procedure O. The amount of quenched Drug-Linker Compound is then determined as described in General Procedure P using reverse-phase HPLC. The aggregation state of the Ligand Antibodies of the Drug-Linker-Ligand Conjugates can be determined using size-exclusion HPLC as described in General Procedure R. The Drug-Linker-Ligand Conjugates can be used without further purification.

General Procedure M: Reduction of the interchain disulfide bonds of an Antibody. To a solution of 24 mg of an antibody (2.4 mL of 10 mg/mL solution) in suitable buffer is added 300 µL of Borate buffer (500 mM sodium borate/500 mM sodium chloride, pH 8.0) followed by 300 µL of Dithiothreitol (DTT, 100 mM solution in $H_2O$). The reaction mixture is stirred using a vortex instrument and incubated at 37° C. for 30 min. Three PD10 columns are equilibrated with PBS containing 1 mM DTPA (in PBS) and the reduced antibody is eluted through the three PD10 columns and collected in 4.2 mL PBS/DTPA solution (1.4 mL per column). The reduced antibody is then stored on ice. The number of thiols per antibody and the antibody concentration are determined according to General Procedure N.

General Procedure N: Determination of number of thiols per Ligand.

A reference sample of a Ligand or a sample of an antibody reduced according to General Procedure L is diluted to about 1:40 (w/w) in PBS, and the uv absorbance of the solution is measured at 280 nm using standard uv spectroscopic methods.

Preferably, the ratio of Ligand:PBS in the solution is such that the uv absorbance ranges from about 0.13-0.2 AU (absorbance units).

A test sample of a Ligand or a test sample of an antibody reduced according to General Procedure L is diluted to about 1:20 with a PBS solution containing about 15 µL DTNB stock solution/mL PBS. A blank sample containing DTNB at the same concentration as the test solution (i.e., 15 µL DTNB stock/mL PBS) is then prepared. The spectrophotometer is referenced at zero nm with the blank sample, then the absorbance of the test sample is measured at 412 nm.

The molar concentration of the antibody is then determined using the formula: $[Ligand]=(OD_{280}/2.24e^5) \times$ dilution factor.

The molar concentration of thiol is then determined using the formula: $[—SH]=(OD_{412}/1.415e^4) \times$ dilution factor.

The [SH]/[Ligand] ratio is then calculated. A reduced monoclonal antibody Ligand can have from 1 to about 20 sulfhydryl groups, but typically has between about 6 to about 9 sulfhydryl groups. In a preferred embodiment, the [SH]/[Ligand] ratio range is from about 7 to about 9.

It is understood that the [SH]/[Ligand] ratio is the average number of $-A_a-W_w—Y_y$-D units per Ligand unit.

General Procedure O: Determination of the number of Drug molecules per Antibody in a Drug-Linker-Antibody Conjugate. The Drug:Antibody ratio for a Drug-Linker-Antibody Conjugate is determined by measuring the number of Dithiothreitol (DTT) reducible thiols that remain after conjugation, using the following method: A 200 mL sample of a Drug-Linker-Antibody conjugate is treated with DTT (100 mM solution in water) to bring the concentration to 10 mM DTT. The resulting solution is incubated at 37° C. for 30 min, then eluted through a PD10 column using PBS/DTPA as the eluent. The $OD_{280}$ of the reduced conjugate is then measured and the molar concentration is measured according to General Procedure Q.

The molar concentration of thiol is determined using DTNB as described in General Procedure M. The ratio of thiol concentration to antibody concentration is then calculated and the Drug:Ligand ratio is the difference between the Thiol:Antibody ratio (determined using General Procedure N) and the Drug:Antibody ratio as determined in the previous paragraph.

General Procedure P: Determination of the amount of quenched Drug-Linker compound in a Drug-Linker-Antibody Conjugate. This assay provides a quantitative determination of the Drug-Linker in the Drug-Linker-Antibody conjugate that is not covalently bound to Antibody. Assuming that all maleimide groups of Drug-Linker in the reaction mixture have been quenched with Cysteine, the unbound drug is the Cysteine quenched adduct of the Drug-Linker Compound, i.e. Drug-Linker-Cys. The proteinaceous Drug-Linker-Antibody Conjugate is denatured, precipitated, and isolated by centrifugation under conditions in which the Drug-Linker-Cys is soluble. The unbound Drug-Linker-Cys is detected quantitatively by HPLC, and the resulting chromatogram is compared to a standard curve to determine the concentration of unbound Drug-Linker-Cys in the sample. This concentration is divided by the total concentration of Drug in the conjugate as determined using General Procedure O and General Procedure Q.

Specifically, 100 mL of a 100 µM Drug-Linker-Cys adduct "working solution" is prepared by adding 1 µL of 100 mM Cysteine in PBS/DTPA and an appropriate volume of stock solution of a Drug-Linker compound to 98 µL of 50% methanol/PBS. The "appropriate volume" in liters is calculated using the formula: V=1e-8/[Drug-Linker]. Six tubes are then labelled as follows: "0", "0.5", "1", "2", "3", and "5", and appropriate amounts of working solution are placed in each tube and diluted with 50% methanol/PBS to give a total volume of 100 mL in each tube. The labels indicate the µM concentration of the standards.

A 50 µL solution of a Drug-Linker-Antibody Conjugate and a 50 µL solution of the Cysteine quenched reaction mixture ("qrm") are collected in separate test tubes and are each diluted with 50 µL of methanol that has been cooled to −20° C. The samples are then cooled to −20° C. over 10 min.

The samples are then centrifuged at 13000 rpm in a desktop centrifuge for 10 min. The supernatants are transferred to HPLC vials, and 90 µL aliquots of each sample are separately analyzed using HPLC(C12 RP column (Phenomenex); monitored at the absorbance maximum of the Drug-Linker Compound using a flow rate of 1.0 mL/min. The eluent used is a linear gradient of MeCN ranging from 10 to 90% in aqueous 5 mM ammonium phosphate, pH 7.4, over 10 min; then 90% MeCN over 5 min.; then returning to initial conditions). The Drug-Linker-Cys adduct typically elutes between about 7 and about 10 minutes.

A standard curve is then prepared by plotting the Peak Area of the standards vs. their concentration (in µM). Linear regression analysis is performed to determine the equation and correlation coefficient of the standard curve. $R^2$ values are typically >0.99. From the regression equation is determined the concentration of the Drug-Linker-Cys adduct in the HPLC sample and in the conjugate, using the formulas:

$$[\text{Drug-Linker-Cys}]_{(HPLC\,spl)} = (\text{Peak area} - \text{intercept})/\text{slope};$$

$$[\text{Drug-Linker-Cys}]_{(conjugate)} = 2 \times [\text{Drug-Linker-Cys}]_{(HPLC\,spl)}$$

The percent of Drug-Linker-Cys adduct present can be determined using the formula:

% Drug-Linker-Cys=100×[Drug-Linker-Cys]$_{(conjugate)}$/[drug]

where [drug]=[Conjugate]×drug/Ab, [Conjugate] is determined using the conjugate concentration assay, and the Drug: Antibody ratio is determined using the Drug: Antibody ratio assay.

General Procedure Q: Determination of Drug-Linker-Antibody Conjugate concentration for drug linkers with minimal uv absorbance at 280 nm. The concentration of Drug-Linker-Antibody conjugate can be determined in the same manner for the concentration of the parent antibody, by measuring the absorbance at 280 nm of an appropriate dilution, using the following formula:

[Conjugate](mg/mL)=(OD$_{280}$×dilution factor/1.4)×0.9

Determination of Drug-Linker-Antibody Conjugate concentration for drug linkers with substantial uv absorbance at 280 nm (e.g. Compounds 68 and 69). Because the absorbances of Compounds 68 and 69 overlap with the absorbances of an antibody, spectrophotometric determination of the conjugate concentration is most useful when the measurement is performed using the absorbances at both 270 nm and 280 nm. Using this data, the molar concentration of Drug-Linker-Ligand conjugate is given by the following formula:

[Conjugate]=(OD$_{280}$×1.23e$^{-5}$−OD$_{270}$×9.35e$^{-6}$)×dilution factor where the values 1.23e$^{-5}$ and 9.35e$^{-6}$ are calculated from the molar extinction coefficients of the drug and the antibody, which are estimated as:

$e_{270}$ Drug=2.06e$^4$ $e_{270}$ Antibody=1.87e$^5$
$e_{280}$ Drug=1.57e$^4$ $e_{280}$ Antibody=2.24e$^5$ General Procedure R: Determination of the aggregation state of The Antibody in a Drug-Linker-Antibody Conjugate. A suitable quantity (~10 μg) of a Drug-Linker-Antibody Conjugate is eluted through a size-exclusion chromatography (SEC) column (Tosoh Biosep SW3000 4.6 mm×30 cm eluted at 0.35 mL/min. with PBS) under standard conditions. Chromatograms are obtained at 220 nm and 280 nm and the OD$_{280}$/OD$_{220}$ ratio is calculated. The corresponding aggregate typically has a retention time of between about 5.5 and about 7 min, and has about the same OD$_{280}$/OD$_{220}$ ratio as the monomeric Drug-Linker-Antibody Conjugate.

5.8 Compositions

In other aspects, the present invention provides a composition comprising an effective amount of a Compound of the Invention and a pharmaceutically acceptable carrier or vehicle. For convenience, the Drug units, Drug-Linker Compounds and Drug-Linker-Ligand Conjugates of the invention can simply be referred to as compounds of the invention. The compositions are suitable for veterinary or human administration.

The compositions of the present invention can be in any form that allows for the composition to be administered to an animal. For example, the composition can be in the form of a solid, liquid or gas (aerosol). Typical routes of administration include, without limitation, oral, topical, parenteral, sublingual, rectal, vaginal, ocular, and intranasal. Parenteral administration includes subcutaneous injections, intravenous, intramuscular, intrasternal injection or infusion techniques. Preferably, the compositions are administered parenterally. Pharmaceutical compositions of the invention can be formulated so as to allow a Compound of the Invention to be bioavailable upon administration of the composition to an animal. Compositions can take the form of one or more dosage units, where for example, a tablet can be a single dosage unit, and a container of a Compound of the Invention in aerosol form can hold a plurality of dosage units.

Materials used in preparing the pharmaceutical compositions can be non-toxic in the amounts used. It will be evident to those of ordinary skill in the art that the optimal dosage of the active ingredient(s) in the pharmaceutical composition will depend on a variety of factors. Relevant factors include, without limitation, the type of animal (e.g., human), the particular form of the Compound of the Invention, the manner of administration, and the composition employed.

The pharmaceutically acceptable carrier or vehicle can be particulate, so that the compositions are, for example, in tablet or powder form. The carrier(s) can be liquid, with the compositions being, for example, an oral syrup or injectable liquid. In addition, the carrier(s) can be gaseous, so as to provide an aerosol composition useful in, e.g., inhalatory administration.

When intended for oral administration, the composition is preferably in solid or liquid form, where semi-solid, semi-liquid, suspension and gel forms are included within the forms considered herein as either solid or liquid.

As a solid composition for oral administration, the composition can be formulated into a powder, granule, compressed tablet, pill, capsule, chewing gum, wafer or the like form. Such a solid composition typically contains one or more inert diluents. In addition, one or more of the following can be present: binders such as carboxymethylcellulose, ethyl cellulose, microcrystalline cellulose, or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin, a flavoring agent such as peppermint, methyl salicylate or orange flavoring, and a coloring agent.

When the composition is in the form of a capsule, e.g., a gelatin capsule, it can contain, in addition to materials of the above type, a liquid carrier such as polyethylene glycol, cyclodextrin or a fatty oil.

The composition can be in the form of a liquid, e.g., an elixir, syrup, solution, emulsion or suspension. The liquid can be useful for oral administration or for delivery by injection. When intended for oral administration, a composition can comprise one or more of a sweetening agent, preservatives, dye/colorant and flavor enhancer. In a composition for administration by injection, one or more of a surfactant, preservative, wetting agent, dispersing agent, suspending agent, buffer, stabilizer and isotonic agent can also be included.

The liquid compositions of the invention, whether they are solutions, suspensions or other like form, can also include one or more of the following: sterile diluents such as water for injection, saline solution, preferably physiological saline, Ringer's solution, isotonic sodium chloride, fixed oils such as synthetic mono or digylcerides which can serve as the solvent or suspending medium, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. A parenteral composition can be enclosed in ampoule, a disposable syringe or a multiple-dose vial made of glass, plastic or other material. Physiological saline is a preferred adjuvant. An injectable composition is preferably sterile.

The amount of the Compound of the Invention that is effective in the treatment of a particular disorder or condition will depend on the nature of the disorder or condition, and can be determined by standard clinical techniques. In addition, in vitro or in vivo assays can optionally be employed to help identify optimal dosage ranges. The precise dose to be employed in the compositions will also depend on the route of administration, and the seriousness of the disease or disorder, and should be decided according to the judgment of the practitioner and each patient's circumstances.

The compositions comprise an effective amount of a Compound of the Invention such that a suitable dosage will be obtained. Typically, this amount is at least about 0.01% of a Compound of the Invention by weight of the composition. When intended for oral administration, this amount can be varied to range from about 0.1% to about 80% by weight of the composition. Preferred oral compositions can comprise from about 4% to about 50% of the Compound of the Invention by weight of the composition. Preferred compositions of the present invention are prepared so that a parenteral dosage unit contains from about 0.01% to about 2% by weight of the Compound of the Invention.

For intravenous administration, the composition can comprise from about 1 to about 250 mg of a Compound of the Invention per kg of the animal's body weight. Preferably, the amount administered will be in the range from about 4 to about 25 mg/kg of body weight of the Compound of the Invention.

Generally, the dosage of Compound of the Invention administered to an animal is typically about 0.1 mg/kg to about 250 mg/kg of the animal's body weight. Preferably, the dosage administered to an animal is between about 0.1 mg/kg and about 20 mg/kg of the animal's body weight, more preferably about 1 mg/kg to about 10 mg/kg of the animal's body weight.

The Compounds of the Invention or compositions can be administered by any convenient route, for example by infusion or bolus injection, by absorption through epithelial or mucocutaneous linings (e.g., oral mucosa, rectal and intestinal mucosa, etc.). Administration can be systemic or local. Various delivery systems are known, e.g., encapsulation in liposomes, microparticles, microcapsules, capsules, etc., and can be used to administer a Compound of the Invention or composition. In certain embodiments, more than one Compound of the Invention or composition is administered to an animal. Methods of administration include, but are not limited to, oral administration and parenteral administration; parenteral administration including, but not limited to, intradermal, intramuscular, intraperitoneal, intravenous, subcutaneous; intranasal, epidural, sublingual, intranasal, intracerebral, intraventricular, intrathecal, intravaginal, transdermal, rectally, by inhalation, or topically to the ears, nose, eyes, or skin. The preferred mode of administration is left to the discretion of the practitioner, and will depend in-part upon the site of the medical condition (such as the site of cancer or autoimmune disease).

In a preferred embodiment, the present Compounds of the Invention or compositions are administered parenterally.

In a more preferred embodiment, the present Compounds of the Invention or compositions are administered intravenously.

In specific embodiments, it can be desirable to administer one or more Compounds of the Invention or compositions locally to the area in need of treatment. This can be achieved, for example, and not by way of limitation, by local infusion during surgery; topical application, e.g., in conjunction with a wound dressing after surgery; by injection; by means of a catheter; by means of a suppository; or by means of an implant, the implant being of a porous, non-porous, or gelatinous material, including membranes, such as sialastic membranes, or fibers. In one embodiment, administration can be by direct injection at the site (or former site) of a cancer, tumor or neoplastic or pre-neoplastic tissue.

In another embodiment, administration can be by direct injection at the site (or former site) of a manifestation of an autoimmune disease.

In certain embodiments, it can be desirable to introduce one or more Compounds of the Invention or compositions into the central nervous system by any suitable route, including intraventricular and intrathecal injection. Intraventricular injection can be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, the Compounds of the Invention or compositions can be formulated as a suppository, with traditional binders and carriers such as triglycerides.

In another embodiment, the Compounds of the invention can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

In yet another embodiment, the Compounds of the Invention or compositions can be delivered in a controlled release system. In one embodiment, a pump can be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J. Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled-release system can be placed in proximity of the target of the Compounds of the Invention or compositions, e.g., the brain, thus requiring only a fraction of the systemic dose (see, e.g., Goodson, in Medical Applications of Controlled Release, supra, vol. 2, pp. 115-138 (1984)). Other controlled-release systems discussed in the review by Langer (Science 249:1527-1533 (1990)) can be used.

The term "carrier" refers to a diluent, adjuvant or excipient, with which a Compound of the Invention is administered. Such pharmaceutical carriers can be liquids, such as water and oils, including those of petroleum, animal, vegetable or synthetic origin, such as peanut oil, soybean oil, mineral oil, sesame oil and the like. The carriers can be saline, gum acacia, gelatin, starch paste, talc, keratin, colloidal silica, urea, and the like. In addition, auxiliary, stabilizing, thickening, lubricating and coloring agents can be used. In one embodiment, when administered to an animal, the Compounds of the Invention or compositions and pharmaceutically acceptable carriers are sterile. Water is a preferred carrier when the Compounds of the Invention are administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable carrier is a capsule (see e.g., U.S. Pat. No. 5,698,155). Other examples of suitable pharmaceutical carriers are described in "Remington's Pharmaceutical Sciences" by E. W. Martin.

In a preferred embodiment, the Compounds of the Invention are formulated in accordance with routine procedures as a pharmaceutical composition adapted for intravenous administration to animals, particularly human beings. Typically, the carriers or vehicles for intravenous administration are sterile isotonic aqueous buffer solutions. Where necessary, the compositions can also include a solubilizing agent. Compositions for intravenous administration can optionally comprise a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where a Compound of the Invention is to be administered by infusion, it can be dispensed, for example, with an infusion bottle containing sterile pharmaceutical grade water or saline. Where the Compound of the Invention is administered by injection, an ampoule of sterile water for injection or saline can be provided so that the ingredients can be mixed prior to administration.

Compositions for oral delivery can be in the form of tablets, lozenges, aqueous or oily suspensions, granules, powders, emulsions, capsules, syrups, or elixirs, for example. Orally administered compositions can contain one or more optionally agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving compound are also suitable for orally administered compounds. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be used. Oral compositions can include standard carriers such as mannitol, lactose, starch, magnesium stearate, sodium saccharine, cellulose, magnesium carbonate, etc. Such carriers are preferably of pharmaceutical grade.

The compositions can be intended for topical administration, in which case the carrier may be in the form of a solution, emulsion, ointment or gel base. The base, for example, can comprise one or more of the following: petrolatum, lanolin, polyethylene glycols, beeswax, mineral oil, diluents such as water and alcohol, and emulsifiers and stabilizers. Thickening agents can be present in a composition for topical administration. If intended for transdermal administration, the composition can be in the form of a transdermal patch or an iontophoresis device. Topical formulations can comprise a concentration of a Compound of the Invention of from about 0.1% to about 10% w/v (weight per unit volume of composition).

The composition can be intended for rectal administration, in the form, e.g., of a suppository which will melt in the rectum and release the Compound of the Invention. The composition for rectal administration can contain an oleaginous base as a suitable nonirritating excipient. Such bases include, without limitation, lanolin, cocoa butter and polyethylene glycol.

The composition can include various materials that modify the physical form of a solid or liquid dosage unit. For example, the composition can include materials that form a coating shell around the active ingredients. The materials that form the coating shell are typically inert, and can be selected from, for example, sugar, shellac, and other enteric coating agents. Alternatively, the active ingredients can be encased in a gelatin capsule.

The compositions can consist of gaseous dosage units, e.g., it can be in the form of an aerosol. The term aerosol is used to denote a variety of systems ranging from those of colloidal nature to systems consisting of pressurized packages. Delivery can be by a liquefied or compressed gas or by a suitable pump system that dispenses the active ingredients. Aerosols of Compounds of the Invention can be delivered in single phase, bi-phasic, or tri-phasic systems in order to deliver the Compound(s) of the Invention. Delivery of the aerosol includes the necessary container, activators, valves, subcontainers, Spacers and the like, which together can form a kit. Preferred aerosols can be determined by one skilled in the art, without undue experimentation.

Whether in solid, liquid or gaseous form, the compositions of the present invention can comprise a pharmacological agent used in the treatment of cancer, an autoimmune disease or an infectious disease.

The pharmaceutical compositions can be prepared using methodology well known in the pharmaceutical art. For example, a composition intended to be administered by injection can be prepared by combining a Compound of the Invention with water so as to form a solution. A surfactant can be added to facilitate the formation of a homogeneous solution or suspension. Surfactants are compounds that non-covalently interact with a Compound of the Invention so as to facilitate dissolution or homogeneous suspension of the active compound in the aqueous delivery system.

5.9 Therapeutic Uses of the Compounds of the Invention

The Compounds of the Invention are useful for treating cancer, an autoimmune disease or an infectious disease in an animal.

5.10 Treatment of Cancer

The Compounds of the Invention are useful for inhibiting the multiplication of a tumor cell or cancer cell, or for treating cancer in an animal. The Compounds of the Invention can be used accordingly in a variety of settings for the treatment of animal cancers. The Drug-Linker-Ligand Conjugates can be used to deliver a Drug or Drug unit to a tumor cell or cancer cell. Without being bound by theory, in one embodiment, the Ligand unit of a Compound of the Invention binds to or associates with a cancer-cell or a tumor-cell-associated antigen, and the Compound of the Invention can be taken up inside a tumor cell or cancer cell through receptor-mediated endocytosis. The antigen can be attached to a tumor cell or cancer cell or can be an extracellular matrix protein associated with the tumor cell or cancer cell. Once inside the cell, one or more specific peptide sequences within the Linker unit are hydrolytically cleaved by one or more tumor-cell or cancer-cell-associated proteases, resulting in release of a Drug or a Drug-Linker Compound. The released Drug or Drug-Linker Compound is then free to migrate in the cytosol and induce cytotoxic activities. In an alternative embodiment, the Drug or Drug unit is cleaved from the Compound of the Invention outside the tumor cell or cancer cell, and the Drug or Drug-Linker Compound subsequently penetrates the cell.

In one embodiment, the Ligand unit binds to the tumor cell or cancer cell.

In another embodiment, the Ligand unit binds to a tumor cell or cancer cell antigen which is on the surface of the tumor cell or cancer cell.

In another embodiment, the Ligand unit binds to a tumor cell or cancer cell antigen which is an extracellular matrix protein associated with the tumor cell or cancer cell.

In one embodiment, the tumor cell or cancer cell is of the type of tumor or cancer that the animal needs treatment or prevention of.

The specificity of the Ligand unit for a particular tumor cell or cancer cell can be important for determining those tumors or cancers that are most effectively treated. For example, Compounds of the Invention having a BR96 Ligand unit can be useful for treating antigen positive carcinomas including those of the lung, breast, colon, ovaries, and pancreas. Compounds of the Invention having an Anti-CD30 or an anti-CD40 Ligand unit can be useful for treating hematologic malignancies.

Other particular types of cancers that can be treated with Compounds of the Invention include, but are not limited to, those disclosed in Table 3.

TABLE 3

Solid tumors, including but not limited to:

fibrosarcoma
myxosarcoma
liposarcoma
chondrosarcoma
osteogenic sarcoma
chordoma
angiosarcoma
endotheliosarcoma
lymphangiosarcoma
lymphangioendotheliosarcoma
synovioma
mesothelioma
Ewing's tumor
leiomyosarcoma
rhabdomyosarcoma
colon cancer
colorectal cancer
kidney cancer
pancreatic cancer
bone cancer
breast cancer
ovarian cancer
prostate cancer
esophogeal cancer
stomach cancer
oral cancer
nasal cancer TABLE 3-continued throat cancer
squamous cell carcinoma
basal cell carcinoma
adenocarcinoma
sweat gland carcinoma
sebaceous gland carcinoma
papillary carcinoma
papillary adenocarcinomas
cystadenocarcinoma
medullary carcinoma
bronchogenic carcinoma
renal cell carcinoma
hepatoma
bile duct carcinoma
choriocarcinoma
seminoma
embryonal carcinoma
Wilms' tumor
cervical cancer
uterine cancer
testicular cancer
small cell lung carcinoma
bladder carcinoma
lung cancer
epithelial carcinoma
glioma
glioblastoma multiforme
astrocytoma
medulloblastoma
craniopharyngioma
ependymoma
pinealoma
hemangioblastoma
acoustic neuroma
oligodendroglioma
meningioma
skin cancer
melanoma
neuroblastoma
retinoblastoma
blood-borne cancers, including but not limited to:

acute lymphoblastic leukemia "ALL"
acute lymphoblastic B-cell leukemia
acute lymphoblastic T-cell leukemia
acute myeloblastic leukemia "AML"
acute promyelocytic leukemia "APL"
acute monoblastic leukemia
acute erythroleukemic leukemia
acute megakaryoblastic leukemia
acute myelomonocytic leukemia
acute nonlymphocytic leukemia
acute undifferentiated leukemia
chronic myelocytic leukemia "CML"
chronic lymphocytic leukemia "CLL"
hairy cell leukemia
multiple myeloma
acute and chronic leukemias:

lymphoblastic
myelogenous
lymphocytic
myelocytic leukemias
Lymphomas:

Hodgkin's disease
non-Hodgkin's Lymphoma
Multiple myeloma
Waldenström's macroglobulinemia
Heavy chain disease
Polycythemia vera The Compounds of the Invention can also be used as chemotherapeutics in the untargeted form. For example, the Drugs themselves, or the Drug-Linker Compounds are useful for treating ovarian, CNS, renal, lung, colon, melanoma, or hematologic cancers or tumors.

The Compounds of the Invention provide Conjugation specific tumor or cancer targeting, thus reducing general toxicity of these compounds. The Linker units stabilize the Compounds of the Invention in blood, yet are cleavable by tumor-specific proteases within the cell, liberating a Drug.

5.10.1 Multi-Modality Therapy for Cancer

Cancer, including, but not limited to, a tumor, metastasis, or any disease or disorder characterized by uncontrolled cell growth, can be treated or prevented by administration of a Compound of the Invention.

In other embodiments, the invention provides methods for treating or preventing cancer, comprising administering to an animal in need thereof an effective amount of a Compound of the Invention and a chemotherapeutic agent. In one embodiment the chemotherapeutic agent is that with which treatment of the cancer has not been found to be refractory. In another embodiment, the chemotherapeutic agent is that with which the treatment of cancer has been found to be refractory. The Compounds of the Invention can be administered to an animal that has also undergone surgery as treatment for the cancer.

In one embodiment, the additional method of treatment is radiation therapy.

In a specific embodiment, the Compound of the Invention is administered concurrently with the chemotherapeutic agent or with radiation therapy. In another specific embodiment, the chemotherapeutic agent or radiation therapy is administered prior or subsequent to administration of a Compound of the Invention, preferably at least an hour, five hours, 12 hours, a day, a week, a month, more preferably several months (e.g., up to three months), prior or subsequent to administration of a Compound of the Invention.

A chemotherapeutic agent can be administered over a series of sessions, any one or a combination of the chemotherapeutic agents listed in Table 4 can be administered. With respect to radiation, any radiation therapy protocol can be used depending upon the type of cancer to be treated. For example, but not by way of limitation, x-ray radiation can be administered; in particular, high-energy megavoltage (radiation of greater that 1 MeV energy) can be used for deep tumors, and electron beam and orthovoltage x-ray radiation can be used for skin cancers. Gamma-ray emitting radioisotopes, such as radioactive isotopes of radium, cobalt and other elements, can also be administered.

Additionally, the invention provides methods of treatment of cancer with a Compound of the Invention as an alternative to chemotherapy or radiation therapy where the chemotherapy or the radiation therapy has proven or can prove too toxic, e.g., results in unacceptable or unbearable side effects, for the subject being treated. The animal being treated can, optionally, be treated with another cancer treatment such as surgery, radiation therapy or chemotherapy, depending on which treatment is found to be acceptable or bearable.

The Compounds of the Invention can also be used in an in vitro or ex vivo fashion, such as for the treatment of certain cancers, including, but not limited to leukemias and lymphomas, such treatment involving autologous stem cell transplants. This can involve a multi-step process in which the animal's autologous hematopoietic stem cells are harvested and purged of all cancer cells, the patient's remaining bone-marrow cell population is then eradicated via the administration of a high dose of a Compound of the Invention with or without accompanying high dose radiation therapy, and the stem cell graft is infused back into the animal. Supportive care is then provided while bone marrow function is restored and the animal recovers.

5.10.2 Multi-Drug Therapy for Cancer

The present invention includes methods for treating cancer, comprising administering to an animal in need thereof an effective amount of a Compound of the Invention and another therapeutic agent that is an anti-cancer agent. Suitable anti-cancer agents include, but are not limited to, methotrexate, taxol, L-asparaginase, mercaptopurine, thioguanine, hydroxyurea, cytarabine, cyclophosphamide, ifosfamide, nitrosoureas, cisplatin, carboplatin, mitomycin, dacarbazine, procarbizine, topotecan, nitrogen mustards, cytoxan, etoposide, 5-fluorouracil, BCNU, irinotecan, camptothecins, bleomycin, doxorubicin, idarubicin, daunorubicin, dactinomycin, plicamycin, mitoxantrone, asparaginase, vinblastine, vincristine, vinorelbine, paclitaxel, and docetaxel. In a preferred embodiment, the anti-cancer agent includes, but is not limited to, a drug listed in Table 4.

TABLE 4

| | |
|---|---|
| Alkylating agents | |
| Nitrogen mustards: | cyclophosphamide |
| | Ifosfamide |
| | trofosfamide |
| | Chlorambucil |
| Nitrosoureas: | carmustine (BCNU) |
| | Lomustine (CCNU) |
| Alkylsulphonates | busulfan |
| | Treosulfan |
| Triazenes: | Dacarbazine |
| Platinum containing compounds: | Cisplatin |
| | carboplatin |
| Plant Alkaloids | |
| Vinca alkaloids: | vincristine |
| | Vinblastine |
| | Vindesine |
| | Vinorelbine |
| Taxoids: | paclitaxel |
| | Docetaxol |
| DNA Topoisomerase Inhibitors | |
| Epipodophyllins: | etoposide |
| | Teniposide |
| | Topotecan |
| | 9-aminocamptothecin |
| | camptothecin |
| | crisnatol |
| mitomycins: | Mitomycin C |
| Anti-metabolites | |
| Anti-folates: | |
| DHFR inhibitors: | methotrexate |
| | Trimetrexate |
| IMP dehydrogenase Inhibitors: | mycophenolic acid |
| | Tiazofurin |
| | Ribavirin |
| | EICAR |
| Ribonuclotide reductase Inhibitors: | hydroxyurea |
| | deferoxamine |
| Pyrimidine analogs: | |
| Uracil analogs | 5-Fluorouracil |
| | Floxuridine |
| | Doxifluridine |
| | Ratitrexed |
| Cytosine analogs | cytarabine (ara C) |
| | Cytosine arabinoside |
| | fludarabine |
| Purine analogs: | mercaptopurine |
| | Thioguanine |
| Hormonal therapies: | |
| Receptor antagonists: | |
| Anti-estrogen | Tamoxifen |
| | Raloxifene |
| | megestrol |

TABLE 4-continued

| | |
|---|---|
| LHRH agonists: | goscrelin |
| | Leuprolide acetate |
| Anti-androgens: | flutamide |
| | bicalutamide |
| Retinoids/Deltoids | |
| Vitamin D3 analogs: | EB 1089 |
| | CB 1093 |
| | KH 1060 |
| Photodynamic therapies: | vertoporfin (BPD-MA) |
| | Phthalocyanine |
| | photosensitizer Pc4 |
| | Demethoxy-hypocrellin A |
| | (2BA-2-DMHA) |
| Cytokines: | Interferon-$\alpha$ |
| | Interferon-$\gamma$ |
| | Tumor necrosis factor |
| Others: | |
| Isoprenylation inhibitors: | Lovastatin |
| Dopaminergic neurotoxins: | 1-methyl-4-phenylpyridinium ion |
| Cell cycle inhibitors: | staurosporine |
| Actinomycins: | Actinomycin D |
| | Dactinomycin |
| Bleomycins: | bleomycin A2 |
| | Bleomycin B2 |
| | Peplomycin |
| Anthracyclines: | daunorubicin |
| | Doxorubicin (adriamycin) |
| | Idarubicin |
| | Epirubicin |
| | Pirarubicin |
| | Zorubicin |
| | Mitoxantrone |
| MDR inhibitors: | verapamil |
| $Ca^{2+}$ ATPase inhibitors: | thapsigargin |

5.11 Treatment of Autoimmune Diseases

The Compounds of the Invention are useful for killing or inhibiting the replication of a cell that produces an autoimmune disease or for treating an autoimmune disease. The Compounds of the Invention can be used accordingly in a variety of settings for the treatment of an autoimmune disease in an animal. The Drug-Linker-Ligand Conjugates can be used to deliver a Drug to a target cell. Without being bound by theory, in one embodiment, the Drug-Linker-Ligand Conjugate associates with an antigen on the surface of a target cell, and the Compound of the Invention is then taken up inside a target-cell through receptor-mediated endocytosis. Once inside the cell, one or more specific peptide sequences within the Linker unit are enzymatically or hydrolytically cleaved, resulting in release of a Drug. The released Drug is then free to migrate in the cytosol and induce cytotoxic activities. In an alternative embodiment, the Drug is cleaved from the Compound of the Invention outside the target cell, and the Drug subsequently penetrates the cell.

In one embodiment, the Ligand unit binds to an autoimmune antigen.

In another embodiment, the Ligand unit binds to an autoimmune antigen which is on the surface of a cell.

In another embodiment, the target cell is of the type of cell that produces the autoimmune antigen which causes the disease the animal needs treatment or prevention of.

In a preferred embodiment, the Ligand binds to activated lympocytes that are associated with the autoimmune disease state.

In a further embodiment, the Compounds of the Invention kill or inhibit the multiplication of cells that produce an autoimmune antibody associated with a particular autoimmune disease.

Particular types of autoimmune diseases that can be treated with the Compounds of the Invention include, but are not limited to, Th2-lymphocyte related disorders (e.g., atopic dermatitis, atopic asthma, rhinoconjunctivitis, allergic rhinitis, Omenn's syndrome, systemic sclerosis, and graft versus host disease); Th1 lymphocyte-related disorders (e.g., rheumatoid arthritis, multiple sclerosis, psoriasis, Sjorgren's syndrome, Hashimoto's thyroiditis, Grave's disease, primary biliary cirrhosis, Wegener's granulomatosis, and tuberculosis); activated B lymphocyte-related disorders (e.g., systemic lupus erythematosus, Goodpasture's syndrome, rheumatoid arthritis, and type I diabetes); and those disclosed in Table 5.

TABLE 5

Active Chronic Hepatitis
Addison's Disease
Allergic Alveolitis
Allergic Reaction
Allergic Rhinitis
Alport's Syndrome
Anaphlaxis
Ankylosing Spondylitis
Anti-phosholipid Syndrome
Arthritis
Ascariasis
Aspergillosis
Atopic Allergy
Atropic Dermatitis
Atropic Rhinitis
Behcet's Disease
Bird-Fancier's Lung
Bronchial Asthma
Caplan's Syndrome
Cardiomyopathy
Celiac Disease
Chagas' Disease
Chronic Glomerulonephritis
Cogan's Syndrome
Cold Agglutinin Disease
Congenital Rubella Infection
CREST Syndrome
Crohn's Disease
Cryoglobulinemia
Cushing's Syndrome
Dermatomyositis
Discoid Lupus
Dressler's Syndrome
Eaton-Lambert Syndrome
Echovirus Infection
Encephalomyelitis
Endocrine opthalmopathy
Epstein-Barr Virus Infection
Equine Heaves
Erythematosis
Evan's Syndrome
Felty's Syndrome
Fibromyalgia
Fuch's Cyclitis
Gastric Atrophy
Gastrointestinal Allergy
Giant Cell Arteritis
Glomerulonephritis
Goodpasture's Syndrome
Graft v. Host Disease
Graves' Disease
Guillain-Barre Disease
Hashimoto's Thyroiditis
Hemolytic Anemia
Henoch-Schonlein Purpura
Idiopathic Adrenal Atrophy
Idiopathic Pulmonary Fibritis
IgA Nephropathy
Inflammatory Bowel Diseases

TABLE 5-continued

Insulin-dependent Diabetes Mellitus
Juvenile Arthritis
Juvenile Diabetes Mellitus (Type I)
Lambert-Eaton Syndrome
Laminitis
Lichen Planus
Lupoid Hepatitis
Lupus
Lymphopenia
Meniere's Disease
Mixed Connective Tissue Disease
Multiple Sclerosis
Myasthenia Gravis
Pernicious Anemia
Polyglandular Syndromes
Presenile Dementia
Primary Agammaglobulinemia
Primary Biliary Cirrhosis
Psoriasis
Psoriatic Arthritis
Raynauds Phenomenon
Recurrent Abortion
Reiter's Syndrome
Rheumatic Fever
Rheumatoid Arthritis
Sampter's Syndrome
Schistosomiasis
Schmidt's Syndrome
Scleroderma
Shulman's Syndrome
Sjorgen's Syndrome
Stiff-Man Syndrome
Sympathetic Ophthalmia
Systemic Lupus Erythematosis
Takayasu's Arteritis
Temporal Arteritis
Thyroiditis
Thrombocytopenia
Thyrotoxicosis
Toxic Epidermal Necrolysis
Type B Insulin Resistance
Type I Diabetes Mellitus
Ulcerative Colitis
Uveitis
Vitiligo
Waldenstrom's Macroglobulemia
Wegener's Granulomatosis

5.11.1 Multi-Drug Therapy of Autoimmune Diseases

The present invention also provides methods for treating an autoimmune disease, comprising administering to an animal in need thereof an effective amount of a Compound of the Invention and another therapeutic agent that known for the treatment of an autoimmune disease. In one embodiment, the anti-autoimmune disease agent includes, but is not limited to, agents listed in Table 6.

TABLE 6 cyclosporine
cyclosporine A
mycophenylate mofetil
sirolimus
tacrolimus
enanercept
prednisone
azathioprine
methotrexate cyclophosphamide
prednisone
aminocaproic acid
chloroquine
hydroxychloroquine
hydrocortisone

TABLE 6-continued dexamethasone
chlorambucil
DHEA
danazol
bromocriptine
meloxicam
infliximab

5.12 Treatment of Infectious Diseases

The Compounds of the Invention are useful for killing or inhibiting the multiplication of a cell that produces an infectious disease or for treating an infectious disease. The Compounds of the Invention can be used accordingly in a variety of settings for the treatment of an infectious disease in an animal. The Drug-Linker-Ligand Conjugates can be used to deliver a Drug to a target cell. Without being bound by theory, in one embodiment, the Drug-Linker-Ligand Conjugate associates with an antigen on the surface of a target cell, and the Compound of the Invention is then taken up inside a target-cell through receptor-mediated endocytosis. Once inside the cell, one or more specific peptide sequences within the Linker unit are enzymatically or hydrolytically cleaved, resulting in release of a Drug. The released Drug is then free to migrate in the cytosol and induce cytotoxic activities. In an alternative embodiment, the Drug is cleaved from the Compound of the Invention outside the target cell, and the Drug subsequently penetrates the cell.

In one embodiment, the Ligand unit binds to the infectious disease cell.

In one embodiment, the infectious disease type of infectious disease that the animal needs treatment or prevention of.

In one embodiment, the Compounds of the Invention kill or inhibit the multiplication of cells that produce a particular infectious disease.

Particular types of infectious diseases that can be treated with the Compounds of the Invention include, but are not limited to, those disclosed in Table 7.

TABLE 7

Bacterial Diseases:

Diptheria
Pertussis
Occult Bacteremia
Urinary Tract Infection
Gastroenteritis
Cellulitis
Epiglottitis
Tracheitis
Adenoid Hypertrophy
Retropharyngeal Abcess
Impetigo
Ecthyma
Pneumonia
Endocarditis
Septic Arthritis
Pneumococcal
Peritonitis
Bactermia
Meningitis
Acute Purulent Meningitis
Urethritis
Cervicitis
Proctitis
Pharyngitis
Salpingitis
Epididymitis TABLE 7-continued Gonorrhea
Syphilis
Listeriosis
Anthrax
Nocardiosis
Salmonella
Typhoid Fever
Dysentery
Conjuntivitis
Sinusitis
Brucellosis
Tullaremia
Cholera
Bubonic Plague
Tetanus
Necrotizing Enteritis
Actinomycosis
Mixed Anaerobic Infections
Syphilis
Relapsing Fever
Leptospirosis
Lyme Disease
Rat Bite Fever
Tuberculosis
Lymphadenitis
Leprosy
Chlamydia
Chlamydial Pneumonia
Trachoma
Inclusion Conjunctivitis
Systemic Fungal Diseases:

Histoplamosis
Coccicidiodomycosis
Blastomycosis
Sporotrichosis
Cryptococcsis
Systemic Candidiasis
Aspergillosis
Mucormycosis
Mycetoma
Chromomycosis
Rickettsial Diseases:

Typhus
Rocky Mountain Spotted Fever
Ehrlichiosis
Eastern Tick-Borne Rickettsioses
Rickettsialpox
Q Fever
Bartonellosis
Parasitic Diseases:

Malaria
Babesiosis
African Sleeping Sickness
Chagas' Disease
Leishmaniasis
Dum-Dum Fever
Toxoplasmosis
Meningoencephalitis
Keratitis
Entamebiasis
Giardiasis
Cryptosporidiasis
Isosporiasis
Cyclosporiasis
Microsporidiosis
Ascariasis
Whipworm Infection
Hookworm Infection
Threadworm Infection
Ocular Larva Migrans
Trichinosis
Guinea Worm Disease
Lymphatic Filariasis
Loiasis
River Blindness
Canine Heartworm Infection TABLE 7-continued Schistosomiasis
Swimmer's Itch
Oriental Lung Fluke
Oriental Liver Fluke
Fascioliasis
Fasciolopsiasis
Opisthorchiasis
Tapeworm Infections
Hydatid Disease
Alveolar Hydatid Disease
Viral Diseases:

Measles
Subacute sclerosing panencephalitis
Common Cold
Mumps
Rubella
Roseola
Fifth Disease
Chickenpox
Respiratory syncytial virus infection
Croup
Bronchiolitis
Infectious Mononucleosis
Poliomyelitis
Herpangina
Hand-Foot-and-Mouth Disease
Bornholm Disease
Genital Herpes
Genital Warts
Aseptic Meningitis
Myocarditis
Pericarditis
Gastroenteritis
Acquired Immunodeficiency Syndrome (AIDS)
Reye's Syndrome
Kawasaki Syndrome
Influenza
Bronchitis
Viral "Walking" Pneumonia
Acute Febrile Respiratory Disease
Acute pharyngoconjunctival fever
Epidemic keratoconjunctivitis
Herpes Simplex Virus 1 (HSV-1)
Herpes Simples Virus 2 (HSV-2)
Shingles
Cytomegalic Inclusion Disease
Rabies
Progressive Multifocal Leukoencephalopathy
Kuru
Fatal Familial Insomnia
Creutzfeldt-Jakob Disease
Gerstmann-Straussler-Scheinker Disease
Tropical Spastic Paraparesis
Western Equine Encephalitis
California Encephalitis
St. Louis Encephalitis
Yellow Fever
Dengue
Lymphocytic choriomeningitis
Lassa Fever
Hemorrhagic Fever
Hantvirus Pulmonary Syndrome
Marburg Virus Infections
Ebola Virus Infections
Smallpox 5.12.1 Multi-Drug Therapy of Infectious Diseases The present invention also provides methods for treating an infectious disease, comprising administering to an animal in need thereof a Compound of the Invention and another therapeutic agent that is an anti-infectious disease agent. In one embodiment, the anti-infectious disease agent is, but not limited to, agents listed in Table 8.

TABLE 8

| Antibacterial Agents: |
| --- |
| β-Lactam Antibiotics: |
| Penicillin G |
| Penicillin V |
| Cloxacilliin |
| Dicloxacillin |
| Methicillin |
| Nafcillin |
| Oxacillin |
| Ampicillin |
| Amoxicillin |
| Bacampicillin |
| Azlocillin |
| Carbenicillin |
| Mezlocillin |
| Piperacillin |
| Ticarcillin |
| Aminoglycosides: |
| Amikacin |
| Gentamicin |
| Kanamycin |
| Neomycin |
| Netilmicin |
| Streptomycin |
| Tobramycin |
| Macrolides: |
| Azithromycin |
| Clarithromycin |
| Erythromycin |
| Lincomycin |
| Clindamycin |
| Tetracyclines: |
| Demeclocycline |
| Doxycycline |
| Minocycline |
| Oxytetracycline |
| Tetracycline |
| Quinolones: |
| Cinoxacin |
| Nalidixic Acid |
| Fluoroquinolones: |
| Ciprofloxacin |
| Enoxacin |
| Grepafloxacin |
| Levofloxacin |
| Lomefloxacin |
| Norfloxacin |
| Ofloxacin |
| Sparfloxacin |
| Trovafloxicin |
| Polypeptides: |
| Bacitracin |
| Colistin |
| Polymyxin B |
| Sulfonamides: |
| Sulfisoxazole |
| Sulfamethoxazole |
| Sulfadiazine |
| Sulfamethizole |
| Sulfacetamide |
| Miscellaneous Antibacterial Agents: |
| Trimethoprim |
| Sulfamethazole |
| Chloramphenicol |
| Vancomycin |
| Metronidazole |
| Quinupristin |
| Dalfopristin |
| Rifampin |

TABLE 8-continued

| Antibacterial Agents: |
| --- |
| Spectinomycin |
| Nitrofurantoin |
| Antiviral Agents: |
| General Antiviral Agents: |
| Idoxuradine |
| Vidarabine |
| Trifluridine |
| Acyclovir |
| Famcicyclovir |
| Pencicyclovir |
| Valacyclovir |
| Gancicyclovir |
| Foscarnet |
| Ribavirin |
| Amantadine |
| Rimantadine |
| Cidofovir |
| Antisense Oligonucleotides |
| Immunoglobulins |
| Inteferons |
| Drugs for HIV infection: |
| Zidovudine |
| Didanosine |
| Zalcitabine |
| Stavudine |
| Lamivudine |
| Nevirapine |
| Delavirdine |
| Saquinavir |
| Ritonavir |
| Indinavir |
| Nelfinavir |

5.13 Other Therapeutic Agents

The present methods can further comprise the administration of a Compound of the Invention and an additional therapeutic agent or pharmaceutically acceptable salts or solvates thereof. The Compound of the Invention and the other therapeutic agent can act additively or, more preferably, synergistically. In a preferred embodiment, a composition comprising a Compound of the Invention is administered concurrently with the administration of one or more additional therapeutic agent(s), which can be part of the same composition or in a different composition from that comprising the Compound of the Invention. In another embodiment, a Compound of the Invention is administered prior to or subsequent to administration of another therapeutic agent(s).

In the present methods for treating cancer, an autoimmune disease or an infectious disease, the other therapeutic agent can be an antiemetic agent. Suitable antiemetic agents include, but are not limited to, metoclopromide, domperidone, proclorperazine, promethazine, chlorpromazine, trimethobenzamide, ondansetron, granisetron, hydroxyzine, acethylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxypemdyl, pipamazine, scopolamine, sulpiride, tetrahydrocannabinols, thiethylperazine, thioproperazine and tropisetron.

In another embodiment, the other therapeutic agent can be an hematopoietic colony stimulating factor. Suitable hematopoietic colony stimulating factors include, but are not limited to, filgrastim, sargramostim, molgramostim and erythropoietin alfa.

In still another embodiment, the other therapeutic agent can be an opioid or non-opioid analgesic agent. Suitable opioid analgesic agents include, but are not limited to, morphine, heroin, hydromorphone, hydrocodone, oxymorphone, oxycodone, metopon, apomorphine, normorphine, etorphine, buprenorphine, meperidine, lopermide, anileridine, ethoheptazine, piminidine, betaprodine, diphenoxylate, fentanil, sufentanil, alfentanil, remifentanil, levorphanol, dextromethorphan, phenazocine, pentazocine, cyclazocine, methadone, isomethadone and propoxyphene. Suitable non-opioid analgesic agents include, but are not limited to, aspirin, celecoxib, rofecoxib, diclofinac, diflusinal, etodolac, fenoprofen, flurbiprofen, ibuprofen, ketoprofen, indomethacin, ketorolac, meclofenamate, mefenamic acid, nabumetone, naproxen, piroxicam and sulindac.

The following examples are provided by way of illustration and not limitation.

6. EXAMPLES

Materials and Methods. Commercially available reagents and solvents were obtained as follows: HPLC-grade solvents, Fisher Scientific (Atlanta, Ga.); anhydrous solvents, Aldrich (St. Louis, Mo.); diisopropylazodicarboxylate (DIAD, 95%), Lancaster (Lancashire, England); 4-aminobenzyl alcohol, Alfa Aesar (Ward Hill, Mass.); L-citrulline, Novabiochem (Laufelfingen, Switzerland); all other amino acids, Advanced ChemTech (Louisville, Ky.) or Novabiochem (Laufelfingen, Switzerland); (1S,2R)-(+)-norephedrine and other commercially available reagents, Aldrich or Acros; all coupling reagents were acquired from Novabiochem or Aldrich. All solvents used as reaction media are assumed to be anhydrous unless otherwise indicated. $^1$H-NMR spectra were recorded on either a Varian Gemini at 300 MHz or Varian Mercury 400 MHz spectrophotometer. Flash column chromatography was performed using 230-400 mesh ASTM silica gel from Fisher. Analtech silica gel GHLF plates were used for thin-layer chromatography. Analytical HPLC was performed using a Waters Alliance system using a photodiode array detector. Preparative HPLC purification was performed using a Varian Prostar system that had either a photodiode array or dual wavelength detector. Combustion analyses were determined by Quantitative Technologies, Inc., Whitehouse, N.J.

Examples 5-12 relate to Drugs that can be used as Drug units in the invention.

Example 1

Preparation of Compound 21

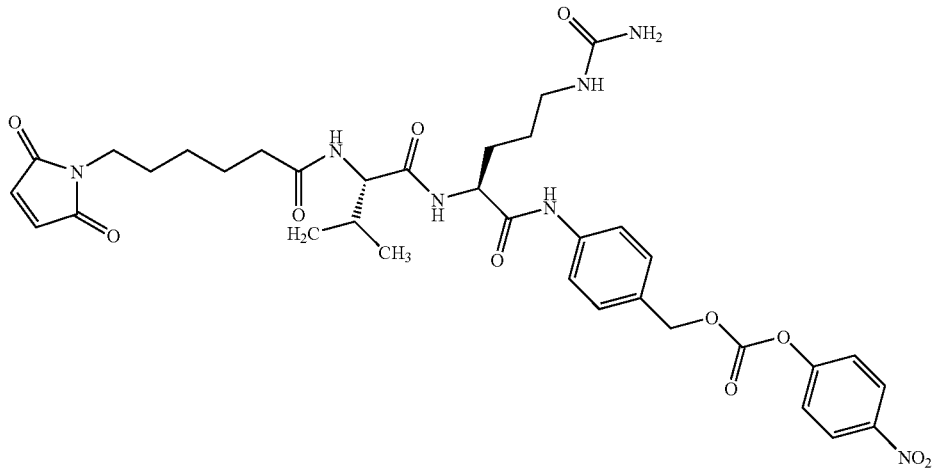

21

Fmoc-(L)-val-(L)-cit-PAB-OH (19)(14.61 g, 24.3 mmol, 1.0 eq., U.S. Pat. No. 6,214,345 to Firestone et al.) was diluted with DMF (120 mL, 0.2 M) and to this solution was added a diethylamine (60 mL). The reaction was monitored by HPLC and found to be complete in 2 h. The reaction mixture was concentrated and the resulting residue was precipitated using ethyl acetate (about 100 mL) under sonication over for 10 min. Ether (200 mL) was added and the precipitate was further sonicated for 5 min. The solution was allowed to stand for 30 min. without stirring and was then filtered and dried under high vacuum to provide Val-cit-PAB-OH, which was used in the next step without further purification. Yield: 8.84 g (96%).

Val-cit-PAB-OH (8.0 g, 21 mmol) was diluted with DMF (110 mL) and the resulting solution was treated with MC-OSu (Willner et al., *Bioconjugate Chem.* 4, 521, 1993, 6.5 g, 21 mmol, 1.0 eq.). Reaction was complete according to HPLC after 2 h. The reaction mixture was concentrated and the resulting oil was precipitated using ethyl acetate (50 mL). After sonicating for 15 min, ether (400 mL) was added and the mixture was sonicated further until all large particles were broken up. The solution was then filtered and the solid dried to provide Compound 20 as an off-white solid. Yield: 11.63 g (96%); ES-MS m/z 757.9 [M−H]$^-$ Compound 20 (8.0 g, 14.0 mmol) was diluted with DMF (120 mL, 0.12 M) and to the resulting solution was added bis(4-nitrophenyl)carbonate (8.5 g, 28.0 mmol, 2.0 eq.) and diisopropylethylamine (3.66 mL, 21.0 mmol, 1.5 eq.). The reaction was complete in 1 h according to HPLC. The reaction mixture was concentrated to provide an oil that was precipitated with EtOAc, and then triturated using EtOAc (about 25 mL). The solute was further precipitated with ether (about 200 mL) and triturated for 15 min. The solid was filtered and dried under high vacuum to provide Compound 21 which was 93% pure according to HPLC and used in the next step without further purification. Yield: 9.7 g (94%).

Example 2

Preparation of Compound 27

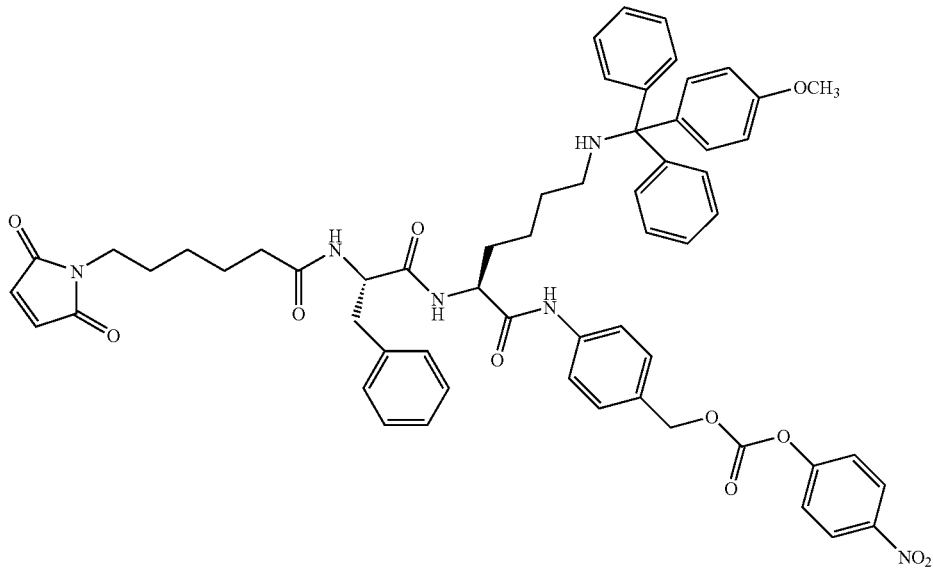

27

Compound 26 (2.0 g, 2.31 mmol, 1.0 eq.) was diluted with dichloromethane (30 mL), and to the resulting solution was added bis(4-nitrophenyl)carbonate (2.72 g, 8.94 mmol, 3.8 eq.) followed by diisopropylethylamine (1.04 mL, 5.97 mmol, 2.6 eq.). The reaction was complete in 3 d, according to HPLC. The reaction mixture was concentrated and the resulting residue was triturated using ether, then filtered and dried under high vacuum to provide Compound 27 as a yellow solid (2.37 g, 97%).

Example 3

Preparation of Compound 28

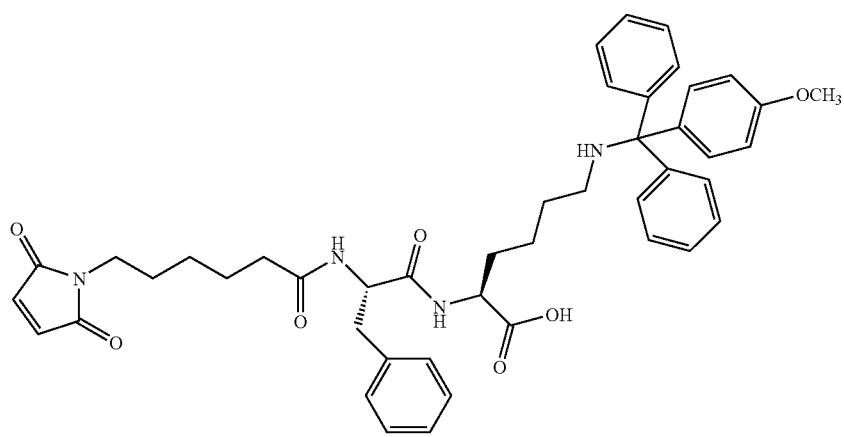

28

Fmoc-phe-lys(Mtr)-OH (24) (0.5 g, 0.63 mmol, U.S. Pat. No. 6,214,345 to Firestone et al.) was diluted with dichloromethane to a concentration of 0.5 M and to this solution was added diethylamine in an amount that was approximately one-third of the volume of the Compound 24/dichloromethane solution. The reaction was allowed to stir and was monitored using HPLC. It was shown to be complete by HPLC in 3 h. The reaction mixture was concentrated in vacuo, and the resulting residue was diluted with ethyl acetate and then reconcentrated. The resulting residue was triturated using ether and filtered. The residual solid was diluted with dichloromethane to a concentration of 0.2M, and to the resulting solution was added MC-OSu (0.20 g, 0.63 mmol, 1.0 eq.) and diisopropylethylamine (0.12 mL, 0.70 mmol, 1.1 eq.). The reaction mixture was allowed to stir under a nitrogen atmosphere for 16 h, after which time HPLC showed very little starting material. The reaction mixture was then concentrated and the resulting residue was triturated using ether to provide Compound 28 as a colored solid. Yield: 100 mg (21%); ES-MS m/z 757.9 [M−H]⁻.

Example 4

Preparation of Compound 19A

Compound 19 (1.0 g, 1.66 mmol) was diluted with DMF (10 mL) and to the resulting solution was added bis(4-nitrophenyl)carbonate (1.0 g, 3.3 mmol, 2.0 eq.).

The reaction mixture was immediately treated with diisopropylethylamine (0.43 mL, 2.5 mmol, 1.5 eq.) and the reaction was allowed to stir under an argon atmosphere. The reaction was complete in 2.5 h according to HPLC. The reaction mixture was concentrated to provide a light brown oil that was precipitated using ethyl acetate (5 mL), then precipitated again using ether (about 100 mL). The resulting precipitate was allowed to stand for 30 min, and was then filtered and dried under high vacuum to provide Compound 19a as an off-white powder. Yield: 1.05 g (83%); ES-MS m/z 767.2 [M+H]⁺; UV $\lambda_{max}$ 215, 256 nm.

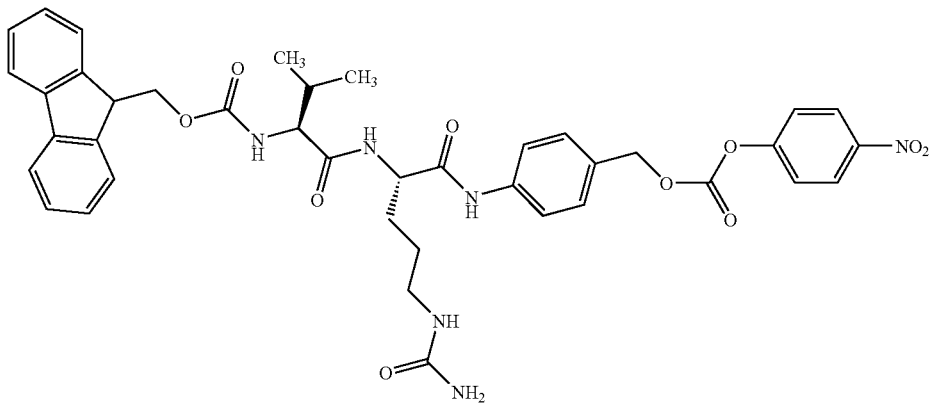

19A

Example 5

Preparation of Compound 49

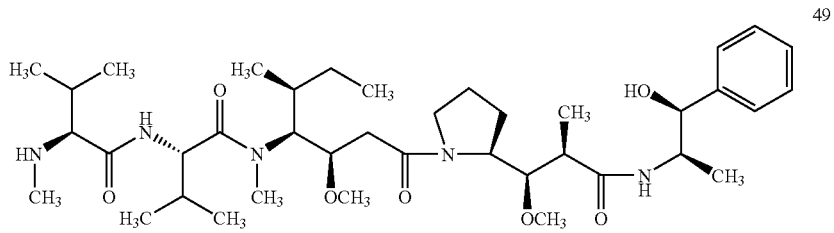

49

Compound 49 was made according to General Procedure D using Fmoc-Me-val-val-dil-O-t-Bu 39 (0.40 g, 0.57 mmol) as the tripeptide and Boc-dap-nor 44 (0.26 g, 0.62 mmol, 1.1 eq.) as the dipeptide. The reaction mixture was purified using flash column chromatography (silica gel column, eluant -100% EtOAc). Two Fmoc-containing products eluted: the Fmoc derivative of Compound 49 ($R_f$ 0.17 in 100% EtOAc) and what was believed to be the Fmoc derivative of the TFA acetate of Compound 49 ($R_f$ 0.37). The products were combined to provide a white foam that was subjected to General Procedure E. Reaction was complete after 2 h. Solvents were removed to provide an oil that was purified using flash column chromatography (eluant -9:1 Dichloromethane-methanol) to provide Compound 49.

Example 6

Preparation of Compound 50 a reverse phase preparative-HPLC column (Varian Dynamax column 21.4 mm×25 cm, 5µ, 100 Å, using a gradient run of MeCN and 0.1M TEA/$CO_2$ at 20 mL/min from 10% to 100% over 40 min followed by 100% MeCN for 20 min). The relevant fractions were pooled and concentrated, and the resulting residue was diluted with 10 mL of dichloromethane-ether (1:1). The solution was cooled to 0° C. and 1.0M ethereal HCl was added dropwise (approx. 10 eq.). The precipitate, Compound 50, was filtered and dried and was substantially pure by HPLC. Yield: 71 mg (43%); ES-MS m/z 731.6 [M+H]$^+$; UV $\lambda_{max}$ 215, 238, 290 nm. Anal. Calc. $C_{40}H_{70}N_6O_6 \cdot 4H_2O \cdot 2HCl$: C, 54.84; H, 9.20; N, 9.59. Found: C, 55.12; H, 9.41; N, 9.82.

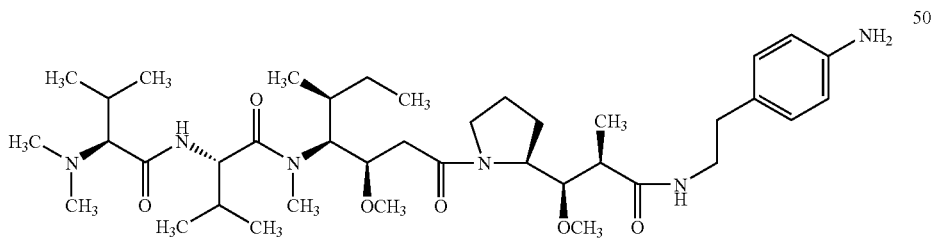

Example 7

Preparation of Compound 51

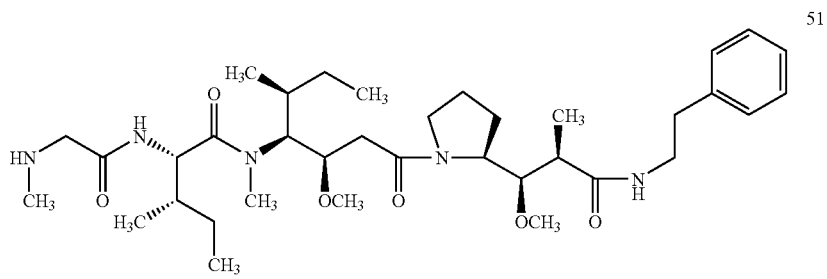

Compound 50 was prepared by reacting tripeptide 42 and dipeptide 48 according to General Procedure D using triethylamine (5.0 eq.) as the base. After concentration of the reaction mixture, the resulting residue was directly injected onto Compound 51 was prepared by reacting Fmoc-tripeptide 41 and dipeptide 46 according to General Procedure D using triethylamine as the base. After concentration of the reaction mixture, the residue was directly injected onto a reverse phase preparative-HPLC column (Varian Dynamax column 21.4 mm×25 cm, 5μ, 100 Å, using a gradient run of MeCN and 0.1M TEA/CO$_2$ at 20 mL/min from 10% to 100% over 40 min followed by 100% MeCN for 20 min). The relevant fractions were pooled and concentrated to provide a white solid intermediate that was used in the next step without further purification. ES-MS m/z 882.9 [M+NH$_4$]$^+$, 899.9 [M+Na]$^+$; UV λ$_{max}$ 215, 256 nm.

Deprotection of the white solid intermediate was performed according to General Procedure E. The crude product was purified using preparative-HPLC (Varian Dynamax column 21.4 mm×25 cm, 5μ, 100 Å, using a gradient run of MeCN and 0.1M TEA/CO$_2$ at 20 mL/min from 10% to 100% over 40 min followed by 100% MeCN for 20 min). The relevant fractions were pooled and concentrated to provide Compound 51 as a sticky solid. ES-MS m/z 660.1 [M+H]$^+$, 682.5 [M+Na]$^+$; UV λ$_{max}$ 215 nm.

Example 8

Preparation of Compound 52

Boc-dolaproine (0.33 g, 1.14 mmol) and (1S,2S)-(−)-1,2-diphenylethylenediamine (0.5 g, 2.28 mmol, 2.0 eq.) were diluted with dichloromethane, (10 mL) and to the resulting solution was added triethylamine (0.32 mL, 2.28 mmol, 2.0 eq.), then DEPC (0.39 mL, 2.28 mmol, 2.0 eq.). After 4 h, additional DEPC (0.39 mL) was added and the reaction was allowed to stir overnight. The reaction mixture was concentrated and the resulting residue was purified using preparative-HPLC (Varian Dynamax C$_{18}$ column 21.4 mm×25 cm, 5μ, 100 Å, using a gradient run of MeCN and water at 20 mL/min from 10% to 100% over 40 min followed by 100% MeCN for 20 min). The relevant fractions were pooled and concentrated to provide a yellow gummy solid peptide intermediate that was used without further purification. R$_f$ 0.15 (100% EtOAc); ES-MS m/z 482.4 [M+H]$^+$; UV λ$_{max}$ 215, 256 nm.

The yellow gummy peptide intermediate (0.24 g, 0.50 mmol) was diluted with dichloromethane, and to the resulting solution was added diisopropylethylamine (0.18 mL, 1.0 mmol, 2.0 eq.) and Fmoc-Cl (0.15 g, 0.55 mmol, 1.1 eq.). The reaction was allowed to stir for 3 h, after which time HPLC showed a complete reaction. The reaction mixture was concentrated to an oil, and the oil was diluted with EtOAc and extracted successively with 10% aqueous citric acid, water, saturated aqueous sodium bicarbonate, and brine. The EtOAc layer was dried, filtered, and concentrated, and the resulting residue was purified using flash column chromatography (silica gel 230-400 mesh; eluant gradient 4:1 hexanes-EtOAc to 1:1 hexanes-EtOAc) to provide Compound 45 as a white solid. Yield: 0.37 g (46% overall); R$_f$ 0.47 (1:1 hexanes-EtOAc); ES-MS m/z 704.5 [M+H]$^+$, 721.4 [M+NH$_4$]$^+$; UV λ$_{max}$ 215, 256 nm.

Compound 52 was prepared by reacting tripeptide 42 (94 mg, 0.13 mmol) and dipeptide compound 45 (65 mg, 0.13 mmol) according to General Procedure D (using 3.6 eq. of diisopropylethylamine as the base). After concentration of the reaction mixture, the resulting residue was diluted with EtOAc and washed successively with 10% aqueous citric acid, water, saturated aqueous sodium bicarbonate, and brine.

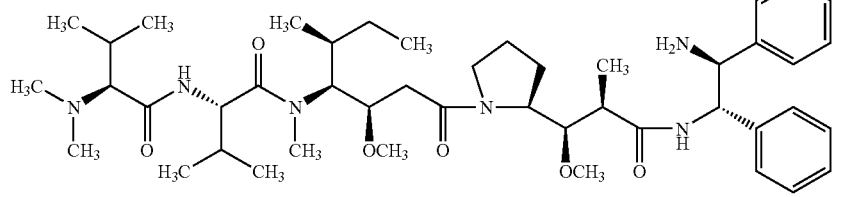

The organic phase was dried, filtered and concentrated to provide a white solid residue which was diluted with dichloromethane and deprotected according to General Procedure E. According to HPLC, reaction was complete after 2 h. The reaction mixture was concentrated to an oil. The oil was diluted with DMSO, and the resulting solution was purified using a reverse phase preparative-HPLC (Varian Dynamax column 21.4 mm×25 cm, 5μ, 100 Å, using a gradient run of MeCN and 0.1% TFA at 20 mL/min from 10% to 100% over 40 min followed by 100% MeCN for 20 min). Two products having similar UV spectra were isolated. The major product, Compound 52, was provided as an off-white solid. Overall yield: 24 mg (23%); ES-MS m/z 793.5 [M+H]$^+$; UV λ$_{max}$ 215 nm.

Example 9

Preparation of Compound 53

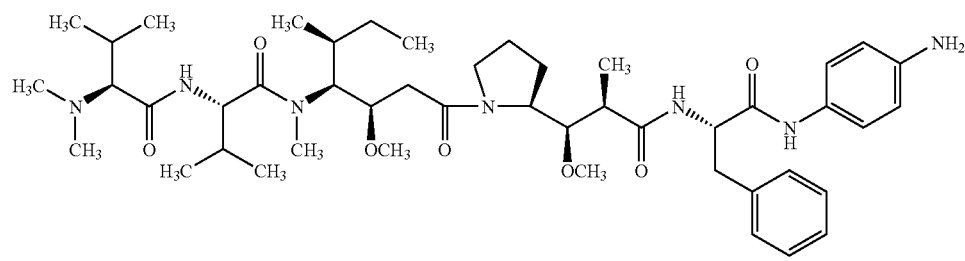

Boc-phenylalanine (1.0 g, 3.8 mmol) was added to a suspension of 1,4-diaminobenzene-HCl (3.5 g, 19.0 mmol, 5.0 eq.) in triethylamine (10.7 mL, 76.0 mmol, 20 eq.) and dichloromethane (50 mL). To the resulting solution was added DEPC (3.2 mL, 19.0 mmol, 5.0 eq.) via syringe. HPLC showed no remaining Boc-phe after 24 h. The reaction mixture was filtered, and the filtrate was concentrated to provide a dark solid. The dark solid residue was partitioned between 1:1 EtOAc-water, and the EtOAc layer was washed sequentially with water and brine. The EtOAc layer was dried and concentrated to provide a dark brown/red residue that was purified using HPLC (Varian Dynamax column 41.4 mm×25 cm, 5μ, 100 Å, using a gradient run of MeCN and water at 45 mL/min form 10% to 100% over 40 min followed by 100% MeCN for 20 min). The relevant fractions were combined and concentrated to provide a red-tan solid intermediate. Yield: 1.4 g (100%); ES-MS m/z 355.9 [M+H]$^+$; UV $\lambda_{max}$ 215, 265 nm; $^1$H NMR (CDCl$_3$) δ 7.48 (1H, br s), 7.22-7.37 (5H, m), 7.12 (2H, d, J=8.7 Hz), 7.61 (2H, d, J=8.7 Hz), 5.19 (1H, br s), 4.39-4.48 (1H, m), 3.49 (2H, s), 3.13 (2H, d, J=5.7 Hz), 1.43 (9H, s).

The red-tan solid intermediate (0.5 g, 1.41 mmol) and diisopropylethylamine (0.37 mL, 2.11 mmol, 1.5 eq.) were diluted with dichloromethane (10 mL), and to the resulting solution was added Fmoc-Cl (0.38 g, 1.41 mmol). The reaction was allowed to stir, and a white solid precipitate formed after a few minutes. Reaction was complete according to HPLC after 1 h. The reaction mixture was filtered, and the filtrate was concentrated to provide an oil. The oil was precipitated with EtOAc, resulting in a reddish-white intermediate product, which was collected by filtration and dried under vacuum. Yield: 0.75 g (93%); ES-MS m/z 578.1 [M+H]$^+$, 595.6 [M+NH$_4$]$^+$.

The reddish-white intermediate (0.49 g, 0.85 mmol), was diluted with 10 mL of dichloromethane, and then treated with 5 mL of trifluoroacetic acid. Reaction was complete in 30 min according to reverse-phase HPLC. The reaction mixture was concentrated and the resulting residue was precipitated with ether to provide an off-white solid. The off-white solid was filtered and dried to provide an amorphous powder, which was added to a solution of Boc-dap (0.24 g, 0.85 mmol) in dichloromethane (10 mL). To this solution was added triethylamine (0.36 mL, 2.5 mmol, 3.0 eq.) and PyBrop (0.59 g, 1.3 mmol, 1.5 eq.). The reaction mixture was monitored using reverse-phase HPLC. Upon completion, the reaction mixture was concentrated, and the resulting residue was diluted with EtOAc, and sequentially washed with 10% aqueous citric acid, water, saturated aqueous sodium bicarbonate, water, and brine. The EtOAc layer was dried (MgSO$_4$), filtered, and concentrated. The resulting residue was purified using flash column chromatography (silica gel) to provide Compound 47 as an off-white powder. Yield: 0.57 g (88%); ES-MS m/z 764.7 [M+NH$_4$]$^+$; UV $\lambda_{max}$ 215, 265 nm; $^1$H NMR (DMSO-d$_6$) δ 10.0-10.15 (1H, m), 9.63 (1H, br s), 8.42 (1/2H, d, J=8.4 Hz), 8.22 (1/2H, d, J=8.4 Hz), 7.89 (2H, d, J=7.2 Hz), 7.73 (2H, d, J=7.6 Hz), 7.11-7.55 (13H, m), 4.69-4.75 (1H, m), 4.46 (2H, d, J=6.8 Hz), 4.29 (1H, t, J=6.4 Hz), 3.29 (3H, s), 2.77-3.47 (7H, m), 2.48-2.50 (3H, m), 2.25 (2/3H, dd, J=9.6, 7.2 Hz), 1.41-1.96 (4H, m), 1.36 (9H, s), 1.07 (1H, d, J=6.4 Hz, rotational isomer), 1.00 (1H, d, J=6.4 Hz, rotational isomer).

Tripeptide compound 42 (55 mg, 0.11 mmol) and dipeptide compound 47 (85 mg, 0.11 mmol) were reacted according to General Procedure D (using 3.0 eq. of diisopropylethylamine). After concentration of the reaction mixture, the resulting residue was diluted with EtOAc, and washed sequentially with 10% aqueous citric acid, water, saturated aqueous sodium bicarbonate, and brine. The EtOAc layer was dried, filtered and concentrated to provide a yellow oil. The yellow oil was diluted with dichloromethane (10 mL) and deprotected according to General Procedure E. According to HPLC, reaction was complete after 2 h. The reaction mixture was concentrated to provide an oil. The oil was diluted with DMSO, and the DMSO solution was purified using reverse phase preparative-HPLC (Varian Dynamax column 21.4 mm×25 cm, 5μ, 100 Å, using a gradient run of MeCN and 0.1% TFA at 20 mL/min from 10% to 100% over 40 min followed by 100% MeCN for 20 min). The relevant fractions were combined and concentrated to provide Compound 53 as an off-white solid. Overall yield: 42 mg (44% overall); ES-MS m/z 837.8 [M+H]$^+$, 858.5 [M+Na]$^+$; UV $\lambda_{max}$ 215, 248 nm.

Example 10

Preparation of Compound 54

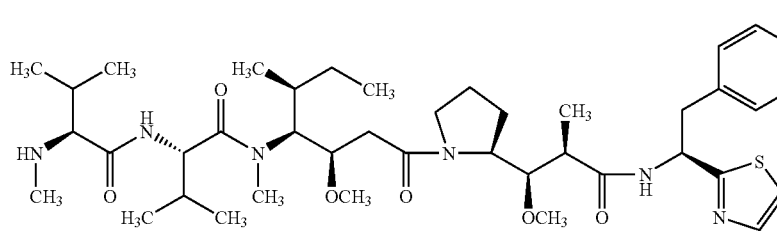

Compound 54 was prepared according to K. Miyazaki, et al. *Chem. Pharm. Bull.* 1995, 43(10), 1706-18.

Example 11

Preparation of Compound 55

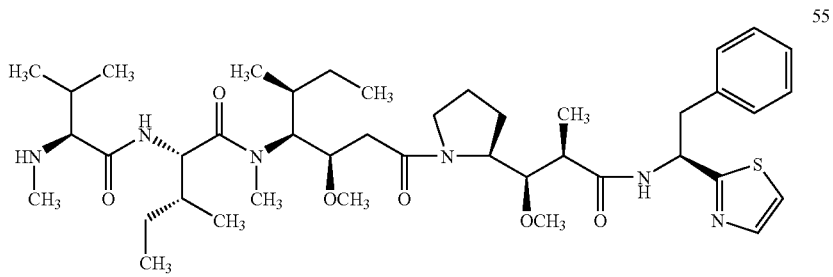

Compound 55 was synthesized in the same manner as Compound 54, but by substituting FmocMeVal-Ile-Dil-tBu (40) for FmocMeVal-Val-Dil-tBu (39) as the starting material.

Example 12

Preparation of Compound 56

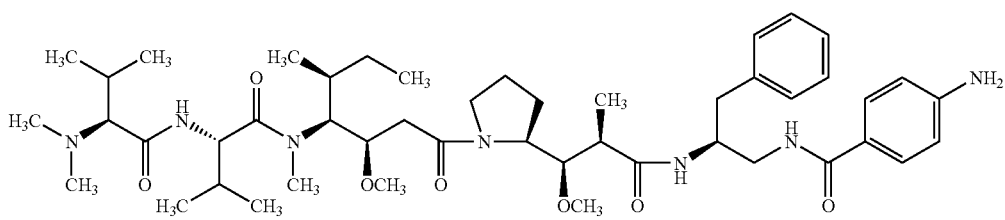

Carbamic acid [(1S)-1-(azidomethyl)-2-phenylethyl]-1,1-dimethylethyl ester (0.56 g, 2 mmol, prepared as described in *J. Chem. Research* (S), 1992, 391), was diluted with a 4 M solution of HCl in dioxane (10 mL) and the resulting solution allowed to stir for 2 hr at room temperature. Toluene (10 mL) was then added to the reaction, the reaction mixture was concentrated and the resulting residue was azeotropically dried under vacuum using toluene (3×15 mL), to provide a white solid intermediate. ES-MS m/z 177.1 [M+H]$^+$.

The white solid intermediate was diluted with dichloromethane (5 mL) and to the resulting solution was added sequentially N-Boc-Dolaproine (0.58 g, 1 eq.), triethylamine (780 μL, 3 eq.) and DEPC (406 μL, 1.2 eq.), and the reaction mixture was allowed to stir for 2 h at room temperature. Reaction progress was monitored using reverse-phase HPLC. Upon completion of reaction as determined by HPLC, the reaction mixture was diluted with dichloromethane (30 mL), the dichloromethane layer was washed successively with 10% aqueous citric acid (20 mL), saturated aqueous NaHCO$_3$ (20 mL), and water (20 mL). The dichloromethane layer was concentrated and the resulting residue was purified via flash column chromatography using a step gradient of 0-5% methanol in dichloromethane. The relevant fractions were combined and concentrated to provide a solid intermediate, 0.78 g (88%). ES-MS m/z 446.1 [M+H]$^+$, 468.3 [M+Na]$^+$.

The solid intermediate (450 mg, 1 mmol) and Tripeptide 42 (534 mg, 1.1 eq.) were diluted with a 50% solution of TFA in dichloromethane (10 mL), and the resulting reaction was allowed to stir for 2 h at room temperature. Toluene (10 mL) was added to the reaction and the reaction mixture was concentrated. The resulting amine intermediate was azeotropically dried using toluene (3×20 mL) and dried under vacuum overnight.

The resulting amine intermediate was diluted with dichloromethane (2 mL) and to the resulting solution was added triethylamine (557 μL, 4 eq.), followed by DEPC (203 μL, 1.4 eq.). The reaction mixture was allowed to stir for 4 h at room temperature and reaction progress was monitored using HPLC. Upon completion of reaction, the reaction mixture was diluted with dichloromethane (30 mL) and the dichloromethane layer was washed sequentially using saturated aqueous NaHCO$_3$ (20 mL) and saturated aqueous NaCl (20 mL). The dichloromethane layer was concentrated and the resulting residue was purified using flash column chromatography in a step gradient of 0-5% methanol in dichloromethane. The relevant fractions were combined and concentrated and the resulting residue was dried using a dichloromethane:hexane (1:1) to provide a white solid intermediate, 0.64 g (84%). ES-MS m/z 757.5 [M+H]$^+$.

The white solid intermediate (536 mg, 0.73 mmol) was diluted with methanol and to the resulting solution was added 10% Pd/C (100 mg). The reaction was placed under a hydrogen atmosphere and was allowed to stir at atmospheric pressure and room temperature for 2 h. Reaction progress was monitored by HPLC and was complete in 2 h. The reaction flask was purged with argon and the reaction mixture was filtered through a pad of Celite. The Celite pad was subsequently washed with methanol (30 mL) and the combined filtrates were concentrated to yield a gray solid intermediate which was used without further purification. Yield=490 mg (91%). ES-MS m/z 731.6 [M+H]$^+$, 366.6 [M+2H]$^{2+}$/2.

The gray solid intermediate (100 mg, 0.136 mmol), N-Boc-4-aminobenzoic acid (39 mg, 1.2 eq.) and triethylamine (90 µL, 4 eq.) were diluted with dichloromethane (2 mL) and to the resulting solution was added DEPC (28 µL, 1.2 eq.). The reaction mixture was allowed to stir at room temperature for 2 h, then the reaction mixture was diluted with dichloromethane (30 mL). The dichloromethane layer was sequentially washed with saturated aqueous NaHCO$_3$ (20 mL) and saturated aqueous NaCl (20 mL). The dichloromethane layer was then concentrated and the resulting residue was purified via flash column chromatography using a step gradient of 0-5% in dichlormethane. The relevant fractions were combined and concentrated and the resulting residue was dried using dichloromethane:hexane (1:1) to provide a white solid intermediate. ES-MS m/z 950.7 [M+H]$^+$.

The white solid intermediate was diluted with a 50% solution of TFA in dichloromethane and allowed to stir for 2 h at room temperature. Toluene (10 mL) was added to the reaction and the reaction mixture was concentrated. The resulting residue was azeotropically dried using toluene (3×15 mL), to provide a yellow oil which was purified using preparative HPLC(C$_{18}$-RP Varian Dynamax column, 5µ, 100 Å, linear gradient of MeCN from 10 to 95% in 0.05 M Triethylammonium carbonate buffer, pH 7.0, in 30 min at a flow rate of 10 mL/min). The relevant fractions were combined and concentrated and the resulting residue was azeotropically dried using MeCN (3×20 mL), to provide Compound 56 as white solid: 101 mg (87% over 2 steps). ES-MS m/z 850.6 [M+H]$^+$, 872.6 [M+Na]$^+$.

Example 13

Preparation of Compound 57

Compound 49 (100 mg, 0.14 mmol), Compound 27 (160 mg, 0.15 mmol, 1.1 eq.), and HOBt (19 mg, 0.14 mmol, 1.0 eq.) were diluted with DMF (2 mL). After 2 min, pyridine (0.5 mL) was added and the reaction mixture was monitored using reverse-phase HPLC. Neither Compound 49 nor Compound 27 was detected after 24 h. The reaction mixture was concentrated, and the resulting residue was purified using reverse phase preparative-HPLC (Varian Dynamax column 21.4 mm×25 cm, 5µ, 100 Å, using a gradient run of MeCN and Et$_3$N—CO$_2$ (pH 7) at 20 mL/min from 10% to 100% over 40 min followed by 100% MeCN for 20 min). The relevant fractions were pooled and concentrated to provide an off-white solid intermediate. ES-MS m/z 1608.7 [M+H]$^+$ The off-white solid intermediate was diluted with MeCN/water/TFA in an 85:5:10 ratio, respectively. The reaction mixture was monitored using HPLC and was complete in 3 h. The reaction mixture was directly concentrated and the resulting residue was purified using reverse phase preparative-HPLC (Varian Dynamax column 21.4 mm×25 cm, 5µ, 100 Å, using a gradient run of MeCN and 0.1% TFA at 20 mL/min from 10% to 100% over 40 min followed by 100% MeCN for 20 min). The relevant fractions were combined and concentrated to provide Compound 57 as an off-white powder. Yield: 46 mg (32% overall); ES-MS m/z 1334.8 [M+H]$^+$; UV $\lambda_{max}$ 215, 256 nm.

57

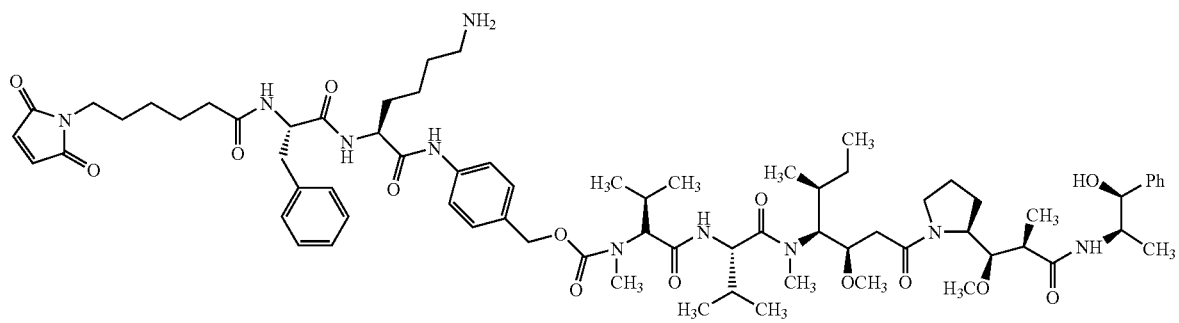

Example 14

Preparation of Compound 58

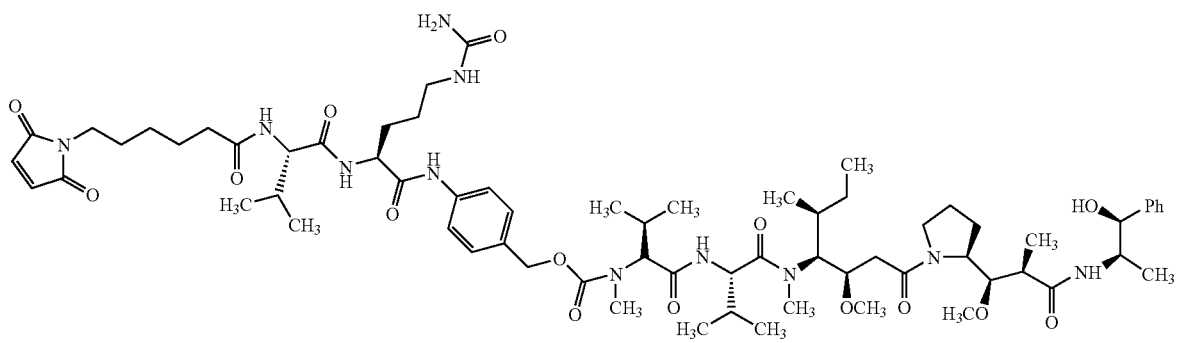

58

Compound 49 (1.69 g, 2.35 mmol), Compound 21 (2.6 g, 3.52 mmol, 1.5 eq.), and HOBt (64 mg, 0.45 mmol, 0.2 eq.) were diluted with DMF (25 mL). After 2 min, pyridine (5 mL) was added and the reaction was monitored using reverse-phase HPLC. The reaction was shown to be complete in 24 h. The reaction mixture was concentrated to provide a dark oil, which was diluted with 3 mL of DMF. The DMF solution was purified using flash column chromatography (silica gel, eluant gradient: 100% dichloromethane to 4:1 dichloromethane-methanol). The relevant fractions were combined and concentrated to provide an oil that solidified under high vacuum to provide a mixture of Compound 58 and unreacted Compound 49 as a dirty yellow solid ($R_f$ 0.40 in 9:1 dichloromethane-methanol). The dirty yellow solid was diluted with DMF and purified using reverse-phase preparative-HPLC (Varian Dynamax $C_{18}$ column 41.4 mm×25 cm, 8 m, 100 Å, using a gradient run of MeCN and 0.1% aqueous TFA at 45 mL/min from 10% to 100% over 40 min followed by 100% MeCN for 20 min) to provide Compound 58 as an amorphous white powder (Rf 0.40 in 9:1 dichloromethane-methanol) which was >95% pure by HPLC and which contained less than 1% of Compound 49. Yield: 1.78 g (57%); ES-MS m/z 1316.7 [M+H]$^+$; UV $\lambda_{max}$ 215, 248 nm.

Example 15

Preparation of Compound 59

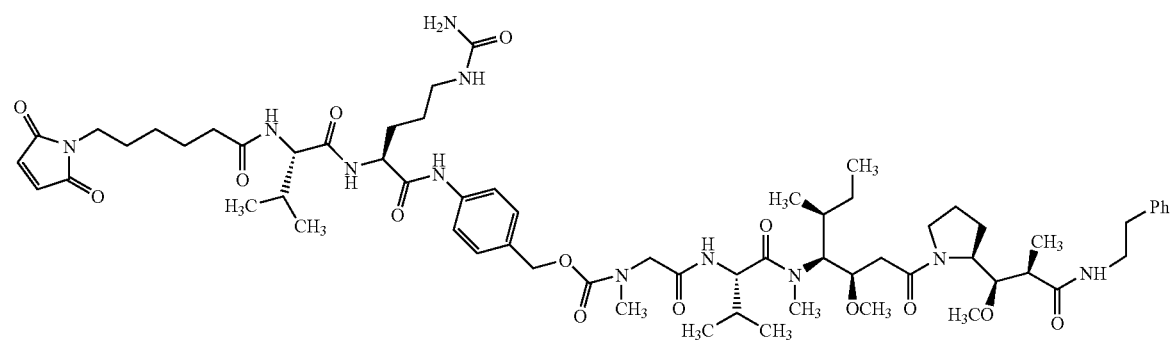

59

The hydrochloride salt of Compound 51 (11 mg, 15.2 mmol) and Compound 21 (11 mg, 15.2 mmol) were diluted with 1-methyl-2-pyrollidinone (1 mL) and to the resulting solution was added diisopropylethylamine (5.3 mL, 30.3 mmol, 2.0 eq.). The mixture was allowed to stir under argon atmosphere for 3 d while being monitored using HPLC. After this time, much unreacted starting material still remained, HOBt (1.0 eq.) was added and the reaction mixture was allowed to stir for 24 h, after which time no starting material remained according to HPLC. The reaction mixture was concentrated and the resulting residue was purified using preparative-HPLC (Varian Dynamax $C_{18}$ column 21.4 mm×25 cm, 5 m, 100 Å, using a gradient run of MeCN and water at 20 mL/min from 10% to 100% over 30 min followed by 100% MeCN for 20 min). The relevant fractions were combined and concentrated to provide Compound 59 as a white solid. Yield:

13 mg (67%); ES-MS m/z 1287.2 [M+H]$^+$, 1304.3 [M+NH$_4$]$^+$; UV $\lambda_{max}$ 215, 248 nm.

Example 16

Preparation of Compound 60

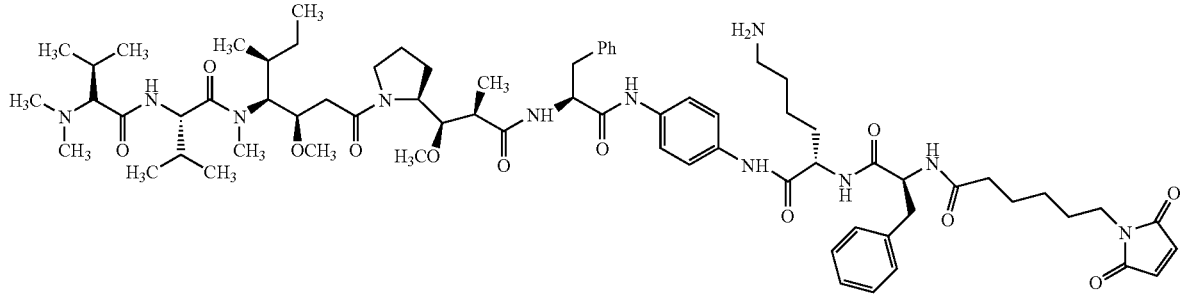

60

Compound 60 as an off-white powder. Yield: 14.9 mg (90%); ES-MS m/z 1304.6 [M+H]$^+$; UV $\lambda_{max}$ 215, 275 nm.

Example 17

Preparation of Compound 61

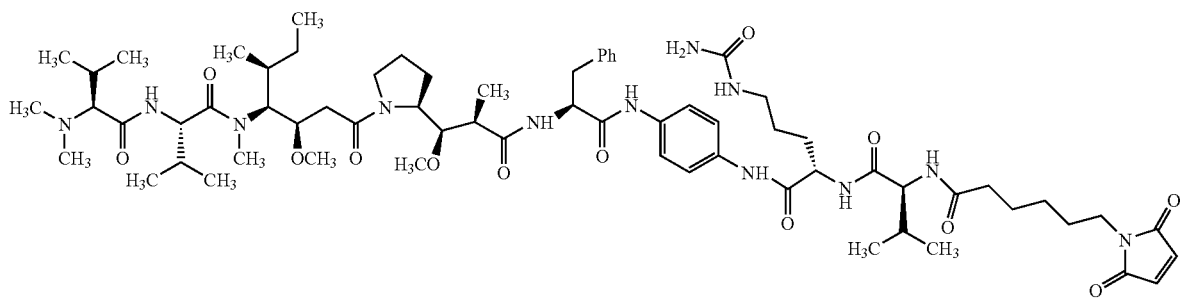

61

Compound 53 (9 mg, 10.8 μmol) and Compound 28 (5.2 mg, 10.8 μmol) were diluted with dichloromethane (1 mL) and to the resulting solution was added HATU (6.3 mg, 16.1 μmol, 1.5 eq.), followed by pyridine (1.3 μL, 16.1 μmol, 1.5 eq.). The reaction mixture was allowed to stir under argon atmosphere while being monitored using HPLC. The reaction was complete after 6 h. The reaction mixture was concentrated and the resulting residue was diluted with DMSO. The DMSO solution was purified using reverse phase preparative-HPLC (Varian Dynamax column 21.4 mm×25 cm, 5μ, 100 Å, using a gradient run of MeCN and 0.1% TFA at 20 mL/min from 10% to 100% over 40 min followed by 100% MeCN for 20 min) and the relevant fractions were combined and concentrated to provide an off-white solid intermediate which was >95% pure according to HPLC.

The off-white solid intermediate was diluted with dichloromethane (2 mL) and the resulting solution was treated with TFA (0.5 mL). The reaction was monitored using HPLC, and was complete in 2 h. The reaction mixture was concentrated, and the resulting residue was diluted with DMSO and purified under the same conditions as described in Example 13. The relevant fractions were combined and concentrated to provide The trifluoroacetate salt of Compound 53 (0.37 g, 0.39 mmol, 1.0 eq.) and Compound 18 (0.30 g, 0.58 mmol, 1.5 eq.) were diluted with DMF (5 mL, 0.1 M), and to the resulting solution was added pyridine (95 μL, 1.2 mmol, 3.0 eq.). HATU (0.23 g, 0.58 mmol, 1.5 eq.) was then added as a solid and the reaction mixture was allowed to stir under argon atmosphere while being monitored using HPLC. The reaction progressed slowly, and 4 h later, 1.0 eq. of diisopropylethylamine was added. Reaction was complete in 1 h. The reaction mixture was concentrated in vacuo and the resulting residue was purified using preparative-HPLC (Varian Dynamax C18 column 41.4 mm×25 cm, 5μ, 100 Å, using a gradient run of MeCN and 0.1% aqueous TFA at 45 mL/min from 10% to 100% over 40 min followed by 100% MeCN for 20 min) to provide a faint pink solid intermediate.

The pink solid intermediate was diluted with DMF (30 mL) and to the resulting solution was added diethylamine (15 mL). Reaction was complete by HPLC in 2 h. The reaction mixture was concentrated and the resulting residue was washed twice with ether. The solid intermediate was dried under high vacuum and then used directly in the next step.

The solid intermediate was diluted with DMF (20 mL) and to the resulting solution was added MC-OSu (0.12 g, 0.39 mmol, 1.0 eq.). After 4 d, the reaction mixture was concentrated to provide an oil which was purified using preparative-HPLC (Varian Dynamax C18 column 41.4 mm×25 cm, 5μ, 100 Å, using a gradient run of MeCN and 0.1% aqueous TFA at 45 mL/min from 10% to 100% over 40 min followed by 100% MeCN for 20 min). Compound 61 was isolated as a white flaky solid. Yield: 0.21 g (38% overall); ES-MS m/z 1285.9 [M+H]$^+$; 13.07.8 [M+Na]$^+$; UV $\lambda_{max}$ 215, 266 nm.

Example 18

Preparation of Compound 62 fractions were pooled and concentrated to yield an oil that was precipitated with ether to provide an off-white solid intermediate. Yield: 0.77 g (74%); ES-MS m/z 1345.7 [M+H]$^+$; UV $\lambda_{max}$ 215, 254 nm.

The off-white solid intermediate (about 85 mg) was deprotected using diethylamine (1 mL) in DMF (3 mL). After 1 h, the reaction was complete. The reaction mixture was concentrated, and the resulting residue was precipitated in 1 mL of EtOAc followed by addition of excess ether (about 20 mL). The amine intermediate was filtered and dried under high vacuum and used in the next step without further purification.

The amine intermediate (70 mg, 61 μmol, 1.0 eq.) was taken up in DMF (10 mL), and to the resulting solution was added sequentially, bromoacetamidocaproic acid (17 mg, 67

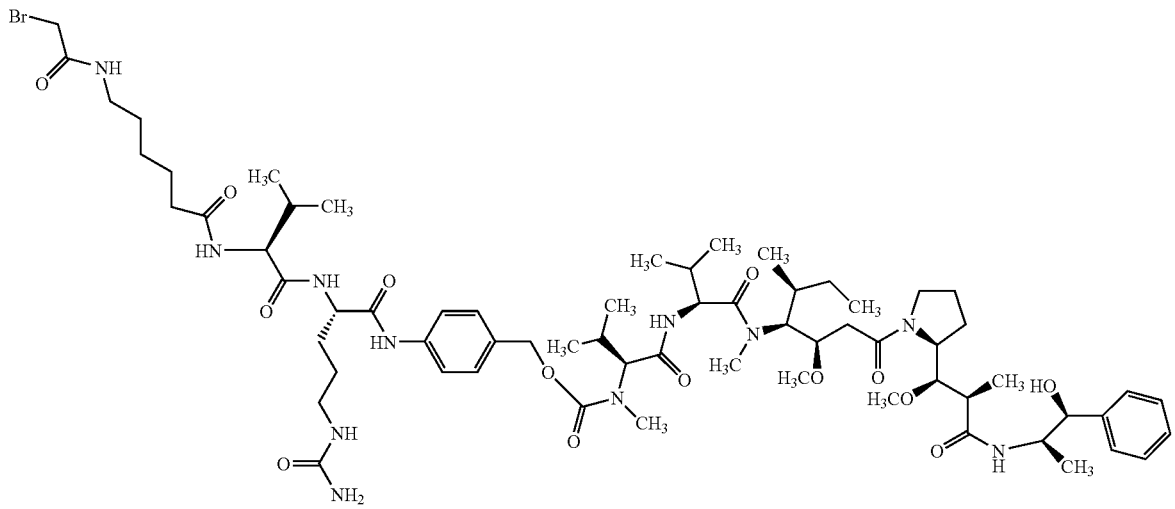

62

Fmoc-val-cit-PAB-OCO-Pnp (19a) (0.65 g, 0.85 mmol, 1.1 eq.), Compound 49 (0.55 g, 0.77 mmol, 1.0 eq.), and HOBt (21 mg, 0.15 mmol, 2.0 eq.) were diluted with DMF (2.0 mL) and dissolved using sonication. To the resulting solution was added pyridine (0.5 mL) and the reaction was monitored using HPLC. After 24 h, diisopropylethylamine (1.0 eq.) was added and the reaction was allowed to stand without stirring for 24 h. The reaction mixture was concentrated to provide an oil residue. The oil residue was purified using reverse phase preparative-HPLC (Varian Dynamax column 41.4 mm×25 cm, 5μ, 100 Å, using a gradient run of MeCN and 0.1% TFA at 45 mL/min from 10% to 100% over 40 min followed by 100% MeCN for 20 min.) The desired μmol, 1.1. eq.), PyBrop (32 mg, 67 μmol, 1.1 eq.), and diisopropylethylamine (16 μL, 92 μmol, 1.5 eq.). After 24 h, an additional 1.0 eq. of bromoacetamidocaproic acid was added. Reaction was stopped after 30 h. The reaction mixture was concentrated to an oil and the oil purified using reverse phase preparative-HPLC (Synergi MaxRP C$_{12}$ column 21.4 mm×25 cm, 5μ, 80 Å, using a gradient run of MeCN and 0.1% TFA at 20 mL/min from 10% to 100% over 40 min followed by 100% MeCN for 20 min.). The relevant fractions were combined and concentrated to provide Compound 62 as a white solid. Yield: 23 mg (27%); ES-MS m/z 1356.7 [M+H]$^+$; UV $\lambda_{max}$ 215, 247 nm.

Example 19

Preparation of Compound 63

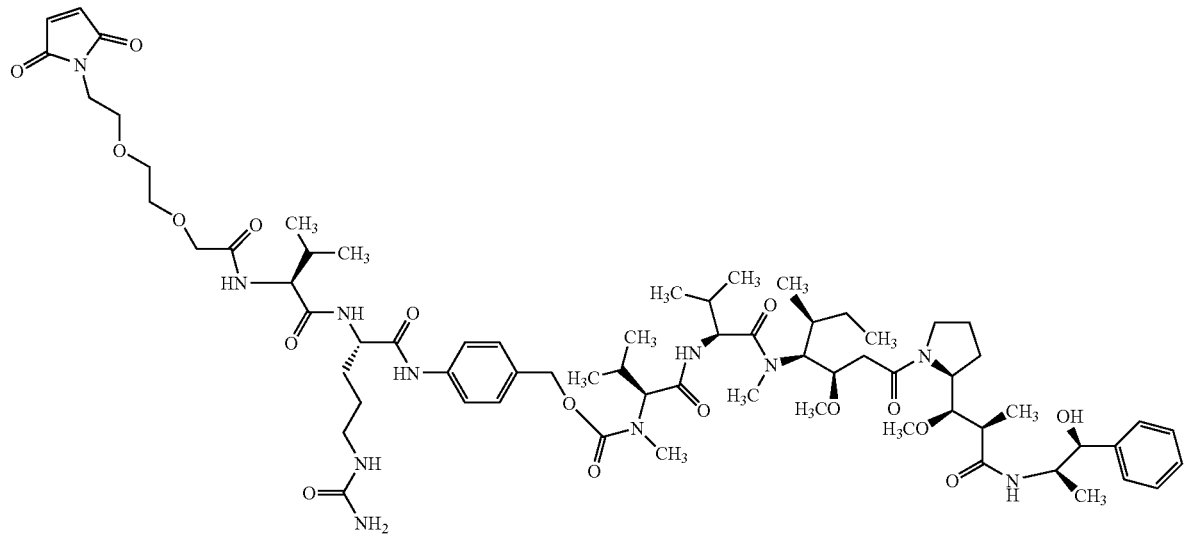

63

Fmoc-val-cit-PAB-OC(O)-Me-val-val-dil-dap-nor (about 48 mg, obtained according to Example 18) was subjected to Fmoc-removal by treating with diethylamine (1 mL) in DMF (3 mL). After 1 h, the reaction was complete. The reaction mixture was concentrated and the resulting residue was precipitated using 1 mL of EtOAc followed by addition of excess ether (about 20 mL). The amine intermediate was filtered and dried under high vacuum and used in the next step without further purification.

The amine intermediate (35 μmol, 1.1 eq.) was diluted with DMF (2 mL), and to the resulting solution was added sequentially maleimido-PEG acid (Frisch, B.; Boeckler, C.; Schuber, F. *Bioconjugate Chem.* 1996, 7, 180-6; 7.8 mg, 32 μmol, 1.0 eq.), DEPC (10.7 μL, 64 μmol, 2.0 eq.), and diisopropylethylamine (11.3 μL, 64 μmol, 2.0 eq.). The reaction was complete in 15 min according to HPLC. The reaction mixture was concentrated to provide an oil. The oil was diluted with 1 mL of DMSO and purified using reverse phase preparative-HPLC (Synergi MaxRP $C_{12}$ column 21.4 mm×25 cm, 5μ, 80 Å, using a gradient run of MeCN and 0.1% TFA at 20 mL/min from 10% to 100% over 40 min followed by 100% MeCN for 20 min). The relevant fractions were combined and concentrated to provide Compound 63 as a white solid.

Yield: 16.2 mg (34%); ES-MS m/z 1348.6 [M+H]$^+$; UV λmax 215, 247 nm.

Examples 20-25 describe the conjugation of the monoclonal antibodies cBR96 and cAC10 to a Drug-Linker Compound. These antibodies were obtained as described in Bowen, et al., *J. Immunol.* 1993, 151, 5896; and Trail, et al., *Science* 1993, 261, 212, respectively.

The number of Drug-Linker moieties per Ligand in a Drug-Linker-Ligand Conjugate varies from conjugation reaction to conjugation reaction, but typically ranges from about 7 to about 9, particularly when the Ligand is cBR96 or cAC10.

Example 20

Preparation of Compound 64

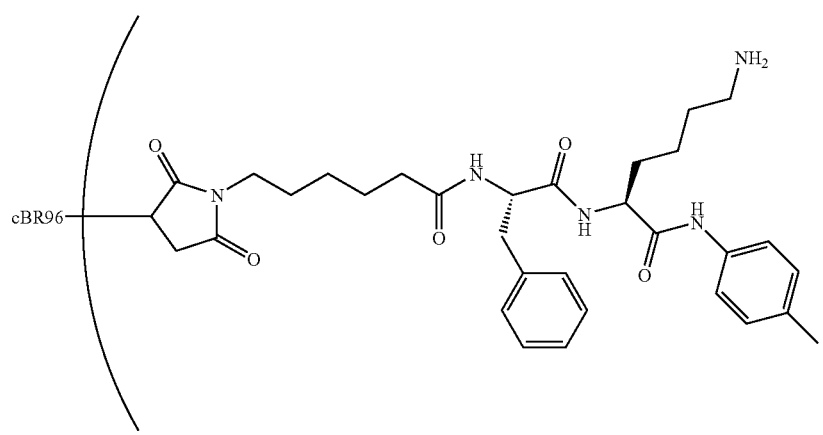

64

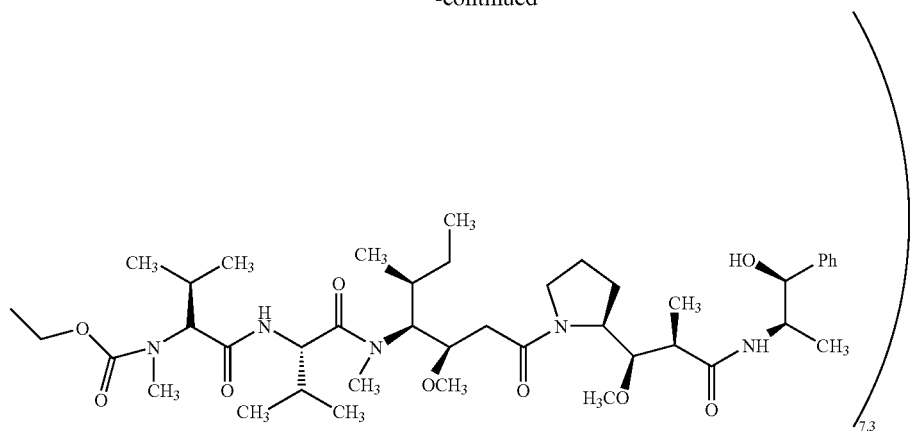

cBR96 Antibody (24 mg) was reduced using DTT as described in General Procedure L, then the number of thiols per antibody and the antibody concentration were determined as described in General Procedure M and General Procedure N, respectively.

Result: [Ab]=4.7 mg/mL=29.4 µM; [thiol]=265 µM; SH/Ab=9.0 (Typical SH/Ab range is from about 7.8 to about 9.5).

Conjugation:

A solution of PBS/DTPA (2.2 mL) as defined above herein, was added to 4.2 mL of reduced antibody and the resulting solution was cooled to 0° C. using an ice bath. In a separate flask, a 130.5 µL stock solution of Compound 57 (8.4 mM in DMSO, 8.5 mol Compound 57 per mol reduced antibody) was diluted with MeCN (1.48 mL, pre-chilled to 0° C. in an ice bath). The MeCN solution of Compound 57 was rapidly added to the antibody solution and the reaction mixture was stirred using a vortex instrument for 5-10 sec., returned to the ice bath and allowed to stir at 0° C. for 1 hr, after which time 218 µL of a cysteine solution (100 mM in PBS/DTPA) was then added to quench the reaction. 60 µL of the quenched reaction mixture was saved as a "qrm" sample.

While the reaction proceeded, three PD10 columns (Sephadex G25, available from Sigma-Aldrich, St. Louis, Mo.) were placed in a cold room and equilibrated with PBS (which had been pre-cooled to 0° C. using an ice bath).

The quenched reaction mixture, which contained Compound 64, was concentrated to ≦3 mL by ultracentrifugation using two Ultrafree 4 centrifuge filtering devices (30K molecular weight cutoff membrane; Millipore Corp.; Bedford, Mass.; used according to manufacturer's instructions) which were pre-cooled to 4° C. in a refrigerator and the concentrated reaction mixture was eluted through the three pre-chilled PD 10 columns using PBS as the eluent (1 mL for each column). The eluted conjugate was collected in a volume of 1.4 mL per column, for a total eluted volume of 4.2 mL. The eluted Conjugate solution was then filtered using a sterile 0.2 micron syringe-end filter, 250 µL of Conjugate solution was set aside for analysis, and the remainder of the Conjugate solution was frozen in sterile vials.

The concentration of Compound 64, the number of Drug molecules per Antibody, the amount of quenched Drug-Linker and the percent of aggregates were determined using General Procedures P, N, O and Q, respectively.

Assay Results:

[Compound 64]=3.8 mg/mLg

% Aggregate=trace

Residual Thiol Titration: Residual thiols=1.7/Ab. Drug/Ab~9.0−1.7=7.3

Quenched Drug-Linker: undetectable

Yield: 4.2 mL, 16 mg, 66%.

Example 21

Preparation of Compound 65

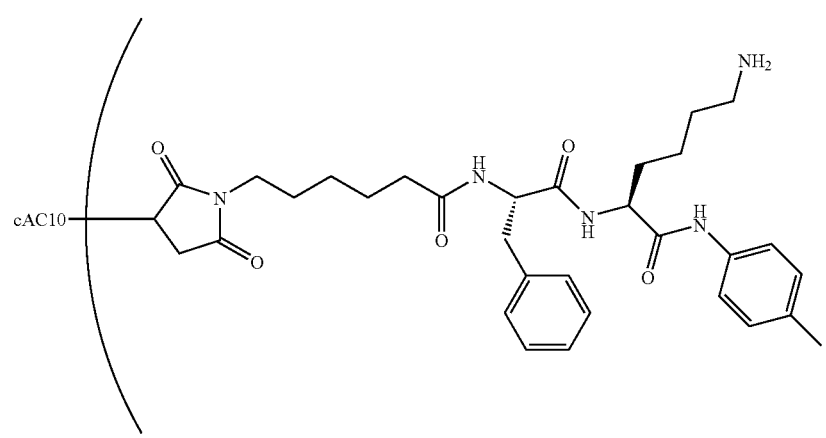

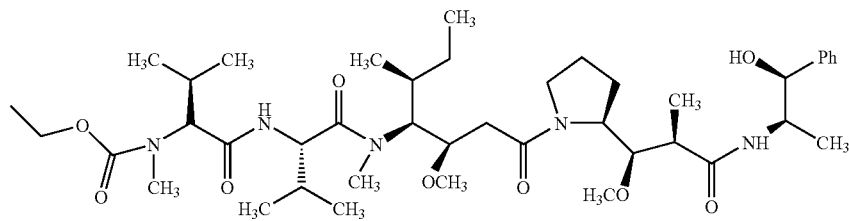

cAC10 Antibody (24 mg) was reduced using DTT as described in General Procedure L, then the number of thiols per antibody and the antibody concentration were determined as described in General Procedure M and General Procedure N, respectively.

Results: [Ab]=4.9 mg/mL=30.7 µM;
[thiol]=283 µM; 9.2 SH/Ab
Conjugation:

A solution of PBS/DTPA (2.2 mL) as defined above herein, was added to 4.2 mL of reduced antibody and the resulting solution was cooled to 0° C. using an ice bath. In a separate flask, 125 µL of a stock solution of Compound 57 (8.4 mM in DMSO, 8.5 mol Compound 57 per mol reduced antibody) was diluted with MeCN (1.48 mL, pre-chilled to 0° C. in an ice bath). The MeCN solution of Compound 57 was rapidly added to the antibody solution and the reaction mixture was stirred using a vortex instrument for 5-10 sec., then returned to the ice bath and allowed to stir at 0° C. for 1 hr, after which time 218 µL of a cysteine solution (100 mM in PBS/DTPA) was then added to quench the reaction. 60 µL of the quenched reaction mixture was saved as a "qrm" sample.

While the reaction proceeded, four PD10 columns (Sephadex G25, available from Sigma-Aldrich, St. Louis, Mo.) were placed in a cold room and equilibrated with PBS (which had been pre-cooled to 0° C. using an ice bath).

The quenched reaction mixture, which contained Compound 65, was concentrated to ≦3 mL by ultracentrifugation using two Ultrafree 4 centrifuge filtering devices (30K molecular weight cutoff membrane; Millipore Corp.; Bedford, Mass.; used according to manufacturer's instructions) which were pre-cooled to 4° C. in a refrigerator and the concentrated reaction mixture was eluted through the four pre-chilled PD 10 columns using PBS as the eluent (1 mL for each column). The eluted conjugate was collected in a volume of 1.4 mL per column, for a total eluted volume of 5.6 mL. The eluted Conjugate solution was then filtered using a sterile 0.2 micron syringe-end filter, 250 µL of Conjugate solution was set aside for analysis, and the remainder of the Conjugate solution was frozen in sterile vials.

The concentration of Compound 65, the number of Drug molecules per Antibody, the amount of quenched Drug-Linker and the percent of aggregates were then determined using General Procedures P, N, O and Q, respectively.

Assay Results:
[Compound 65]=2.8 mg/mL
% Aggregate=trace
Residual Thiol Titration: Residual thiols=1.6/Ab. Drug/Ab~9.2−1.6=7.6
Not covalently bound Drug-Linker: undetectable
Yield: 5.6 mL, 15.7 mg, 65%.

Example 22

Preparation of Compound 66

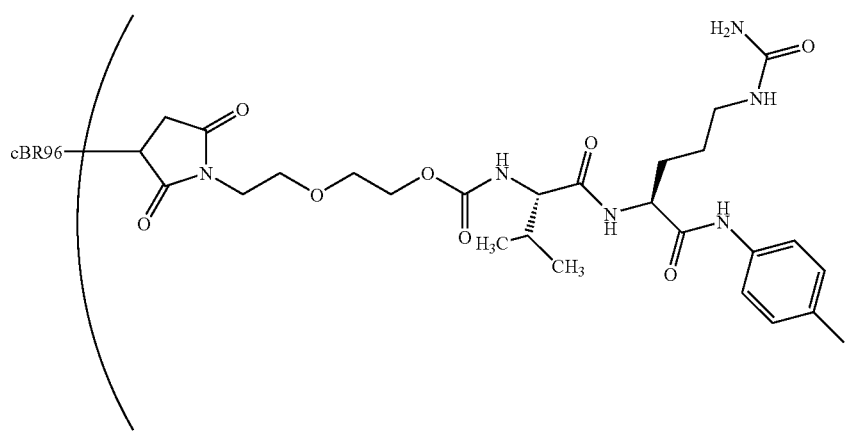

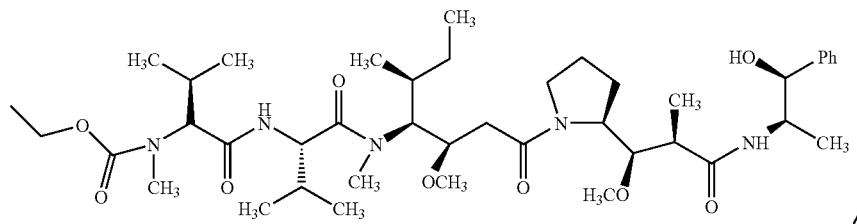

cBR96 Antibody (24 mg) was reduced using DTT as described in General Procedure L, then the number of thiols per antibody and the antibody concentration were determined as described in General Procedure M and General Procedure N, respectively.

Result: [Ab]=3.7 mg/mL=23.1 µM; [thiol]=218 µM; 9.4 SH/Ab

Conjugation:

A solution of PBS/DTPA (2.2 mL) as defined above herein, was added to 4.2 mL of reduced antibody and the resulting solution was cooled to 0° C. using an ice bath. In a separate flask, 145.5 µL of a stock solution of Compound 58 (8.3 mM in DMSO, 9.0 mol Compound 58 per mol reduced antibody) was diluted with MeCN (1.48 mL, pre-chilled to 0° C. in an ice bath). The MeCN solution of Compound 58 was rapidly added to the antibody solution and the reaction mixture was stirred using a vortex instrument for 5-10 sec., then returned to the ice bath and allowed to stir at 0° C. for 1 hr, after which time 249 µL of a cysteine solution (100 mM in PBS/DTPA) was then added to quench the reaction. 60 µL of the quenched reaction mixture was saved as a "qrm" sample.

While the reaction proceeded, three PD 10 columns (Sephadex G25, available from Sigma-Aldrich, St. Louis, Mo.) were placed in a cold room and equilibrated with PBS (which had been pre-cooled to 0° C. using an ice bath).

The quenched reaction mixture, which contained Compound 66, was concentrated to ≦3 mL by ultracentrifugation using two Ultrafree 4 centrifuge filtering devices (30K molecular weight cutoff membrane; Millipore Corp.; Bedford, Mass.; used according to manufacturer's instructions) which were pre-cooled to 4° C. in a refrigerator and the concentrated reaction mixture was eluted through the three pre-chilled PD 10 columns using PBS as the eluent (1 mL for each column). The eluted conjugate was collected in a volume of 1.4 mL per column, for a total eluted volume of 4.2 mL. The eluted Conjugate solution was then filtered using a sterile 0.2 micron syringe-end filter, 250 µL of Conjugate solution was set aside for analysis, and the remainder of the Conjugate solution was frozen in sterile vials.

The concentration of Compound 66, the number of Drug molecules per

Antibody, the amount of quenched Drug-Linker and the percent of aggregates were determined using General Procedures P, N, O and Q, respectively.

Assay Results:

[Compound 66]=3.0 mg/mL

% Aggregate=trace

Residual Thiol Titration: Residual thiols=0.4/Ab. Drug/Ab~9.5−0.4=9.1

Not covalently bound Drug-Linker: 0.3% of 57-Cys adduct

Yield: 5.3 mL, 15.9 mg, 66%.

Example 23

Preparation of Compound 67

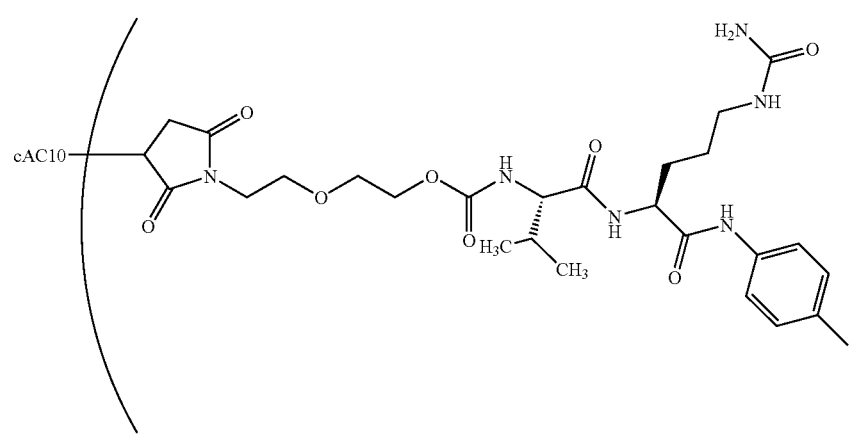

67

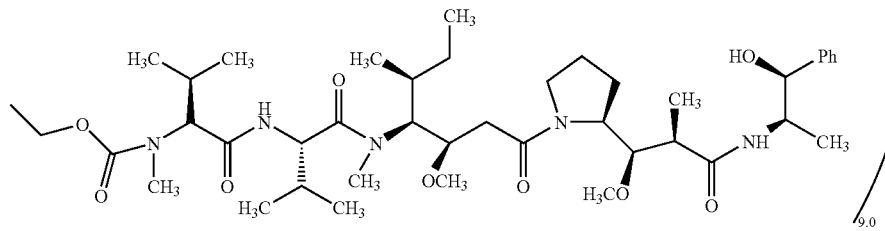

cAC10 Antibody (24 mg) was reduced using DTT as described in General Procedure L, then the number of thiols per antibody and the antibody concentration were determined as described in General Procedure M and General Procedure N, respectively.

Result: [Ab]=3.9 mg/mL=24.5 µM; [thiol]=227 µM; 9.3 SH/Ab

Conjugation:

A solution of PBS/DTPA (2.2 mL) as defined above herein, was added to 4.2 mL of reduced antibody and the resulting solution was cooled to 0° C. using an ice bath. In a separate flask, 154.4 µL of a stock solution of Compound 58 (8.3 mM in DMSO, 9.0 mol Compound 58 per mol reduced antibody) was diluted with MeCN (1.46 mL, pre-chilled to 0° C. in an ice bath). The MeCN solution of Compound 58 was rapidly added to the antibody solution and the reaction mixture was stirred using a vortex instrument for 5-10 sec., then returned to the ice bath and allowed to stir at 0° C. for 1 hr, after which time 249 µL of a cysteine solution (100 mM in PBS/DTPA) was then added to quench the reaction. 60 µL of the quenched reaction mixture was saved as a "qrm" sample.

While the reaction proceeded, four PD10 columns (Sephadex G25, available from Sigma-Aldrich, St. Louis, Mo.) were placed in a cold room and equilibrated with PBS (which had been pre-cooled to 0° C. using an ice bath).

The quenched reaction mixture, which contained Compound 67, was concentrated to ≦3 mL by ultracentrifugation using two Ultrafree 4 centrifuge filtering devices (30K molecular weight cutoff membrane; Millipore Corp.; Bedford, Mass.; used according to manufacturer's instructions) which were pre-cooled to 4° C. in a refrigerator and the concentrated reaction mixture was eluted through the four pre-chilled PD 10 columns using PBS as the eluent (1 mL for each column). The eluted conjugate was collected in a volume of 1.4 mL per column, for a total eluted volume of 5.6 mL. The eluted Conjugate solution was then filtered using a sterile 0.2 micron syringe-end filter, 250 µL of Conjugate solution was set aside for analysis, and the remainder of the Conjugate solution was frozen in sterile vials.

The concentration of Compound 67, the number of Drug molecules per

Antibody, the amount of quenched Drug-Linker and the percent of aggregates were determined using General Procedures P, N, O and Q, respectively.

Assay Results:

[Compound 67]=3.0 mg/mL

% Aggregate=trace

Residual Thiol Titration: Residual thiols=0.5/Ab. Drug/Ab~9.5~0.5=9.0

Quenched Drug-Linker: 1.1% of 58-Cys adduct

Yield: 5.3 mL, 15.9 mg, 66%.

Example 24

Preparation of Compound 68

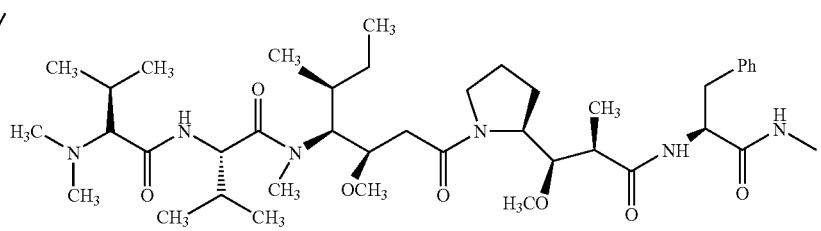

-continued

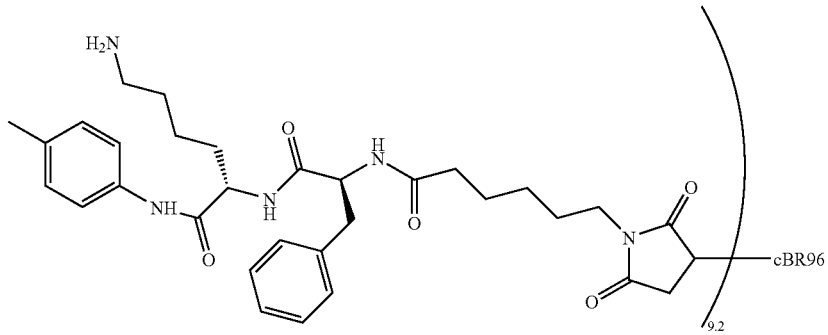

cBR96 Antibody (24 mg) was reduced using DTT as described in General Procedure L, then the number of thiols per antibody and the antibody concentration were determined as described in General Procedure M and General Procedure N, respectively.

Result: [Ab]=4.4 mg/mL=27.2 µM; [thiol]=277 µM; 10.2 SH/Ab

Conjugation:

The reduced antibody was diluted with DMSO (1.47 mL, pre-chilled to 0° C. in an ice bath) so that the resulting solution was 20% DMSO. The solution was allowed to stir for 10 min. at 0° C., then 127.8 µL of a stock solution of Compound 60 (7.6 mM solution in DMSO; 9 mol Compound 60 per mol antibody) was rapidly added. The reaction mixture was immediately stirred using a vortex instrument and return to the ice bath and allowed to stir at 0° C. for 1 hr, after which time 213 µL of a cysteine solution (100 mM in PBS/DTPA) was then added to quench the reaction. 60 µL of the quenched reaction mixture was saved as a "qrm" sample.

While the reaction proceeded, four PD10 columns (Sephadex G25, available from Sigma-Aldrich, St. Louis, Mo.) were placed in a cold room and equilibrated with PBS (which had been pre-cooled to 0° C. using an ice bath).

The quenched reaction mixture, which contained Compound 68, was concentrated to ≦3 mL by ultracentrifugation using two Ultrafree 4 centrifuge filtering devices (30K molecular weight cutoff membrane; Millipore Corp.; Bedford, Mass.; used according to manufacturer's instructions) which were pre-cooled to 4° C. in a refrigerator and the concentrated reaction mixture was eluted through the four pre-chilled PD 10 columns using PBS as the eluent (1 mL for each column). The eluted conjugate was collected in a volume of 1.4 mL per column, for a total eluted volume of 5.6 mL.

The eluted Conjugate solution was then filtered using a sterile 0.2 micron syringe-end filter, 250 µL of Conjugate solution was set aside for analysis, and the remainder of the Conjugate solution was frozen in sterile vials.

The concentration of Compound 68, the number of Drug molecules per Antibody, the amount of quenched Drug-Linker and the percent of aggregates were determined using General Procedures P, N, O and Q, respectively.

Because the absorbances of Compound 60 and antibody largely overlap, spectrophotometric determination of the conjugate concentration requires the measurement of absorbance at 270 and 280 nm. The molar concentration of conjugate is given by the following formula:

[Conjugate]=($OD_{280}$×1.08$e^{-5}$−$OD_{270}$×8.20$e^{-6}$)×dilution factor, where the values 1.08$e^{-5}$ and 8.20$e^{-6}$ are calculated from the molar extinction coefficients of the drug and the antibody, which are estimated as:

$\epsilon_{270}$ Compound 60=2.06e4 $\epsilon_{270}$ cBR96=1.87e5
$\epsilon_{280}$ Compound 60=1.57e4 $\epsilon_{280}$ cBR96=2.24e5

Assay Results:
[Compound 68]=3.2 mg/mL
% Aggregate=trace
Residual Thiol Titration: Residual thiols=1.0/Ab. Drug/Ab~10.2−1.0=9.2
Quenched Drug-Linker: trace
Yield: 5.6 mL, 17.9 mg, 75%.

Example 25

Preparation of Compound 69

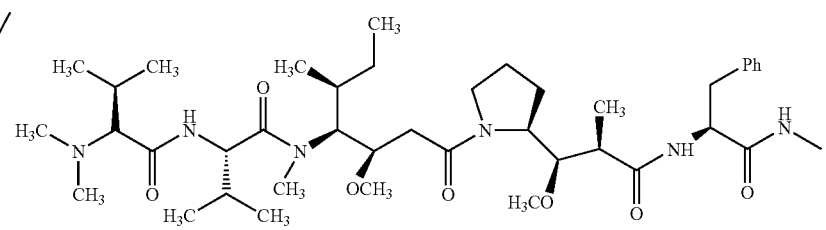

-continued

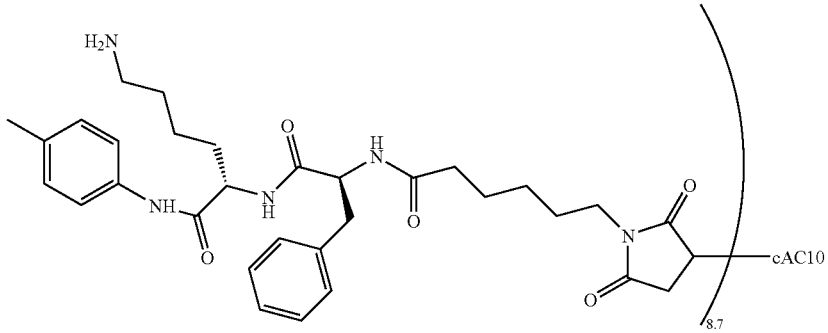

cAC10 Antibody (24 mg) was reduced using DTT as described in General Procedure L, then the number of thiols per antibody and the antibody concentration were determined as described in General Procedure M and General Procedure N, respectively.

Result: [Ab]=4.8 mg/mL=29.8 µM; [thiol]=281 µM; 9.4 SH/Ab

Conjugation:

The reduced antibody was diluted with DMSO (1.47 mL, pre-chilled to 0° C. in an ice bath) so that the resulting solution was 20% DMSO. The solution was allowed to stir for 10 min. at 0° C., then 140 µL of a stock solution of Compound 60 (7.6 mM solution in DMSO; 8.5 mol Compound 60 per mol antibody) was rapidly added. The reaction mixture was immediately stirred using a vortex instrument and return to the ice bath and allowed to stir for 1 hr at 0° C., after which time 213 µL of a cysteine solution (100 mM in PBS/DTPA) was then added to quench the reaction. 60 µL of the quenched reaction mixture was saved as a "qrm" sample.

While the reaction proceeded, four PD10 columns (Sephadex G25, available from Sigma-Aldrich, St. Louis, Mo.) were placed in a cold room and equilibrated with PBS (which had been pre-cooled to 0° C. using an ice bath).

The quenched reaction mixture, which contained Compound 69, was concentrated to ≦3 mL by ultracentrifugation using two Ultrafree 4 centrifuge filtering devices (30K molecular weight cutoff membrane; Millipore Corp.; Bedford, Mass.; used according to manufacturer's instructions) which were pre-cooled to 4° C. in a refrigerator and the concentrated reaction mixture was eluted through the four pre-chilled PD 10 columns using PBS as the eluent (1 mL for each column). The eluted conjugate was collected in a volume of 1.4 mL per column, for a total eluted volume of 5.6 mL. The eluted Conjugate solution was then filtered using a sterile 0.2 micron syringe-end filter, 250 µL of Conjugate solution was set aside for analysis, and the remainder of the Conjugate solution was frozen in sterile vials.

The concentration of Compound 69, the number of Drug molecules per Antibody, the amount of quenched Drug-Linker and the percent of aggregates were determined using General Procedures P, N, O and Q, respectively.

Because the absorbances of Compound 60 and antibody largely overlap, spectrophotometric determination of the conjugate concentration requires the measurement of absorbance at 270 and 280 nm. The molar concentration of conjugate is given by the following formula:

[Conjugate]=(OD$_{280}$×1.08$e^{-5}$−OD$_{270}$×8.20$e^{-6}$)×dilution factor, where the values 1.08$e^{-5}$ and 8.20$e^{-6}$ are calculated from the molar extinction coefficients of the drug and the antibody, which are estimated as:

$\epsilon_{270}$ Compound 60=2.06$e^4$ $\epsilon_{270}$ cAC10=2.10$e^5$
$\epsilon_{280}$ Compound 60=1.57$e^4$ $\epsilon_{280}$ cAC10=2.53$e^5$ Assay Results:
[Compound 69]=3.0 mg/mL
% Aggregate=trace
Residual Thiol Titration: Residual thiols=0.7/Ab. Drug/Ab~9.4−0.7=8.7
Quenched Drug-Linker: trace
Yield: 5.6 mL, 16.8 mg, 70%.

Example 26

Preparation of Compound 75

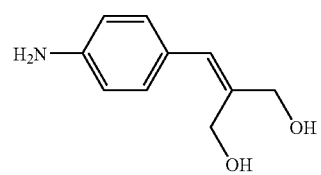

75

Diethyl (4-nitrobenzyl)phosphonate (1.1 g, 4.02 mmol) was diluted in anhydrous THF (4 mL) and the resulting mixture was cooled to 0° C. Sodium hydride (0.17 g, 4.22 mmol, 1.05 eq., 60% dispersion in mineral oil) was added and the resulting reaction was allowed to stir for 5 min. At this time gas evolution from the reaction mixture had ceased. 2,2-Dimethyl-1,3-dioxan-5-one (0.52 g, 4.02 mmol) in 1 mL of a hydrous THF was then added to the reaction mixture via syringe and the reaction was allowed to warm to room temperature with stirring. Additional THF (1 mL) was added after 30 min to help dilute the resulting precipitate and the resulting mixture was stirred for an additional 30 min., was transferred to a separatory funnel containing EtOAc (10 mL) and water (10 mL). The organic phase was collected, washed with brine, and the combined aqueous extracts were washed with ethyl acetate (2×). The combined organic extracts were dried over MgSO$_4$, filtered, and concentrated to provide a dark red crude oil that was purified using flash chromatography on a silica gel column (300×25 mm) and eluting with 9:1 hexanes-EtOAc to provide a pale yellow solid intermediate. Yield: 0.57 g (57%); R$_f$ 0.24 (9:1 hexanes-EtOAc); UV λ$_{max}$ 225, 320 nm. $^1$H NMR (CDCl$_3$) δ 8.19 (2H, d, J=8.4 Hz), 7.24 (2H, d, J=8.4 Hz), 6.33 (1H, s), 4.62 (2H, s), 4.42 (2H, s), 1.45 (6H, s). $^{13}$C NMR (CDCl$_3$) δ 146.6, 142.7, 141.3, 129.4, 123.9, 121.1, 99.9, 64.4, 60.8, 24.1.

The pale yellow solid intermediate (0.25 g, 1.0 mmol) was diluted using THF (20 mL), the resulting mixture was treated with 1 N HCl (10 mL) and allowed to stir for 5 min. To the reaction mixture was added diethyl ether (150 mL) and water and the resulting mixture was transferred to a separatory funnel. The organic layer was dried (MgSO$_4$), filtered and concentrated to give an oil. The resulting diol was then taken up in THF-methanol (1:1, 4 mL each, 0.3 M) followed by the addition of Raney Nickel (100 µL, 100 µL/mmol nitro-group, 50% slurry in water) and hydrazine (74 µL, 1.5 eq.). Gas evolution occurred while the reaction mixture was heated to 50-60° C. After 30 min and 1 h, 1.5 eq. of hydrazine was added each time. The yellow mixture was filtered through celite and washed with methanol. The filtrated was concentrated to provide Compound 75 as an oil which later crystallized to a yellow solid. Yield: 0.14 g (78%); UV λ$_{max}$ 215, 260 nm. 1H NMR (DMSO) δ 7.00 (2H, d, J=8.4 Hz), 6.51 (2H, d, J=8.4 Hz), 6.33 (1H, s), 5.20 (2H, bs), 4.64 (2H, bd), 4.04 (2H, s). $^{13}$C NMR (DMSO) δ 147.2, 138.1, 129.6, 126.1, 124.6, 113.7, 63.6, 57.5.

Example 27

Preparation of Compound 79

2.84-3.06 (2H, m), 1.91-2.03 (1H, m), 1.29-1.74 (4H, m), 0.86 (3H, d, J=6.8 Hz), 0.84 (3H, d, J=6.8 Hz).

The tan solid intermediate was diluted with DMF (10 mL) and the resulting mixture was treated with diethylamine (5 mL), allowed to stir for 1 hour and concentrated to provide a tan solid which was dried under high vacuum for 3 days. The tan solid was triturated using EtOAc (10 mL) and further precipitated using ether (80 mL) to provide a crude residue which was filtered through a sintered glass funnel and dried in vacuo to afford a light tan intermediate. ES-MS m/z 436 [M+H]$^+$, 458 [M+Na]$^+$; UV λ$_{max}$ 215, 270 nm.

The light tan intermediate was diluted with DMF (10 mL) and treated with 6-maleimidocaproic acid hydroxysuccinimde ester (0.16 g, 0.53 mmol, 1 eq.). The reaction was allowed to stir for 18 h, additional diisopropylethylamine (1.0 eq) was added followed by additional 6-maleimidocaproic acid hydroxysuccinimde ester (0.5 eq.). The resulting reaction was allowed to stir for 4 hours, after which time, HPLC indicated that the starting material had been consumed. The reaction mixture was concentrated to provide a crude residue that was triturated using EtOAc (10 mL) and then further precipitated using ether (75 mL). The precipitate was and dried overnight to provide a tan/orange powdered intermediate. Overall yield: 0.42 g (quant.). ES-MS m/z 629 [M+H]$^+$, 651 [M+Na]$^+$; UV λ$_{max}$ 215, 270 nm.

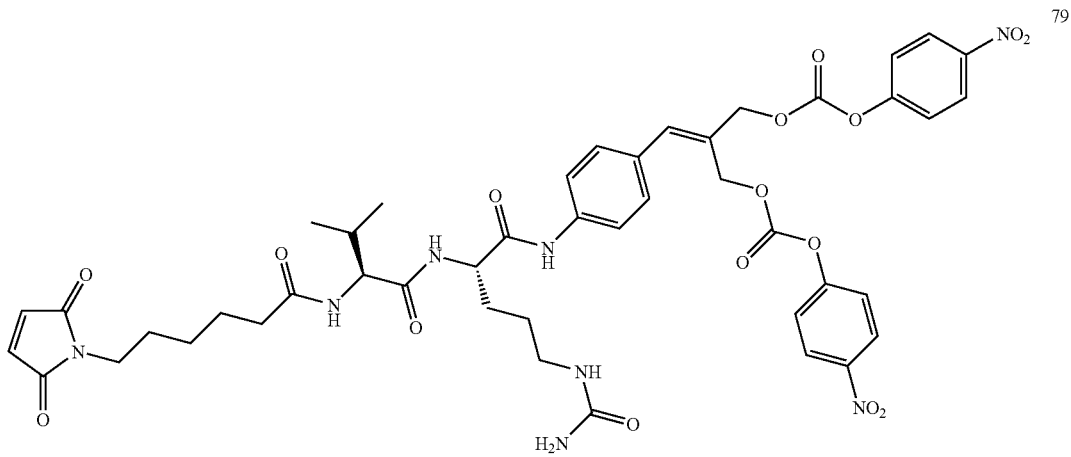

To a mixture of Compound 75 (BHMS, 0.12 g, 0.67 mmol) in methanol-dichloromethane (1:2, 4.5 mL total) was added Fmoc-Val-Cit (0.33 g, 0.67 mmol) followed by EEDQ (0.25 g, 1.0 mmol, 1.5 eq.) and the resulting reaction was allowed to stir for 15 hours under inert atmosphere. Additional EEDQ (1.5 eq.) and Fmoc-Val-Cit (1.0 eq.) were then added due to the presence of unreacted BHMS and the resulting reaction was allowed to stir for 2 days and concentrated. The resulting residue was triturated using ether to provide a tan solid intermediate. ES-MS m/z 659 [M+H]$^+$, 681 [M+Na]$^+$; UV λ$_{max}$ 215, 270 nm. $^1$H NMR (DMSO) δ 10.04 (1H, s), 8.10 (1H, d, J=7.2 Hz), 7.87 (2H, d, J=7.6 Hz), 7.72 (2H, t, J=7.6 Hz), 7.55 (2H, d, J=8.4 Hz), 7.37-7.43 (3H, m), 7.30 (2H, t, J=7.2 Hz), 7.24 (2H, d, J=8.4 Hz), 6.47 (1H, s), 5.96 (1H, t, J=5.2 Hz), 5.39 (1H, s), 4.83 (1H, t, J=5.2 Hz), 4.78 (1H, t, J=5.2 Hz), 4.40 (1H, dd, J=5.2, 8.0 Hz), 4.20-4.30 (3H, m), 4.11 (2H, d, J=4.4 Hz), 4.04 (2H, d, J=5.2 Hz), 3.91 (1H, t, J=7.2 Hz), The tan/orange powdered intermediate (0.40 g, 0.64 mmol) was partially dissolved in DMF (20 mL) and to the resulting mixture was added bis(4-nitrophenyl) carbonate (0.98 g, 3.2 mmol, 5.0 eq.) and diisopropylethylamine (0.45 mL, 2.5 mmol, 4.0 eq.). The resulting reaction was allowed to stir for about 4 hours, after which time, HPLC monitoring indicated that no starting material remained and that the reaction mixture contained 2 products in a 3:2 ratio (the desired biscarbonate and the 1,3-dioxan-2-one, respectively). The reaction mixture was concentrated and the resulting residue was triturated using EtOAc (10 mL), then further precipitated using ether (80 mL) in a one-pot manner. The EtOAc-ether mixture was filtered and the solid was dried to provide Compound 79 as a tan powder which was used without further purification.

Example 28

Preparation of Compound 80

Compound 49 (202 mg, 0.22 mmol, 2.0 eq., 80% pure) and Compound 79 (180 mg, 0.11 mmol, 1.0 eq., 60% pure) were suspended in dry DMF (2 mL, 0.1 M) and to the resulting mixture was added HOBt (3 mg, 22 μmol, 0.2 eq.) followed by pyridine (400 μL, ¼ v/v DMF). The resulting reaction was allowed to stir for 16 h, diluted with DMSO (2 mL) and the resulting mixture was purified using preparative HPLC(C$_{18}$-RP column, 5μ, 100 Å, linear gradient of MeCN in water 10 to 100% in 40 min followed by 20 min at 100%, at a flow rate of 50 mL/min) to provide Compound 80 as a white solid.

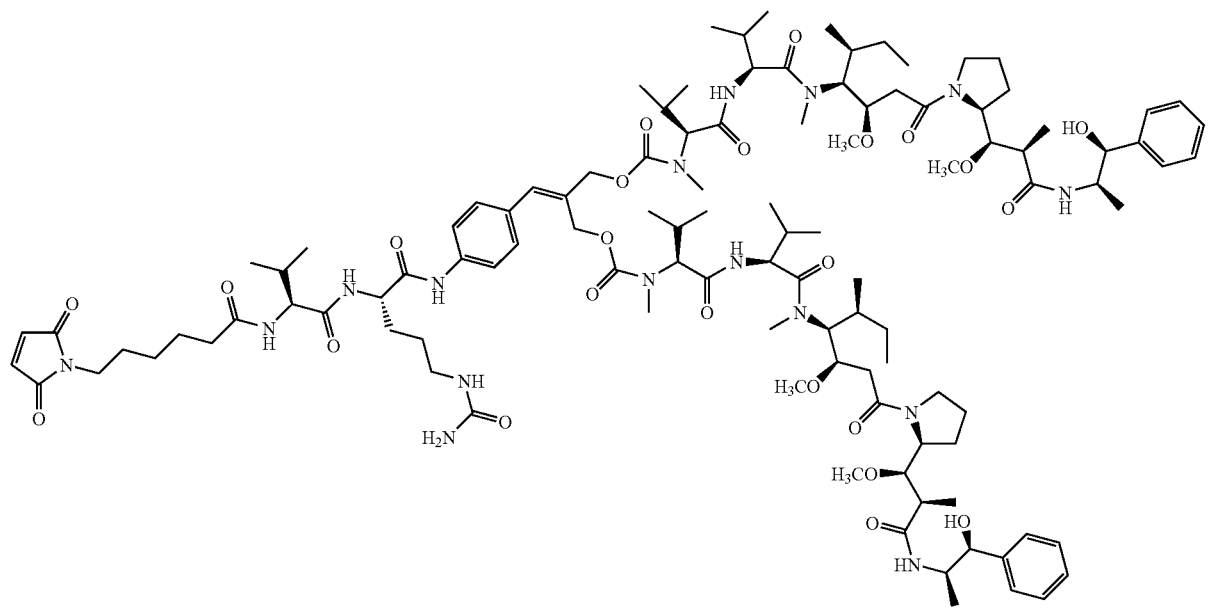

80

Yield: 70 mg (18%). MALDI-TOF MS m/z 2138.9 [M+Na]$^+$, 2154.9 [M+K]$^+$.

Example 29

Preparation of Compound 81

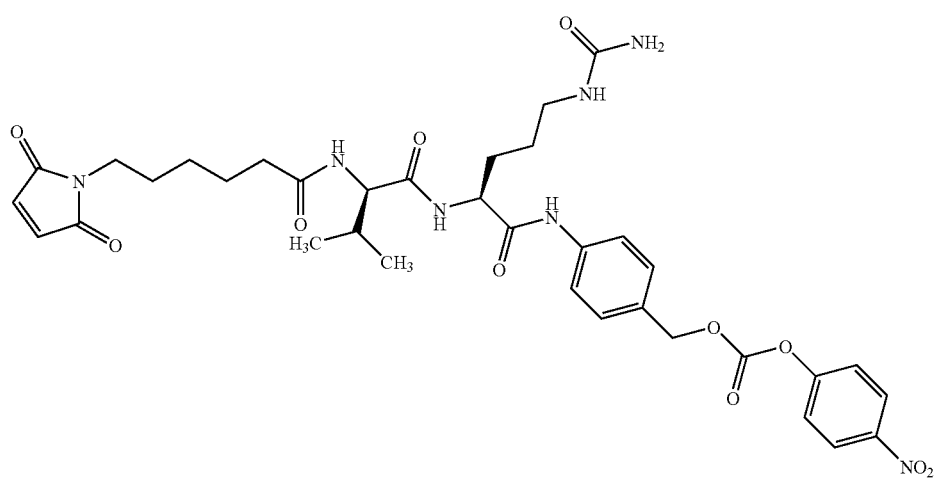

81

Compound 81 was made using the method described in Example 1 and substituting Fmoc-(D)-val-(L)-cit-PAB-OH for Compound 19.
Example 30
Preparation of Compound 82
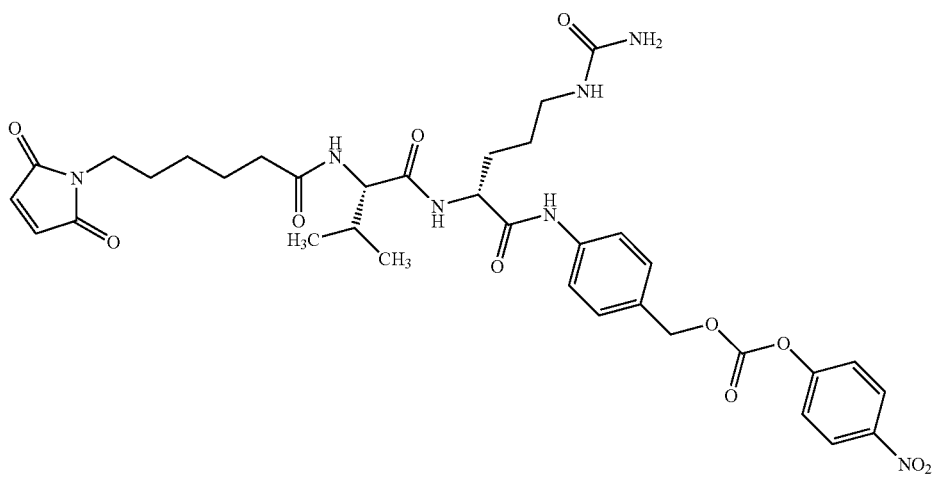
82
Compound 82 was made using the method described in Example 1 and substituting Fmoc-(L)-val-(D)-cit-PAB-OH for Compound 19.
Example 31
Preparation of Compound 83
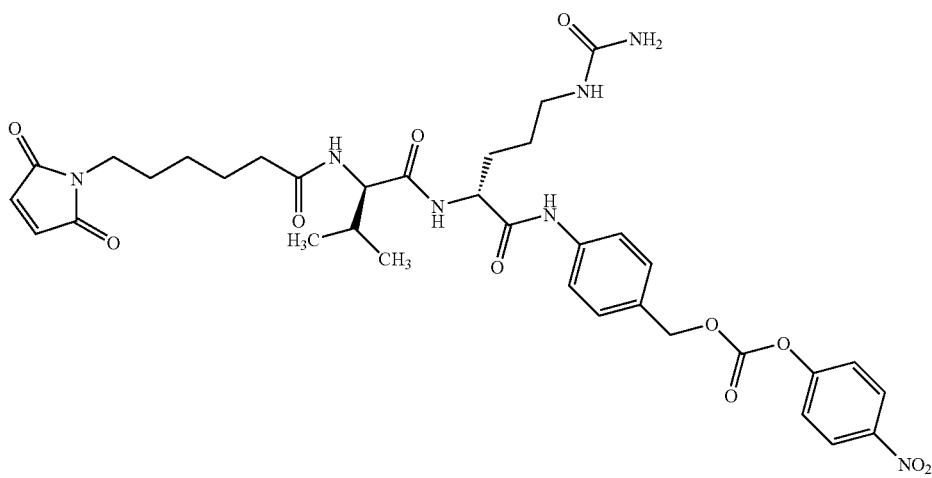
83

Compound 83 was made using the method described in Example 1 and substituting Fmoc-(D)-val-(D)-cit-PAB-OH for Compound 19.
Example 32
Preparation of Compound 84
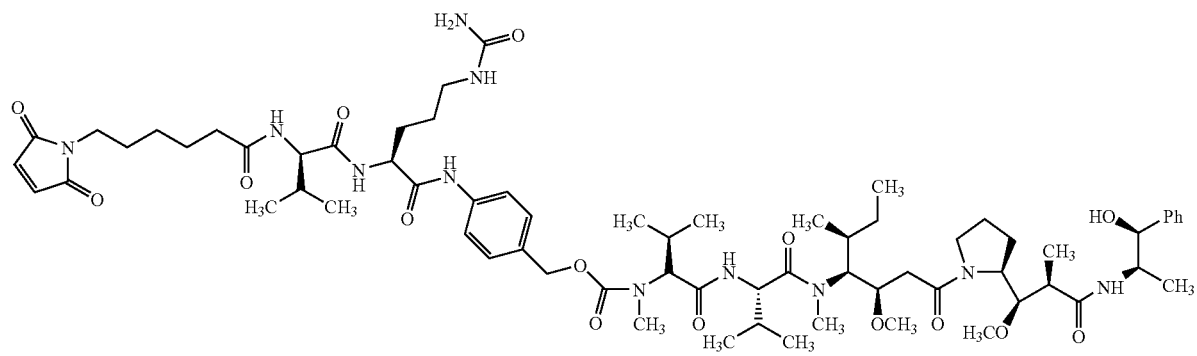
84
Compound 84 was made using the method described in Example 14 and substituting Compound 81 for Compound 21.
Example 33
Preparation of Compound 85
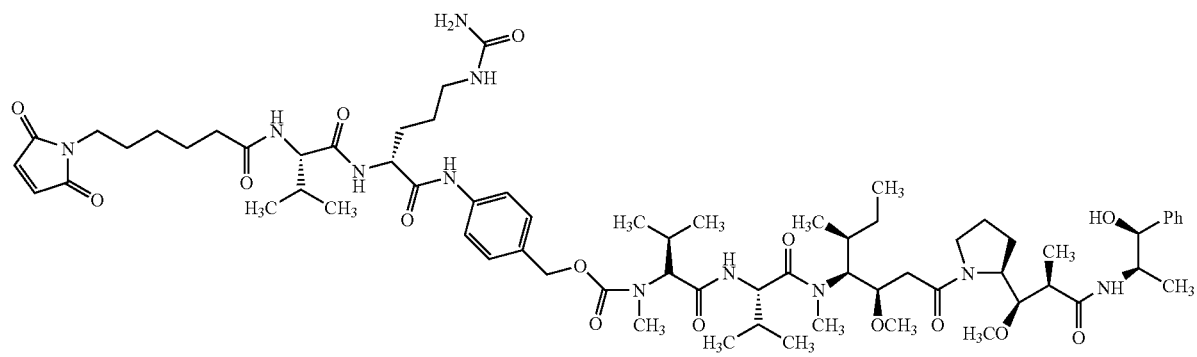
85

Compound 85 was made using the method described in Example 14 and substituting Compound 82 for Compound 21.

Example 34

Preparation of Compound 86

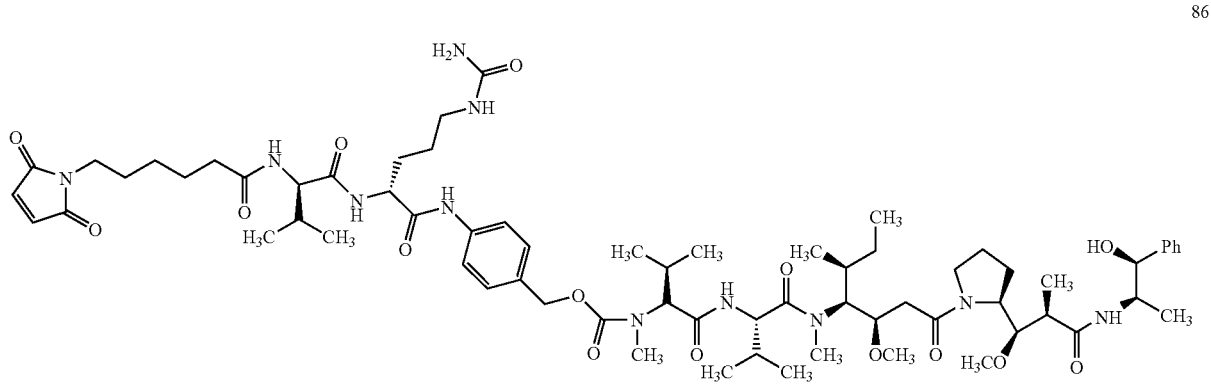

Compound 86 was made using the method described in Example 14 and substituting Compound 83 for Compound 21.

Example 35

Preparation of Compound 87

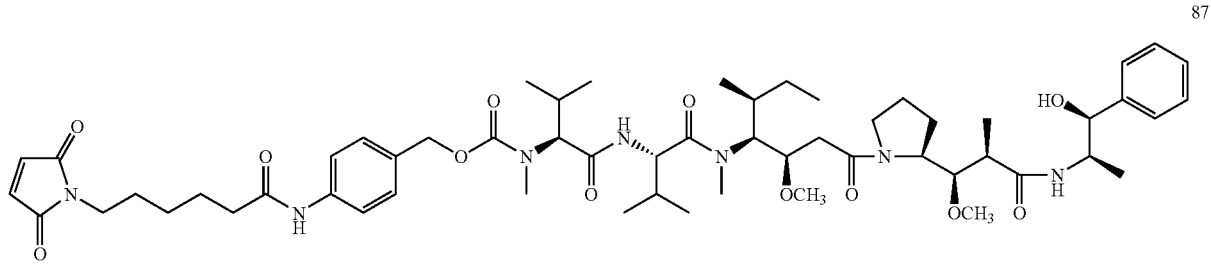

A mixture of 6-Maleimidocaproic acid (1.00 g, 4.52 mmol, 1.0 eq.), p-aminobenzyl alcohol (1.11 g, 9.04 mmol, 2.0 eq.) and EEDQ (2.24 g, 9.04 mmol, 2.0 eq.) were diluted in dichloromethane (13 mL). The resulting reaction was stirred about 16 hr., then concentrated and purified using flash column chromatography in a step gradient 25-100% EtOAc in hexanes to provide a solid intermediate. Yield: 1.38 g (96%); ES-MS m/z 317.22 [M+H]$^+$, 339.13 [M+Na]$^+$; UV $\lambda_{max}$ 215, 246 nm.

The solid intermediate (0.85 g, 2.69 mmol, 1.0 eq.) and bis(4-nitrophenyl) carbonate (2.45 g, 8.06 mmol, 3.0 eq.) were diluted in DMF (10 mL), and to the resulting mixture was added diisopropylethylamine (0.94 mL, 5.37 mmol, 2.0 eq.). The resulting reaction was stirred for about 1 hr, after which time RP-HPLC indicated that the reaction was complete. The reaction mixture was concentrated in vacuo, and the resulting crude residue was triturated using diethyl ether (about 250 mL) to provide a white solid intermediate upon filtration. Yield: 1.25 g (96%); UV $\lambda_{max}$ 215, 252 nm.

The white solid intermediate (259 mg, 0.0538 mmol, 1.0 eq.), MMAE (464 mg, 0.646 mmol, 1.2 eq.), and HOBt (14.5 mg, 0.108 mmol, 0.2 eq.) were diluted in pyridine/DMF (1:5, 6 mL), and the resulting reaction was stirred for about 10 h, after which time RP-HPLC indicated incomplete reaction. The reaction mixture was concentrated, the resulting crude residue was diluted using DMF (3 mL), and to the resulting mixture was added diisopropylethylamine (0.469 mL, 0.538 mmol, 1.0 eq.) and the resulting reaction was allowed to stir for about 16 hr. The reaction mixture was directly purified using Chromatotron® (radial thin-layer chromatography) with a step gradient (0-5% methanol in dichloromethane), to provide Compound 87 as a white solid. Yield: 217 mg (38%); ES-MS m/z 1082.64 [M+Na]$^+$; UV $\lambda_{max}$ 215, 248 nm.

Example 36

Preparation of Compound 88

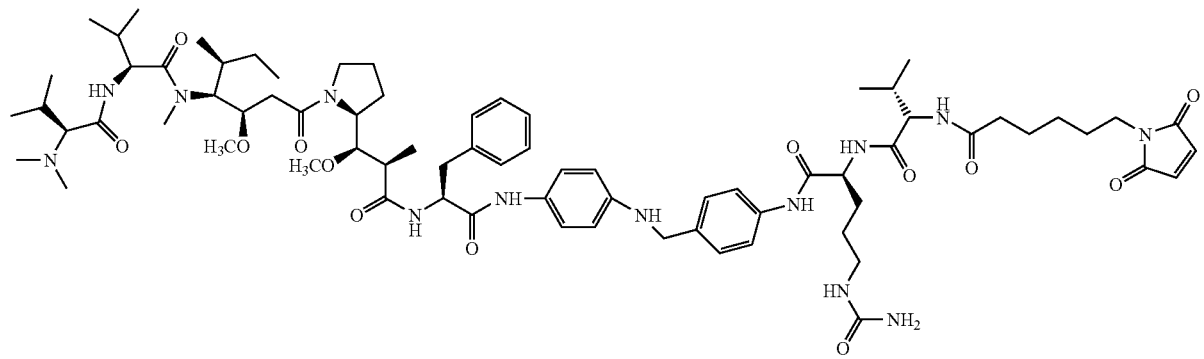

Fmoc-val-cit (U.S. Pat. No. 6,214,345 to Firestone et al.) was suspended in dichloromethane (50 mL) and the resulting mixture was treated with 33% HBr in HOAc (20 mL), which was added via pipette over about 5 minutes. After stirring for about 10 minutes, the reaction mixture was shown to be complete using HPLC. The reaction mixture was diluted with ice (about 500 mL) and saturated aqueous sodium bicarbonate was slowly added while stirring until gas evolution ceased. The resulting gelatinous mass was filtered and washed with distilled water to provide a solid which was dried under high vacuum in the presence of $P_2O_5$ for 24 h. The resulting tan powdered intermediate (Fmoc-val-cit-PAB-Br) was about 70% pure by HPLC and was used without further purification.

The tan powdered intermediate (30 mg, 40.6 μmol) and Compound 53 (34 mg, 40.6 μmol) were dissolved in DMF (1 mL), and to the resulting mixture was added diisopropylethylamine (21 μL, 0.12 mmol, 3.0 eq.). The resulting reaction was allowed to stir for 6 h, diluted with DMSO (1 mL) and immediately purified using preparative-HPLC ($C_{12}$-RP column, 5μ, 100 Å, linear gradient of MeCN in water (containing 0.1% formic acid) 10 to 100% in 40 min followed by 20 min at 100%, at a flow rate of 25 mL/min), to provide as a slight tan powdered intermediate. Yield: 5 mg (8%); ES-MS m/z 1420 $[M+H]^+$, 1443 $[M+Na]^+$; UV $\lambda_{max}$ 205, 258 nm.

The slight tan powdered intermediate (4 mg, 9.5 μmol) was diluted using DMF (1 mL) and the resulting mixture was treated with diethylamine (0.5 mL). The resulting reaction was complete in 1 h according to HPLC. The reaction mixture was concentrated to provide an oily solid residue which was triturated with ether (3×) to provide a crude residue. The crude residue was diluted with DMF (1 mL) and to the resulting mixture was added 6-maleimidocaproic acid hydroxysuccinimide ester (3 mg, 9.5 μmol). The resulting reaction was allowed to stir at room temperature for about 16 h. The reaction mixture was directly purified using preparative-HPLC ($C_{12}$-RP column, 5μ, 100 Å, linear gradient of MeCN in water (containing 0.1% formic acid) 10 to 100% in 40 min followed by 20 min at 100%, at a flow rate of 25 mL/min) to provide Compound 88 as a slight tan solid. Yield: 3.9 mg (quant); ES-MS m/z 1391 $[M+H]^+$; UV $\lambda_{max}$ 205, 250 nm.

Example 37

Preparation of Compound 89

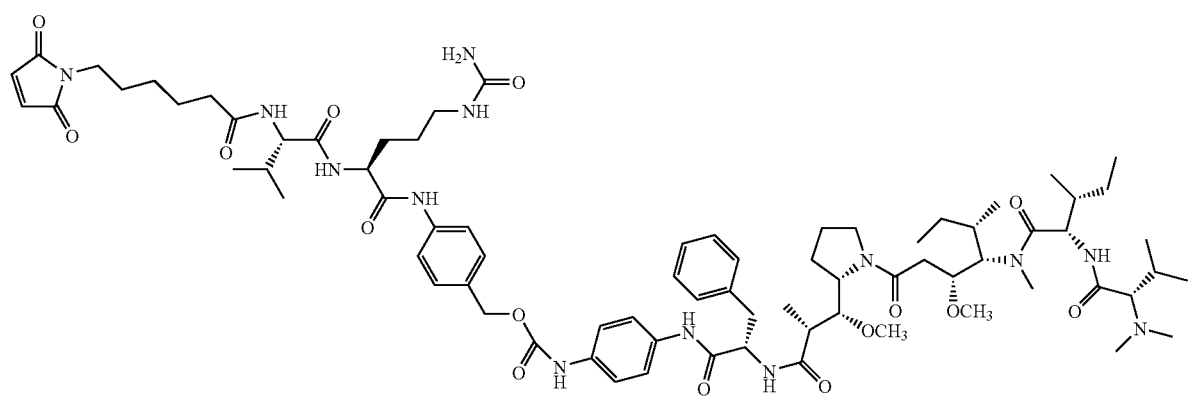

Preparation of Compound 89A

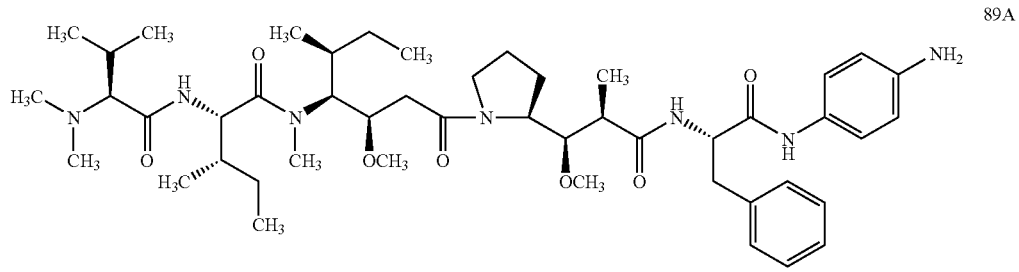

Compound 89A was prepared using the method described in Example 9 and substituting tripeptide Compound 43 for tripeptide Compound 42, intermediate Preparation of Compound 89

Compound 89a (0.13 g, 0.15 μmol, 1.0 mmol), Compound 21 (0.12 g, 0.17 mmol, 1.1 eq.), and HOBt (4 mg, 31 μmol, 0.2 eq.) were suspended in DMF/pyridine (2 mL/0.5 mL, respectively). The resulting reaction was allowed to stir for about 4 h, then diisopropylethylamine (27 μL, 0.15 mmol, 1.0 eq.) was added and the resulting reaction was allowed to stirred for about 54 h and concentrated in vacuo. The resulting crude oil was diluted with DMSO and purified using preparative-HPLC($C_{12}$-RP column, 5μ, 100 Å, linear gradient of MeCN in water (containing 0.1% TFA) 10 to 100% in 40 min followed by 20 min at 100%, at a flow rate of 25 mL/min) to provide to a yellow oil that was taken up in a minimum amount of dichloromethane and precipitated with excess ether to afford Compound 89 as a tan powder. Yield: 0.15 mg (68%). ES-MS m/z 1449.14 [M+H]$^+$; UV $\lambda_{max}$ 215, 258 nm.

Example 38

Preparation of Compound 90

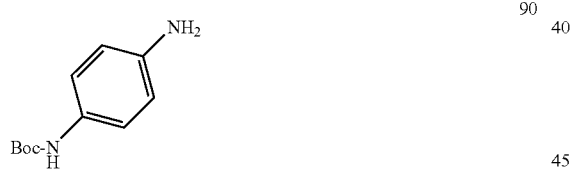

1,4-Phenylenediamine dihydrochloride (3.06 g, 17 mmoles) and di-t-butyl dicarbonate (3.69 g, 17 mmoles) were diluted with 30 mL of dichloromethane. To the resulting mixture was added diisopropylethylamine (8.83 ml, 50.7 mmoles, 3.0 eq.) and the resulting reaction was allowed to stirred for 1 hr. The reaction mixture was transferred to a separatory funnel and the organic phase was washed water (3×10 ml). The organic layer was stored at 4° C. for about 15 h and crystallization of the product occurred. The crystals were collected by filtration and washed with cold dichloromethane to provide Compound 90 as a crystalline solid. (1.2 g, 34%). UV $\lambda_{max}$ 215, 250 nm. $^1$H NMR (DMSO) δ 8.78 (1H, bs), 7.04 (2H, bd, J=7.2 Hz), 6.43 (2H, d, J=7.2 Hz), 4.72 (2H, s), 1.41 (9H, s).

Example 39

Preparation of Compound 91

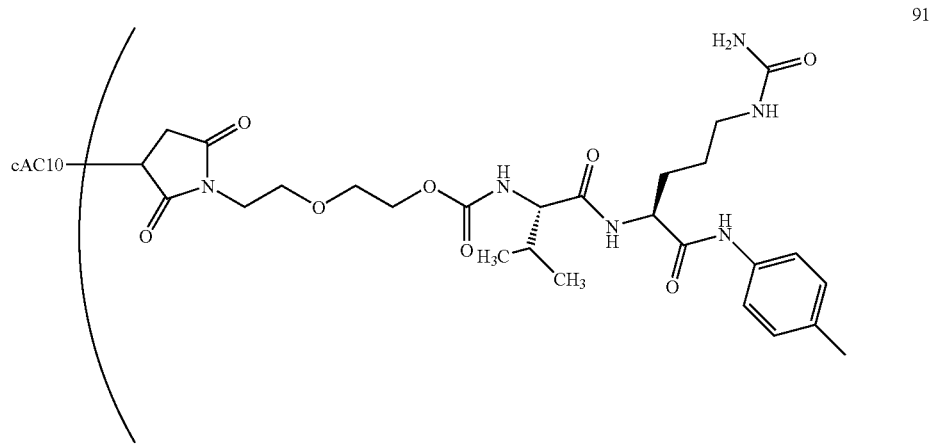

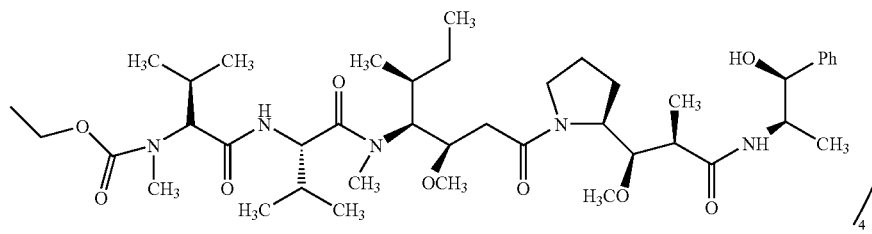

A solution of cAC10 (10 mg/mL in 25 mM sodium citrate, 250 mM sodium chloride, 0.02% Tween 80, pH 6.5) was adjusted to pH 7.5 by addition of 0.3 M sodium phosphate, dibasic. To this pH-adjusted cAC10 solution, EDTA was added to a final concentration of 5 mM. The cAC10 solution was then pre-heated to 37° C. by incubation in a temperature-controlled oven. After the temperature of the cAC10 solution has equilibrated to 37° C., DTT (from a stock solution of 10 mM) was added to achieve a final DTT-to-cAC10 molar ratio of about 3.0 in the reduction reaction (a molecular weight of 148,500 Da was used for cAC10). The reduction reaction was then allowed to proceed for 2 hours at 37° C.

At the end of the incubation, the reduction reaction was cooled to an internal temperature of 2 to 8° C. in an ice-water bath. The temperature of the solution was kept at 2 to 8° C. throughout the remaining conjugation steps. The chilled reduction reaction was subjected to constant-volume diafiltration to remove excess DTT using a 30 kDa membrane and the buffer was exchanged into phosphate buffered saline, pH 7.4 (PBS). Following diafiltration, the concentration of free thiol in the reduced and diafiltered cAC10 was determined using General Procedure M. Conjugation is then carried out by addition of a 15% molar excess of Compound 58 (from a stock solution of 13 mg/mL in DMSO) relative to the total thiols determined using General Procedure M. Additional DMSO was added to the conjugation reaction to achieve a final DMSO concentration of 15% (v/v). The conjugation reaction was allowed to proceed for a total of 30 min.

At the end of the conjugation reaction, any unreacted excess Drug-Linker compound was quenched by addition of excess Cysteine (2× molar excess relative to the total thiols determined using General Procedure M, performed on the reduced and diafiltered cAC10 to produce the quenched reaction mixture. The quenched reaction mixture is then purified free of small-molecule contaminants via constant-volume diafiltration using a 30 kDa membrane and the buffer was exchanged into PBS, pH 7.4. After diafiltration, the conjugate was sterile-filtered using a 0.22 micron filter to provide Compound 91 in a clear, colorless solution.

Example 40

Preparation of Compound 92

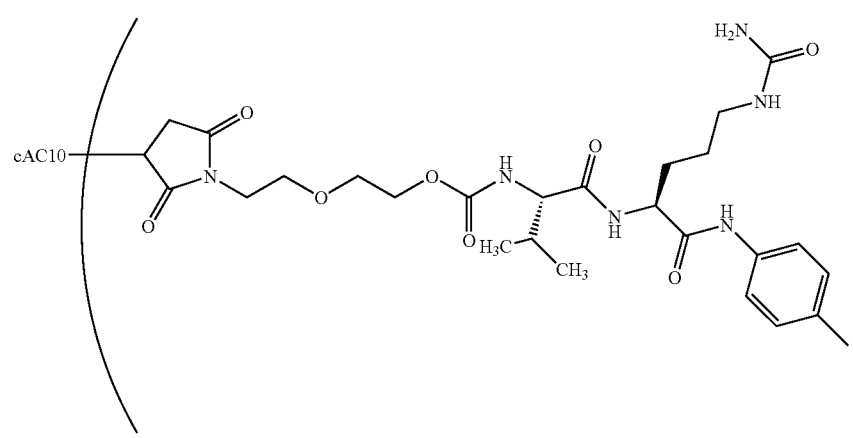

-continued

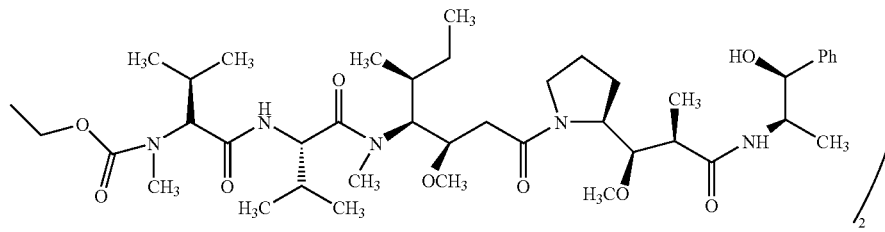

Compound 92 was prepared using the method described in Example 39 using an amount of DTT (from a stock solution of 10 mM) which provides a final DTT-to-cAC10 molar ratio of about 1.5 in the reduction reaction.

6.2 In Vitro Cytotoxicity Experiments

The cell lines used were H3396 human breast carcinoma (cBR96 antigen positive, cAC10 antigen negative), HCT-116 human colorectal carcinoma (cBR96 and cAC10 antigen negative), and Karpas human anaplastic large cell lymphoma (ALCL) (cBR96 antigen negative, cAC10 antigen positive). These cell lines are available from ATCC. CD30-positive Hodgkin's Disease (HD) cell line L540 and the ALCL cell line Karpas 299 were obtained from the Deutsche Sammlung von Mikroorganism und Zellkulturen GmbH (Braunschweig, Germany). L540cy, a derivative of the HD line L540 adapted to xenograft growth, was provided by Dr. Phil Thorpe (U of Texas Southwestern Medical Center, Dallas, Tex.). Cell lines were grown in RPMI-1640 media (Life Technologies Inc., Gaithersburg, Md.) supplemented with 10% fetal bovine serum. H3396 cells in RPMI containing 10% fetal bovine serum (referred to as medium) were plated in 96-well plates at approximately 3,000-10,000 cells/well and allowed to adhere overnight. The non-adherent Karpas cell line was plated out at approximately 10,000 cells/well at the initiation of the assay. Various concentrations of illustrative Compounds of the Invention in medium were added in triplicate, and after the times indicated IN FIGS. 1-7, the medium was removed, and the cells were washed with fresh medium three times. After a 96 hour incubation period at 37° C., Alamar Blue was added and cell viability was determined 4 hours later as described by Ahmed S A, Gogal R M Jr, Walsh J E., J. Immunol. Methods, 170, 211-224, 1994.

C.B.-17 SCID (Harlan, Indianapolis, Ind.) mice were used for in vivo experiments.

Example 41

In Vitro Cytotoxicity Data

Figure 1:
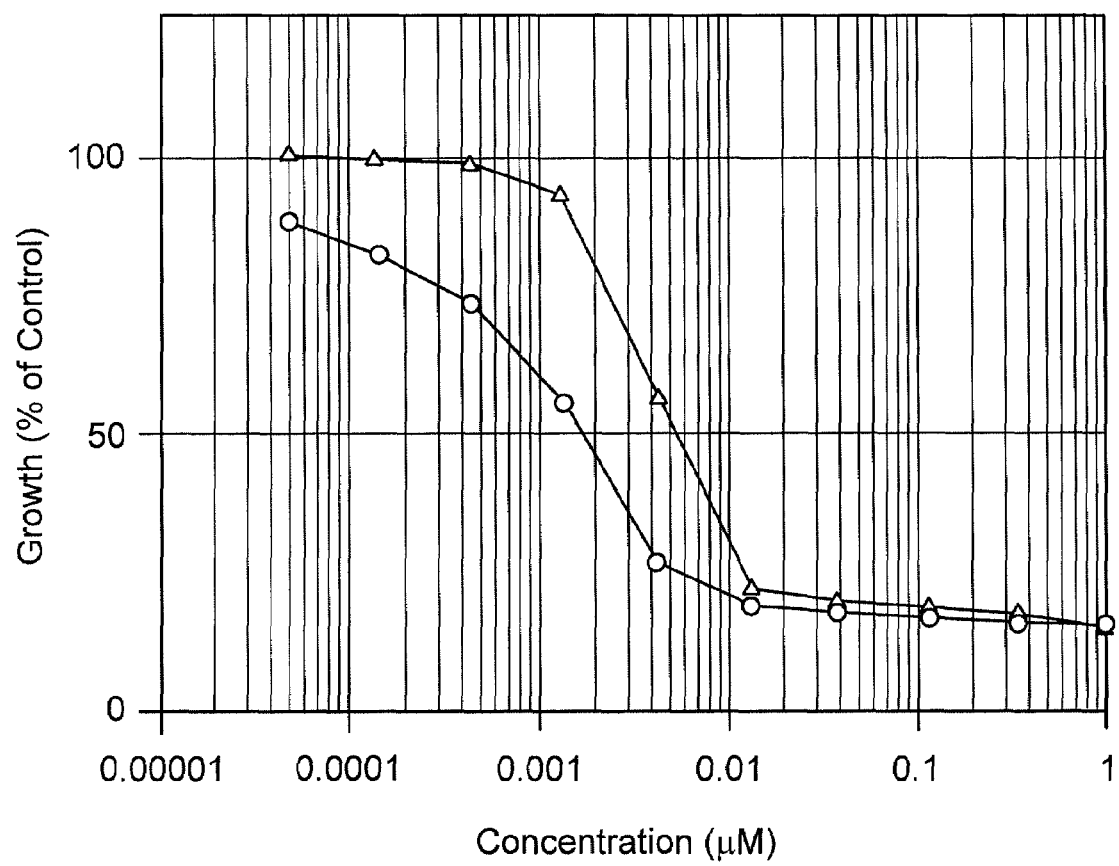
FIG. 1 shows the cytotoxicity of Compound 49 and Compound 53 against the H3396 cell line. Line -Δ- represents Compound 49 and line -o- represents Compound 53.

The cytotoxic effects of Compound 49 and Compound 53 on H3396 human breast carcinoma cells are shown in FIG. 1. The data show that after exposure for 1 hour, Compound 53 is more cytotoxic than Compound 49 at concentrations of up to 0.01 mM. The compounds show substantially equal cytotoxicity at concentrations between 0.01 mM and 1.0 mM.

Example 42

In Vitro Cytotoxicity Data

Figure 2:
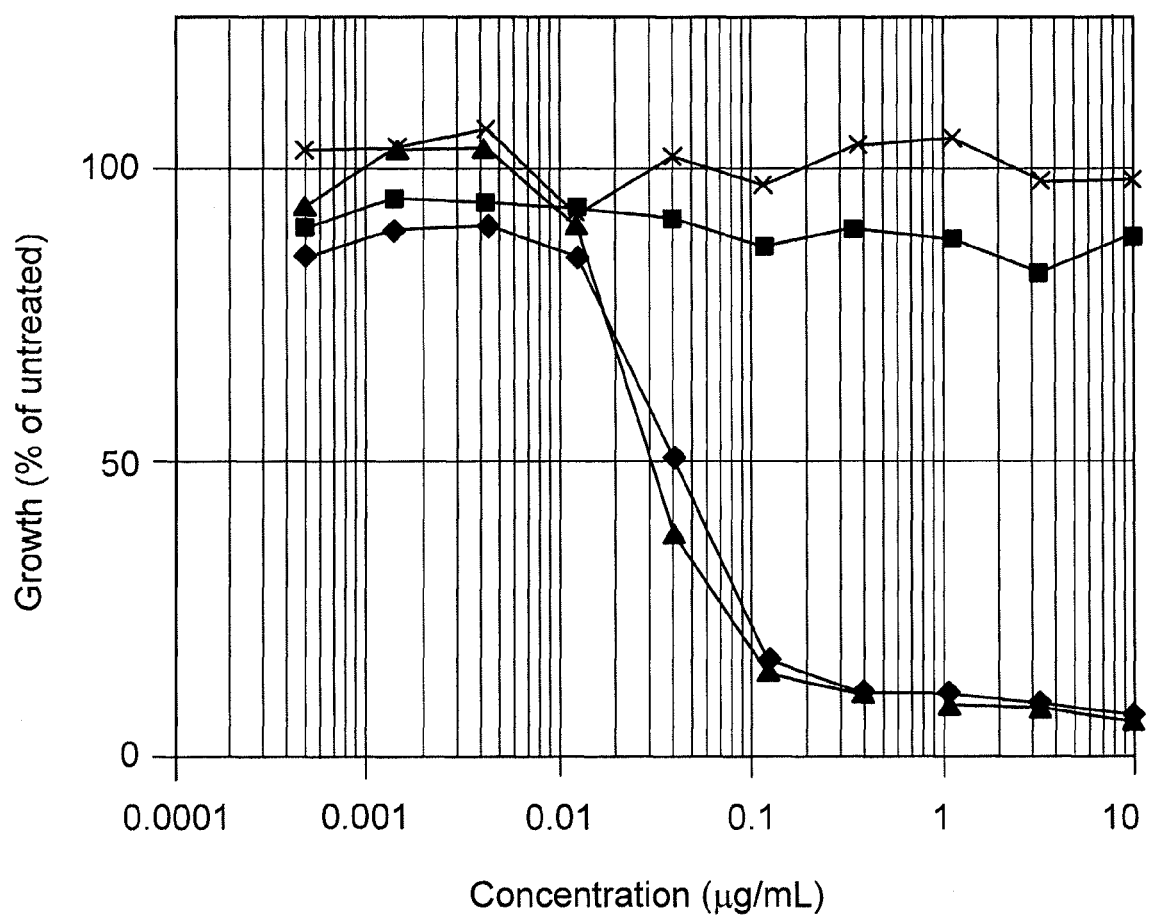
FIG. 2 shows the cytotoxicity of Compounds 64, 65, 68 and 69 against the H3396 cell line. Line -♦- represents Compound 64, line -■- represents Compound 65, line -Δ- represents Compound 68, and line -X- represents Compound 69.

FIG. 2 shows the cytotoxic effects of Compounds 64, 65, 68 and 69 on H3396 human breast carcinoma cells (cBR96 antigen positive, cAC10 antigen negative). The data show that the Compounds 64 and 68 demonstrate similar and significant cytotoxicity, while Compounds 65 and 69 are less efficacious, but nevertheless cytotoxic against H3396 cells in this particular assay.

Example 43

In Vitro Cytotoxicity Data

Figure 3:
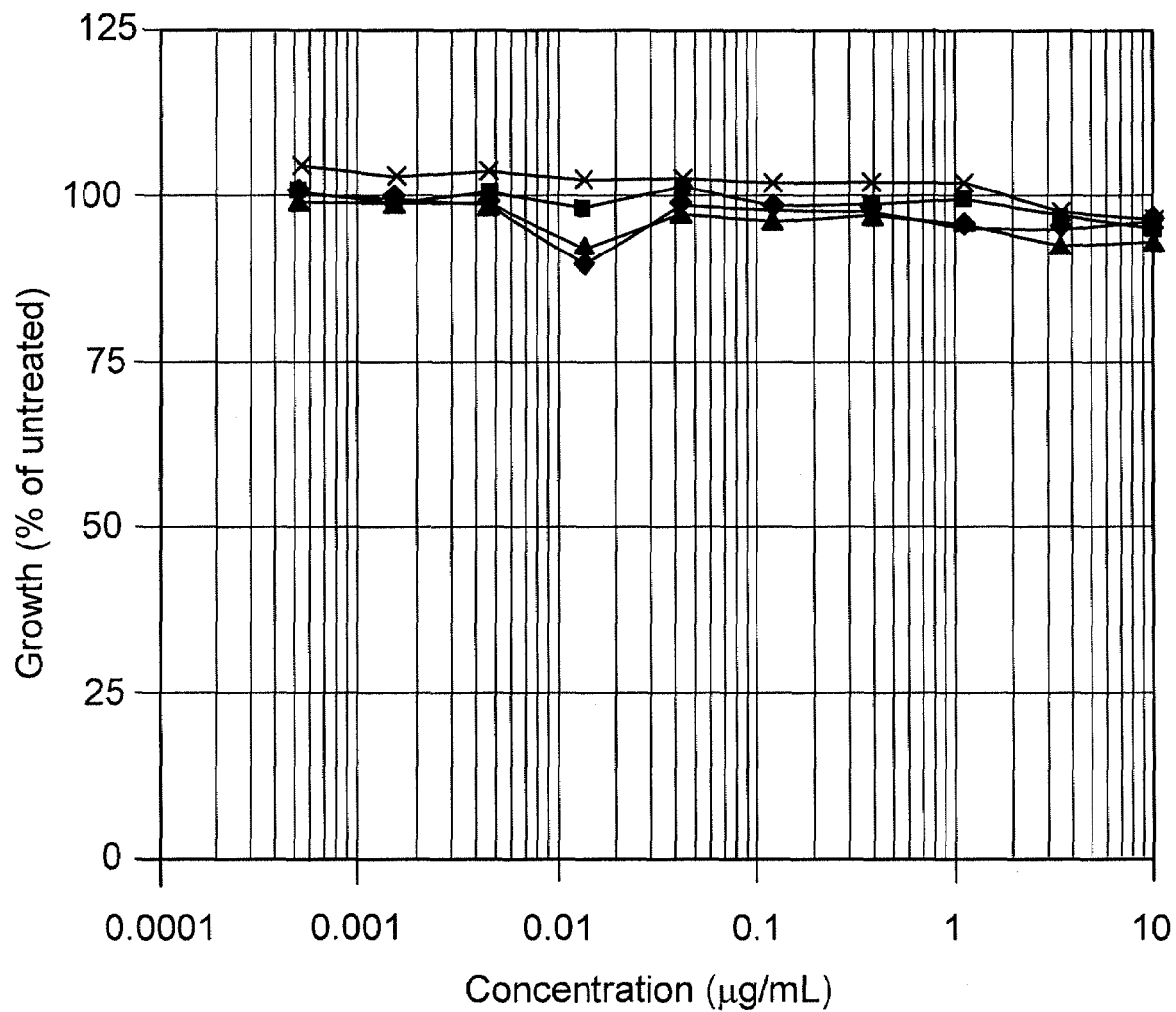
FIG. 3 shows the cytotoxicity of Compounds 64, 65, 68 and 69 against the HCT-116 cell line. Line -♦- represents Compound 64, line -■- represents Compound 65, Line -Δ- represents Compound 68, and line -X- represents Compound 69.

FIG. 3 shows the cytotoxic effects of Compounds 64, 65, 68 and 69 on HCT-116 human colorectal carcinoma cells (cBR96 antigen negative, cAC10 antigen negative). The data illustrate that none of Compounds 64, 65, 68 and 69 is cytotoxic toward the antigen negative HCT-116 cells in this assay.

Example 44

In Vitro Cytotoxicity Data

Figure 4:
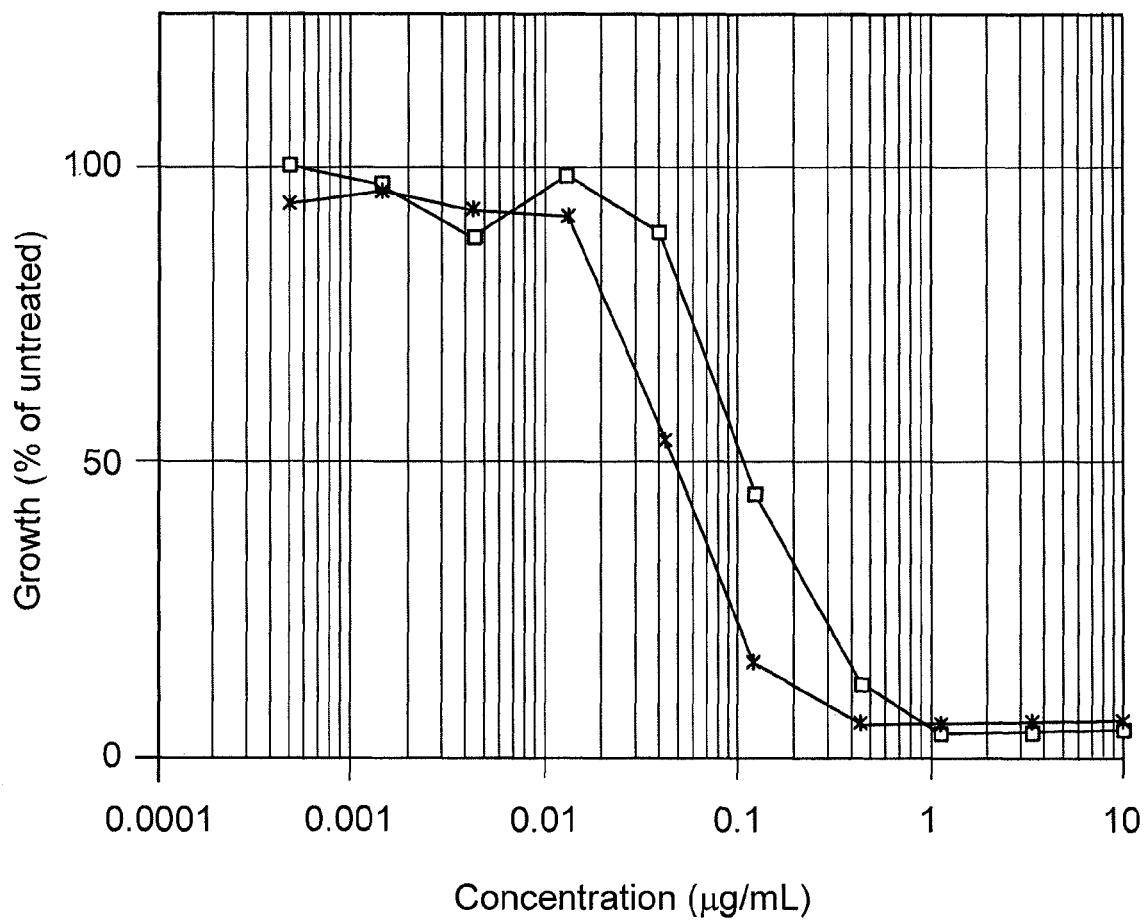
FIG. 4 shows the cytotoxicity of Compounds 66 and 68 against the H3396 cell line. Line -□- represents Compound 66 and line -*- represents Compound 68.

FIG. 4 illustrates the cytotoxicity of Compounds 66 and 68 on H3396 human breast carcinoma cells (cBR96 antigen positive). The data show that both Compounds are highly cytotoxic at concentrations above 0.1 mM and that Compound 68 demonstrates greater cytotoxicity than Compound 66 at concentrations between 0.01 mg/mL and 0.4 mg/mL.

Example 45

In Vitro Cytotoxicity Data

Figure 5:
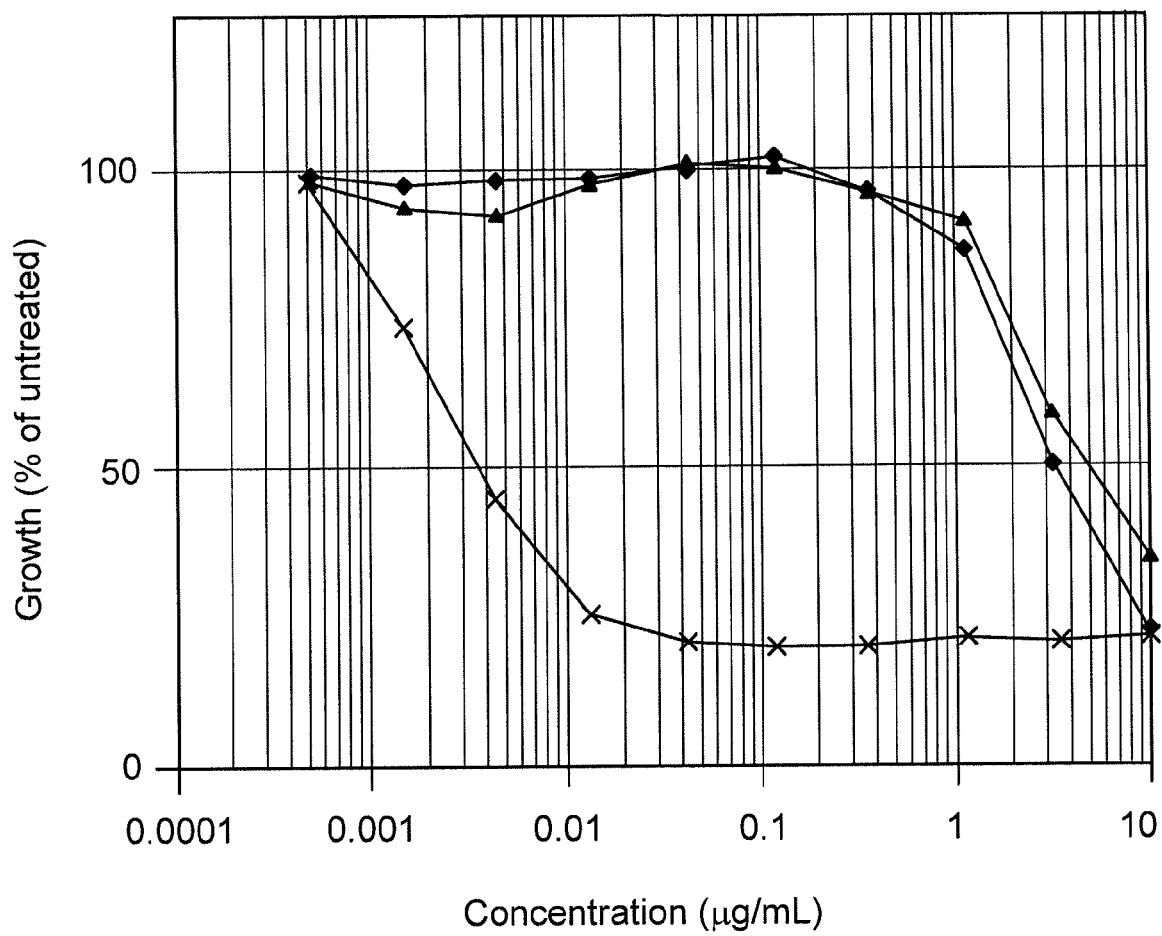
FIG. 5 shows the cytotoxicity of Compounds 66, 68 and 69 against the Karpas human colorectal cell line. Line -♦- represents Compound 66, line -▲- represents Compound 68, and line -X- represents Compound 69.

FIG. 5 illustrates the cytotoxicity of Compounds 66, 68 and 69 on Karpas human anaplastic large cell lymphoma (cBR96 antigen negative, cAC10 antigen positive). The data show that Compound 69 was more cytotoxic toward Karpas cells than compared to Compounds 68 and 66 in this assay. Compound 69 demonstrated significant cytotoxicity at concentrations above 0.001 mM, while Compound 66 and Compound 68 were not cytotoxic at concentrations below 1.0 mg/mL.

Example 46

In Vitro Cytotoxicity Data

FIG. 6 illustrates the cytotoxicity of Compound 66 and 67 at 2 h and 96 h on H3396 human breast carcinoma cells (cBR96 antigen positive, cAC10 antigen negative). The data show that Compound 66 is highly cytotoxic at concentrations above 100 mg/mL at short-term exposure (2 h) mg/mL, and at concentrations above 100 mg/mL over long-term exposure (96 h). Compound 67 did not demonstrate cytotoxicity against H3396 cells in this assay at concentrations up to 1000 mg/mL.

General Procedure S: In Vivo Testing of Selected Drug-Linker-Antibody Conjugates. For the L2987 human adenocarcinoma cell line, Athymic nude mice (8-10 weeks old) were implanted with xenograft tumors or tumor cells. For the Karpas human anaplastic large cell lymphoma model, CB-17 SCID mice were implanted subcutaneously with $5 \times 10^6$ cells. In both tumor models, therapy was initiated once the tumors reached an average volume of 100 mm$^3$. Groups of mice were injected with one of Compounds 66-69 in phosphate buffered saline intravenously every fours days for a total of 6 injections for L2987 animals and 2 injections for Karpas animals. Tumor volume was computed using the formula: 0.5 (longest dimension×perpendicular dimension$^2$). Mice were removed from the study when their tumors were approximately 1000 mm$^3$, at which point the average tumor sizes from the particular group were no longer plotted.

Example 47

In Vivo Therapeutic Efficacy on L2987 Tumors

FIG. 7 shows the therapeutic effects of Compounds 66-69 on L2987 human lung adenocarcinoma xenograft tumors (cBR96 antigen positive, cAC10 antigen negative) implanted in athymic nude mice. General Procedure S was followed using subcutaneous L2987 human lung tumors (from in vivo passaging). Mice were administered by injection with one of Compounds 66, 67, 68 or 69 at four day intervals for a total of 6 injections. The first injection was given at 15 days post tumor-implant. The data illustrate that administration of Compound 66 and Compound 68 markedly reduced tumor volume and no additional growth was noted in treated mice for at approximately 25 days after the last injection. Compound 67 and Compound 69 were less efficacious but nevertheless inhibited tumor cell multiplication in the treated mice. Testing was stopped in animals receiving Compounds 67 and 69 when tumor volume exceeded 1000 mm$^3$.

Example 48

In Vivo Therapeutic Efficacy on Karpas Tumors

FIG. 8 shows the therapeutic effects of compounds 66-69 on Karpas human anaplastic large cell lymphoma xenograft tumors (cAC10 antigen positive, cBR96 antigen negative) implanted in nude mice. General Procedure S was followed using Karpas human anaplastic large cell lymphoma model, CB-17 SCID mice were implanted subcutaneously with $5 \times 10^6$ cells. Mice were dosed intravenously with one of Compounds 66, 67, 68 or 69 at four day intervals for a total of 2 injections starting on day 8. The data illustrate that Compounds 67 and 69 induced complete regressions, and that the tumors progressed in animals that received substantially equivalent amounts of Compounds 66 and 68.

Example 49

Determination of Cytotoxicity of Selected Compounds in CD30– and Cd30+ Cells

Following their physical characterization, the in vitro cytotoxicity of Compounds 67, 91 and 92 was evaluated in CD30$^+$ Karpas 299 and CD30$^-$ Raji cells using the Alamar Blue assay as described above. The percent viable cells was plotted versus concentration for each molecule to determine the IC$_{50}$ (defined as the mAb concentration that gave 50% cell kill).

Compound 67 demonstrated activity against Karpas 299 cells with an IC$_{50}$ of 4 ng/mL. The IC$_{50}$ was inversely proportional to drug loading as it increased from 4 ng/mL for Compound 67 to 7 ng/mL for Compound 91, to 40 ng/mL for Compound 92. Selectivity of the tested compounds was evaluated using the antigen-negative Raji cell line which were insensitive to all cAC10-containing Compounds with IC$_{50}$ values >1000 ng/ml for Compounds 67, 91 and 92.

Example 50

Cytotoxicity of Selected Compounds in Xenograft Models of HD and ALCL

Cytotoxicity of Compounds 67, 91 and 92 was evaluated in subcutaneous Karpas 299 human anaplastic large cell lymphoma and L540cy Hodgkin's Disease xenograft models in C.B.-17 SCID mice. Evaluations were initiated when tumor volumes averaged 50-100 mm$^3$. Cohorts of Karpas-299 bearing mice were injected q4d×4 with Compound 92, Compound 91, or Compound 67 at either 0.25 mg/kg or 0.5 mg/kg. None of the animals treated at 0.25 mg/kg had a regression, although there was a delay in tumor growth compared to untreated controls for the animals treated with Compound 91 and Compound 67. Treatment of Karpas tumors with Compound 91 and Compound 67 at 0.5 mg/kg given q4d×4 achieved 5/5 complete regressions and 4/5 complete regressions, respectively. A delay in tumor growth compared to untreated animals was observed for Compound 92 at 0.5 mg/kg given q4d×4, but no complete regressions were obtained.

Efficacy was also tested in a subcutaneous Karpas model with selected compounds administered as a single dose. Compound 91 and Compound 67 were injected at single doses of 0.25, 0.5 and 2.0 mg/kg. At the dose of 0.25 mg/kg there was no antitumor activity in either group and mean tumor volume did not deviate from the untreated controls. A delay in the tumor growth was demonstrated by both molecules at 0.5 mg/kg, but no complete regressions were obtained. Treating the mice with Compound 91 and Compound 67 at 2 mg/kg achieved 100% complete regressions in both groups.

Compound 91 and Compound 67 were also compared in mice bearing subcutaneous L540cy human HD tumors treated q4d×4 with Compound 91 and Compound 67 at 1 and 3 mg/kg. At 1 mg/kg, mice treated with Compound 91 and Compound 67 had significant delays in tumor growth compared to the untreated animals. Complete regressions were observed in mice administered with both Compound 91 and Compound 67 at 3 mg/kg.

The present invention is not to be limited in scope by the specific embodiments disclosed in the examples which are intended as illustrations of a few aspects of the invention and

What is claimed is:

1. A drug-linker-antibody conjugate of Formula Ia:

L-(A$_a$-W$_w$—Y$_y$-D)$_p$      Ia or a pharmaceutically acceptable salt thereof,
wherein,
L- is an antibody that immunospecifically binds to a cancer cell antigen which is on the surface of a cancer cell;
-A$_a$-W$_w$—Y$_y$— is an enzymatically cleavable linker unit that links the Drug unit and the antibody, wherein:
-A- is a Stretcher unit;
a is 1;
each —W— is independently an Amino Acid unit;
—Y— is a self-immolative Spacer unit;
w is an integer ranging from 2 to 12,
y is 1 or 2;
p ranges from 1 to about 20; and
-D is a Drug unit of the formula

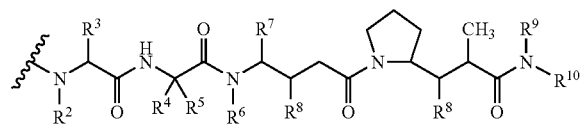

wherein, the wavy line indicates the point of attachment to the Spacer unit, and for each D:
$R^2$ is selected from the group consisting of —H and —C$_1$-C$_8$ alkyl;
$R^3$ is selected from the group consisting of —H, —C$_1$-C$_8$ alkyl, —C$_3$-C$_8$ carbocycle, —O—(C$_1$-C$_8$ alkyl), -aryl, —C$_1$-C$_8$ alkyl-aryl, —C$_1$-C$_8$ alkyl-(C$_3$-C$_8$ carbocycle), —C$_3$-C$_8$ heterocycle and —C$_1$-C$_8$ alkyl-(C$_3$-C$_8$ heterocycle);
$R^4$ is selected from the group consisting of —H, —C$_1$-C$_8$ alkyl, —C$_3$-C$_8$ carbocycle, —O—(C$_1$-C$_8$ alkyl), -aryl, —C$_1$-C$_8$ alkyl-aryl, —C$_1$-C$_8$ alkyl-(C$_3$-C$_8$ carbocycle), —C$_3$-C$_8$ heterocycle and —C$_1$-C$_8$ alkyl-(C$_3$-C$_8$ heterocycle) wherein $R^5$ is selected from the group consisting of —H and -methyl; or $R^4$ and $R^5$ join and form a ring with the carbon atom to which they are attached and $R^4$ and $R^5$ have the formula —(CR$^a$R$^b$)$_n$— wherein R$^a$ and R$^b$ are independently selected from the group consisting of —H, —C$_1$-C$_8$ alkyl and —C$_3$-C$_8$ carbocycle and n is selected from the group consisting of 2, 3, 4, 5 and 6;
$R^6$ is selected from the group consisting of —H and —C$_1$-C$_8$ alkyl;
$R^7$ is selected from the group consisting of —H, —C$_1$-C$_8$ alkyl, —C$_3$-C$_8$ carbocycle, —O—(C$_1$-C$_8$ alkyl), -aryl, —C$_1$-C$_8$ alkyl-aryl, —C$_1$-C$_8$ alkyl-(C$_3$-C$_8$ carbocycle), —C$_3$-C$_8$ heterocycle and —C$_1$-C$_8$ alkyl-(C$_3$-C$_8$ heterocycle);
each $R^8$ is independently selected from the group consisting of —H, —OH, —C$_1$-C$_8$ alkyl, —C$_3$-C$_8$ carbocycle and —O—(C$_1$-C$_8$ alkyl);
$R^9$ is selected from the group consisting of —H and —C$_1$-C$_8$ alkyl;

$R^{10}$ is selected from the group consisting of:

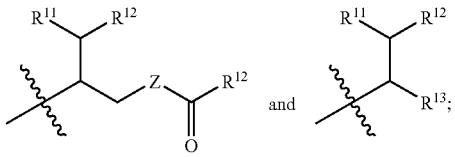

Z is —O—, —S—, —NH— or —N(R$^{14}$)—;
$R^{11}$ is selected from the group consisting of —H, —OH, —NH$_2$, —NHR$^{14}$, —N(R$^{14}$)$_2$, —C$_1$-C$_8$ alkyl, —C$_3$-C$_8$ carbocycle, —O—(C$_1$-C$_8$ alkyl), -aryl, —C$_1$-C$_8$ alkyl-aryl, —C$_1$-C$_8$ alkyl-(C$_3$-C$_8$ carbocycle); —C$_3$-C$_8$ heterocycle and —C$_1$-C$_8$ alkyl-(C$_3$-C$_8$ heterocycle); or $R^{11}$ is an oxygen atom which forms a carbonyl unit (C=O) with the carbon atom to which it is attached and a hydrogen atom on this carbon atom is replaced by one of the bonds in the (C=O) double bond;
each $R^{12}$ is independently selected from the group consisting of -aryl and —C$_3$-C$_8$ heterocycle;
$R^{13}$ is selected from the group consisting of —H, —OH, —NH$_2$, —NHR$^{14}$, —N(R$^{14}$)$_2$, —C$_1$-C$_8$ alkyl, —C$_3$-C$_8$ carbocycle, —O—(C$_1$-C$_8$ alkyl), -aryl, —C$_1$-C$_8$ alkyl-aryl, —C$_1$-C$_8$ alkyl-(C$_3$-C$_8$ carbocycle), C$_3$-C$_8$ heterocycle and —C$_{1-8}$ alkyl-(C$_3$-C$_8$ heterocycle); and
each $R^{14}$ is independently —H or —C$_1$-C$_8$ alkyl.

2. A drug-linker-antibody conjugate of the formula Ia:

L-(A$_a$-W$_w$—Y$_y$-D)$_p$      Ia or a pharmaceutically acceptable salt thereof,
wherein,
L- is an antibody that immunospecifically binds to a cancer cell antigen which is on the surface of a cancer cell;
-A$_a$-W$_w$—Y$_y$— is an enzymatically cleavable linker unit that links the Drug unit and the antibody, wherein:
-A- is a Stretcher unit;
a is 1;
each —W— is independently an Amino Acid unit;
—Y— is a self-immolative Spacer unit;
w is an integer ranging from 2 to 12;
y is 1 or 2;
p ranges from 1 to about 20; and
-D is a Drug unit having the structure

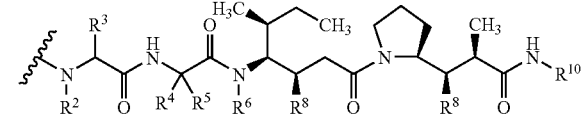

wherein, the wavy line indicates the point of attachment to the Spacer unit, and for each D:
$R^2$ is selected from the group consisting of —H and -methyl;
$R^3$ is selected from the group consisting of —H, -methyl, and -isopropyl;
$R^4$ is selected from the group consisting of —H and -methyl;
$R^5$ is selected from the group consisting of -isopropyl, -isobutyl, -sec-butyl, -methyl and -t-butyl or $R^4$ and $R^5$ join and form a ring with the carbon atom to which they are attached and $R^4$ and $R^5$ have the formula —(CR$^a$R$^b$)$_n$— where R$^a$ and R$^b$) are independently selected from the group consisting of —H, —C$_1$-C$_8$ alkyl, and —$C_3$-$C_8$ carbocycle, and n is selected from the group consisting of 2, 3, 4, 5 and 6;

$R^6$ is selected from the group consisting of —H and -methyl;

each $R^8$ is independently selected from the group consisting of —OH, -methoxy and -ethoxy;

$R^{10}$ is selected from the group consisting of:

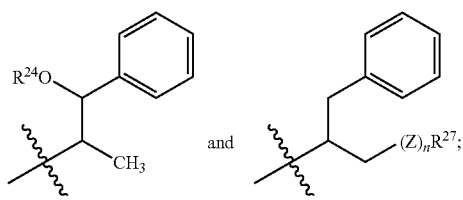

and

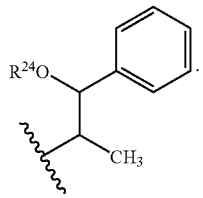

5. The drug-linker-antibody conjugate of claim 3 or a pharmaceutically acceptable salt thereof wherein $R^2$ is —$C_1$-$C_8$ alkyl.

6. The drug-linker-antibody conjugate of claim 4 or a pharmaceutically acceptable salt thereof wherein $R^2$ is methyl.

7. The drug-linker-antibody conjugate of claim 1 or a pharmaceutically acceptable salt thereof where -D is a Drug unit having the structure

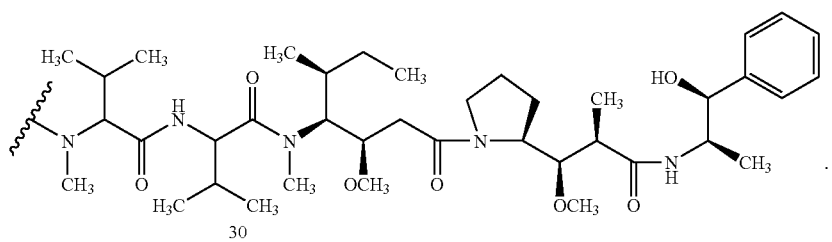

$R^{24}$ is selected from the group consisting of H and —C(O)$R^{25}$; wherein $R^{25}$ is selected from the group consisting of —$C_1$-$C_8$ alkyl, —$C_3$-$C_8$ carbocycle, -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle);

Z is —O—, —NH—, —OC(O)—, —NHC(O)—, or —$NR^{28}$C(O)—; where $R^{28}$ is selected from the group consisting of —H and —$C_1$-$C_8$ alkyl;

n is 0 or 1; and $R^{27}$ is selected from the group consisting of —H, —$N_3$, —$C_1$-$C_8$ alkyl, —$C_3$-$C_8$ carbocycle, -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle) when n is 0; and $R^{27}$ is selected from the group consisting of —H, —$C_1$-$C_8$ alkyl, —$C_3$-$C_8$ carbocycle, -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle) when n is 1.

3. The drug-linker-antibody conjugate of claim 1 or a pharmaceutically acceptable salt thereof wherein $R^{10}$ is

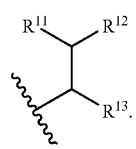

4. The drug-linker-antibody conjugate of claim 2 or a pharmaceutically acceptable salt thereof wherein $R^{10}$ is 8. The drug-linker-antibody conjugate of claim 1 or a pharmaceutically acceptable salt thereof wherein the antibody is a monoclonal antibody.

9. The drug-linker-antibody conjugate of claim 1 or a pharmaceutically acceptable salt thereof wherein the antibody is a full length immunoglobulin molecule.

10. The drug-linker-antibody conjugate of claim 9 or a pharmaceutically acceptable salt thereof wherein the antibody is bound to the Stretcher unit via an interchain thiol of the antibody.

11. The drug-linker-antibody conjugate of claim 8 or a pharmaceutically acceptable salt thereof wherein the antibody is a chimeric antibody.

12. The drug-linker-antibody conjugate of claim 11 or a pharmaceutically acceptable salt thereof wherein the antibody comprises a variable region derived from a murine monoclonal antibody and a human immunoglobulin constant region.

13. The drug-linker-antibody conjugate of claim 12 or a pharmaceutically acceptable salt thereof wherein the antibody immunospecifically binds human CD30 antigen.

14. The drug-linker-antibody conjugate of claim 2 or a pharmaceutically acceptable salt thereof wherein the antibody is a monoclonal antibody.

15. The drug-linker-antibody conjugate of claim 1 or a pharmaceutically acceptable salt thereof where —$W_w$— is represented by Formula VII:

(VII)

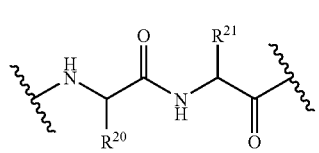

wherein
R²⁰ is benzyl, methyl, or isopropyl and R²¹ is (CH₂)₄NH₂; or
R²⁰ is isopropyl, benzyl, isobutyl, or sec-butyl and R²¹ is (CH₂)₃NHCONH₂; or
R²⁰ is benzyl and R²¹ is methyl or (CH₂)₃NHC(=NH)NH₂; or
R²⁰ is

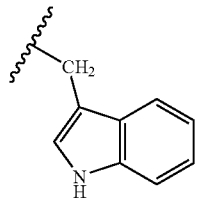

and R²¹ is (CH₂)₃NHCONH₂.

16. The drug-linker-antibody conjugate of claim 1 or a pharmaceutically acceptable salt thereof where —W_w— is -valine-citrulline-, the amino terminus of —W_w— forming a bond with a Stretcher unit, and the C-terminus of —W_w— forming a bond with a Spacer unit.

17. The drug-linker-antibody conjugate of claim 1 or a pharmaceutically acceptable salt thereof wherein p ranges from 1 to about 5.

18. The drug-linker-antibody conjugate of claim 1 or a pharmaceutically acceptable salt thereof wherein p ranges from 1 to 10.

19. The drug-linker-antibody conjugate of claim 1 or a pharmaceutically acceptable salt thereof wherein the linker unit is cleavable by cathepsin B.

20. The drug-linker-antibody conjugate of claim 2 or a pharmaceutically acceptable salt thereof wherein the linker unit is cleavable by cathepsin B.

21. The drug-linker-antibody conjugate of claim 1 having the formula below:

or a pharmaceutically acceptable salt thereof, where E is —CH₂— or —CH₂CH₂O—; e is an integer ranging either from 0-10 when E is —CH₂—, or from 1-10 when E is —CH₂CH₂—O—; F is —CH₂—; f is 0 or 1; and p ranges from 1 to about 20.

22. The drug-linker-antibody conjugate of claim 21 or a pharmaceutically acceptable salt thereof wherein the antibody is a monoclonal antibody.

23. The drug-linker-antibody conjugate of claim 21 or a pharmaceutically acceptable salt thereof wherein the antibody is a full length immunoglobulin molecule.

24. The drug-linker-antibody conjugate of claim 23 or a pharmaceutically acceptable salt thereof wherein the antibody is bound to the Stretcher unit via an interchain thiol of the antibody.

25. The drug-linker-antibody conjugate of claim 22 or a pharmaceutically acceptable salt thereof wherein the antibody is a chimeric antibody.

26. The drug-linker-antibody conjugate of claim 25 or a pharmaceutically acceptable salt thereof wherein the chimeric antibody comprises a variable region derived from a murine monoclonal antibody and a human immunoglobulin constant region.

27. The drug-linker-antibody conjugate of claim 21 or a pharmaceutically acceptable salt thereof wherein p ranges from 1 to about 5.

28. The drug-linker-antibody conjugate of claim 21 or a pharmaceutically acceptable salt thereof wherein p ranges from 1 to 10.

29. The drug-linker-antibody conjugate of claim 1 having the formula below:

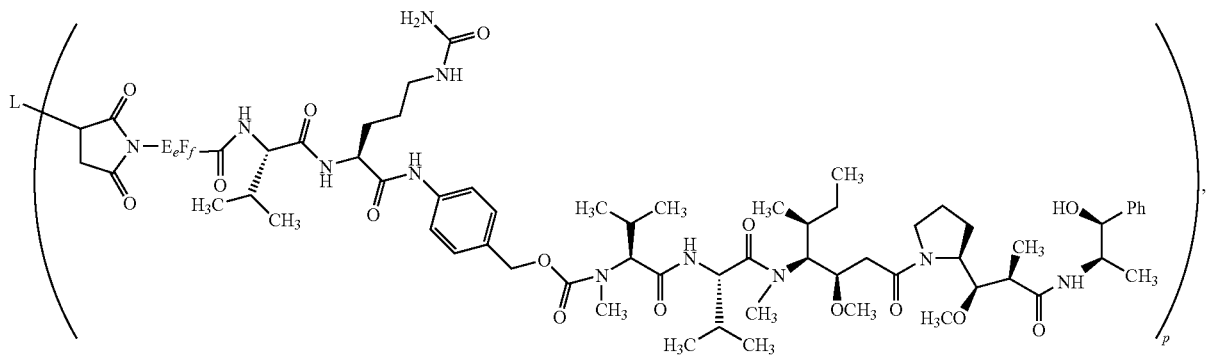

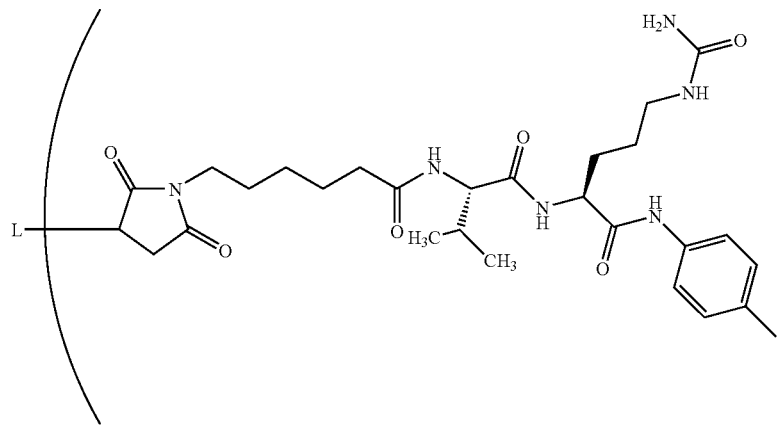

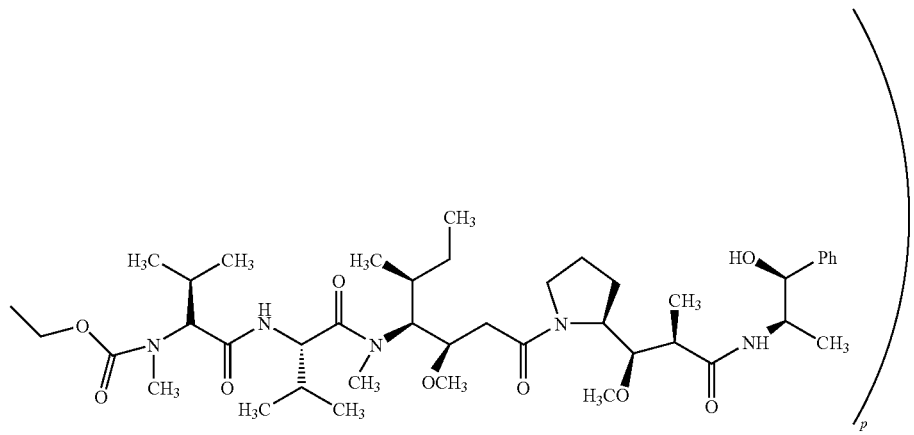

or a pharmaceutically acceptable salt thereof.

30. The drug-linker-antibody conjugate of claim 29 or a pharmaceutically acceptable salt thereof wherein the antibody is a monoclonal antibody.

31. The drug-linker-antibody conjugate of claim 30 or a pharmaceutically acceptable salt thereof wherein the antibody comprises a variable region derived from a murine monoclonal antibody and a human immunoglobulin constant region.

32. A composition comprising drug-linker-antibody conjugates having Formula Ia:

or a pharmaceutically acceptable salt thereof;
wherein,
L- is an antibody that immunospecifically binds to a cancer cell antigen which is on the surface of a cancer cell;
-$A_a$-$W_w$—$Y_y$— is an enzymatically cleavable linker unit that links the Drug unit and the antibody, wherein:
-A- is a Stretcher unit;
a is 1;
each —W— is independently an Amino Acid unit;
—Y— is a self-immolative Spacer unit;
w is an integer ranging from 2 to 12;
y is 1 or 2;
p ranges from 1 to 10 and is the average number of -$A_a$-$W_w$—$Y_y$-D units per antibody in the composition; and -D is a Drug unit of the formula

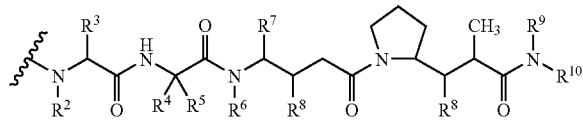

wherein, the wavy line indicates the point of attachment to the Spacer unit, and for each D:

$R^2$ is selected from the group consisting of —H and —$C_1$-$C_8$ alkyl;

$R^3$ is selected from the group consisting of —H, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle);

$R^4$ is selected from the group consisting of —H, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle) wherein $R^5$ is selected from the group consisting of —H and -methyl; or $R^4$ and $R^5$ join and form a ring with the carbon atom to which they are attached and $R^4$ and $R^5$ have the formula —($CR^aR^b$)$_n$— wherein $R^a$ and $R^b$ are independently selected from the group consisting of —H, —$C_1$-$C_8$ alkyl and —$C_3$-$C_8$ carbocycle and n is selected from the group consisting of 2, 3, 4, 5 and 6;

$R^6$ is selected from the group consisting of —H and —$C_1$-$C_8$ alkyl;

$R^7$ is selected from the group consisting of —H, —$C_1$-$C_8$ alkyl, —$C_3$-$C_8$ carbocycle, O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle);

each $R^8$ is independently selected from the group consisting of —H, —OH, —$C_1$-$C_8$ alkyl, —$C_3$-$C_8$ carbocycle and —O—($C_1$-$C_8$ alkyl);

$R^9$ is selected from the group consisting of —H and —$C_1$-$C_8$ alkyl;

$R^{10}$ is selected from the group consisting of:

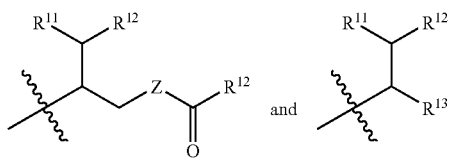

Z is —O—, —S—, —NH— or —N($R^{14}$)—;

$R^{11}$ is selected from the group consisting of —H, —OH, —$NH_2$, —$NHR^{14}$, —$N(R^{14})_2$, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle); or $R^{11}$ is an oxygen atom which forms a carbonyl unit (C=O) with the carbon atom to which it is attached and a hydrogen atom on this carbon atom is replaced by one of the bonds in the (C=O) double bond;

each $R^{12}$ is independently selected from the group consisting of -aryl and —$C_3$-$C_8$ heterocycle;

$R^{13}$ is selected from the group consisting of —H, —OH, —$NH_2$, —$NHR^{14}$, —$N(R^{14})_2$, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), $C_3$-$C_8$ heterocycle and —$C_{1-8}$ alkyl-($C_3$-$C_8$ heterocycle); and each $R^{14}$ is independently —H or —$C_1$-$C_8$ alkyl; and a pharmaceutically acceptable carrier or vehicle.

33. A composition comprising drug-linker-antibody conjugates having Formula Ia:

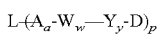

or a pharmaceutically acceptable salt thereof, wherein,

L- is an antibody that immunospecifically binds to a cancer cell antigen which is on the surface of a cancer cell;

-$A_a$-$W_w$—$Y_y$— is an enzymatically cleavable linker unit that links the Drug unit and the antibody, wherein:

-A- is a Stretcher unit;

a is 1;

each —W— is independently an Amino Acid unit;

—Y— is a self-immolative Spacer unit;

w is an integer ranging from 2 to 12;

y is 1 or 2;

p ranges from 1 to 10 and is the average number of -$A_a$-$W_w$—$Y_y$-D units per antibody in the composition; and -D is a Drug unit having the structure

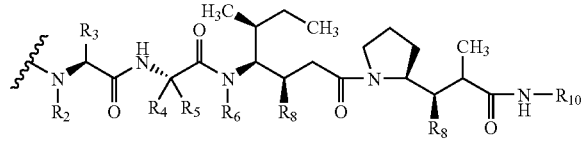

wherein, the wavy line indicates the point of attachment to the Spacer unit, and for each D:

$R^2$ is selected from the group consisting of —H and -methyl;

$R^3$ is selected from the group consisting of —H, -methyl, and -isopropyl;

$R^4$ is selected from the group consisting of —H and -methyl;

$R^5$ is selected from the group consisting of -isopropyl, -isobutyl, -sec-butyl, -methyl and -t-butyl or $R^4$ and $R^5$ join and faun a ring with the carbon atom to which they are attached and $R^4$ and $R^5$ have the formula —$(CR^aR^b)_n$— where $R^a$ and $R^b$ are independently selected from the group consisting of —H, —$C_1$-$C_8$ alkyl, and —$C_3$-$C_8$ carbocycle, and n is selected from the group consisting of 2, 3, 4, 5 and 6;

$R^6$ is selected from the group consisting of —H and -methyl;

each $R^8$ is independently selected from the group consisting of —OH, -methoxy and -ethoxy;

$R^{10}$ is selected from the group consisting of:

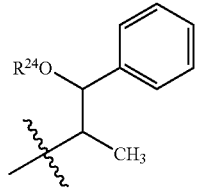 and 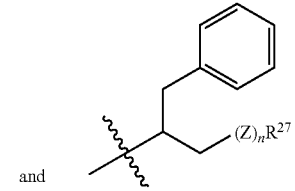

$R^{24}$ is selected from the group consisting of H and —C(O)$R^{25}$—; wherein $R^{25}$ is selected from the group consisting of —$C_1$-$C_8$ alkyl, —$C_3$-$C_8$ carbocycle, -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle);

Z is —O—, —NH—, —OC(O)—, —NHC(O)—, or —$NR^{28}$C(O)—; where $R^{28}$ is selected from the group consisting of —H and —$C_1$-$C_8$ alkyl;

n is 0 or 1; and $R^{27}$ is selected from the group consisting of —H, —$N_3$, —$C_1$-$C_8$ alkyl, —$C_3$-$C_8$ carbocycle, -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle) when n is 0; and $R^{27}$ is selected from the group consisting of —H, —$C_1$-$C_8$ alkyl, —$C_3$-$C_8$ carbocycle, -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle) when n is 1; and a pharmaceutically acceptable carrier or vehicle.

34. The composition of claim 32 wherein in the drug-linker-antibody conjugates or pharmaceutically acceptable salt thereof, $R^2$ is —$C_1$-$C_8$ alkyl.

35. The composition of claim 33 wherein in the drug-linker-antibody conjugates or pharmaceutically acceptable salt thereof, $R^2$ is methyl.

36. The composition of claim 32 wherein in the drug-linker-antibody conjugates or pharmaceutically acceptable salt thereof, -D is a Drug unit having the structure

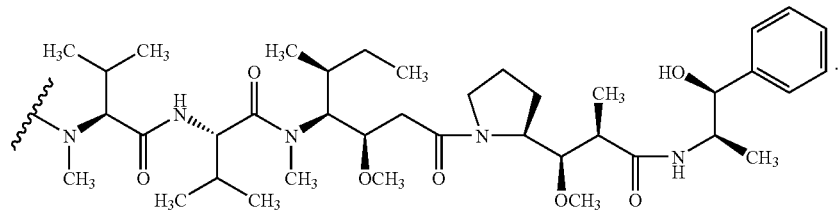

37. The composition of claim 32 wherein the drug-linker-antibody conjugates have the formula

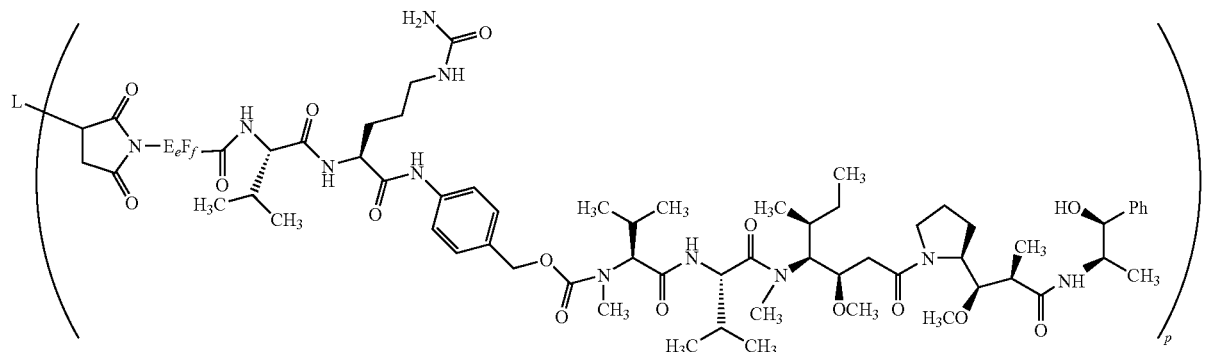

or a pharmaceutically acceptable salt thereof, where E is —CH$_2$— or —CH$_2$CH$_2$O—; e is an integer ranging either from 0-10 when E is —CH$_2$—, or from 1-10 when E is —CH$_2$CH$_2$—O—; F is —CH$_2$—; and f is 0 or 1.

38. The composition of claim 37 wherein in the drug-linker-antibody conjugates or pharmaceutically acceptable salt thereof, the antibody is a monoclonal antibody.

39. The composition of claim 37 wherein in the drug-linker-antibody conjugates or pharmaceutically acceptable salt thereof, the antibody is a full length immunoglobulin molecule.

40. The composition of claim 37 wherein in the drug-linker-antibody conjugates or pharmaceutically acceptable salt thereof, the antibody is bound to the Stretcher unit via an interchain thiol of the antibody.

41. The composition of claim 38 wherein in the drug-linker-antibody conjugates or pharmaceutically acceptable salt thereof, the antibody is a chimeric antibody.

42. The composition of claim 41 wherein in the drug-linker-antibody conjugates or pharmaceutically acceptable salt thereof, the chimeric antibody comprises a variable region derived from a murine monoclonal antibody and a human immunoglobulin constant region.

43. The composition of claim 37 wherein in the drug-linker-antibody conjugates or pharmaceutically acceptable salt thereof, p ranges from 1 to about 5.

44. The composition of claim 32 wherein the drug-linker-antibody conjugates have the formula

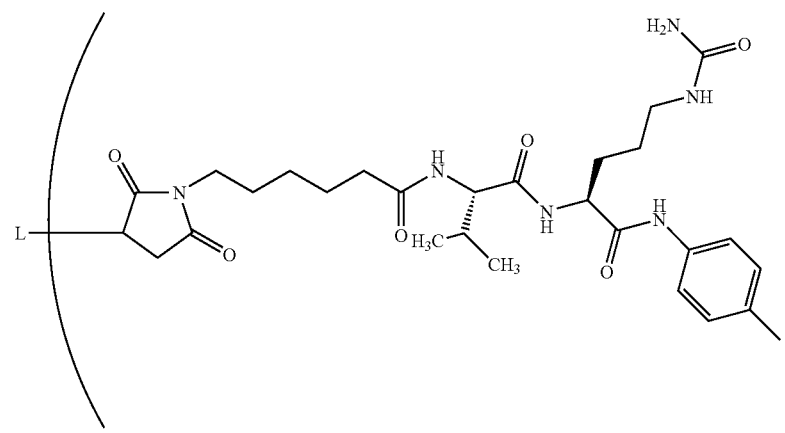

-continued or a pharmaceutically acceptable salt thereof.

45. The composition of claim 44 wherein in the drug-linker-antibody conjugates or pharmaceutically acceptable salt thereof, the antibody is a monoclonal antibody.

46. The composition of claim 45 wherein in the drug-linker-antibody conjugates or pharmaceutically acceptable salt thereof, the antibody comprises a variable region derived from a murine monoclonal antibody and a human immunoglobulin constant region.

47. A method for the treatment of Hodgkin's Disease or Anaplastic Large Cell Lymphoma in a human, the method comprising administering to the human an effective amount of a drug-linker-antibody conjugate wherein the drug-linker-antibody conjugate is taken up inside the cancer cell and, once inside the cancer cell, the linker unit is cleaved, resulting in release of drug; the drug-linker-antibody conjugate having formula Ia:

$$L-(A_a-W_w-Y_y-D)_p \qquad \text{Ia}$$

or a pharmaceutically acceptable salt thereof
wherein,
L- is an antibody that immunospecifically binds to human CD30 antigen;
-$A_a$-$W_w$—$Y_y$— is an enzymatically cleavable linker unit that links the Drug unit and the antibody, wherein:
-A- is a Stretcher unit;
a is 1;
each —W— is independently an Amino Acid unit;
—Y— is a self-immolative Spacer unit;
w is an integer ranging from 2 to 12;
y is 1 or 2;
p ranges from 1 to about 20; and
-D is a Drug unit having the structure wherein, the wavy line indicates the point of attachment to the Spacer unit, and for each D:
$R^2$ is -methyl;
$R^3$ is selected from the group consisting of —H, -methyl, and -isopropyl;

$R^4$ is selected from the group consisting of —H and -methyl;
$R^5$ is selected from the group consisting of -isopropyl, -isobutyl, -sec-butyl, -methyl and -t-butyl or $R^4$ and $R^5$ join and form a ring with the carbon atom to which they are attached and $R^4$ and $R^5$ have the formula —$(CR^aR^b)_n$— where $R^a$ and $R^b$ are independently selected from the group consisting of —H, —$C_1$-$C_8$ alkyl, and —$C_3$-$C_8$ carbocycle, and n is selected from the group consisting of 2, 3, 4, 5 and 6;
$R^6$ is selected from the group consisting of —H and -methyl;
each $R^8$ is independently selected from the group consisting of —OH, -methoxy and -ethoxy;
$R^{10}$ is selected from the group consisting of:

$R^{24}$ is selected from the group consisting of H and —C(O)$R^{25}$—; wherein $R^{25}$ is selected from the group consisting of —$C_1$-$C_8$ alkyl, —$C_3$-$C_8$ carbocycle, -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle);
Z is —O—, —NH—, —OC(O)—, —NHC(O)—, or —NR$^{28}$C(O)—; where $R^{28}$ is selected from the group consisting of —H and —$C_1$-$C_8$ alkyl;
n is 0 or 1; and
$R^{27}$ is selected from the group consisting of —H, —$N_3$, —$C_1$-$C_8$ alkyl, —$C_3$-$C_8$ carbocycle, -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle) when n is 0; and $R^{27}$ is selected from the group consisting of —H, —$C_1$-$C_8$ alkyl, —$C_3$-$C_8$ carbocycle, -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle) when n is 1.

48. The method of claim 47 wherein the method is for treating Hodgkin's Disease.

49. The method of claim 47 wherein the drug-linker-antibody conjugate has the structure

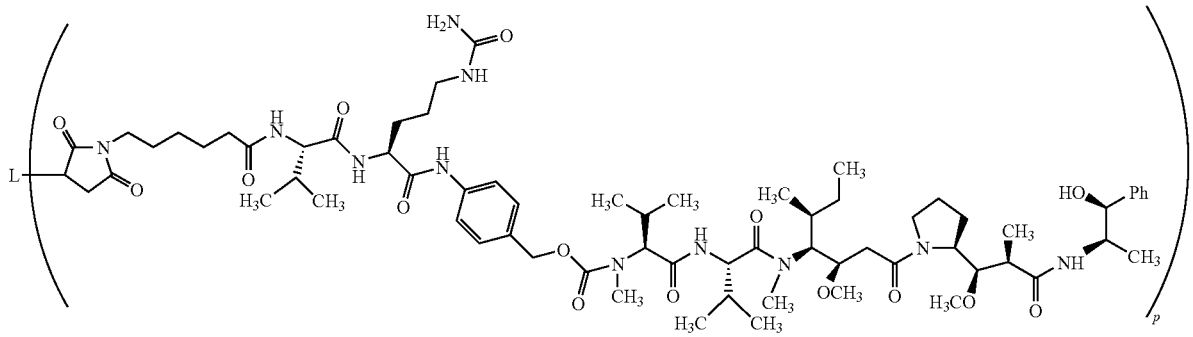

or a pharmaceutically acceptable salt thereof.

50. The method of claim 49 wherein the antibody is a monoclonal antibody.

51. The method of claim 49 wherein the antibody is a chimeric antibody.

52. The method of claim 49 wherein the antibody is a humanized antibody.

53. A method for the treatment of Hodgkin's Disease or Anaplastic Large Cell Lymphoma in a human, the method comprising administering to the human an effective amount of a composition comprising drug-linker-antibody conjugates and a pharmaceutically acceptable carrier wherein the drug-linker-antibody conjugates are taken up inside the cancer cell and, once inside the cancer cell, the linker units of the drug-linker-antibody conjugates are cleaved, resulting in release of drug; the drug-linker-antibody conjugates having Formula Ia:

$$L\text{-}(A_a\text{-}W_w\text{---}Y_y\text{-}D)_p \qquad \text{Ia}$$

or a pharmaceutically acceptable salt thereof;
wherein,
- L- is an antibody that immunospecifically binds to human CD30 antigen;
- $-A_a$-$W_w$—$Y_y$— is an enzymatically cleavable linker unit that links the Drug unit and the antibody, wherein:
- -A- is a Stretcher unit;
- a is 1;
- each —W— is independently an Amino Acid unit;
- —Y— is a self-immolative Spacer unit;
- w is an integer ranging from 2 to 12;
- y is 1 or 2;
- p ranges from 1 to 10 and is the average number of -$A_a$-$W_w$—$Y_y$-D units per antibody in the composition; and
- -D is a Drug unit of the formula

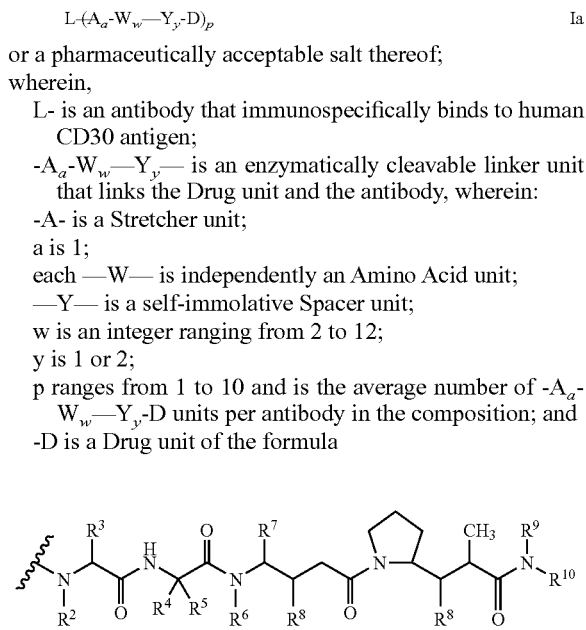

wherein, the wavy line indicates the point of attachment to the Spacer unit, and for each D:
- $R^2$ is —$C_1$-$C_8$ alkyl;
- $R^3$ is selected from the group consisting of —H, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle);
- $R^4$ is selected from the group consisting of —H, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle) wherein $R^5$ is selected from the group consisting of —H and -methyl; or $R^4$ and $R^5$ join and form a ring with the carbon atom to which they are attached and $R^4$ and $R^5$ have the formula —$(CR^aR^b)_n$— wherein $R^a$ and $R^b$ are independently selected from the group consisting of —H, —$C_1$-$C_8$ alkyl and —$C_3$-$C_8$ carbocycle and n is selected from the group consisting of 2, 3, 4, 5 and 6;
- $R^6$ is selected from the group consisting of —H and —$C_1$-$C_8$ alkyl;
- $R^7$ is selected from the group consisting of —H, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle);
- each $R^8$ is independently selected from the group consisting of —H, —OH, —$C_1$-$C_8$ alkyl, —$C_3$-$C_8$ carbocycle and —O—($C_1$-$C_8$ alkyl);
- $R^9$ is selected from the group consisting of —H and —$C_1$-$C_8$ alkyl;
- $R^{10}$ is selected from the group consisting of:

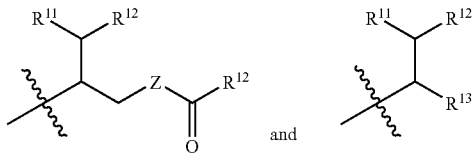

Z is —O—, —S—, —NH— or —N($R^{14}$)—;
$R^{11}$ is selected from the group consisting of —H, —OH, —$NH_2$, —$NHR^{14}$, —$N(R^{14})_2$, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle); or $R^{11}$ is an oxygen atom which forms a carbonyl unit (C=O) with the carbon atom to which it is attached and a hydrogen atom on this carbon atom is replaced by one of the bonds in the (C=O) double bond;

each $R^{12}$ is independently selected from the group consisting of -aryl and —$C_3$-$C_8$ heterocycle;

$R^{13}$ is selected from the group consisting of —H, —OH, —$NH_2$, —$NHR^{14}$, —$N(R^{14})_2$, —$C_1$-$C_8$ alkyl, —$C_3$-$C_8$ carbocycle, —O—($C_1$-$C_8$ alkyl), -aryl, —$C_1$-$C_8$ alkyl-aryl, —$C_1$-$C_8$ alkyl-($C_3$-$C_8$ carbocycle), $C_3$-$C_8$ heterocycle and —$C_{1-8}$ alkyl-($C_3$-$C_8$ heterocycle); and each $R^{14}$ is independently —H or —$C_1$-$C_8$ alkyl.

54. The method of claim 53 wherein the drug-linker-antibody conjugates have the structure

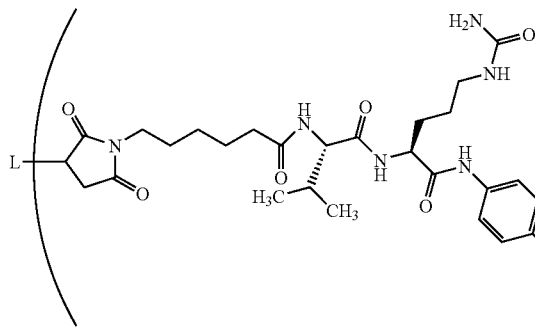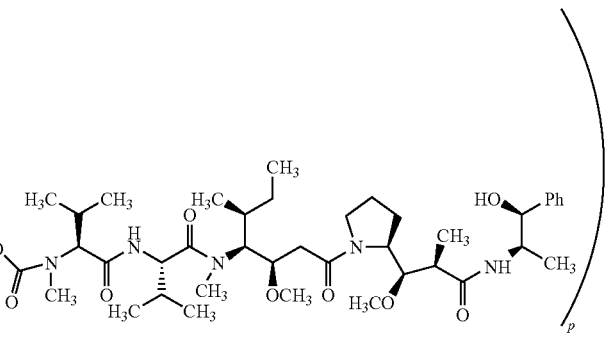

or a pharmaceutically acceptable salt thereof.

55. The method of claim 54 wherein the antibody is a monoclonal antibody.

56. The method of claim 55 wherein the antibody comprises a variable region derived from a murine monoclonal antibody and a human immunoglobulin constant region.

57. The method of claim 54 wherein the antibody is a full length immunoglobulin molecule.

58. The method of claim 55 wherein the antibody is a humanized antibody.

59. The drug-linker-antibody conjugate of claim 14 or a pharmaceutically acceptable salt thereof wherein the antibody is a chimeric antibody.

60. The drug-linker-antibody conjugate of claim 14 or a pharmaceutically acceptable salt thereof wherein the antibody is a humanized antibody.

61. The drug-linker-antibody conjugate of claim 14 or a pharmaceutically acceptable salt thereof wherein the antibody comprises a human immunoglobulin constant region.

62. The drug-linker-antibody conjugate of claim 61 or a pharmaceutically acceptable salt thereof wherein the antibody is an IgG1.

63. The drug-linker-antibody conjugate of claim 59 or a pharmaceutically acceptable salt thereof wherein the antibody comprises a variable region derived from a murine monoclonal antibody and a human immunoglobulin constant region.

64. The drug-linker-antibody conjugate of claim 63 or a pharmaceutically acceptable salt thereof wherein the antibody immunospecifically binds human CD30 antigen.

65. The drug-linker-antibody conjugate of claim 26 or a pharmaceutically acceptable salt thereof wherein the antibody immunospecifically binds human CD30 antigen.

66. The drug-linker-antibody conjugate of claim 22 or a pharmaceutically acceptable salt thereof wherein the antibody comprises a human immunoglobulin constant region.

67. The drug-linker-antibody conjugate of claim 66 or a pharmaceutically acceptable salt thereof wherein the antibody is an IgG1.

68. The drug-linker-antibody conjugate of claim 30 or a pharmaceutically acceptable salt thereof wherein the antibody immunospecifically binds human CD30 antigen.

69. The composition of claim 38 wherein in the drug-linker-antibody conjugates or pharmaceutically acceptable salt thereof, the antibody is a humanized antibody.

70. The composition of claim 38 wherein in the drug-linker-antibody conjugates or a pharmaceutically acceptable salt thereof, the antibody comprises a human immunoglobulin constant region.

71. The composition of claim 70 wherein in the drug-linker-antibody conjugates or a pharmaceutically acceptable salt thereof, the antibody is an IgG1.

72. The composition of claim 42 wherein in the drug-linker-antibody conjugates or pharmaceutically acceptable salt thereof, the antibody immunospecifically binds human CD30 antigen.

73. The composition of claim 45 wherein in the drug-linker-antibody conjugates or pharmaceutically acceptable salt thereof, the antibody is a humanized antibody.

74. The composition of claim 46 wherein in the drug-linker-antibody conjugates or pharmaceutically acceptable salt thereof, the antibody immunospecifically binds human CD30 antigen.

75. The drug-linker-antibody conjugate of claim 1 or a pharmaceutically acceptable salt thereof wherein p ranges from about 7 to about 9.

76. The drug-linker-antibody conjugate of claim 21 or a pharmaceutically acceptable salt thereof wherein p ranges from about 7 to about 9.

77. The drug-linker-antibody conjugate of claim 29 or a pharmaceutically acceptable salt thereof wherein p ranges from 1 to 10.

78. The composition of claim 37 wherein in the drug-linker antibody conjugates or pharmaceutically acceptable salt thereof, p ranges from about 7 to about 9.

79. The composition of claim 44 wherein in the drug-linker antibody conjugates or pharmaceutically acceptable salt thereof, p ranges from 1 to about 5.

80. The method of claim 53 wherein in the drug-linker antibody conjugates or pharmaceutically acceptable salt thereof, p ranges from 1 to about 5.

81. The method of claim 54 wherein in the drug-linker antibody conjugates or pharmaceutically acceptable salt thereof, p ranges from 1 to about 5.

* * * * *

UNITED STATES PATENT AND TRADEMARK OFFICE
CERTIFICATE OF CORRECTION

PATENT NO. : 7,829,531 B2  
APPLICATION NO. : 12/408646  
DATED : November 9, 2010  
INVENTOR(S) : Senter et al.

Page 1 of 2

It is certified that error appears in the above-identified patent and that said Letters Patent is hereby corrected as shown below:

Claim 2, Column 220, Line 66: delete "and $R^b$)" and insert --and $R^b$-- (in other words, delete the parenthesis after $R^b$ in the instance of $R^b$ that is not in the formula).

Claim 7, Column 222, Line 29: please delete the chemical structure and insert:

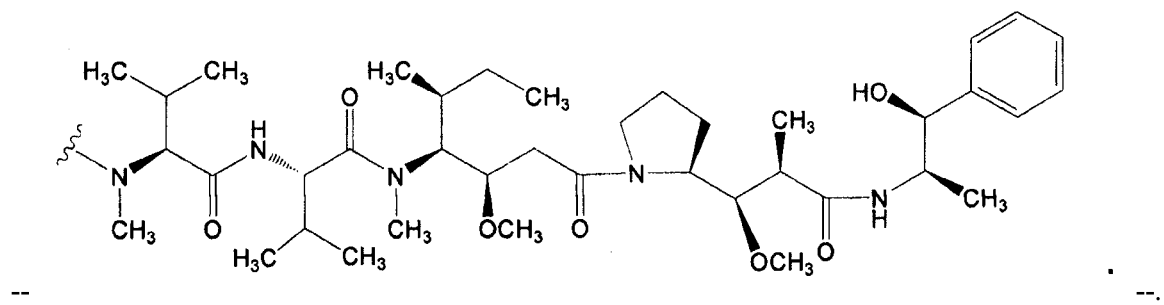

--           --.

Claim 29, Column 225, Line 1: please delete the chemical structure and insert:

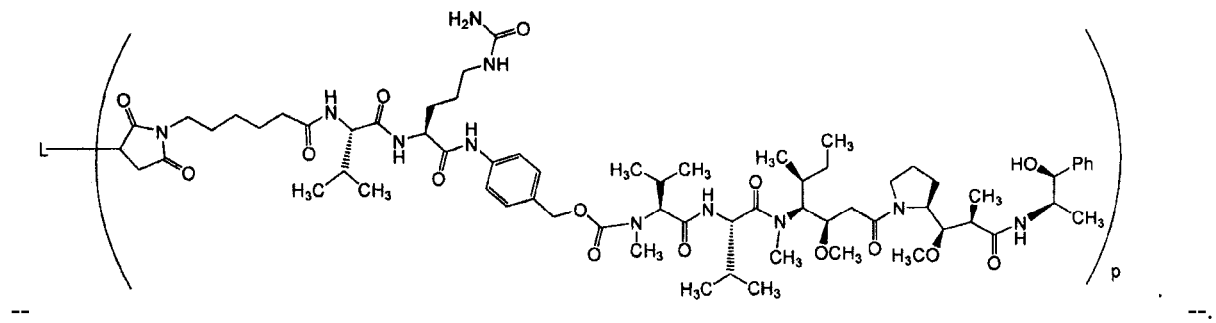

--           --.

Column 228, Claim 33, Line 21: delete "faun" and replace with --form--.

Signed and Sealed this  
Fifth Day of April, 2011

David J. Kappos  
*Director of the United States Patent and Trademark Office*

CERTIFICATE OF CORRECTION (continued)

U.S. Pat. No. 7,829,531 B2

Claim 44, Columns 230, Line 48 - Column 231, Line 1: delete the chemical structure that spans those columns and insert:

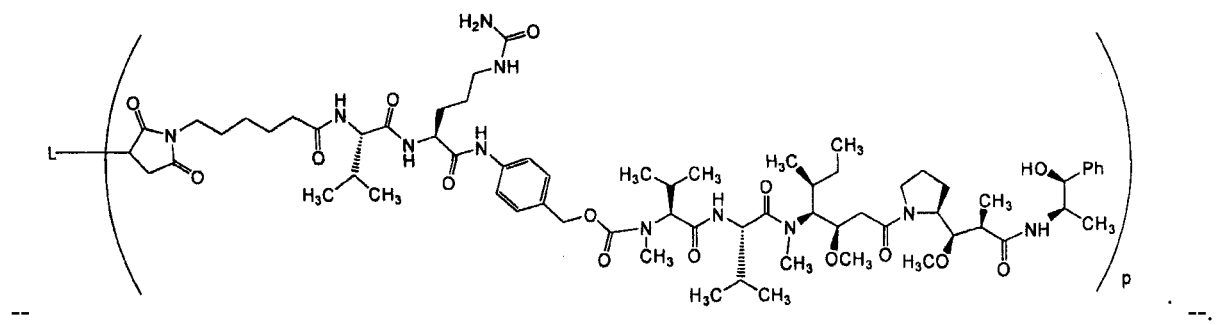

-- --.

Column 236, Claim 68, Line 1: delete "claim 30" and replace with --claim 31--.